US012780904B2

(12) United States Patent
Crowe, Jr.

(10) Patent No.: US 12,780,904 B2
(45) Date of Patent: Nov. 3, 2026

(54) HUMAN ANTIBODIES TO ALPHAVIRUSES

(71) Applicant: VANDERBILT UNIVERSITY, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1068 days.

(21) Appl. No.: 17/638,918

(22) PCT Filed: Aug. 31, 2020

(86) PCT No.: PCT/US2020/048708
§ 371 (c)(1),
(2) Date: Feb. 28, 2022

(87) PCT Pub. No.: WO2021/042021
PCT Pub. Date: Mar. 4, 2021

(65) Prior Publication Data

US 2023/0065377 A1 Mar. 2, 2023

Related U.S. Application Data

(60) Provisional application No. 62/933,735, filed on Nov. 11, 2019, provisional application No. 62/896,382, filed on Sep. 5, 2019, provisional application No. 62/894,740, filed on Aug. 31, 2019.

(51) Int. Cl.

| | |
|---|---|
| ***C07K 16/10*** | (2026.01) |
| ***A61K 39/00*** | (2006.01) |
| ***A61P 31/14*** | (2006.01) |
| ***G01N 33/569*** | (2006.01) |

(52) U.S. Cl.
CPC .............. *C07K 16/10* (2013.01); *A61P 31/14* (2018.01); *G01N 33/56983* (2013.01); *A61K 2039/505* (2013.01); *C07K 2317/24* (2013.01); *C07K 2317/31* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 7,973,140 B2 * | 7/2011 | Green | ....................... | A61P 9/00 530/387.9 |
| 2011/0143333 A1 | 6/2011 | Brehin et al. | | |
| 2012/0244150 A1 | 9/2012 | Goodchild et al. | | |
| 2017/0015733 A1 | 1/2017 | Warter et al. | | |
| 2018/0079802 A1 | 3/2018 | Crowe, Jr. et al. | | |

FOREIGN PATENT DOCUMENTS

WO WO 2010/004276 A2 1/2010

OTHER PUBLICATIONS

Hatami, et al., Trends in Microbio, 2025, in press, 1-12 (Year: 2025).*

Fox, J. M. et al., "Broadly neutralizing alphavirus antibodies bind an epitope on E2 and inhibit entry and egress," *Cell*, 163 (2015): 1095-1107.

Griffin, D. E., "Alphaviruses," *Fields Virology*, 6th edition (2013): 651-686.

Jin, J. et al., "Neutralizing Monoclonal Antibodies Block Chikungunya Virus Entry and Release by Targeting an Epitope Critical to Viral Pathogenesis," *Cell reports*, 13.11 (2015): 2553-2564.

Kim, A. S. et al., "Protective antibodies against Eastern equine encephalitis virus bind to epitopes in domains A and B of the E2 glycoprotein," *Nat Microbiol.*, 4 (2019): 187-197.

Long, F. et al., "Cryo-EM structures elucidate neutralizing mechanisms of anti-chikungunya human monoclonal antibodies with therapeutic activity," *PNAS*, 112.45 (2015): 13898-13903.

PCT International Search Report and Written Opinion issued in International Patent Application No. PCT/US2020/048708, mailed Feb. 1, 2021.

PCT International Preliminary Report on Patentability issued in International Patent Application No. PCT/US2020/048708, mailed Mar. 10, 2022.

Porta, J. et al., "Locking and blocking the viral landscape of an alphavirus with neutralizing antibodies," *Journal of Virology*, 88.17 (2014):9616-9623.

Sun, S. et al., "Structural analyses at pseudo atomic resolution of Chikungunya virus and antibodies show mechanisms of neutralization," *eLife.* 2 (2013): e00435, 1-27.

Sun, E, et al., "Comprehensive mapping of common immunodominant epitopes in the eastern equine encephalitis virus E2 protein recognized by avian antibody responses," *PLoS One*, 8.7 (2013): e69349, 1-9.

Voss, J. E. et al., "Glycoprotein organization of Chikungunya virus particles revealed by X-ray crystallography," *Nature*, 468 (2010): 709-712.

Williamson, L. E. et al., "Neutralization of Eastern equine encephalitis virus by human monoclonal antibodies," *Department of Pathology, Microbiology and Immunology, Pediatrics, Vanderbilt Vaccine Center, Vanderbilt University Medical Center, Poster*, 2019.

* cited by examiner

*Primary Examiner* — Misook Yu
*Assistant Examiner* — Samantha Lake Hopkins
(74) *Attorney, Agent, or Firm* — pH IP Law

(57) ABSTRACT

The present disclosure is directed to antibodies binding to and neutralizing alphavirus, such as EEEV, WEEV or VEEV, and methods for use thereof. Thus, in accordance with the present disclosure, a method of detecting an alphavirus infection in a subject comprising (a) contacting a sample from said subject with an antibody or antibody fragment having clone-paired heavy and light chain CDR sequences from Tables 3 and 4, respectively; and (b) detecting alphavirus in said sample by binding of said antibody or antibody fragment to an alphavirus antigen in said sample.

27 Claims, 39 Drawing Sheets

Specification includes a Sequence Listing.

A. SINV/EEEV

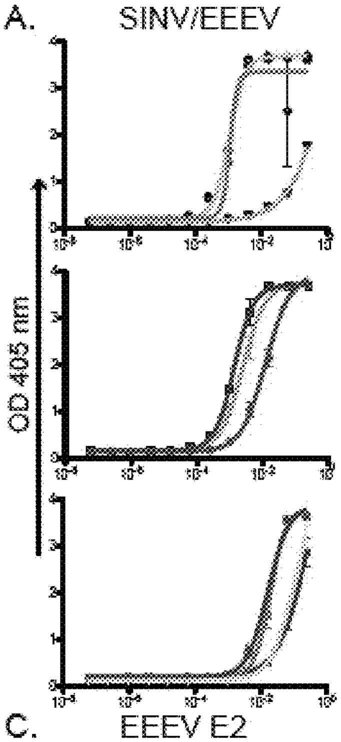

| Endpoint titer (1/dilution) | Donor | Endpoint titer (1/dilution) |
|---|---|---|
| SINV/EEV Binding | Natural EEEV Infection | SINV/EEV Neutralization |
| 4,096 | 1069 | 16,384 |
| 4,096 | 982 | 16,384 |
| 64 | 1065 | 0 |
| | SIP | |
| 4,096 | 921 | 4,096 |
| 4,096 | 1008 | 4,096 |
| 1,024 | 1093 | 1,024 |
| | VEEV | |
| 1,024 | 933 | 1,024 |
| 1,024 | 932 | 1,024 |
| 64 | 1140 | 64 |
| 64 | 117 | 0 |
| | Negative | |
| 0 | 269 | 64 |

B. SINV/EEEV

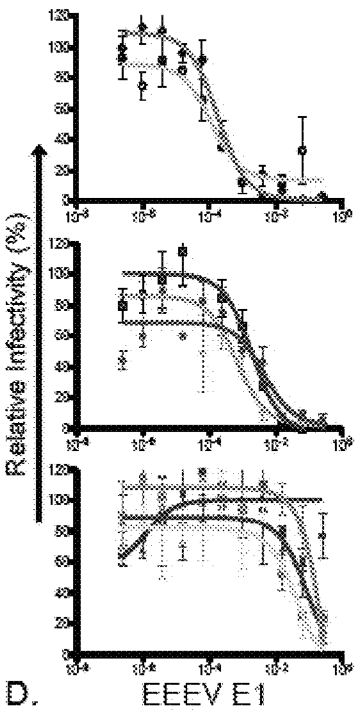

C. EEEV E2 glycoprotein

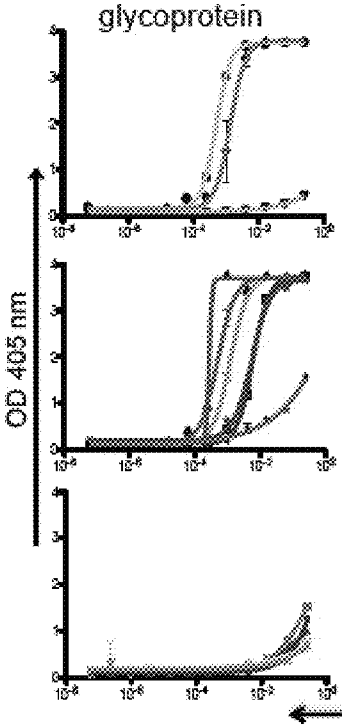

| Endpoint titer (1/dilution) | Donor | Endpoint titer (1/dilution) |
|---|---|---|
| EEEV E2 glycoprotein | Natural EEEV Infection | EEEV E1 glycoprotein |
| 1,024 | 1069 | 16,384 |
| 4,096 | 982 | 4,096 |
| 4 | 1065 | 64 |
| | SIP | |
| 4,096 | 1047 | 1,024 |
| 4,096 | 975 | 1,024 |
| 1,024 | 921 | 1,024 |
| 256 | 1008 | 1,024 |
| 256 | 1093 | 1,024 |
| 64 | 1109 | 1,024 |
| | VEEV | |
| 4 | 933 | 256 |
| 16 | 932 | 64 |
| 4 | 1140 | 256 |
| 16 | 117 | 64 |
| | Negtaive | |
| 4 | 269 | 256 |

D. EEEV E1 glycoprotein

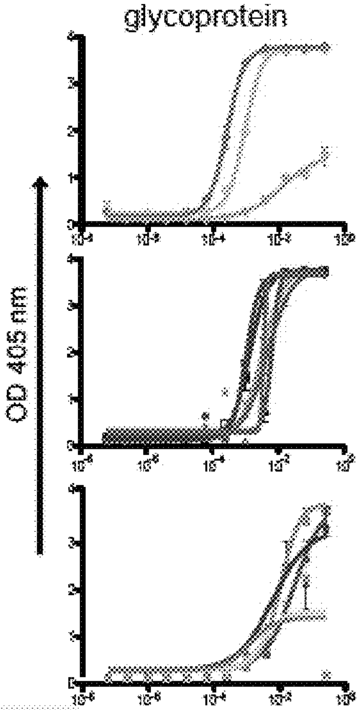

Serum Serial Dilution

FIGS. 1A-D

A.
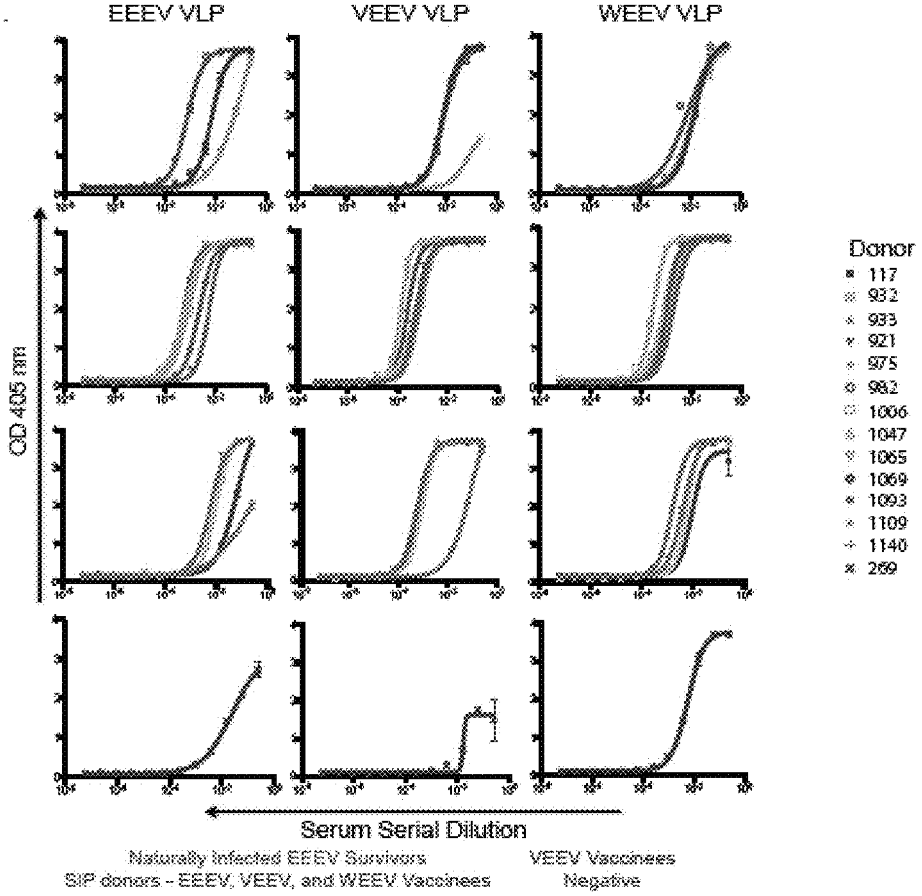
B.
| Endpoint Titer (1/dilution) | | | | |
|---|---|---|---|---|
| | Donor | EEEV VLP | VEEV VLP | WEEV VLP |
| Naturally Infected EEEV | 982 | 4096 | 256 | 256 |
| | 1069 | 1024 | 256 | 256 |
| | 1065 | 256 | 16 | 256 |
| | | | | |
| SIP Donors | 921 | 4096 | 16384 | 4096 |
| | 975 | 4096 | 4096 | 1024 |
| | 1006 | 4096 | 16384 | 4096 |
| | 1047 | 16384 | 4096 | 4096 |
| | 1093 | 1024 | 4096 | 1024 |
| | 1109 | 1024 | 4096 | 1024 |
| | | | | |
| VEEV Vaccinees | 933 | 1024 | 4096 | 1024 |
| | 932 | 256 | 4096 | 256 |
| | 117 | 64 | 4096 | 256 |
| | 1140 | 64 | 64 | 1024 |
| | | | | |
| Negative | 269 | 256 | 64 | 256 |
FIGS. 2A-B

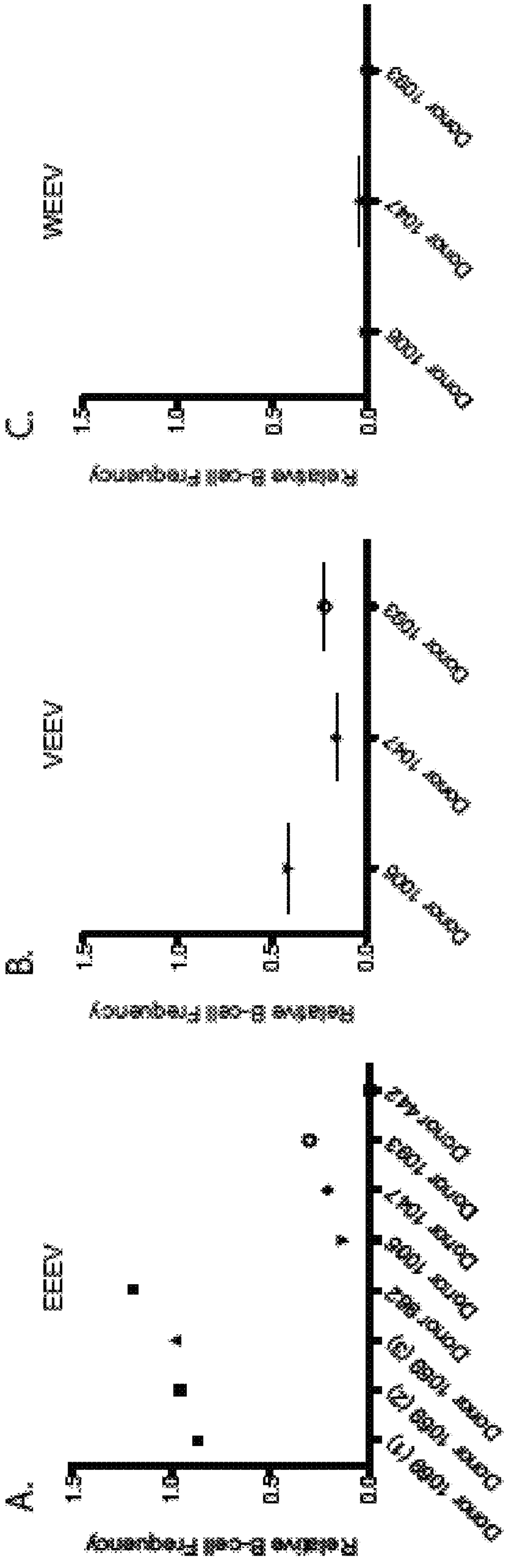
FIGS. 3A-C

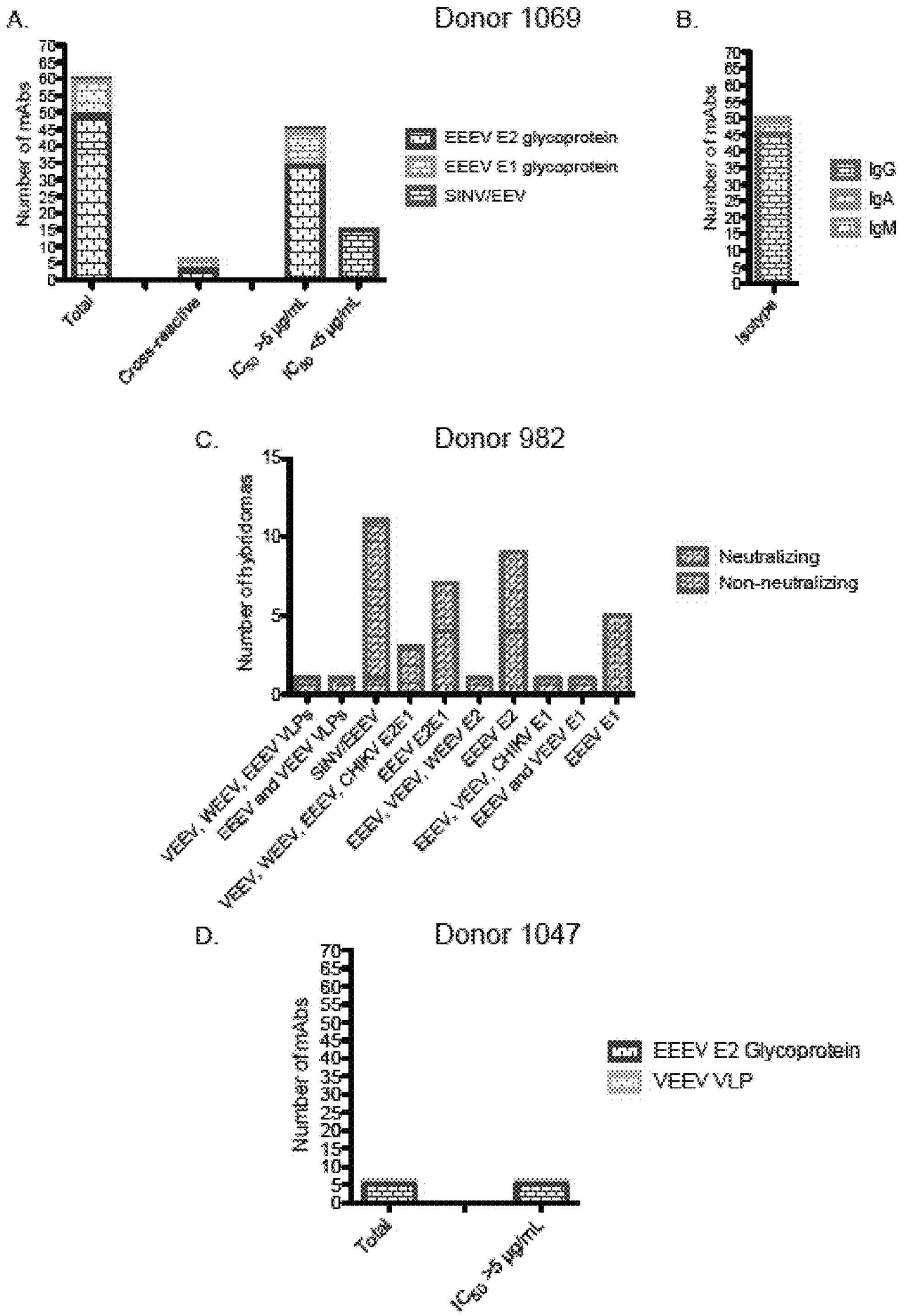
FIGS. 4A-D

A.

| | mAb | Reactivity | Protein/Virus $EC_{50}$ Ratio | Binding $EC_{50}$ (ng/mL) SINV/NA-EEEV | Binding $EC_{50}$ (ng/mL) EEEV E2 glycoprotein |
|---|---|---|---|---|---|
| * | EEEV-7 | EEEV E2 glycoprotein | 39.4 | 0.1 | 3.8 |
| * | EEEV-94 | | 18.9 | 0.3 | 6.8 |
| * | EEEV-66 | | 1,054.7 | 0.3 | 318.4 |
| * | EEEV-33 | | 135.2 | 0.4 | 54.1 |
| * | EEEV-16 | | 10.5 | 0.5 | 5.3 |
| | EEEV-63 | | 6.6 | 0.6 | 3.8 |
| * | EEEV-129 | | 8.5 | 0.6 | 5.1 |
| ** | EEEV-81 | | 9.7 | 0.6 | 5.8 |
| | EEEV-58 | | 3.0 | 1.0 | 3.0 |
| * | EEEV-108 | | 3.7 | 1.1 | 4.1 |
| | EEEV-154 | | 4.5 | 1.1 | 5.1 |
| | EEEV-55 | | 2.3 | 1.2 | 4.2 |
| | EEEV-173 | | 3.5 | 1.8 | 6.4 |
| * | EEEV-21 | | 5.8 | 2.1 | 12.2 |
| | EEEV-93 | | 2.1 | 3.0 | 6.3 |
| | EEEV-17 | | 1.9 | 3.4 | 6.4 |
| * | EEEV-27 | | 1.9 | 3.7 | 7.1 |
| | EEEV-30 | | 0.79 | 9.9 | 7.9 |
| | EEEV-43 | | 0.22 | 12.6 | 2.8 |
| | EEEV-168 | | 0.83 | 15.0 | 12.5 |
| * | EEEV-147 | | 0.26 | 17.1 | 4.5 |
| | EEEV-35 | | 0.28 | 17.2 | 4.7 |
| | EEEV-23 | | 0.11 | 51.4 | 5.5 |
| | EEEV-28 | | 0.11 | 53.2 | 5.7 |
| | EEEV-144 | | 3.4 | 53.8 | 182.8 |
| | EEEV-169 | | 0.08 | 75.2 | 6.2 |
| | EEEV-67 | | 0.09 | 80.6 | 7.6 |
| | EEEV-180 | | 0.04 | 85.4 | 3.5 |
| * | EEEV-54 | | 0.05 | 102.3 | 5.2 |
| * | EEEV-12 | | 0.03 | 136.2 | 4.0 |
| | EEEV-164 | | 0.24 | 139.4 | 33.8 |
| | EEEV-153 | | 0.01 | 143.8 | 2.0 |
| | EEEV-88 | | 0.06 | 217.9 | 13.6 |
| * | EEEV-42 | | 0.02 | 358.3 | 5.8 |
| | EEEV-68 | | 0.06 | 447.0 | 28.4 |
| | EEEV-47 | | 0.03 | 508.0 | 15.1 |
| ** | EEEV-107 | | 0.004 | 693.1 | 2.9 |
| | EEEV-181 | | 0.003 | 1,180 | 3.7 |
| | EEEV-182 | | ND | ND | 3.4 |
| * | EEEV-97 | | ND | ND | 3.5 |
| | EEEV-34 | | ND | ND | 4.6 |
| | EEEV-102 | | ND | ND | 4.9 |
| | EEEV-29 | | ND | ND | 5.7 |
| | EEEV-183 | | ND | ND | 8.7 |
| | EEEV-103 | | ND | ND | 15.9 |
| * | EEEV-143 | | ND | ND | 18.7 |
| | EEEV-84 | | ND | ND | 22.3 |
| | EEEV-160 | | ND | ND | 39.8 |
| | EEEV-158 | | ND | ND | 375.9 |
| | EEEV-51 | | ND | ND | 2,289 |

B.

| | mAb | Reactivity | Protein/Virus $EC_{50}$ Ratio | Binding $EC_{50}$ (ng/mL) SINV/NA-EEEV | Binding $EC_{50}$ (ng/mL) EEEV E1 glycoprotein |
|---|---|---|---|---|---|
| ** | EEEV-157 | EEEV E1 glycoprotein | 0.79 | 3.8 | 3.0 |
| | EEEV-109 | | 0.10 | 14.9 | 1.5 |
| | EEEV-104 | | 1.4 | 26.4 | 36.4 |
| | EEEV-76 | | 0.16 | 45.8 | 7.4 |
| | EEEV-126 | | 0.28 | 47.2 | 13.1 |
| | EEEV-127 | | 0.05 | 149.8 | 7.3 |
| ** | EEEV-179 | | 0.09 | 386.7 | 34.2 |
| | EEEV-98 | | 0.003 | 897.7 | 2.6 |
| ** | EEEV-138 | | ND | ND | 35.9 |
| | EEEV-141 | | ND | ND | 39.5 |

C.

| mAb | Reactivity | Binding $EC_{50}$ (ng/mL) SINV/NA-EEEV | Binding $EC_{50}$ (ng/mL) EEEV E2 glycoprotein | Binding $EC_{50}$ (ng/mL) EEEV E1 glycoprotein |
|---|---|---|---|---|
| EEEV-145 | SINV/NA-EEEV | 1.1 | > | > |

*Neutralizing
**Cross-reactive
ND = not determined

| $EC_{50}$ (ng/mL) | Protein/Virus $EC_{50}$ Ratio |
|---|---|
| 0-10 | >10 |
| 11-100 | 1.0-10 |
| 101-1,000 | 0.1-1.0 |
| 1,001-5,000 | <0.1 |
| >5,001 | |

FIGS. 5A-C

A.

| | mAb | Reactivity | Binding EC$_{50}$ (ng/mL): Virus or Virus-Like Particle (VLP) | | | | | Protein | | | |
|---|---|---|---|---|---|---|---|---|---|---|---|
| | | | SINV/NA-EEEV | EEEV VLP | WEEV VLP | VEEV VLP | CHIKV | EEEV E2 glycoprotein | VEEV E2 glycoprotein | EEEV E1 glycoprotein | CHIKV E2E1 glycoproteins |
| ** | EEEV-138 | EEEV, VEEV, WEEV, CHIKV E1 glycoproteins | ND | 11.2 | 66.5 | 43.2 | 377.1 | > | > | 35.9 | 12.6 |
| ** | EEEV-179 | EEEV, VEEV, WEEV E1 glycoproteins | 386.7 | 183.5 | 195.1 | 353.5 | ND | > | > | 34.2 | > |
| ** | EEEV-157 | EEEV and VEEV E1 glycoproteins | 3.8 | 23.1 | > | 1,642 | ND | > | > | 3.0 | ND |
| ** | EEEV-107 | EEEV and VEEV E2 glycoproteins | 693.1 | 34.9 | > | 13.9 | ND | 2.9 | 41.2 | > | > |
| * | EEEV-21 | | 2.1 | 2.5 | > | > | ND | 12.2 | 266.5 | > | > |
| ** | EEEV-81 | | 0.6 | 14.4 | > | > | ND | 5.8 | 34.3 | > | > |

FIG. 6A

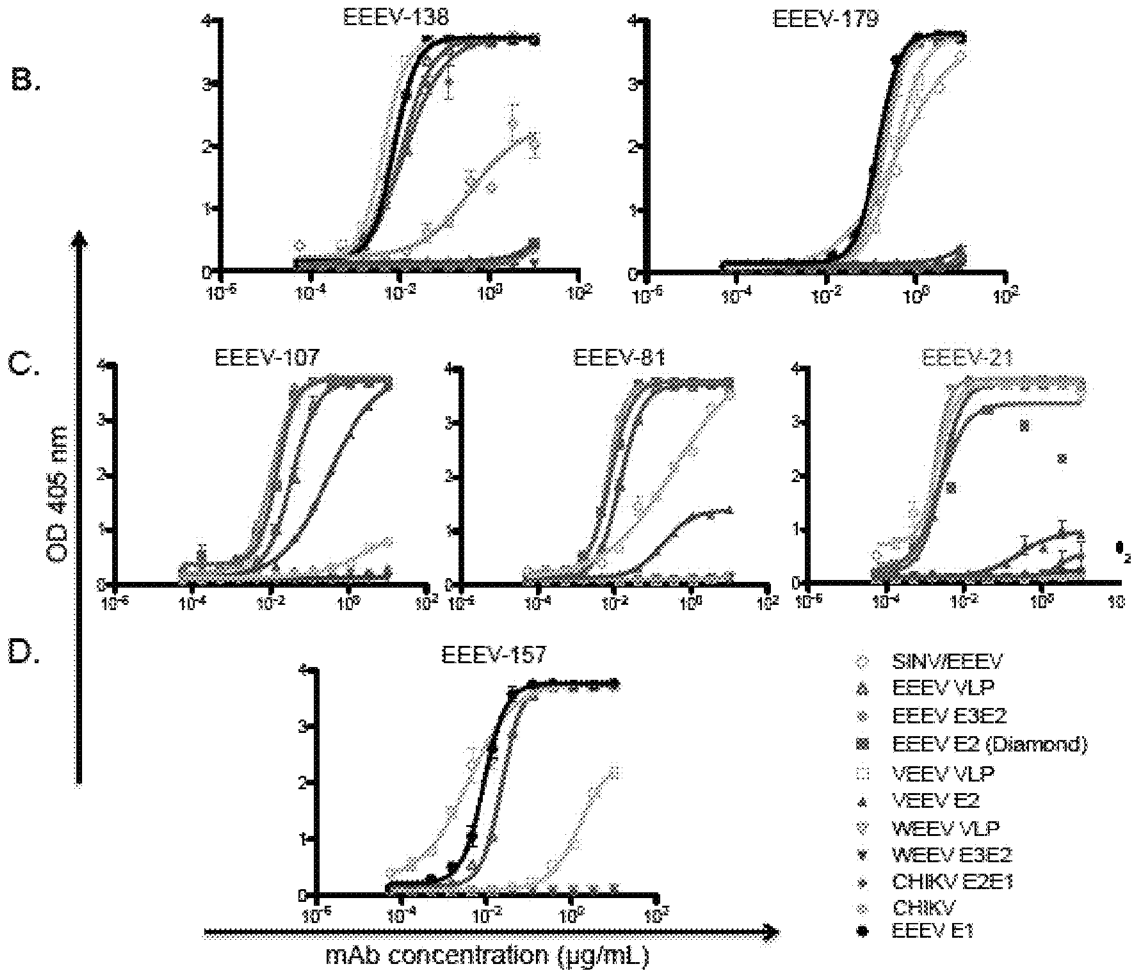
FIGS. 6B-D

A. SINV/EEEV
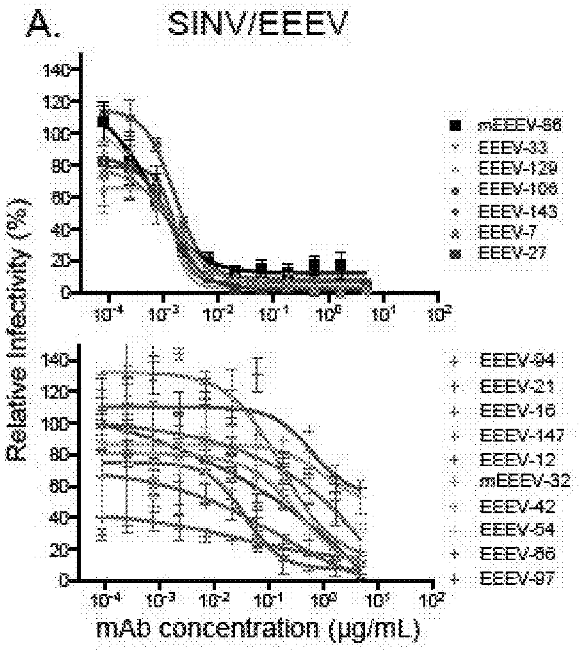
| mAb | $IC_{50}$ (ng/mL) | $IC_{90}$ (ng/mL) | $IC_{99}$ (ng/mL) |
|---|---|---|---|
| mEEEV-86 | 0.6 | 4.9 | 46.9 |
| EEEV-129 | 0.8 | 3.7 | 62.0 |
| EEEV-27 | 1.4 | 6.1 | 30.7 |
| EEEV-106 | 1.5 | 6.4 | 28.7 |
| EEEV-143 | 1.6 | 3.5 | 9.1 |
| EEEV-7 | 1.7 | 11.3 | 90.7 |
| EEEV-33 | 1.7 | 3.3 | 7.2 |
| | | | |
| EEEV-94 | 22.4 | 2,909 | > |
| EEEV-21 | 36.4 | 193.6 | 1,199 |
| EEEV-16 | 159.7 | > | > |
| EEEV-147 | 171 | 1,972 | > |
| EEEV-12 | 191 | 1,717 | > |
| mEEEV-32 | 371.1 | 4,329 | > |
| EEEV-42 | 950 | > | > |
| EEEV-54 | 1,048 | > | > |
| EEEV-97 | 1,222 | > | > |
| EEEV-66 | 1,404 | > | > |
B. EEEV
| mAb | $IC_{50}$ (ng/mL) |
|---|---|
| EEEV-129 | 2,700 |
| | 3,400 |
| EEEV-27 | >10,000 |
| | >10,000 |
| EEEV-106 | 4,200 |
| | 5,900 |
| EEEV-143 | >10,000 |
| | >10,000 |
| EEEV-7 | >10,000 |
| | >10,000 |
| EEEV-33 | [illegible] |
| | [illegible] |
| EEEV-94 | 3,200 |
| | 4,000 |
| EEEV-21 | 4,200 |
| | 5,300 |
| EEEV-16 | 10,000 |
| | >10,000 |
| EEEV-147 | 560 |
| | 600 |
| EEEV-12 | 3,200 |
| | 3,100 |
| EEEV-42 | >10,000 |
| | >10,000 |
| EEEV-54 | >10,000 |
| | >10,000 |
| EEEV-66 | >10,000 |
| | >10,000 |
| Infergen | [illegible] |
| | [illegible] |
| IC ng/mL |
|---|
| 0-10 |
| 11-100 |
| 101-1,000 |
| 1,001-5,000 |
| >5,001 |
FIGS. 7A-B

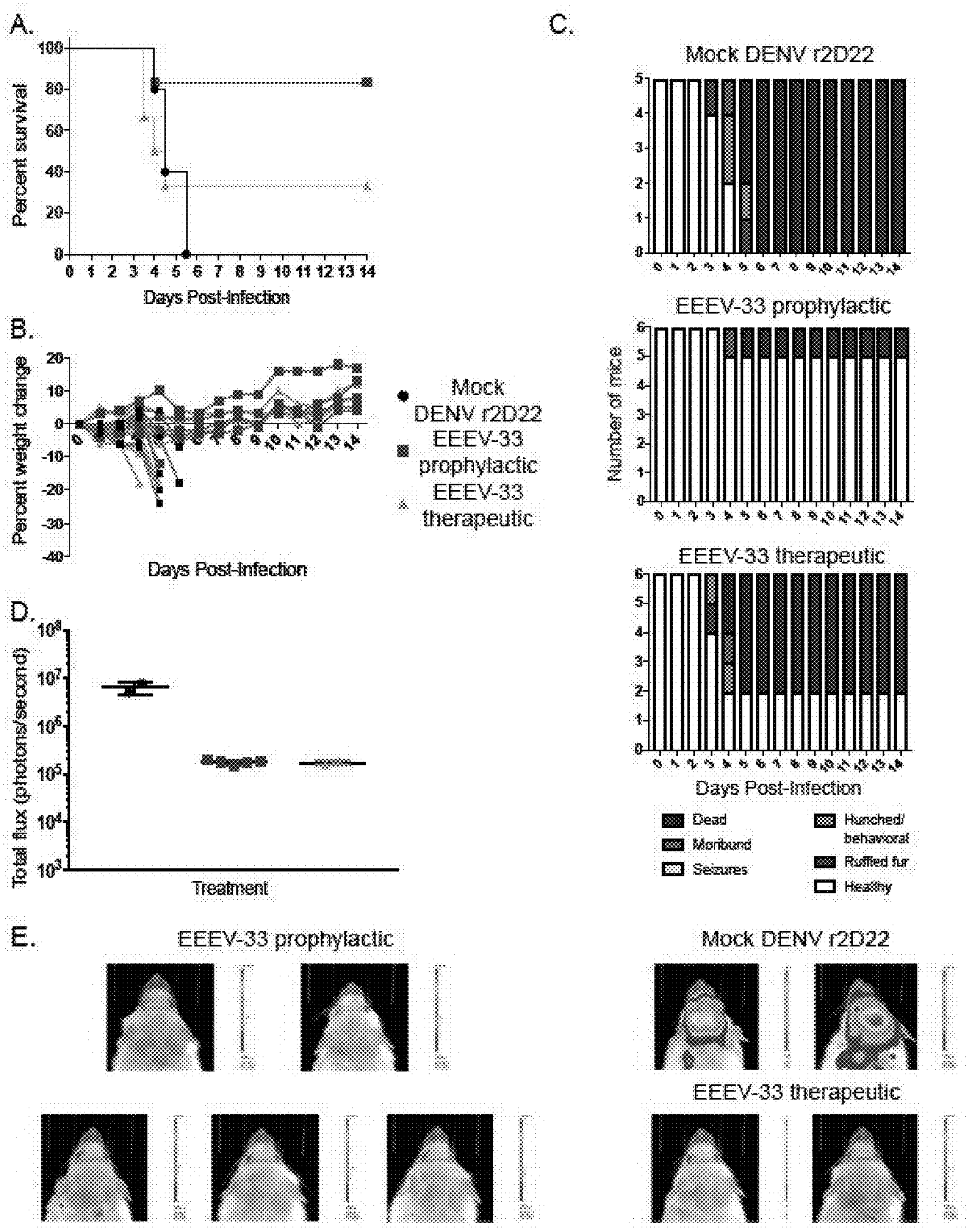
FIGS. 8A-E

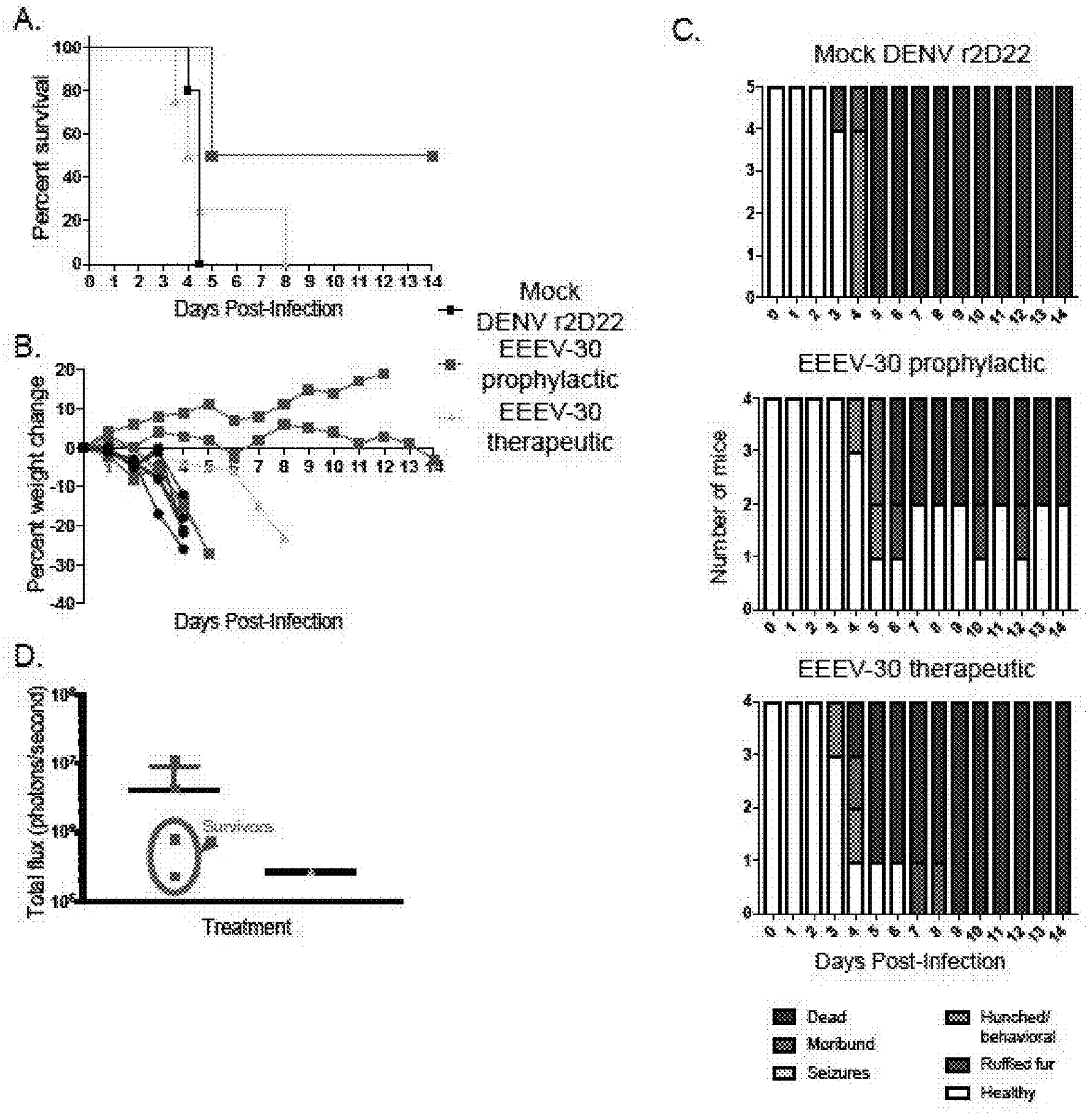
FIGS. 9A-D

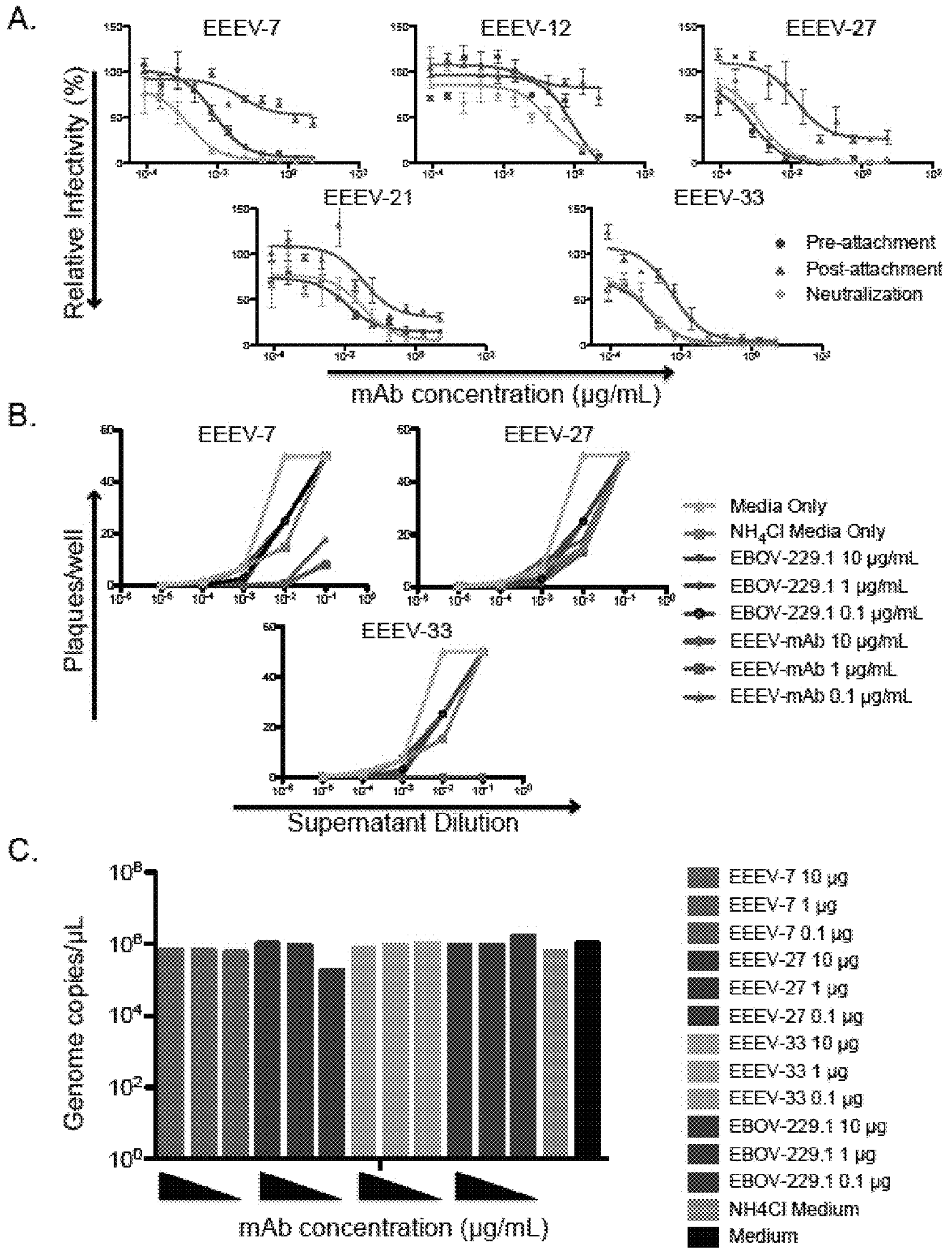
FIGS. 10A-C

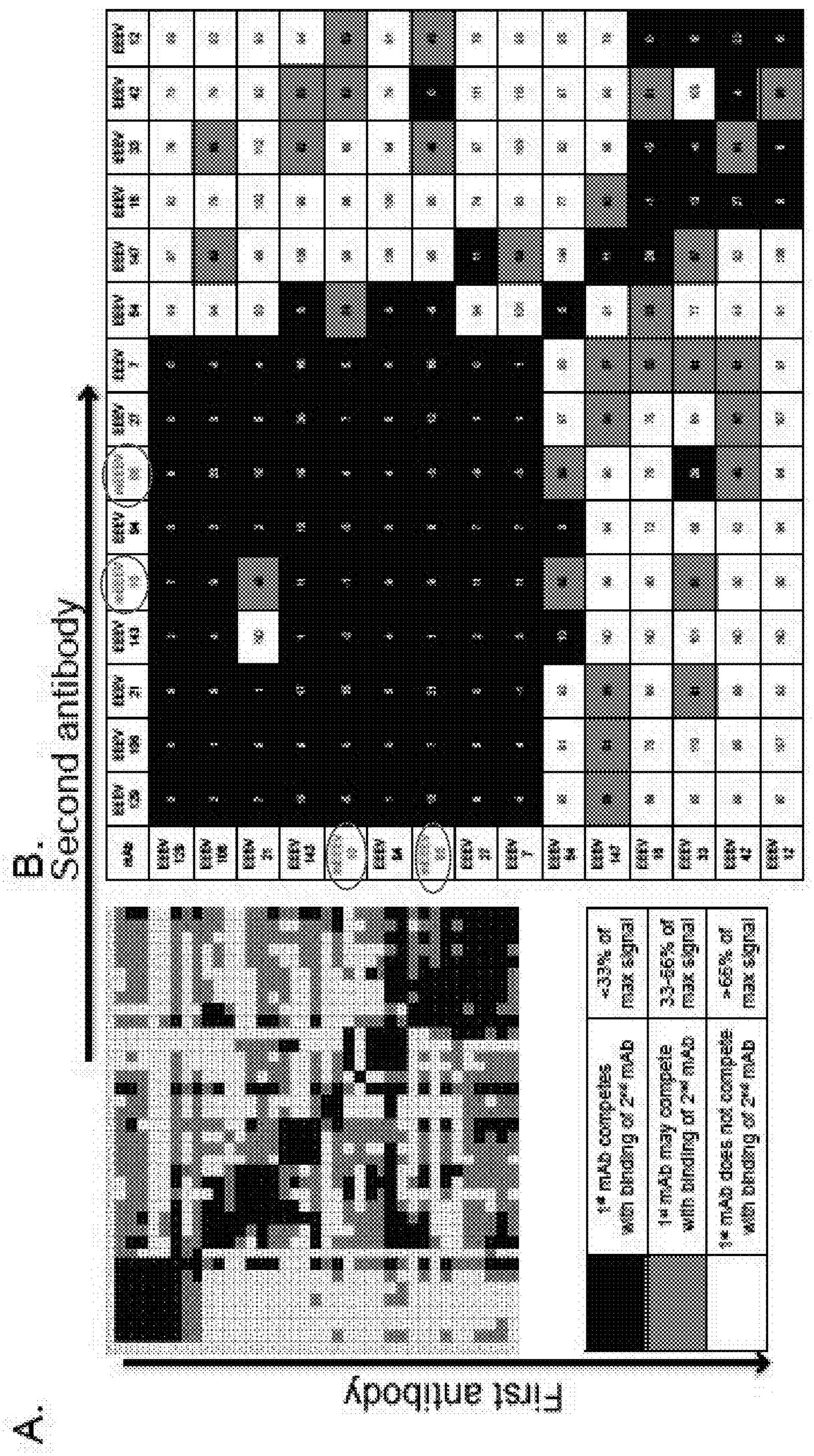
FIGS. 11A-B

C.

A.
| | | Binding | | | | |
|---|---|---|---|---|---|---|
| | | $EC_{50}$ (ng/mL) | | | | |
| | | Virus or Virus-Like Particle (VLP) | | | Protein | |
| mAb | Reactivity | EEEV VLP | WEEV VLP | VEEV VLP | EEEV E2 glycoprotein | EEEV E1 glycoprotein |
| EEEV-237 | EEEV E2 glycoprotein | 36.4 | > | > | 40.5 | > |
| EEEV-239 | | 982.3 | > | > | 1,696 | > |
| EEEV-275 | | 1,991 | > | > | 1,203 | > |
| EEEV-250 | | > | > | > | 1,006 | > |
| EEEV-255 | | > | > | > | ~3,972 | > |
| VEEV-47 | VEEV VLP | > | > | 16.8 | > | > |
B.
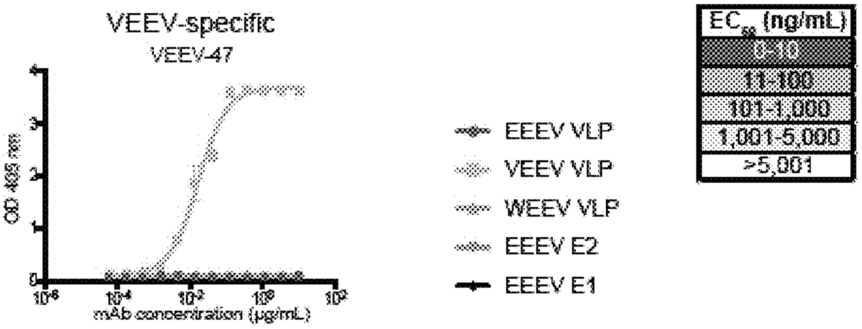
C.
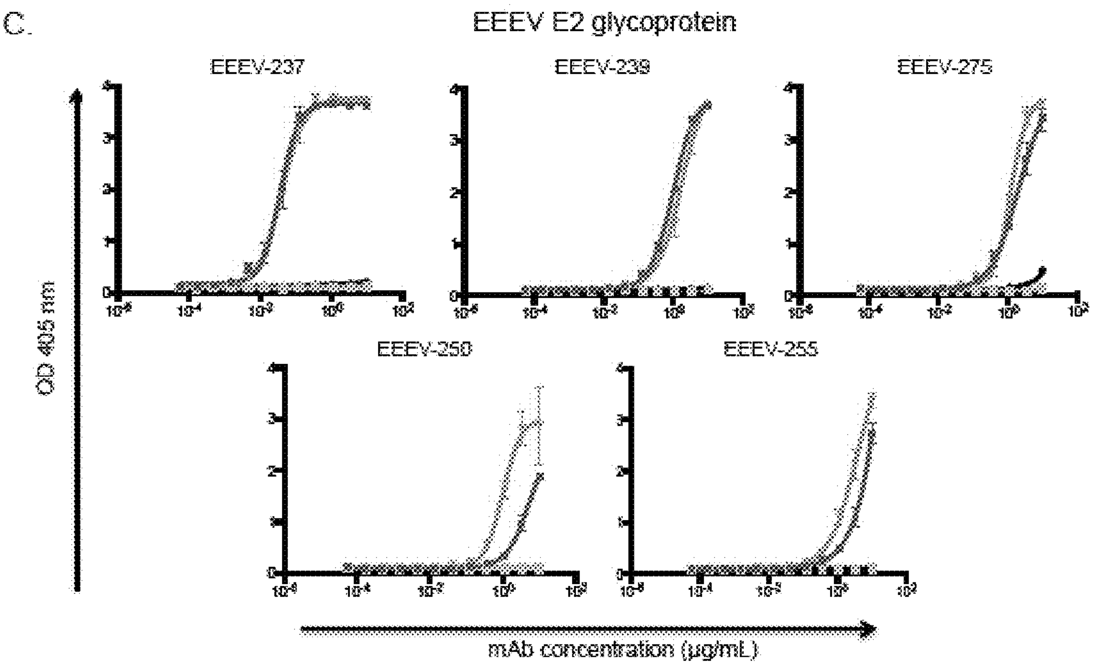
FIGS. 12A-C A.
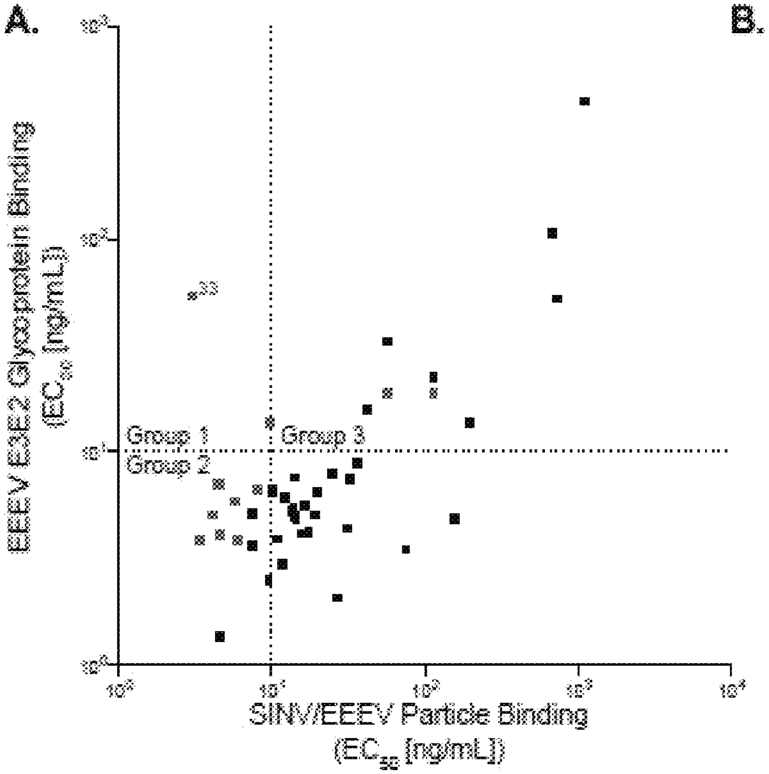
B.
| Group | mAb | Virus/Protein $EC_{50}$ Ratio | Half-maximal effective concentration ($EC_{50}$) for ELISA binding (ng/mL) | |
|---|---|---|---|---|
| | | | SINV/EEEV Virus Particles | EEEV E3E2 Glycoprotein |
| 1 | EEEV-33 | 0.06 | 3.1 | 54.1 |
| 2 | EEEV-7 | 0.89 | 3.4 | 3.8 |
| | EEEV-129 | 0.80 | 4.0 | 5.1 |
| | EEEV-93 | 0.62 | 4.4 | 7.0 |
| | EEEV-106 | 1.10 | 4.5 | 4.1 |
| | EEEV-27 | 0.64 | 4.5 | 7.1 |
| | EEEV-12 | 0.96 | 5.6 | 5.8 |
| | EEEV-97 | 1.53 | 5.9 | 3.8 |
| | EEEV-147 | 1.18 | 7.9 | 6.7 |
| | EEEV-21 | 0.71 | 9.8 | 13.8 |
| 3 | EEEV-143* | 3.06 | 57.2 | 18.7 |
| | EEEV-94 | 6.02 | 113.6 | 18.9 |
FIGS. 13A-B

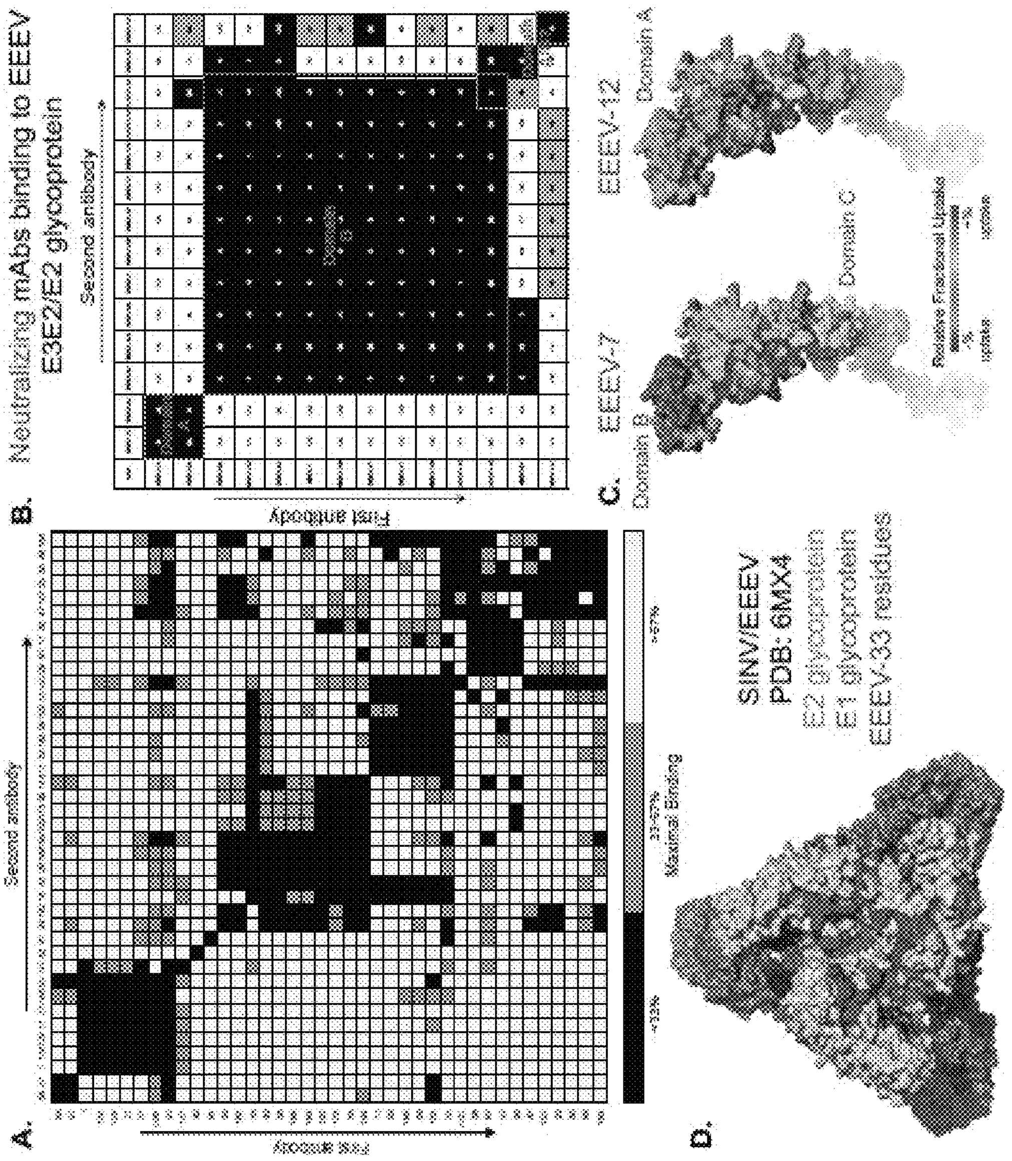
FIGS. 14A-D

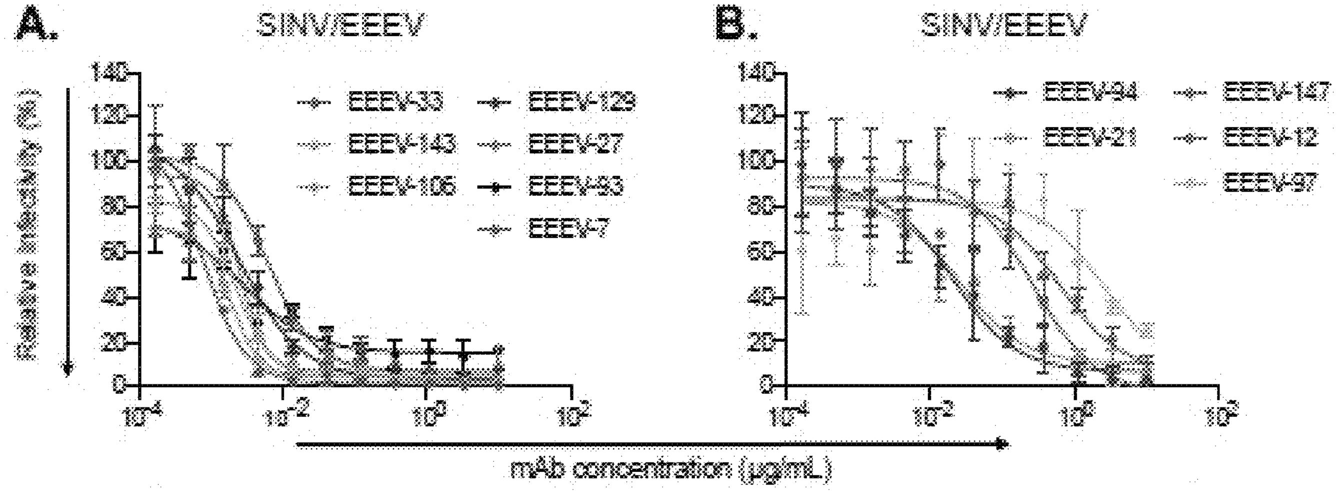
| mAb | $IC_{50}$ (ng/mL) |
|---|---|
| EEEV-33 | [illegible] |
| EEEV-106 | [illegible] |
| EEEV-143* | [illegible] |
| EEEV-129 | [illegible] |
| EEEV-27 | [illegible] |
| EEEV-93 | [illegible] |
| EEEV-7 | [illegible] |
| $IC_{50}$ (ng/mL) |
|---|
| [illegible] |
| 51-500 |
| 501-5,000 |
| 5,001-10,000 |
| >10,000 |
| mAb | $IC_{50}$ (ng/mL) |
|---|---|
| EEEV-94 | [illegible] |
| EEEV-21 | [illegible] |
| EEEV-147 | 272.2 |
| EEEV-12 | 627.2 |
| EEEV-97 | 2,571 |
FIGS. 15A-B

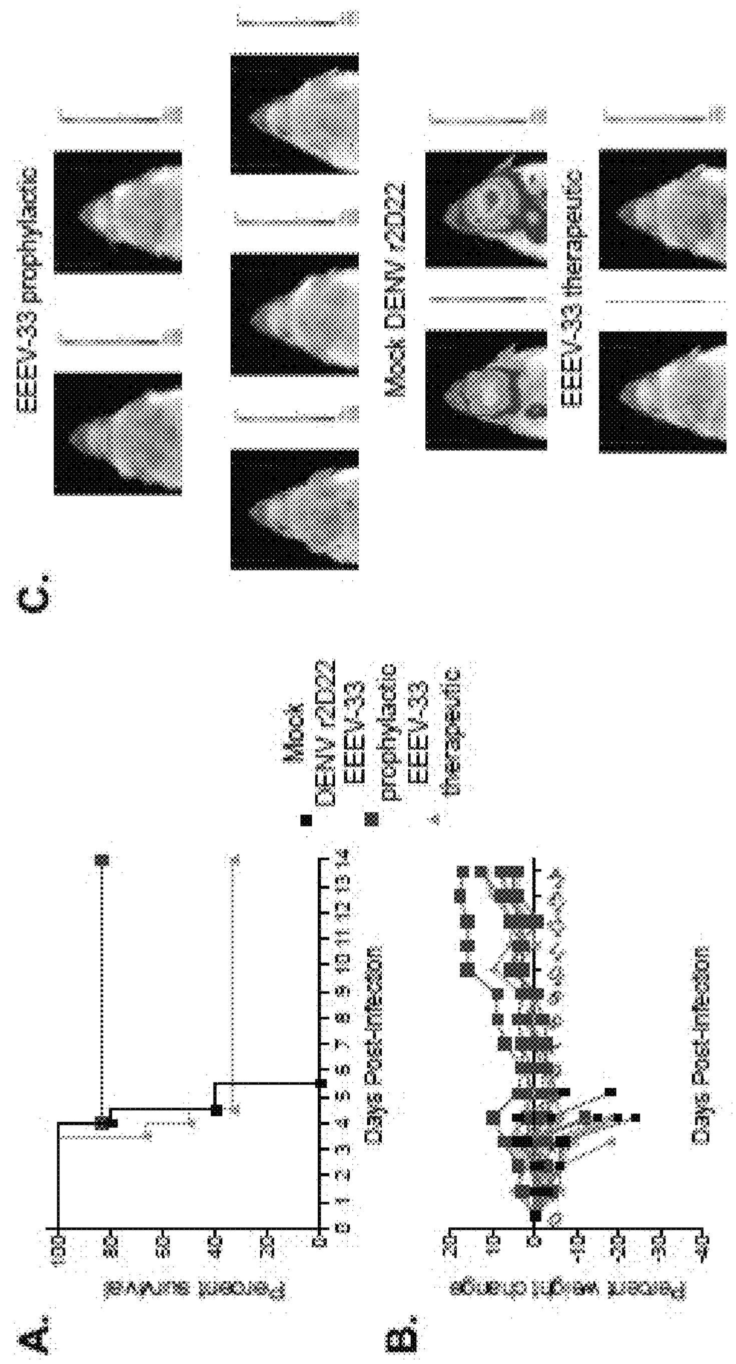
FIGS. 17A-C

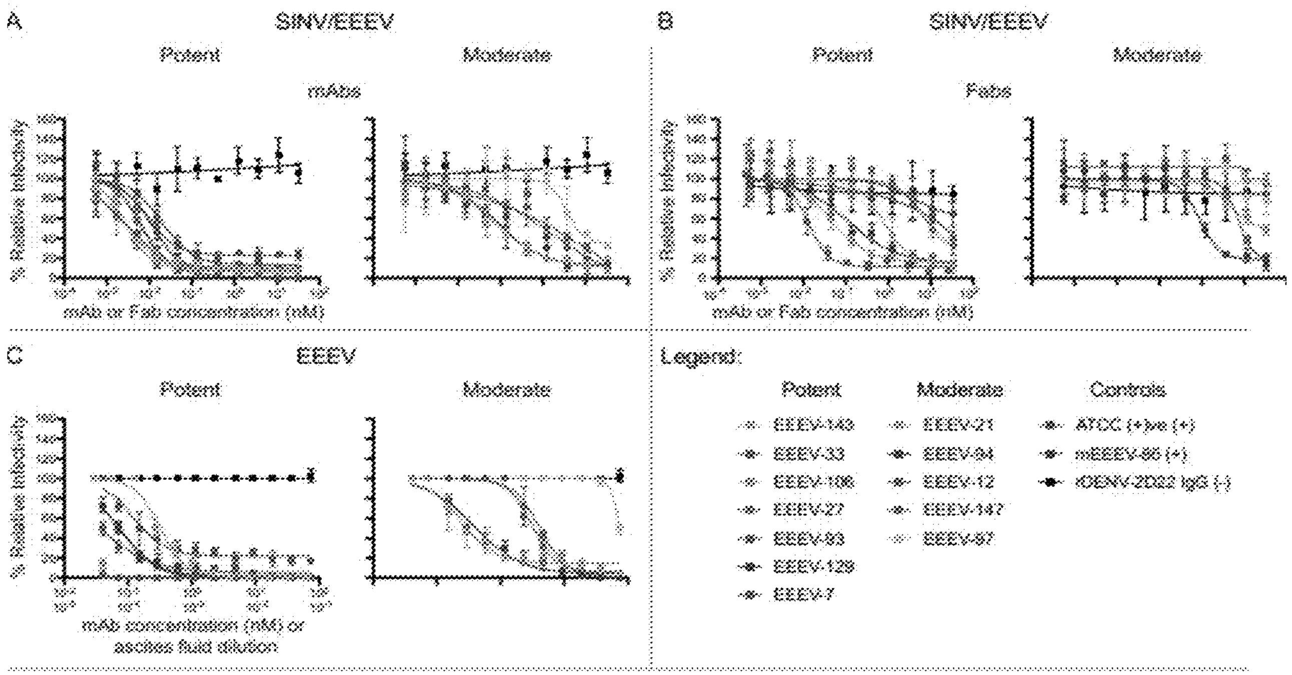

D

Potent Abs

| $IC_{50}$ (pM) | Isotype | SINV/EEEV | | EEEV |
|---|---|---|---|---|
| | | mAb | Fab | mAb |
| EEEV-143 | IgA1,κ | [illegible] | 772.0 | 315.5 |
| EEEV-33 | IgG1,λ | [illegible] | [illegible] | [illegible] |
| EEEV-106 | IgG1,κ | [illegible] | 46.5 | [illegible] |
| mEEEV-86 | IgG2c | [illegible] | NT | NT |
| EEEV-27 | IgG1,λ | [illegible] | 6,835 | [illegible] |
| EEEV-93 | IgG1,λ | [illegible] | > | 120.5 |
| EEEV-129 | IgG1,λ | [illegible] | 112.5 | 69.6 |
| EEEV-7 | IgG1,κ | [illegible] | > | [illegible] |

Moderate Abs and Controls

| $IC_{50}$ (pM) | Isotype | SINV/EEEV | | EEEV |
|---|---|---|---|---|
| | | mAb | Fab | mAb |
| EEEV-21 | IgG1,λ | 76.3 | > | 238.9 |
| EEEV-94 | IgG1,κ | 84.1 | 876.0 | 393.6 |
| EEEV-12 | IgG1,λ | 381.3 | 7,110 | 3,144 |
| EEEV-147 | IgG1,κ | 1,574 | > | 4,128 |
| EEEV-97 | IgG1,λ | 3,653 | > | > |
| ATCC (+)ve | NA | NT | NT | 1/10,240 |
| rDENV-2D22 | IgG1,κ | > | IgG (>) | > |

FIGS. 18A-D

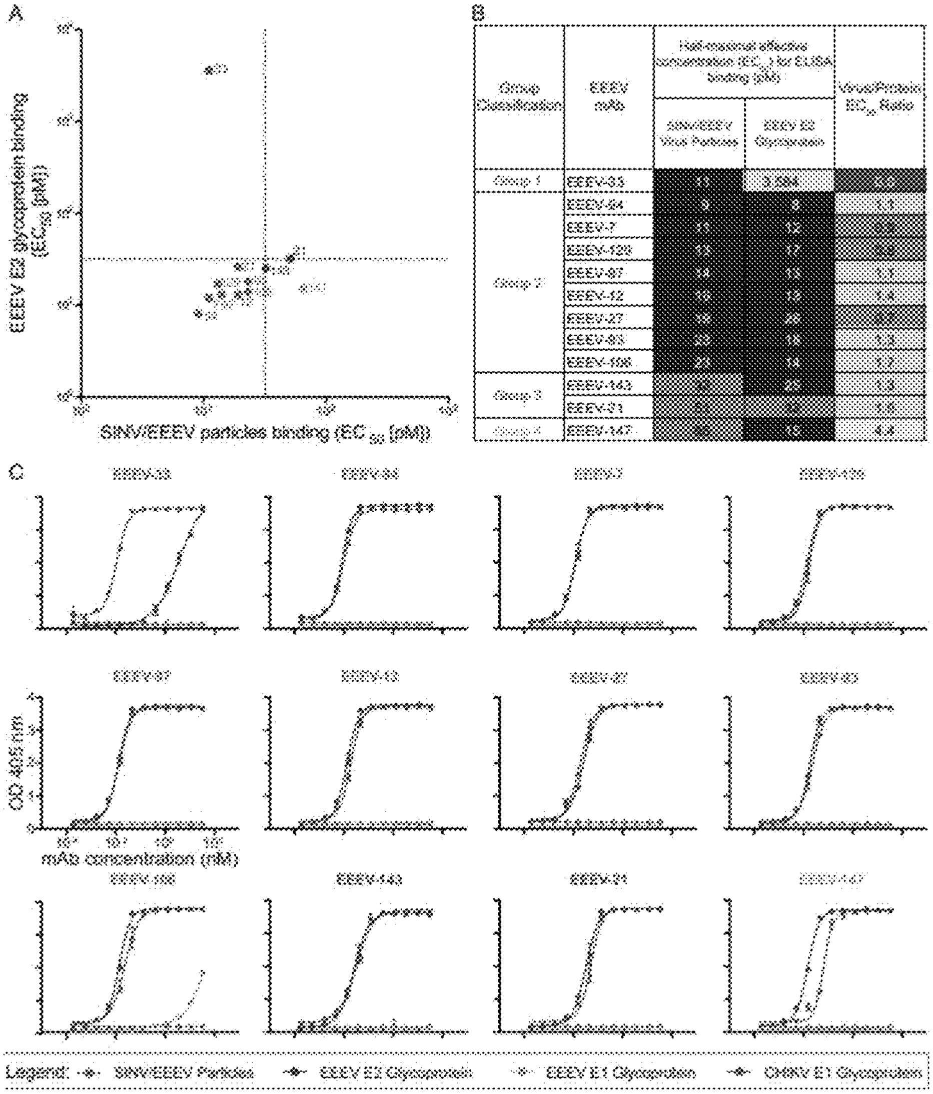
FIGS. 19A-C

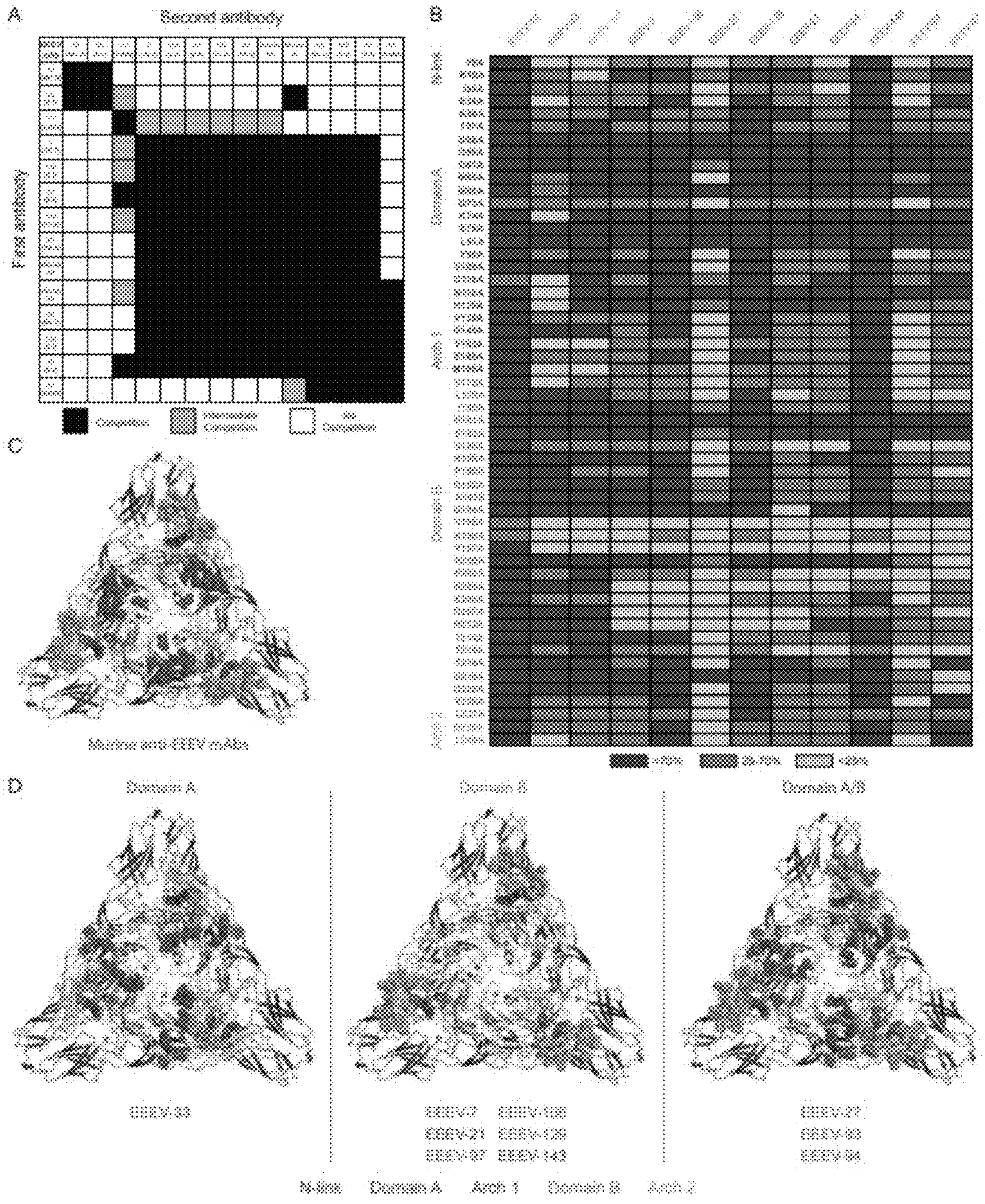
FIGS. 20A-D

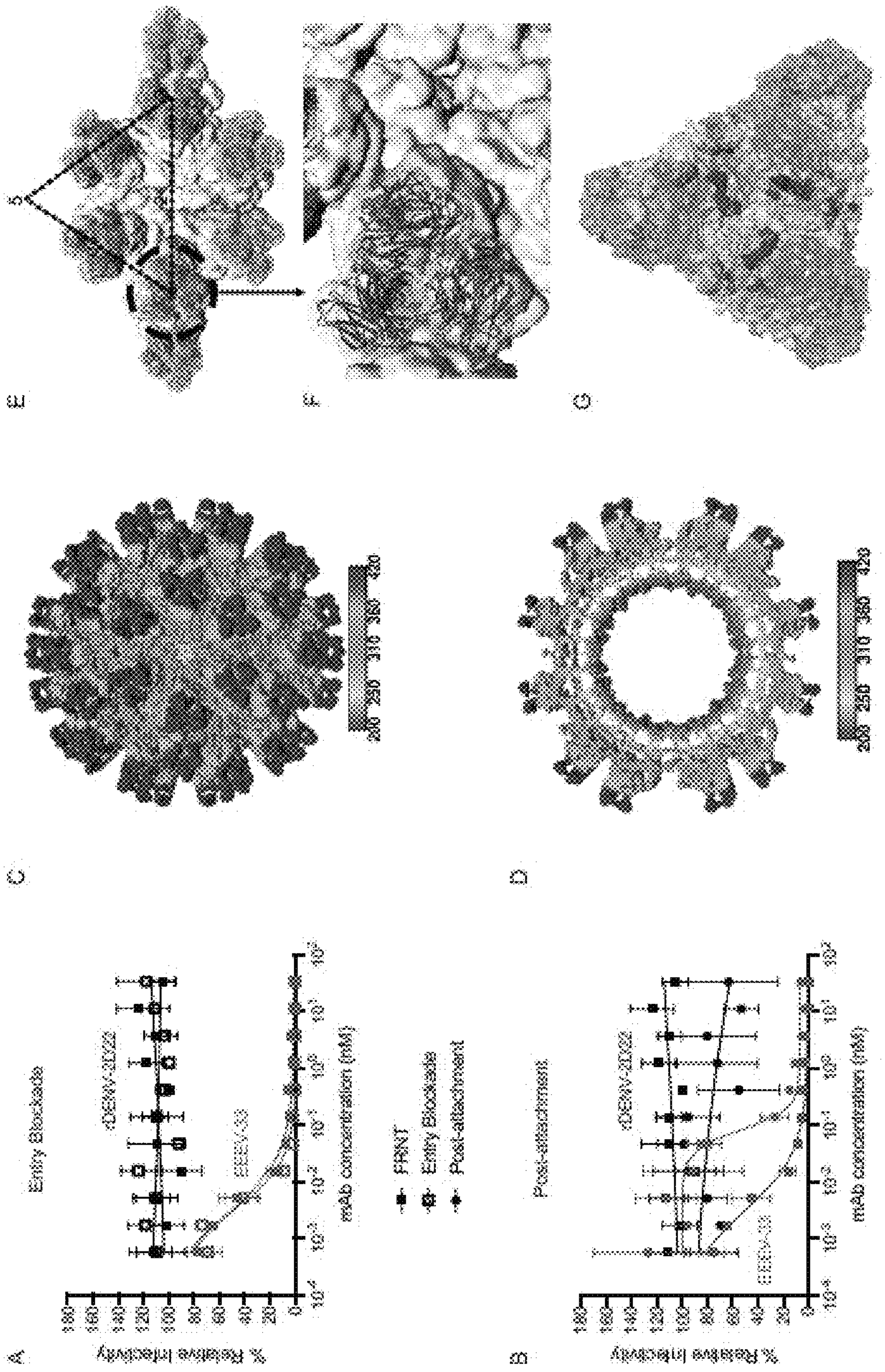
FIGS. 21A-G

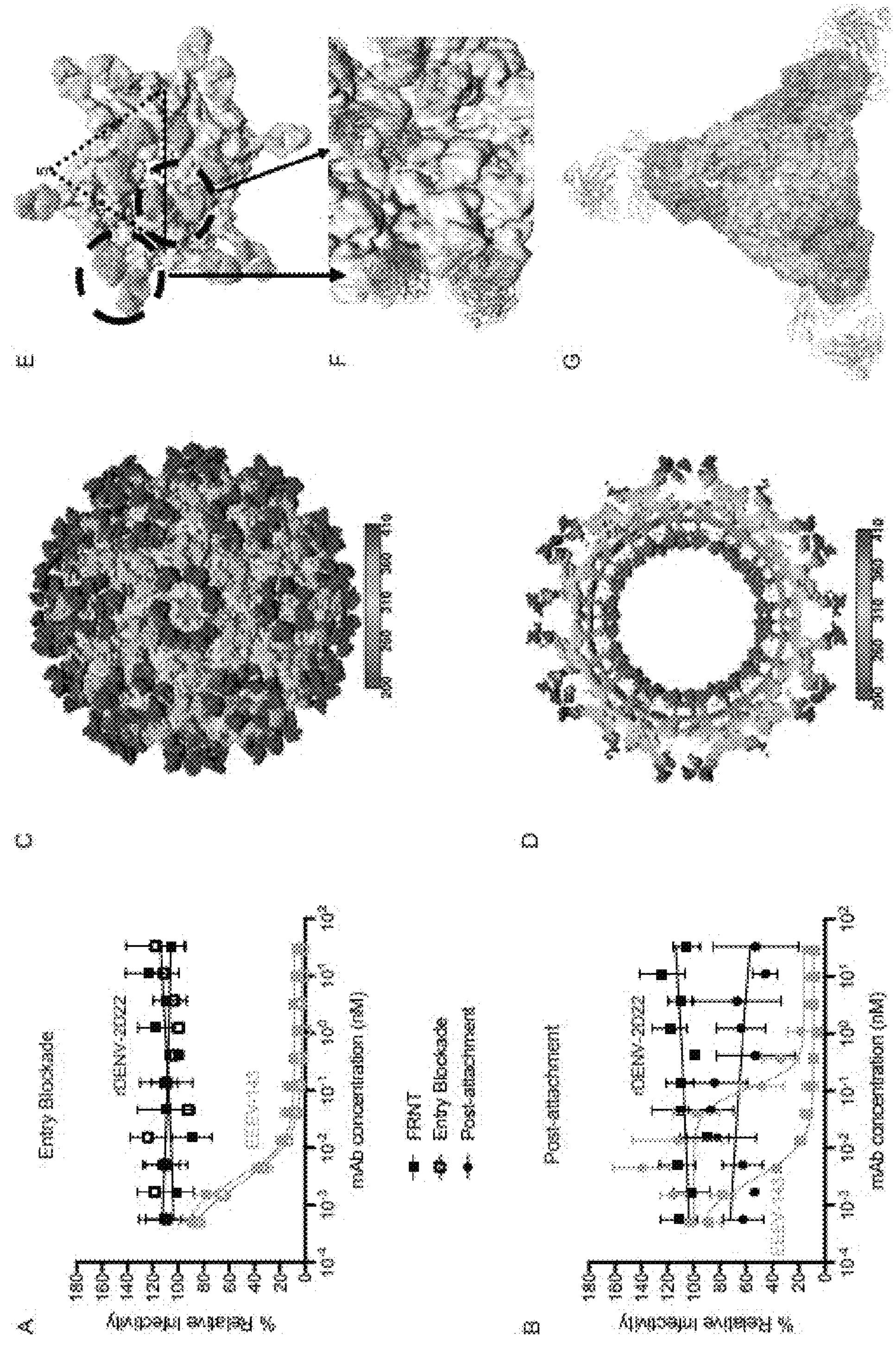
FIGS. 22A-G

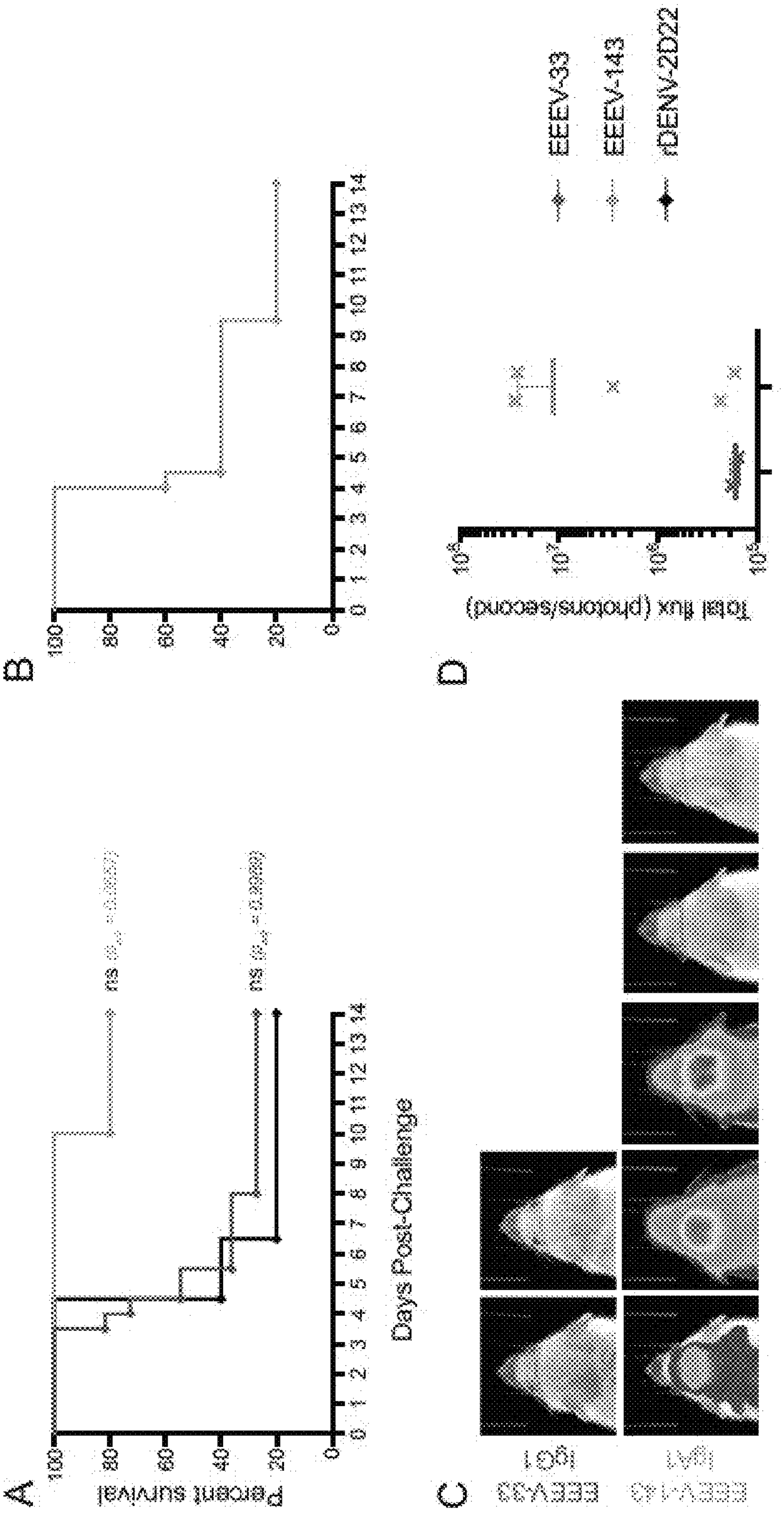
FIGS. 24A-D

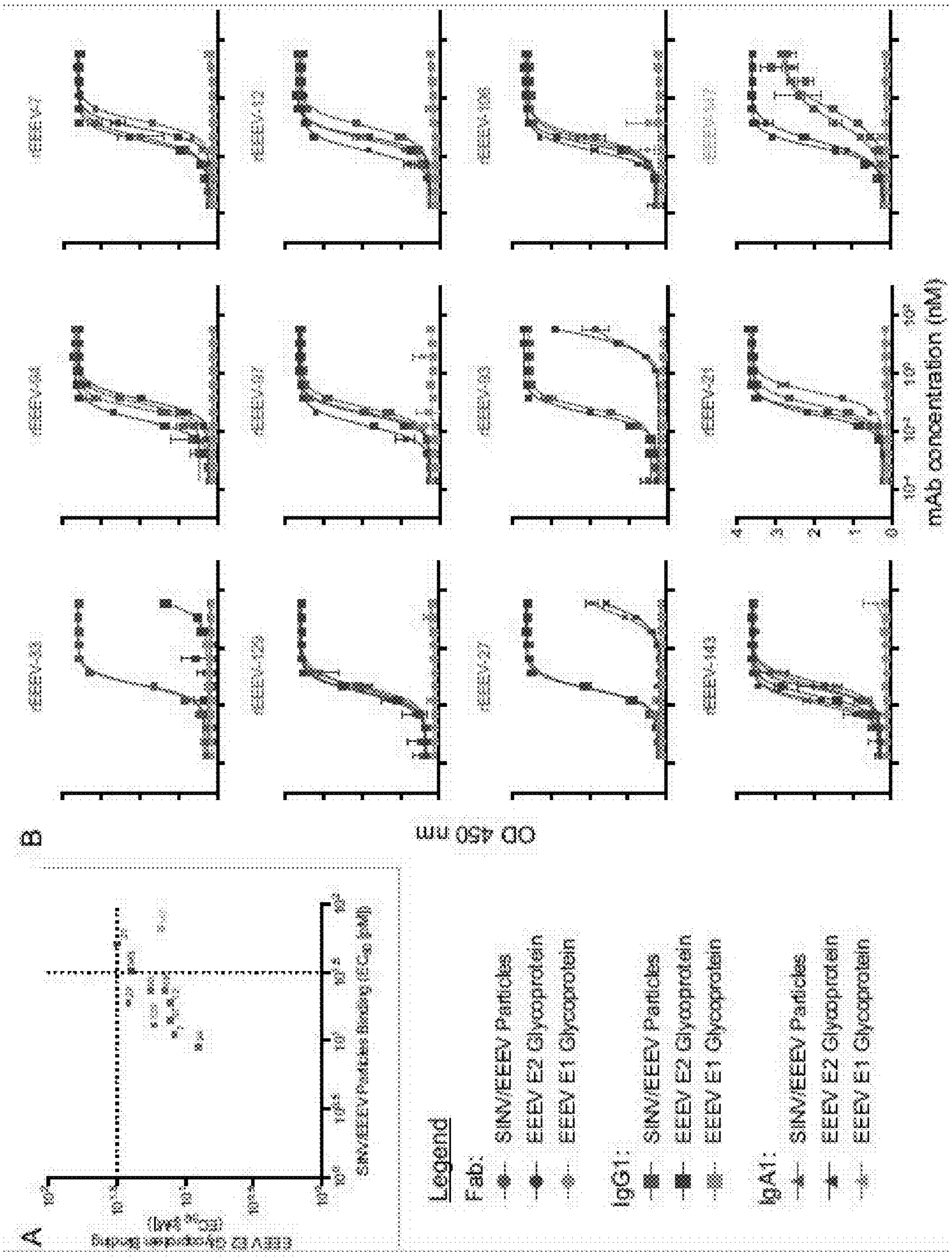
FIGS. 25A-B

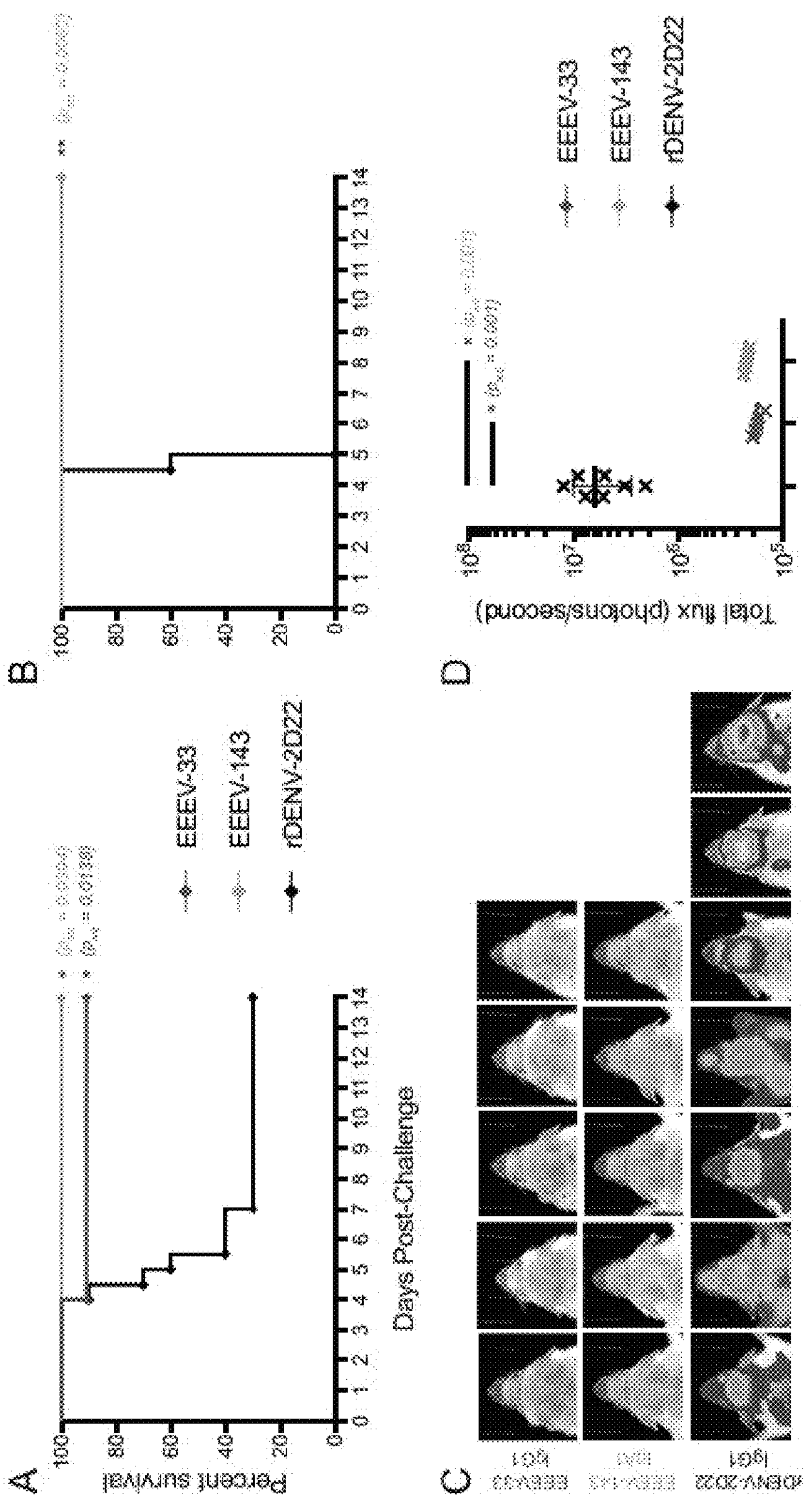
FIGS. 23A-D

C

| EEEV mAb | Antibody Isotype (Heavy Chain, Light Chain) | IgG1 (IgA1) | Fab | IgG1 (IgA1) | Fab | IgG1 | Fab | SINV/EEEV particles | EEEV E2 glycoprotein |
|---|---|---|---|---|---|---|---|---|---|
| | | SINV/EEEV particles | | EEEV E2 glycoprotein | | Virus/Protein $EC_{50}$ Ratio | | IgG/Fab $EC_{50}$ Ratio | |
| EEEV-33 | IgG1,λ | 51.1 | 52.5 | > | > | 0.9 | 0.9 | 1.0 | NA |
| EEEV-94 | IgG1,κ | 63.1 | 80.4 | 24.3 | 119.9 | 2.6 | 0.7 | 0.7 | 0.2 |
| EEEV-7 | IgG1,κ | 42.7 | 154.1 | 32.5 | 85.5 | 1.3 | 1.8 | 0.3 | 0.4 |
| EEEV-129 | IgG1,λ | 39.9 | 45.0 | 30.2 | 29.0 | 1.3 | 1.6 | 0.9 | 1.0 |
| EEEV-97 | IgG1,λ | 65.9 | 43.8 | 39.9 | 16.0 | 1.7 | 2.7 | 1.5 | 2.5 |
| EEEV-12 | IgG1,λ | 108.1 | 38.0 | 46.7 | 14.7 | 2.3 | 2.6 | 2.8 | 3.2 |
| EEEV-27 | IgG1,λ | 37.6 | > | 37.6 | > | 1.0 | > | NA | NA |
| EEEV-93 | IgG1,λ | 62.1 | > | 40.8 | > | 1.5 | > | NA | NA |
| EEEV-108 | IgG1,κ | 41.7 | 32.3 | 24.6 | 15.1 | 1.7 | 2.1 | 1.3 | 1.8 |
| EEEV-143 | IgA1,κ | 48.3 (87.5) | 11.9 | 22.3 (39.6) | 15.4 | 2.2 | 0.8 | 4.1 | 1.4 |
| EEEV-21 | IgG1,λ | 78.2 | 216.2 | 49.5 | 34.9 | 1.6 | 6.2 | 0.4 | 1.4 |
| EEEV-147 | IgG1,κ | 385.0 | 158.5 | 19.9 | 32.0 | 19.3 | 5.0 | 2.4 | 0.6 |

FIG. 25C

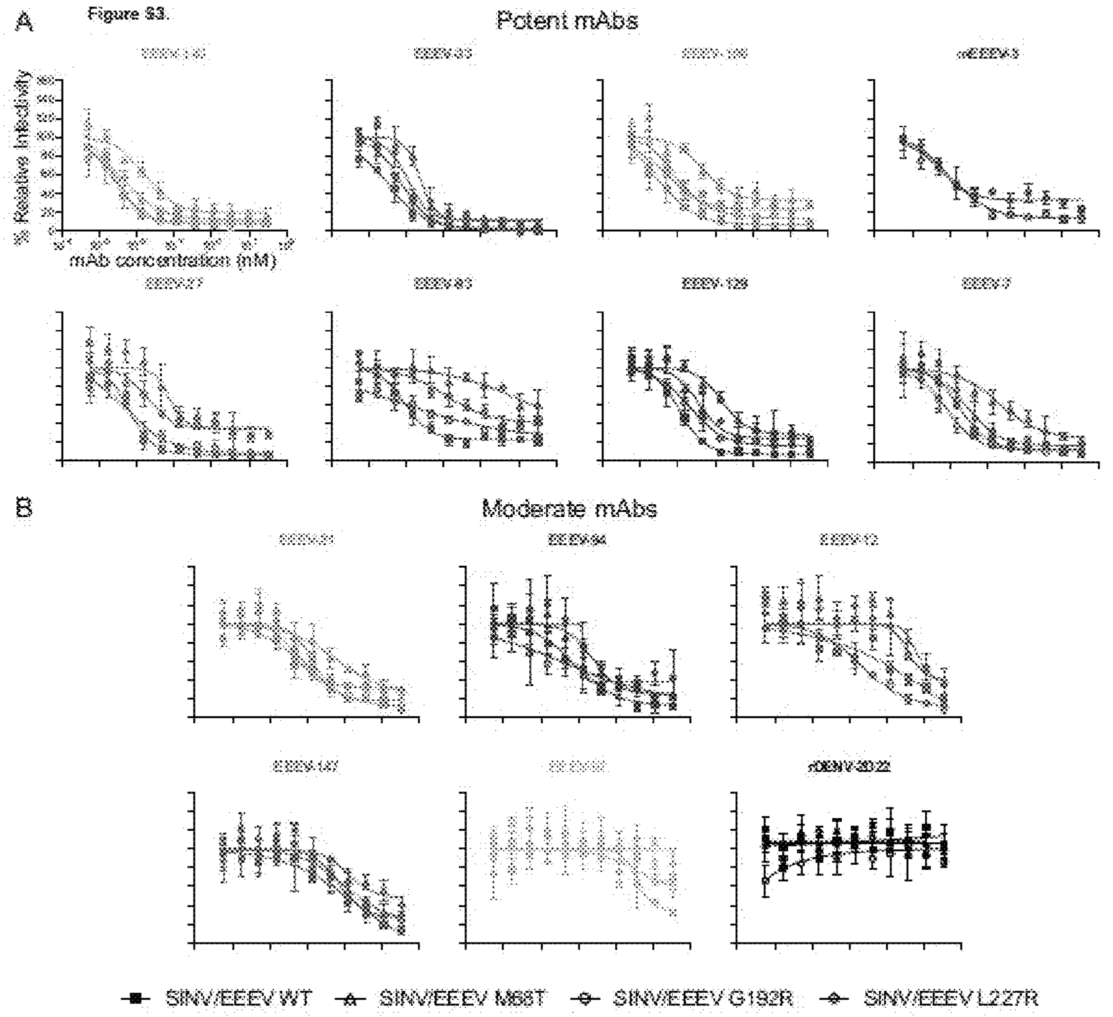
C
| EEEV mAb | SINV/EEEV $IC_{50}$ (pM) | | | | Fold Difference in $IC_{50}$ ratio to SINV/EEEV WT | | |
|---|---|---|---|---|---|---|---|
| | WT | M68T | G192R | L227R | M68T | G192R | L227R |
| EEEV-143 | 2.8 | 16.3 | 2.6 | 3.6 | 6 | 1 | 1 |
| EEEV-33 | 3.1 | 23.7 | 7.3 | 10.7 | 8 | 2 | 3 |
| EEEV-106 | 3.3 | 44.7 | 6.0 | 7.7 | 14 | 2 | 2 |
| mEEEV-3 | NT | NT | 9.9 | 5.8 | NT | NT | NT |
| EEEV-27 | 6.5 | 72.6 | 5.8 | 19.1 | 11 | 1 | 3 |
| EEEV-93 | 9.3 | > | 7.7 | 114.5 | > | 1 | 12 |
| EEEV-129 | 11.2 | 145.6 | 20.6 | 34.9 | 13 | 2 | 3 |
| EEEV-7 | 19.7 | 212.4 | 9.4 | 28.7 | 11 | 0 | 2 |
| EEEV-21 | 76.3 | 567.3 | 143.9 | 58.2 | 7 | 2 | 1 |
| EEEV-94 | 84.1 | 244.9 | 41.3 | 142.6 | 3 | 0 | 2 |
| EEEV-12 | 381.3 | 6,057 | 204.9 | 3,607 | 16 | 1 | 9 |
| EEEV-147 | 1,574 | 1,273 | 705.0 | 928.0 | 1 | 0 | 1 |
| EEEV-97 | 3,653 | > | > | > | > | > | > |
| rDENV-2D22 | > | > | > | > | > | > | > |
FIGS. 27A-C

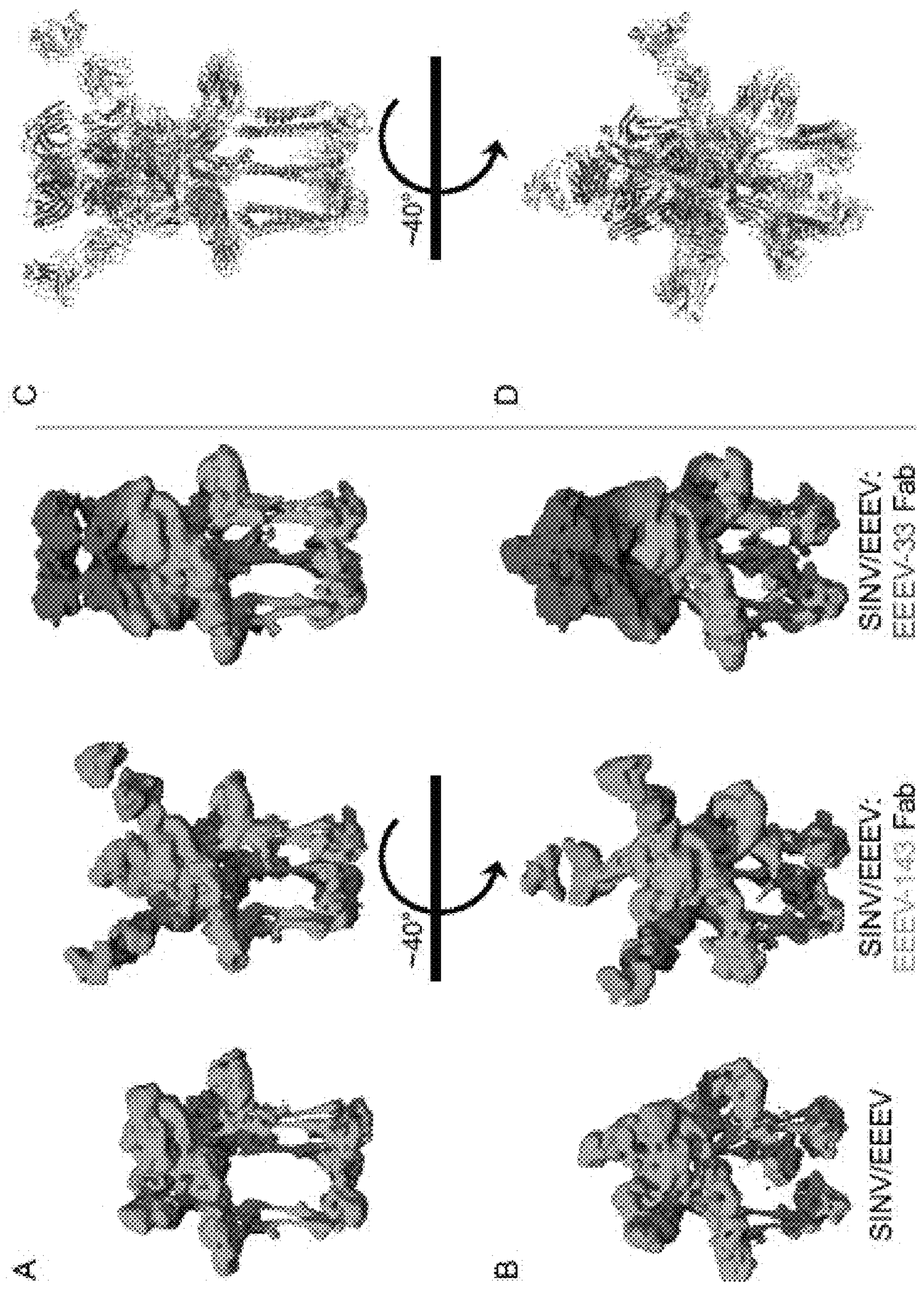
FIGS. 28A-D

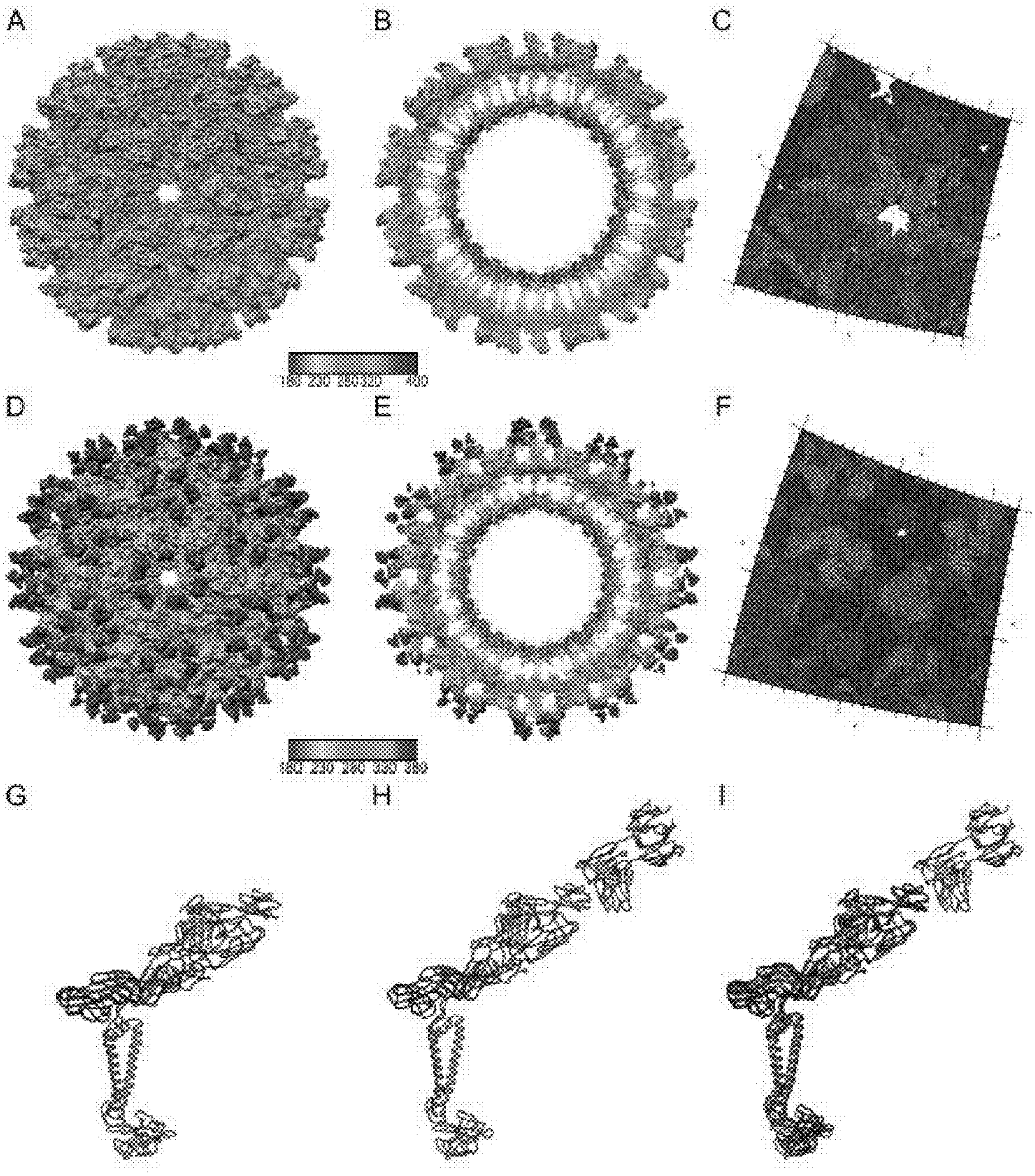
FIGS. 29A-I

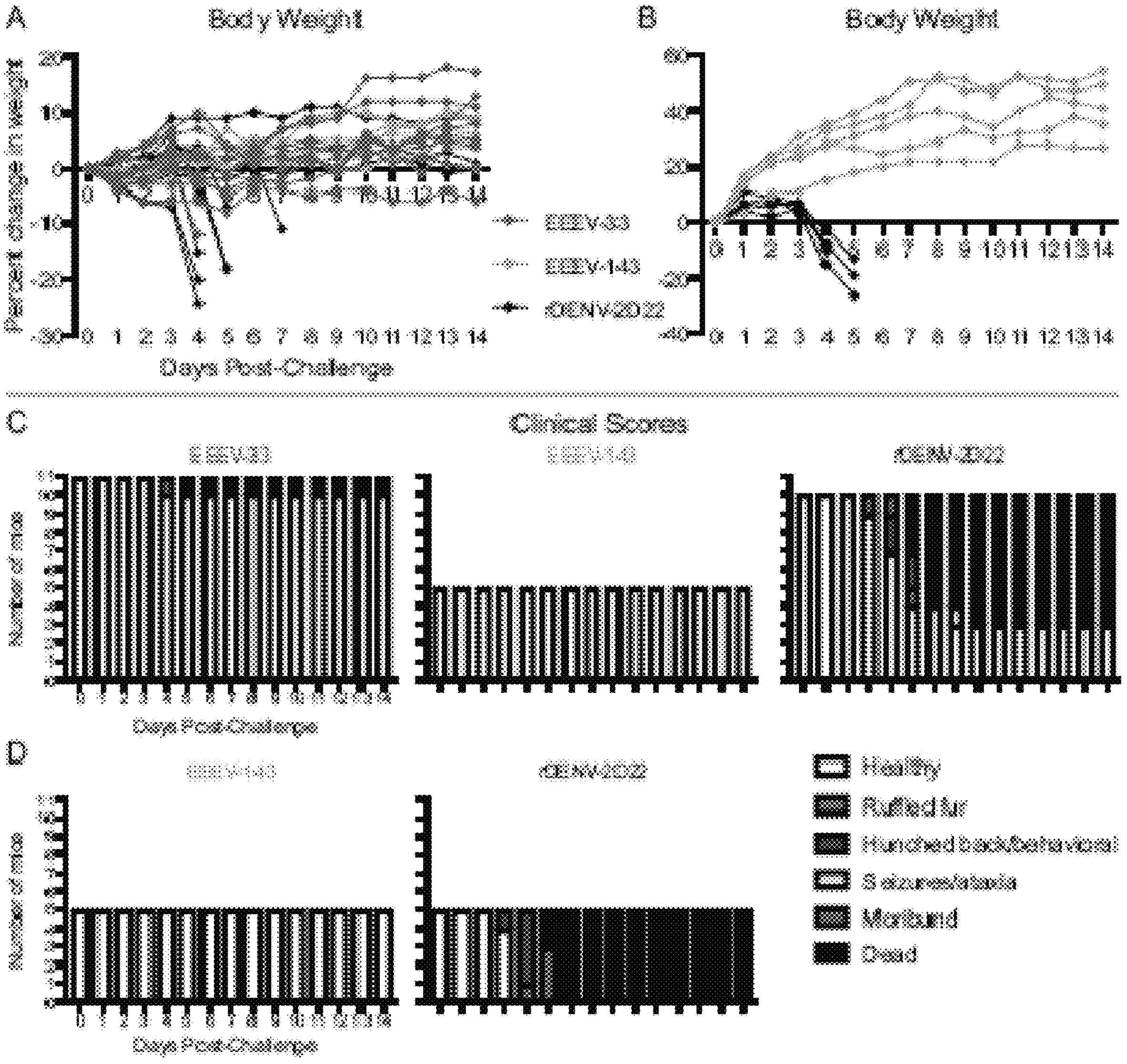
FIGS. 30A-D

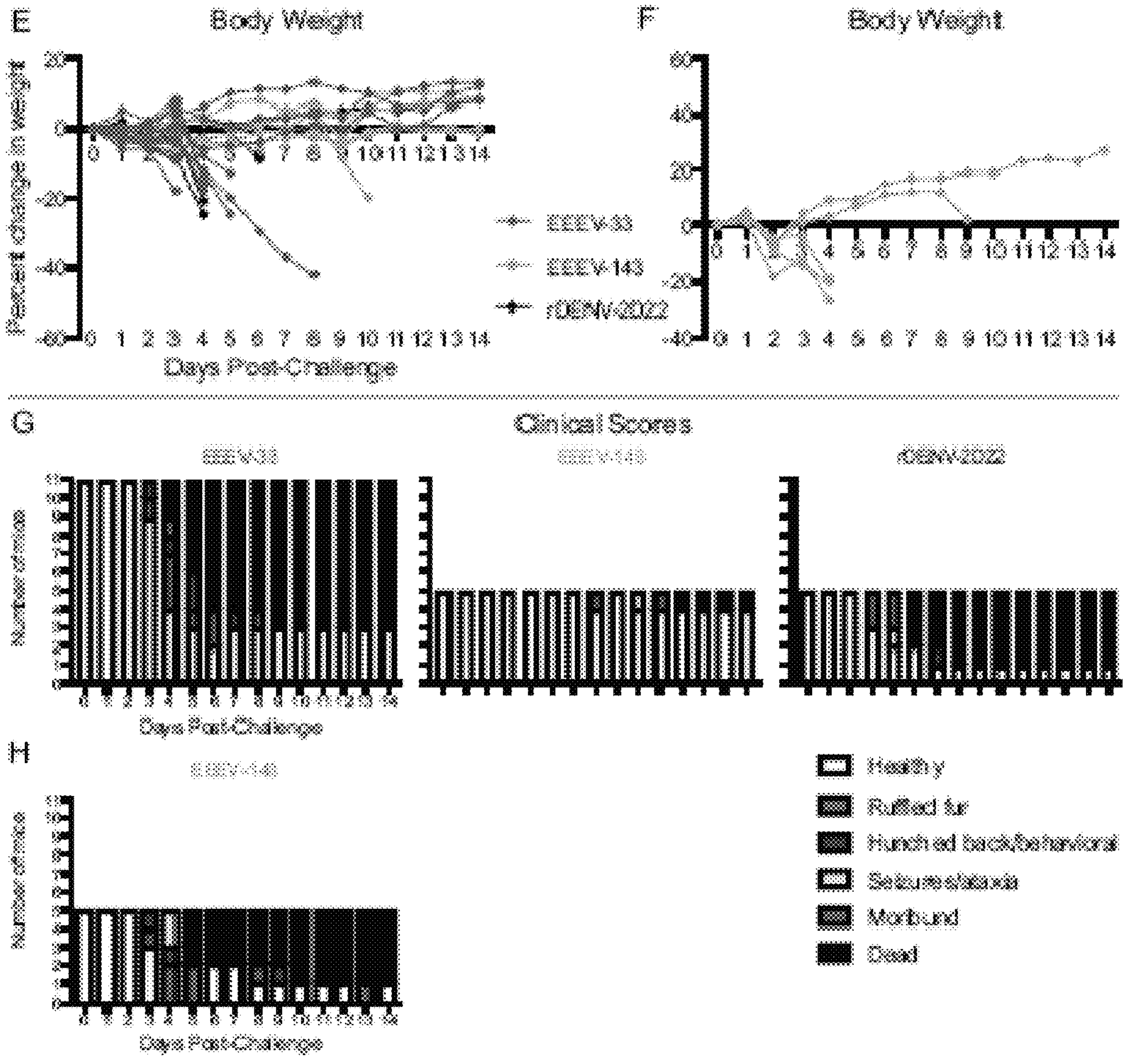
FIGS. 30E-H

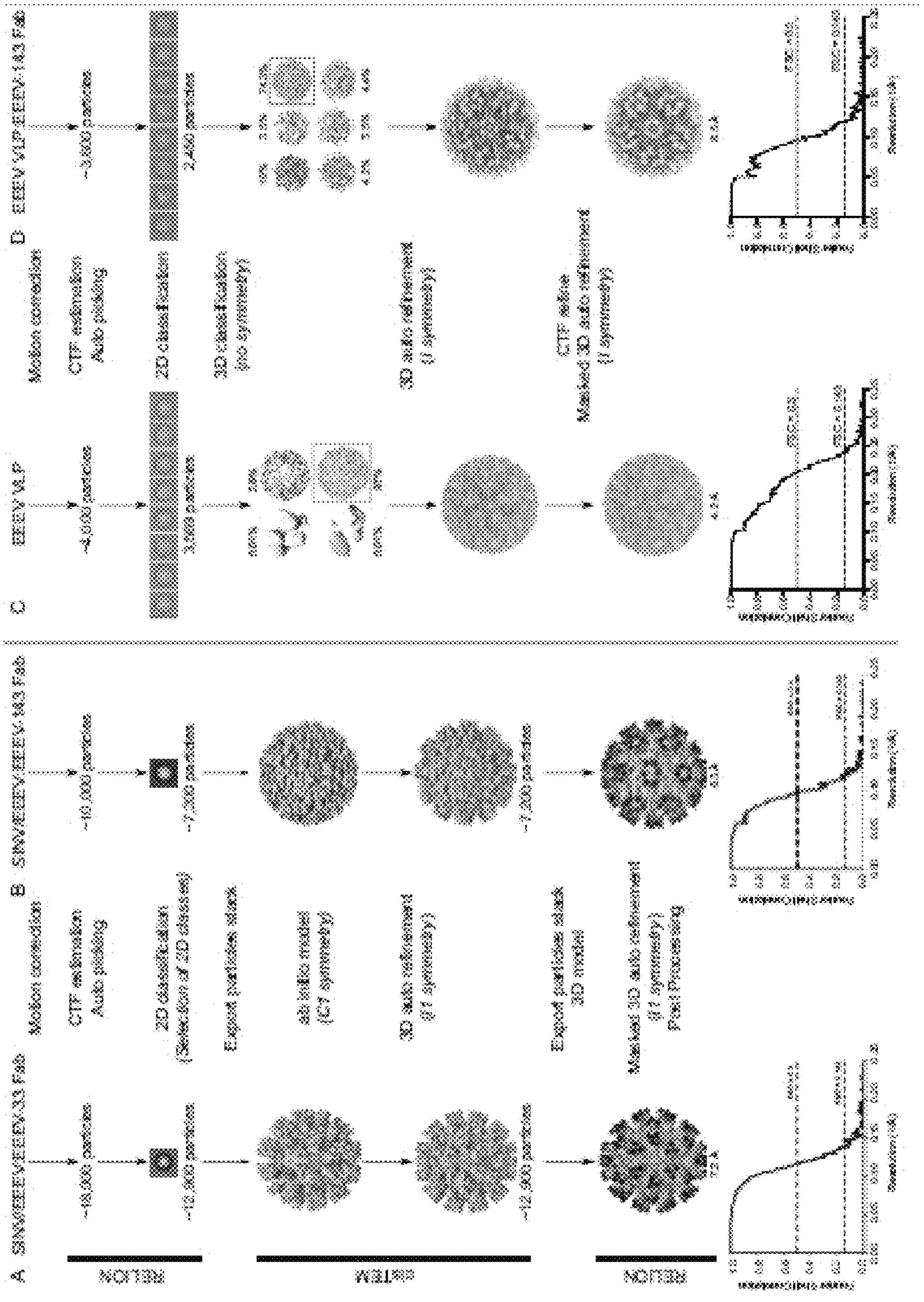
FIGS. 31A-D

HUMAN ANTIBODIES TO ALPHAVIRUSES

CROSS-REFERENCES TO RELATED APPLICATIONS

The present is a national phase application under 35 U.S.C. § 371 of International Application No. PCT/US2020/048708, filed Aug. 31, 2020, which application claims priority to U.S. Provisional Application Nos. 62/894,740, 62/896,382 and 62/933,735, filed Aug. 31, 2019, Sep. 5, 2019, and Nov. 11, 2019, respectively, the entire contents of each application being hereby incorporated by reference.

GOVERNMENT SUPPORT CLAUSE

This invention was made with government support under grant number HDTRA1-13-1-0034 awarded by the Department of Defense. The government has certain rights in the invention.

INCORPORATION-BY-REFERENCE OF SEQUENCE LISTING

This application contains a Sequence Listing, which has been submitted electronically and is hereby incorporated by reference in its entirety. Said Sequence Listing, created on Feb. 28, 2022, is named VBLTP0295US_ST25.txt, and is 290,235 bytes in size.

BACKGROUND

1. Field of the Disclosure

The present disclosure relates generally to the fields of medicine, infectious disease, and immunology. More particular, the disclosure relates to human antibodies binding to alphaviruses such as EEEV, WEEV and VEEV.

2. Background

The Alphavirus genus consists of three major encephalitic viruses: Eastern equine encephalitis virus (EEEV), Venezuelan equine encephalitis virus (VEEV), and Western equine encephalitis virus (WEEV). As indicated by their names, these encephalitic alphaviruses were identified as the cause of several epidemics of fatal encephalitis among horses (Calisher, 1994; Go et al., 2014; Markoff, 2015). Humans can acquire infection with these viruses, in which the mortality rate is approximately 30-70%, 10%, and 1% for EEEV, WEEV, and VEEV, respectively (Griffin, 2013; 2016; Markoff, 2015). EEEV and VEEV are considered category B priority pathogens due to their threat or previous use as bioterrorism agents (Griffin, 2013; 2015; Sidwell and Smee, 2003).

Additionally, the high mortality rate of up to 70% for EEEV and transmission capabilities for VEEV make these viruses of interest in regard to preventative or therapeutic treatment options (Griffin, 2013; 2015). Currently, there are no antiviral drugs or licensed human vaccines available for these viruses (Griffin, 2013; 2015; Reichert et al., 2009). However, experimental vaccines are available, and several vaccination strategies are in clinical trials (Griffin, 2013; 2015; Markoff, 2015). The antibody response to alphaviruses has been shown to be an important part of the immune response in conferring protective immunity and aiding in the clearance and recovery from infection (Matthews and Roehrig, 1982; Hunt et al., 2011; Levin et al., 1991; Griffin et al., 1997). However, the fundamental molecular and structural mechanisms of action of antibodies in humans to the encephalitic alphaviruses, in particular EEEV, remain poorly defined. Comprehensive characterization of potent monoclonal antibodies (mAbs) within the human antibody repertoire to these viruses is of high clinical significance and will help inform vaccine and therapeutic design against these clinically relevant alphaviruses.

Alphaviruses are classified into at least eight antigenic complexes (Calisher et al., 1980) and consist of up to six potential structural proteins: the capsid protein, E3 protein, E2 glycoprotein, E1 glycoprotein, 6K protein, and the TF protein (Griffin, 2013). The E1 and E2 glycoproteins heterodimerize to form trimeric knobs on the surface of the virus and are tethered via transmembrane domains to the capsid protein beneath the viral membrane (Zhang et al., 2002; Mukhopadhyay et al., 2006). Within these trimers, the E2 glycoprotein radially projects from the viral surface and forms the top of the trimeric knobs while the E1 glycoprotein lies tangential to the virus membrane (Li et al., 2010; Kielian et al., 2010; Zhang et al., 2011). The E2 glycoprotein is involved in receptor binding and the E1 glycoprotein contains the fusion loop for fusion of the virus with the endosomal membrane (Li et al., 2010; Kielian et al., 2010; Zhang et al., 2011). For many alphaviruses, the two glycoproteins are the major targets of murine antibodies (Griffin, 2013; 2015; 1995; Voss et al., 2010). As the more surface exposed glycoprotein, the E2 glycoprotein is the primary target for potent neutralizing murine antibodies (Griffin, 2013; 1995). In particular, murine antibodies bind to the E2 glycoprotein and are suspected to interfere with steps in the virus replication cycle from receptor attachment to viral egress (Sun et al., 2013; Porta et al., 2014; Fox et al., 2015; Long et al., 2015; Jin et al., 2015). Murine antibodies have also been isolated against the E1 glycoprotein (Hunt and Roehrig, 1985). However, most of these antibodies are non-neutralizing (Griffin, 2013; Hunt and Roehrig, 1985).

Of the murine neutralizing antibodies to the E1 glycoprotein, these antibodies rely on proximity to the E2 glycoprotein (Griffin, 2013; Roehrig et al., 1982) to do so or recognize transitional epitopes either exposed during low pH conditions or on the surface of an infected cell (Griffin, 1995).

In comparison to the characterization of murine and human antibodies to alphaviruses such as VEEV, WEEV and CHIKV (Selvarajah et al., 2013; Roehrig and Matthews, 1985; Rico-Hesse et al., 1988; Roehrig et al., 1988; Johnson et al., 1990; Hunt et al., 1990; 1991; Agapov et al., 1994; Hunt and Roehrig, 1985; 1995; Hunt et al., 2010; Smith et al., 2015; Hunt et al., 2006; Hulseweh et al., 2014; Pal et al., 2013; Jin et al., 2015), little is known about how antibodies neutralize or interact with EEEV. Previous research focuses on identification of linear epitopes of EEEV for murine and avian antibodies generated through animal immunization with recombinant E2 glycoprotein (Calisher et al., 1986; Pereboev et al., 1996; Zhao et al., 2012; EnCheng et al., 2013a; 2013b). Thus, knowledge of conformational epitopes that are recognized by human antibodies in the context of natural infection of EEEV is lacking. There are many other gaps in knowledge regarding the human antibody response to EEEV. Some questions that have yet to be addressed involve what are the human immunodominant antigenic determinants, are there correlates of protection and/or therapeutic potential, what are the neutralization mechanism(s) utilized by human mAbs, are there cross-reactive mAbs and, if so, are there cross-neutralizing or cross-protective mAbs, and are Fc-mediated effector functions involved?

SUMMARY

Thus, in accordance with the present disclosure, a method of detecting an alphavirus infection in a subject comprising (a) contacting a sample from said subject with an antibody or antibody fragment having clone-paired heavy and light chain CDR sequences from Tables 3 and 4, respectively; and (b) detecting alphavirus in said sample by binding of said antibody or antibody fragment to an alphavirus antigen in said sample. The sample may be is a body fluid, such as blood, sputum, tears, saliva, mucous or serum, semen, cervical or vaginal secretions, amniotic fluid, placental tissues, urine, exudate, transudate, tissue scrapings or feces. The alphavirus may be eastern equine encephalitis virus, western equine encephalitis virus, or Venezuelan equine encephalitis virus. Detection may comprise ELISA, RIA, lateral flow assay or Western blot. The method may further comprise performing steps (a) and (b) a second time and determining a change in alphavirus antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, $F(ab')_2$ fragment, or Fv fragment.

In another embodiment, there is provided a method of treating a subject infected with alphavirus or reducing the likelihood of infection of a subject at risk of contracting alphavirus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, IgA, IgM, polymeric IgA, or polymeric IgM antibody or a recombinant IgG, IgA, IgM, polymeric IgA, or polymeric IgM antibody or IgG, IgA, IgM, polymeric IgA, or polymeric IgM antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The alphavirus may be an eastern equine encephalitis virus, western equine encephalitis virus, or Venezuelan equine encephalitis virus.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody. The alphavirus may be an eastern equine encephalitis virus, western equine encephalitis virus, or Venezuelan equine encephalitis virus.

The monoclonal antibody or antibody fragment may further comprise a domain that facilitates transfer across the blood brain barrier by binding to a transport molecule, thereby facilitating transport into the brain. The transport molecule may be transferrin receptor, heparin-binding EGF, a scavenger receptor AI or BI, EGF receptor, tumor necrosis factor, insulin or insulin-like growth factor receptor, apolipoprotein E receptor 2, leptin receptor, melanotransferrin receptor, or LDL receptor. The domain may be a peptide or an scFv (single chain fragment variable) antibody, Fab fragment, $F(ab')_2$ fragment, Fv fragment, single domain antibody (nanobody) or wherein said domain is a distinct binding specificity as part of a chimeric or bispecific antibody structure. They may further comprise a domain that facilitates transfer across a mucosal surface, such as the respiratory tract barrier, by binding to a transport molecule, thereby facilitating transport across the mucosal surface.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody. The alphavirus may be an eastern equine encephalitis virus, western equine encephalitis virus, or Venezuelan equine encephalitis virus.

In a further embodiment, there is provided a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody. The alphavirus may be eastern equine encephalitis virus, western equine encephalitis virus, or Venezuelan equine encephalitis virus.

In yet a further embodiment there is provided a vaccine formulation comprising one or more expression vectors encoding a first antibody or antibody fragment as defined above. The expression vector(s) may be Sindbis virus or VEE vector(s). The vaccine may be formulated for delivery by needle injection, jet injection, or electroporation. The vaccine formulation may further comprise one or more expression vectors encoding for a second antibody or antibody fragment, such as a distinct antibody or antibody fragment as described herein.

In still yet a further embodiment, there is provided a method of protecting the health of a placenta and/or fetus of a pregnant a subject infected with or at risk of infection with an alphavirus comprising delivering to said subject an antibody or antibody fragment having clone-paired heavy and light chain CDR sequences from Tables 3 and 4, respectively.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, $F(ab')_2$ fragment, or Fv fragment. The antibody may be an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In an additional embodiment, there is provided a method of determining the antigenic integrity, correct conformation and/or correct sequence of an alphavirus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen, or a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, $F(ab')_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, $F(ab')_2$ fragment, or Fv fragment. The method may further comprise performing steps (c) and (d) a second time to determine the antigenic stability of the antigen over time.

In an additional embodiment, there is provided a human monoclonal antibody or antibody fragment, or hybridoma or engineered cell producing the same, wherein said antibody binds to alphavirus glycoprotein E1 or E2 and (a) reacts with one, two or all three of EEEV, VEEV and WEEV; (b) reacts with at least one of EEEV, VEEV, and WEEV, and also reacts with an arthritogenic virus, such as CHIKV; (c) neutralizes alphavirus at pre-attachment or post-attachment; (d) recognizes a neutralizing antigenic site in domain B at the tip of EEEV E2 glycoprotein or a neutralizing antigenic site in domain A of EEEV E2 glycoprotein; and/or (e) is therapeutic for alphavirus infection and/or is prophylactic for alphavirus infection, wherein the antibody may be neutralizing and prophylactic/therapeutic, or may be neutralizing and therapeutic, or non-neutralizing and prophylactic.

The monoclonal antibody or antibody fragment may further comprise a domain that facilitates transfer across the blood brain barrier by binding to a transport molecule, thereby facilitating transport into the brain. The transport molecule may be transferrin receptor, heparin-binding EGF, a scavenger receptor AI or BI, EGF receptor, tumor necrosis factor, insulin or insulin-like growth factor receptor, apolipoprotein E receptor 2, leptin receptor, melanotransferrin receptor, or LDL receptor. The domain may be a peptide or an scFv (single chain fragment variable) antibody, Fab fragment, $F(ab')_2$ fragment, Fv fragment, single domain antibody (nanobody) or wherein said domain is a distinct binding specificity as part of a chimeric or bispecific antibody structure. They may further comprise a domain that facilitates transfer across a mucosal surface, such as the respiratory tract barrier, by binding to a transport molecule, thereby facilitating transport across the mucosal surface.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D. Donor serum binding reactivity and neutralization activity to recombinant EEEV proteins and SINV/EEEV. (FIG. 1A) Representative curves for donor serum binding to SINV/EEEV with serum serial dilutions on the x-axis and optical density at 405 nm on the y-axis. (FIG. 1B) Neutralization curves of donor serum neutralization activity to SINV/EEEV with serum serial dilutions on the x-axis and percent relative infectivity on the y-axis. (FIGS. 1SC and D) Representative curves for donor serum binding to recombinant EEEV E2 (FIG. 1C) and E1 glycoproteins (FIG. 1D). Donor history of either naturally infected EEEV survivors or vaccinated with EEEV, VEEV, WEEV or VEEV alone are indicated in the tables. Endpoint titers for binding or neutralization activity (1/dilution) are indicated in the tables for each respective donor. Data for FIGS. 1A-D represents mean±SD of technical triplicates as determined via ELISA (FIGS. 1A, 1C, 1D) and focus reduction neutralization test (FRNT) (FIG. 1B).

FIGS. 2A-B. Donor serum binding reactivity to EEEV, VEEV, and WEEV virus-like particles (VLPs). (FIG. 2A) Representative curves for donor serum binding to EEEV, VEEV, and WEEV VLPs with serum serial dilutions on the x-axis and optical density at 405 nm on the y-axis. (FIG. 2B) Endpoint titers for binding (1/dilution) to EEEV, VEEV, and WEEV VLPs are indicated in the table for each respective donor. Data for FIGS. 2A-B represents mean±SD of technical triplicates as determined via ELISA.

FIGS. 3A-C. Donor human B-cell response to the encephalitic alphaviruses: EEEV, VEEV, and WEEV. (FIG. 3A) Relative B-cell frequencies obtained from EBV-transformation of PBMCs isolated from donors that naturally survived EEEV infection (average 1.0%) or were vaccinated against EEEV (average 0.21%) to SINV/EEEV and recombinant EEEV structural proteins (E2 and E1 glycoproteins). Donor 442 is a Rift Valley Fever Virus donor that serves a negative control. (FIG. 3B) Relative B-cell frequencies (average 0.26%) of EBV-transformed PBMCs from donors vaccinated against VEEV to the chimeric EILV/VEEV and recombinant VEEV E2 glycoprotein. (FIG. 3C) Relative B-cell frequencies (average 0.01%) of EBV-transformed PBMCs from donors vaccinated against WEEV to recombinant WEEV E2 glycoprotein.

FIGS. 4A-D. Current human hybridoma status of three EBV-transformed donors. (FIG. 4A) Hybridoma status for a naturally infected EEEV survivor (Donor 1069). A total of 64 human mAbs were isolated. Of this panel, a majority of the human mAbs are reactive to recombinant EEEV E2 glycoprotein (×49), several are reactive to recombinant EEEV E1 glycoprotein (×10), and one is specific for a virus-dependent epitope (×1). Three human mAbs are cross-reactive with the E2 (×3) or E1 (×3) glycoprotein of other encephalitic alphaviruses, VEEV and WEEV, and the arthritogenic alphavirus, CHIKV. Fifteen out of the 64 human mAbs isolated from Donor 1069 exhibit neutralization activity towards SINV/EEEV with <2 μg/mL $IC_{50}$ values. These mAbs are reactive to recombinant EEEV E2 glycoprotein. (FIG. 4B) A majority of the human mAb panel are IgG (×49), several are IgA (×4), and one IgM (×1). (FIG. 4C) Hybridoma status for another naturally infected EEEV survivor (Donor 982). A total of 40 human hybridomas are in the process for isolation of human mAbs. Based off of reactivity of the hybridoma supernatants, there is a diverse reactivity to SINV/EEEV (×11), recombinant EEEV structural proteins (×21), and EEEV, VEEV, and WEEV VLPs or structural proteins (×8). Of these, 10 exhibit neutralization activity (>70% reduction) against SINV/EEEV and are reactive to either virus-specific epitopes or recombinant EEEV E2 glycoprotein. (FIG. 4D) Hybridoma status of a SIP donor (Donor 1047) vaccinated for EEEV, VEEV, and WEEV. Several human mAbs were isolated and found to be specific for EEEV (×5) or VEEV (×1). None of the mAbs exhibited neutralization activity against SINV/EEEV (>5 μg/mL $IC_{50}$ value).

FIGS. 5A-C. Binding reactivity of human EEEV mAbs isolated from a naturally infected EEEV survivor to SINV/EEEV and recombinant EEEV structural proteins. (FIG. 5A) Half-maximal effective concentration ($EC_{50}$) values for binding of human EEEV E2-specific mAbs to SINV/EEEV and recombinant EEEV E2 glycoprotein. (FIG. 5B) $EC_{50}$ values for binding of human EEEV E1-specific mAbs to SINV/EEEV and recombinant EEEV E1 glycoprotein. (FIG. 5C) $EC_{50}$ values for binding of a human EEEV SINV/EEEV-specific mAb to SINV/EEEV. Data for FIGS. 5A-C represents mean±SD of technical triplicates as determined via ELISA. Increasing $EC_{50}$ value, or decreasing binding affinity, corresponds with increasing shade from <10, 11-100 ng/mL, 101-1,000, 1,001-5,000, to greater than 5,001 ng/mL. Dependence of each mAb on virus-specific epitopes compared to recombinant monomeric protein is indicated as the ratio of $EC_{50}$ values of protein versus virus. Higher ratio value indicates less dependence on virus-specific epitopes with a ratio of >10, 1.0-10, 0.1-1.0, and <0.1. Human EEEV mAbs with neutralization activity are indicated with * and cross-reactive mAbs are indicated with **. No binding was observed to uninfected baby hamster kidney (BHK-21) cell medium and non-EEEV recombinant viral surface proteins except for cross-reactive mAbs. ND=not determined.

FIGS. 6A-D. Cross-reactivity of human EEEV mAbs to VEEV, WEEV, and CHIKV. (FIG. 6A) $EC_{50}$ values for binding of human EEEV mabs to SINV/EEEV, EEEV, VEEV, and WEEV VLPs, and recombinant EEEV and VEEV E2 glycoproteins. Increasing $EC_{50}$ value corresponds with decreasing binding affinity. Human EEEV mAbs with neutralization activity are indicated with *. ND=not determined. (FIG. 6B) Representative binding curves for pan-alphavirus mAbs, EEEV-138 and EEEV-179, with mAb concentration (μg/mL) on the x-axis and optical density at 405 nm on the y-axis. (FIG. 6C) Representative binding curves for the EEEV and VEEV E2 glycoprotein mAbs: EEEV-107, EEEV-21, and EEEV-81. (FIG. 6D) Representative binding curves for EEEV and VEEV E1 glycoprotein mAb, EEEV-157. Data for FIGS. 6A-D represents mean±SD of technical triplicates as determined via ELISA. No binding was observed to uninfected baby hamster kidney (BHK-21) cell medium.

FIGS. 7A-B. Neutralization activity of human EEEV mAbs to BSL-2 SINV/EEEV and BSL-3 EEEV. (FIG. 7A) Neutralization curves of potently and moderately neutralizing human and mouse EEEV mAbs to SINV/EEEV as determined through FRNTs. In a FRNT, mAb and virus are added together for 1 hour at 37° C. prior to addition to cells at 37° C. for an additional 1.5 hours. After a methylcellulose overlay is added, cells are incubated at 37° C. for 18 hours. Cells are fixed and reduction in foci is observed through immunostain for EEEV structural proteins with mouse ascites fluids. Data represents mean±SD of technical triplicates. $IC_{50}$, $IC_{90}$, and $IC_{99}$ values (ng/ml) are indicated in the table as determined through non-linear regression analysis. Increasing IC value corresponds with decreasing neutralization activity. (FIG. 7B) $IC_{50}$ values (ng/mL) for human EEEV mAbs to wildtype, BSL-3, EEEV as determined through a cytopathic effect (CPE) assay.

FIGS. 8A-E. EEEV-33 protects prophylactically and therapeutically against EEEV in an in vivo aerosol challenge small animal model. (FIG. 8A) Kaplan-Meier survival curve of EEEV-33 (100 μg; i.p.) when given prophylactically (24 hours prior; squares; n=6) or therapeutically (24 hours post; triangles; n=6) against EEEV aerosol challenge (1,825 PFU/mouse; n=5). DENV r2D22 is an isotype control. (FIG. 8B) Percent body weight change of mice over the course of 14 days. (FIG. 8C) Clinical signs of mice over the course of 14 days. (FIG. 8D) IVIS imaging total flux (photons/second) at day 5. ~$1\times10^5$ total flux is background for uninfected mice. (FIG. 8E) IVIS images of mice. Three mice died by day 5 in the mock infected DENV r2D22 control and when EEEV- 33 was given therapeutically. One mouse died by day 5 when EEEV-33 was given prophylactically.

FIGS. 9A-D. EEEV-30 protects prophylactically against EEEV in an in vivo aerosol challenge small animal model. (FIG. 9A) Kaplan-Meier survival curve of EEEV-30 (100 μg; i.p.) when given prophylactically (24 hours prior; squares; n=6) or therapeutically (24 hours post; triangles; n=6) against EEEV aerosol challenge (6,340 PFU/mouse; n=5). DENV r2D22 is an isotype control. (FIG. 9B) Percent body weight change of mice over the course of 14 days. (FIG. 9C) Clinical signs of mice over the course of 14 days. (FIG. 9D) IVIS imaging total flux (photons/second) at day 5. ~$1\times10^5$ total flux is background for uninfected mice.

FIGS. 10A-C. Potential neutralization mechanism(s) of human EEEV mAbs. (FIG. 10A) Pre-vs post-attachment entry inhibition assays for several neutralizing human EEEV mAbs. In the pre-attachment entry inhibition assay, mAb and virus are mixed together and added to cells at 4° C. to allow for virus attachment but not entry. In the post-attachment entry inhibition assay, virus is added to cells at 4° C. followed by addition of the mAb. A shift to 37° C. for 15 minutes allows for the virus to enter the cell. After a methylcellulose overlay is added, cells are incubated at 37° C. for 18 hours. Cells are fixed and reduction in foci is observed through immunostain for EEEV structural proteins with mouse ascites fluids. Pre-attachment is indicated with circles, post-attachment is indicated with triangles, and FRNT is indicated with diamonds. (FIG. 10B) Plaque assay to measure the presence of infectious virus in supernatant taken from cells in an egress inhibition assay. In an egress inhibition assay, cells are incubated with virus for 2 hours at 37° C. Following extensive washing, different concentrations of a human EEEV mAb are incubated with the cells in the presence of ammonium chloride to prevent de novo infection. The cells are incubated at 37° C. for 6 hours. Supernatant is then collected. (FIG. 10C) Viral RNA was extracted from supernatant taken from cells in an egress inhibition assay. A standard curve was generated to determine the relative copies/μL of viral RNA present through qRT-PCR.

FIGS. 11A-C. Epitope mapping of human mAbs to recombinant EEEV E2 glycoprotein. (FIG. 11A) Competition-binding groups of human EEEV mAbs to recombinant EEEV E2 glycoprotein as determined through biolayer interferometry. A total of 36 human EEEV mAbs are shown. The $1^{st}$ mAb loaded onto biosensor is in the left-hand column and $2^{nd}$ mAb loaded is in the top column. Black boxes indicate that the $1^{st}$ mAb competes with the $2^{nd}$ mAb, as the max signal for the $2^{nd}$ mAb is <33%. Grey boxes indicate that the $1^{st}$ mAb may compete with the $2^{nd}$ mAb, as the max signal for the $2^{nd}$ mAb is between 33-66%. White boxes indicate that the $1^{st}$ mAb does not compete with the $2^{nd}$ mAb, as the max signal for the $2^{nd}$ mAb is >66%. (FIG. 11B) Competition-binding groups of neutralizing human EEEV mAbs binding to recombinant EEEV E2 glycoprotein. mAbs indicated with circles are murine EEEV mAbs known to bind residues 180-181 of the EEEV E2 glycoprotein, which correspond to domain B. (FIG. 11C) Mapping of residues recognized by Fab7, Fab12, and Fab16 onto VEEV structural proteins (PDB ID: 3JOC and 3JOG) as determined through hydrogen-deuterium exchange mass spectrometry (HDX-MS).

FIGS. 12A-C. Binding reactivity of human mAbs isolated from a Special Immunizations Program (SIP) donor to SINV/EEEV, recombinant EEEV structural proteins, and EEEV, VEEV, and WEEV virus-like particles (VLPs). (FIG. 12A) $EC_{50}$ values for binding of human EEEV mabs to EEEV, VEEV, and WEEV VLPs, and recombinant EEEV E2 and E1 glycoproteins. Increasing $EC_{50}$ value corresponds with decreasing binding affinity. ND=not determined. (FIG. 12B) Representative binding curve for VEEV-specific mAb, VEEV-47, with mAb concentration (μg/mL) on the x-axis and optical density at 405 nm on the y-axis. (FIG. 12C) Representative binding curves for the EEEV E2 glycoprotein mAbs: EEEV-237, EEEV-239, EEEV-275, EEEV-250, and EEEV-255. Data for FIGS. 12A-C represents mean±SD of technical triplicates as determined via ELISA.

FIGS. 13A-B. (FIG. 13A) $EC_{50}$ (ng/ml) values for binding of human anti-EEEV mAbs to SINV/EEEV particles and recombinant EEEV E3E2/E2 glycoprotein. Different binding patterns are observed with mAbs that bind better to virus than protein (Group 1), bind well to virus and protein (Group 2), bind better to protein than virus (Group 3), and those that bind weakly to both. A majority of the neutralizing mAbs bind well to both virus and protein. (FIG. 13B) $EC_{50}$ (ng/mL) values for neutralizing mAbs binding to SINV/EEEV particles and recombinant EEEV E3E2/E2 glycoprotein, with increase $EC_{50}$ value. The virus/protein $EC_{50}$ ratio is heat mapped, with mAbs that have higher affinity to SINV/EEEV particles with a ratio <1 and are indicated with darker shading. *=IgA.

FIGS. 14A-D. (FIG. 14A) Competition-binding analysis of human anti-EEEV mAbs to EEEV E3E2/E2 glycoprotein. Distinct competition binding groups are indicated in black with <33% maximal binding of the secondary antibody in the presence of the first antibody. There are about four distinct antigenic sites on the E2 glycoprotein recognized by human anti-EEEV mAbs. (FIG. 14B) Competition-binding analysis of neutralizing human anti-EEEV mAbs to EEEV E3E2/E2 glycoprotein. There are at least three distinct neutralizing antigenic sites on the E2 glycoprotein recognized by human anti-EEEV mAbs. (FIG. 14C) Hydrogen-deuterium exchange mass spectrometry of two neutralizing Fab molecules, EEEV-7 and EEEV-12. The footprint of EEEV-7 maps to domain B and of EEEV-12 to domain A of the E2 glycoprotein. (FIG. 14D) Alanine-scanning mutagenesis library analysis of EEEV-33. Alanine mutants of the E2 glycoprotein were screened to detect loss in binding residues for EEEV-33, which correspond to domain A of the E2 glycoprotein.

FIGS. 15A-B. Neutralization curves for human anti-EEEV mAbs. Seven potent neutralizing mAbs (FIG. 15A) and 5 moderate neutralizing mAbs (FIG. 15B). $IC_{50}$ values (ng/mL) are indicated in tables for potent (<10 $IC_{50}$ value) and moderate neutralizing mAbs with fading shading corresponding to increase in values. *=IgA.

FIGS. 17A-C. (FIG. 17A) Kaplan-Meier survival curve of EEEV-33 (100 μg; i.p.) when given prophylactically (24 hours prior; n=6) or therapeutically (24 hours post; n=6) against EEEV aerosol challenge (1,825 PFU/mouse; n=5). DENV r2D22 is an isotype control. (FIG. 17B) Percent body weight change of mice over the course of 14 days. (FIG. 17C) IVIS images of mice. Three mice died by day 5 in the mock infected DENV r2D22 control and when EEEV-33 was given therapeutically. One mouse died by day 5 when EEEV-33 was given prophylactically.

FIGS. 18A-D. Human anti-EEEV mAbs isolated from a naturally infected EEEV survivor potently neutralize Sindbis (SINV)/EEEV and WT EEEV (FL93-939). (FIG. 18A) Representative neutralization curves of potent or moderate neutralizing human anti-EEEV mAbs against SINV/EEEV. Neutralization curves of potent (left) or moderate (right) neutralizing human anti-EEEV mAbs against SINV/EEEV with mAb concentration (nM) on the x-axis and % relative infectivity on the y-axis. A positive control mouse mAb, EEEV-86 (dark purple) (Kim et al., 2019), and a negative control mAb, rDENV-2D22 (black), were included. (FIG. 18B) Representative neutralization curves of potent or moderate human anti-EEEV Fabs against SINV/EEEV. Neutralization curves of potent (left) or moderate (right) human anti-EEEV mAbs as Fab molecules against SINV/EEEV with Fab concentration (nM) on the x-axis and % relative infectivity on the y-axis. A negative control mAb, rDENV-2D22 (black), was included. (FIG. 18C) Neutralization curves of potent or moderate human anti-EEEV mAbs against EEEV. Neutralization curves of potent (left) or moderate (right) neutralizing human anti-EEEV mAbs against EEEV with mAb concentration (nM) on the x-axis and % relative infectivity on the y-axis. A positive control mouse anti-EEEV ascites fluid, ATCC (+) ve, and a negative control mAb, rDENV-2D22 (black), were included. (FIG. 18D) Half-maximal inhibitory concentration ($IC_{50}$) values (pM) for human anti-EEEV mAbs or Fabs against SINV/EEEV and mAbs against EEEV strain FL93-939. $IC_{50}$ values (pM) for neutralizing human anti-EEEV mAbs or Fabs against SINV/EEEV or mAbs against EEEV are indicated in the table. Neutralizing human anti-EEEV mAbs are listed in order of increasing $IC_{50}$ value against SINV/EEEV. $IC_{50}$ value in pM is indicated by the heat map (<33 [dark shade], 33.01 to 333 [medium shade], 333.01 to 3,333 [light shade], <10,000 [lightest shade]). Isotype is indicated as heavy chain (IgG1 or IgA1), light chain (κ or λ) as determined by antibody gene sequencing. Data in FIGS. 18A-B represent mean±SD of technical triplicates and are representative of three independent focus reduction neutralization test (FRNT) experiments. Data in FIG. 18C represent mean±SD of technical triplicates of a plaque reduction neutralization test (PRNT) experiment.

FIGS. 19A-C. Neutralizing human anti-EEEV mAbs bind to SINV/EEEV particles and/or recombinant EEEV E2 glycoprotein. (FIG. 19A) Binding ratio of neutralizing human anti-EEEV mAbs to SINV/EEEV particles versus recombinant monomeric EEEV E2 glycoprotein. A dotted line indicates 32 μM half-maximal effective concentration ($EC_{50}$) values for binding, revealing distinct binding patterns of human anti-EEEV mAbs to SINV/EEEV particles and EEEV E2 glycoprotein. Neutralizing human anti-EEEV mAbs are labeled with the anti-EEEV mAb name (Group 1=virus>protein binding; Group 2=strong (SINV/EEEV $EC_{50}$=<32 μM) virus»protein binding; Group 3=weak (SINV/EEEV $EC_{50}$=>32 PM) virus»protein binding; Group 4=protein>virus binding). (FIG. 19B) $EC_{50}$ values (pM) for binding of neutralizing human anti-EEEV mAbs to SINV/EEEV particles or EEEV E2 glycoprotein. Neutralizing human anti-EEEV mAbs are listed in order of binding group and increasing $EC_{50}$ value for binding to SINV/EEEV particles. $EC_{50}$ value in pM is indicated by the heat map (<32 [dark shade], 32.01 to 100 [medium shade], 100.01 to 320 [light shade], <10,000 [lightest shade]). Ratio of binding to SINV/EEEV particles versus EEEV E2 glycoprotein is indicated as the ratio of $EC_{50}$ values in the final column, corresponding to FIG. 19A. Increasing depth of shade indicates lower ratios (<0.1 [dark shade], 0.1 to 1.0 [medium shade], 1.01 to 2.0 [light shade], >2.0 [lightest shade]), suggesting recognition of a quaternary epitope on virion particles. (FIG. 19C) Representative binding curves of neutralizing human anti-EEEV mAbs to four different antigens. Binding curves of neutralizing human anti-EEEV mAbs to SINV/EEEV particles and EEEV E2 glycoprotein, with mAb concentration (nM) on the x-axis and optical density at 405 nm on the y-axis. Binding to EEEV E1 or CHIKV E1 glycoproteins was not detected. Data in FIGS. 19A-C represent mean±SD of technical triplicates and are representative of three independent ELISA experiments. See also FIGS. 25A-C for recombinant IgG1, IgA1, or Fab neutralizing human anti-EEEV Ab binding reactivity to SINV/EEEV particles or EEEV E2 glycoprotein.

FIGS. 20A-D. Human anti-EEEV mAbs recognize three neutralizing antigenic determinants on the EEEV E2 glycoprotein. (FIG. 20A) Competition-binding groups of neutralizing human anti-EEEV mAbs to recombinant EEEV E2 monomeric glycoprotein as determined through biolayer interferometry. Mouse domain B and neutralizing human anti-EEEV mAbs were incubated with EEEV E2 glycoprotein to identify the number of antigenic determinants recognized by these mAbs. The first mAb incubated with EEEV E2 glycoprotein is shown in the left-hand column and the second mAb is shown in the top column. Black boxes indicate competition, or reduction in maximum signal for binding of the second mAb to <33%. Grey boxes indicate intermediate competition, or reduction in maximum signal for binding of the second mAb to between 33 to 67%. White boxes indicate no competition, or little to no reduction in maximum signal for binding of the second mAb to >67%. $IC_{50}$ (pM) values for neutralization activity against SINV/EEEV are indicated in parentheses (FIG. 18D). (FIG. 20B) Heat map of critical residues for neutralizing human anti-EEEV mAbs as determined through alanine-scanning mutagenesis library analysis. The average percent binding of each neutralizing human anti-EEEV mAbs is indicated for the critical residues identified (<25% binding of mAb in which at least two mAbs exhibited >70% binding to control for expression; D1-L267) and for the previously characterized murine anti-EEEV mAbs (Kim et al., 2019) and the VEEV-specific human mAb, F5 (Hunt et al., 2010; Porta et al., 2014). The heat map displays average percent binding relative to WT EEEV E2 glycoprotein. Residues are grouped based on E2 domain. Each mAb is ordered to correspond with the competition-binding groups as defined in FIG. 20A. Data represents mean of at least two independent experiments. (FIG. 20C) Epitope mapping of critical alanine and arginine residues previously identified for neutralizing murine anti-EEEV mAbs binding to the E2 glycoprotein. Critical residues for binding of neutralizing murine anti-EEEV mAbs as previously determined through alanine and arginine mutagenesis analyses were mapped onto the 4.2 Å cryo-EM reconstruction of EEEV VLP (EMD-22276; PBD ID: 6XO4) for comparison to the critical alanine residues identified for neutralizing human anti-EEEV mAbs (see FIG. 20D). A trimeric top view of the E2 glycoprotein and E1 glycoprotein is shown with critical residues (spheres) for murine anti-EEEV mAbs that recognize the E2 domains A, B, and A/B. (FIG. 20D) Epitope mapping of critical alanine residues identified for neutralizing human anti-EEEV mAbs binding to the E2 glycoprotein. Critical residues for binding of neutralizing human anti-EEEV mAbs as identified through alanine-scanning mutagenesis library analyses (FIG. 20B) were mapped onto the 4.2 Å cryo-EM reconstruction of EEEV VLP (EMD-22276; PBD ID: 6XO4). A trimeric top view of the E2 glycoprotein and E1 glycoprotein is shown with critical residues (spheres) for mAbs that recognize the E2 domains A, B, and A/B. Certain spheres indicate the previously identified SINV/EEEV neutralization escape mutants (M68T, G192R, and L227R) (Kim et al., 2019). Each mAb is presented with its respective E2 domain. See FIG. 26 for a bar graph representation of the percent binding of each human anti-EEEV mAb to the alanine residues described in FIG. 3B. See FIGS. 27A-C for neutralization activity of human anti-EEEV mAbs against the SINV/EEEV escape mutants (M68T, G192R, and L227R). See Table S1 for critical alanine residues identified for each human anti-EEEV mAb.

FIGS. 21A-G. EEEV-33 recognizes a critical domain A epitope on SINV/EEEV particles for inhibition of viral entry or fusion into cells. (FIG. 21A) Entry blockade of SINV/EEEV by EEEV-33. An entry blockade assay (open squares) was performed by extensive washing of EEEV-33 or the DENV-specific negative control mAb, rDENV-2D22 (black), from the medium following internalization of SINV/EEEV into Vero cells. Representative neutralization curves are shown for EEEV-33 and rDENV-2D22 as determined through FRNT (closed squares; see FIG. 18A) or the entry blockade assay with mAb concentration (nM) on the x-axis and percent relative infectivity on the y-axis. (FIG. 21B) Post-attachment neutralization of SINV/EEEV by EEEV-33. A post-attachment neutralization assay (starred circles) was performed by incubation of Vero cells with SINV/EEEV at 4° C. for 1 hour followed by addition of EEEV-33 or rDENV-2D22 (black) at 4° C. for 1 hour. Cells then were incubated at 37° C. for 15 minutes prior to addition of a methylcellulose overlay and incubation at 37° C. for 18 hours. Representative neutralization curves are shown for EEEV-33 and rDENV-2D22 as determined through FRNT (closed squares; see FIG. 18A) or the post-attachment neutralization assay with mAb concentration (nM) on the x-axis and percent relative infectivity on the y-axis. (FIGS. 21C-D) Cryo-EM reconstruction of SINV/EEEV in complex with EEEV-33 Fab molecules. Cryo-EM structure of EEEV-33 Fab complex (~7.2 Å) showing radially colored surface representation of full (FIG. 21C) and cross section (FIG. 21D) of the map. (FIG. 21E) EEEV-33 Fab binding footprint to E2 trimeric spikes on SINV/EEEV particles. View of map surface to illustrate binding of EEEV-33 Fab to the q3 and i3 spikes along the icosahedral 2-fold axis. (FIG. 21F) EEEV-33 Fab constant domain contact interactions. Close-up view of EEEV-33 Fab binding to the i3 spike (black circle in E), in which overlapping Fab constant domain density is observed. (FIG. 21G) Cryo-EM E2 trimeric view of EEEV-33 Fab binding with critical alanine residues. Critical alanine residues identified for EEEV-33 are indicated with spheres to illustrate the epitope of EEEV-33 corresponds with the SINV/EEEV (PDB ID: 6MX4) and EEEV-143 Fab (mutated sequence of PDB: 6MWX) docked and rigid body refined cryo-EM model of rEEEV-33 Fab in complex with SINV/EEEV. Data in FIGS. 21A-B represent mean±SD of technical triplicates and are representative of two independent experiments. See FIGS. 28A-D for additional views of EEEV-33 Fab binding to the E2 trimer on SINV/EEEV particles.

FIGS. 22A-G. EEEV-143 recognizes a critical domain B epitope on SINV/EEEV particles for inhibition of viral entry or fusion into cells. (FIG. 22A) Entry blockade of SINV/EEEV by EEEV-143. An entry blockade assay (open squares) was performed by extensive washing of EEEV-143 or the DENV-specific negative control mAb, rDENV-2D22 (black), from the medium following internalization of SINV/EEEV. Representative neutralization curves are shown for EEEV-143 and rDENV-2D22 as determined through FRNT (closed squares; see FIG. 18A) or the entry blockade assay with mAb concentration (nM) on the x-axis and percent relative infectivity on the y-axis. (FIG. 22B) Post-attachment neutralization of SINV/EEEV by EEEV-143. A post-attachment neutralization assay (starred circles) was performed by incubation of Vero cells with SINV/EEEV at 4° C. for 1 hour followed by addition of EEEV-143 or rDENV-2D22 (black) at 4° C. for 1 hour. Cells then were incubated at 37° C. for 15 minutes prior to addition of a methylcellulose overlay and incubation at 37° C. for 18 hours. Representative neutralization curves are shown for EEEV-143 and rDENV-2D22 as determined through FRNT (closed squares; see FIG. 18A) or the post-attachment neutralization assay with mAb concentration (nM) on the x-axis and percent relative infectivity on the y-axis. (FIGS. 22C-D) Cryo-EM reconstruction of SINV/EEEV in complex with EEEV-143 Fab molecules. Cryo-EM structure of EEEV-143 Fab complex (~8.3 Å) showing radially colored surface representation of full (FIG. 22C) and cross section (FIG. 22D) of the map. (FIG. 22E) EEEV-143 Fab binding footprint to E2 trimeric spikes on EEEV virus-like particles (VLPs). View of map surface to illustrate binding of EEEV-143 Fab to the q3 and i3 spikes along the icosahedral 2-fold axis. (FIG. 22F) EEEV-143 Fab constant domain contact interactions. Close-up view of EEEV-143 Fab binding to the q3 and i3 spikes (black circles in FIG. 22E), in which overlapping Fab constant domain density is observed around the 2-fold axis. Fabs bound to the q3 and i3 spikes across the 3-fold axis are ~11 Å apart, in which the flexibility of the Fab may allow for contacts to occur. (FIG. 22G) Cryo-EM E2 trimeric view of EEEV-143 Fab binding with critical alanine residues. Critical alanine residues identified for EEEV-143 are indicated with spheres to illustrate the epitope of EEEV-143 corresponds with the EEEV VLP (EMD-22276; PDB ID: 6XO4) and EEEV-143 Fab (mutated sequence of PDB: 6MWX) docked and rigid body refined cryo-EM model. Data in A-B represent mean±SD of technical triplicates and are representative of two independent experiments. See FIGS. 28A-D for additional views of EEEV-143 Fab binding to the E2 trimer on SINV/EEEV particles.

FIGS. 23A-D. Prophylaxis administration of mice with EEEV-33 and EEEV-143 protects against EEEV in an in vivo aerosol challenge model. (FIG. 23A) Anti-EEEV mAbs protect against EEEV lethality as prophylaxis. EEEV-33 (n=11) and EEEV-143 (n=5) were administered prophylactically (24 hours prior virus challenge) at 100 μg via the intraperitoneal route to CD-1 female mice (4-6-weeks old). EEEV-33 or EEEV-143 protected mice with 91 or 100% survival, respectively, against EEEV (FL93-939) aerosol challenge (1,631 to 1,825 PFU/mouse) compared to the negative control DENV-specific IgG1 mAb, rDENV-2D22 (n=10) (Fibriansah et al., 2015). Survival curves were compared using the log-rank test with Bonferroni multiple comparison correction. *p<0.05, p<0.01, ns=not significant. (FIG. 23**B) EEEV-143 protects against a higher inoculation dose of EEEV. EEEV-143 (n=5) was administered prophylactically (24 hours prior virus challenge) at 100 μg by the intraperitoneal route to CD-1 female mice (4-6-weeks old). EEEV-143 exhibited 100% prophylactic survival against EEEV (FL93-939) aerosol challenge (2,739 PFU/mouse). rDENV-2D22 (black; n=5), a DENV-specific IgG1 mAb, served as a negative control. Survival curves were compared using the log-rank test with Bonferroni multiple comparison correction. *p<0.05, p<0.01, ns=not significant. (FIG. 23C) In vivo imaging system (IVIS) images of CD-1 mice for EEEV-33, EEEV-143, and rDENV-2D22 prophylactically treated groups at days 4-5 post EEEV aerosol challenge. IVIS images for EEEV-33, EEEV-143, and rDENV-2D22 (black). One of the mice in the EEEV-33 group and three of the mice in the rDENV-2D22 negative control group died prior to IVIS imaging on day 5 after virus challenge. (FIG. 23D) Luminescence intensity of IVIS images. Total flux (photons/second) for the corresponding IVIS images in FIG. 23**C of the EEEV-33, EEEV-143, and rDENV-2D22 groups is indicated. ~1x$10^5$ total flux is the background for uninfected mice. One-way ANOVA with Dunnett's multiple comparisons correction was used to compare luminescence of the images to the rDENV-2D22 control group. *p<0.01. Data FIG. 23A, FIG. 23C, and FIG. 23D represent combined in vivo data for EEEV-33 (n=6, n=5) or rDENV-2D22 (n=5, n=5) in two independent experiments (1,631 to 1,825 PFU/mouse). Data in FIG. 23A represent in vivo data for EEEV-143 (n=5) in one independent experiment (1,631 to 1,825 PFU/mouse). Data in FIGS. 23B-D represent in vivo data for EEEV-143 (n=5) in one independent experiment (2,739 PFU/mouse).

FIGS. 24A-D. Post-exposure therapy with EEEV-33 and EEEV-143 partially protects mice against EEEV in an in vivo aerosol challenge model. (FIG. 24A) Anti-EEEV mAbs protect against EEEV lethality as post-exposure therapy. EEEV-33 (n=11) and EEEV-143 (n=5) were administered therapeutically (24 hours post virus challenge) at 100 μg via the intraperitoneal route to CD-1 female mice (4-6-weeks old). EEEV-33 or EEEV-143 exhibited 27% or 80% therapeutic survival, respectively, against EEEV (FL93-939) aerosol challenge (1,631-1,825 PFU/mouse) compared to the negative control dengue virus-specific IgG1 mAb rDENV-2D22 (n=5) (Fibriansah et al., 2015). Survival curves were compared using the log-rank test with Bonferroni multiple comparison correction. *p<0.05, p<0.01, ns=not significant. (FIG. 24B) EEEV-143 administration at a higher inoculation dose of EEEV. EEEV-143 (n=5) was administered therapeutically (24 hours after virus inoculation) at 100 μg by the intraperitoneal route to CD-1 female mice (4-6-weeks old). EEEV-143 exhibited 20% therapeutic survival against EEEV (FL93-939) aerosol challenge (2,739 PFU/mouse). (FIG. 24C) In vivo imaging system (IVIS) images of CD-1 mice for EEEV-33 and EEEV-143 therapeutically treated group at days 4-5 after EEEV aerosol challenge. IVIS images for EEEV-33 or EEEV-143. Four of the mice in the EEEV-33 group died prior to IVIS imaging on day 5 post virus challenge. (FIG. 24D) Luminescence intensity of IVIS images. Total flux (photons/second) for the corresponding IVIS images in FIG. 24C of the EEEV-33 and EEEV-143 groups are indicated. ~1x$10^5$ total flux is the background for uninfected mice. Data in FIGS. 24A-D represent combined in vivo data for EEEV-33 (n=6, n=5) in two independent experiments (1,631 to 1,825 PFU/mouse). Data in A represent in vivo data for EEEV-143 (n=5) rDENV-2D22 (n=5) in one independent experiment (1,631 to 1,825 PFU/mouse). Data in FIGS. 24**B-D represent in vivo data for EEEV-143 (n=5) in one independent experiment (2,739 PFU/mouse).

FIGS. 25A-C. Related to FIGS. 19A-C. Binding reactivity of neutralizing human anti-EEEV mAbs to SINV/EEEV particles or EEEV E2 glycoprotein. (FIG. 25A) Binding ratio of neutralizing human anti-EEEV mAbs to SINV/EEEV particles vs. recombinant monomeric EEEV E2 glycoprotein. EEEV-33 is removed to display the binding reactivity groups for the rest of the panel of neutralizing human anti-EEEV mAbs at higher resolution. A dotted line indicates 32 μM half-maximal effective concentration ($EC_{50}$) values for binding, revealing distinct binding patterns of human anti-EEEV mAbs to SINV/EEEV particles and EEEV E2 glycoprotein. Neutralizing human anti-EEEV mAbs are labeled with the anti-EEEV mAb name (Group 2=strong (SINV/EEEV $EC_{50}$=<32 μM) virus»protein binding; Group 3=weak (SINV/EEEV $EC_{50}$=>32 μM) virus»protein binding; Group 4=protein>virus binding). (FIG. 25B) Representative binding curves of recombinant neutralizing human anti-EEEV IgG1, IgA1, or Fab molecules to three different antigens. Binding curves of recombinant neutralizing human anti-EEEV IgG1 (square), IgA1 (triangle), or Fab (circle) molecules to SINV/EEEV particles or EEEV E2 glycoprotein, with mAb concentration (nM) on the x-axis and optical density at 405 nm on the y-axis. Binding to EEEV E1 glycoprotein was not detected. (FIG. 25C) $EC_{50}$ values (pM) for binding of recombinant neutralizing human anti-EEEV IgG1, IgA1, or Fab molecules to SINV/EEEV particles or EEEV E2 glycoprotein. $EC_{50}$ value in pM is indicated by shading intensity (<32, 32.01 to 100, 100.01 to 320, <10,000). Ratio of binding to SINV/EEEV particles versus EEEV E2 glycoprotein is indicated as the ratio of $EC_{50}$ values. Increasing depth of shading indicates lower ratios (<0.1, 0.1 to 1.0, 1.01 to 2.0, >2.0), suggesting recognition of a quaternary epitope on virion particles. Ratio of binding of recombinant IgG1 versus Fab molecules to SINV/EEEV particles or EEEV E2 glycoprotein is indicated as the ratio of $EC_{50}$ values. Increasing depth of shading indicates lower ratios (<0.1, 0.1 to 1.0, 1.01 to 2.0, >2.0), suggesting dependence on valency for binding. Antibody isotype is indicated as IgG1 or IgA1 for the heavy chain or k or 1 for the light chain. NA=not applicable. Data in A to C represent mean±SD of technical triplicates and are representative of two independent ELISA experiments.

FIGS. 27A-C. Related to FIGS. 20A-D. Neutralization activity of human anti-EEEV mAbs to SINV/EEEV escape mutant viruses. (FIG. 27A) Representative neutralization curves of potent neutralizing human anti-EEEV mAbs against SINV/EEEV WT, and escape mutant viruses M68T, G192R, and L227R. Neutralization curves of potent human anti-EEEV mAbs against SINV/EEEV WT (closed square), M68T (open triangle), G192R (open circle), and L227R (open diamond), with mAb concentration (nM) on the x-axis and % relative infectivity on the y-axis. mAbs are ordered based on $IC_{50}$ values against SINV/EEEV WT. A positive control mouse mAb, mEEEV-3 (Kim et al., 2019), and a negative control mAb, rDENV-2D22 (black; B), were included. (FIG. 27B) Representative neutralization curves of moderate neutralizing human anti-EEEV mAbs against SINV/EEEV WT and escape mutant viruses M68T, G192R, and L227R. Neutralization curves of moderate human anti-EEEV mAbs against SINV/EEEV WT (closed square), M68T (open triangle), G192R (open circle), and L227R (open diamond), with mAb concentration (nM) on the x-axis and % relative infectivity on the y-axis. A positive control mouse mAb, mEEEV-3 (FIG. 27A) (Kim et al., 2019), and a negative control mAb, rDENV-2D22 (black), were included. (FIG. 27C) Half-maximal inhibitory concentration ($IC_{50}$) values (pM) for human anti-EEEV mAbs against SINV/EEEV WT and escape mutant viruses M68T, G192R, and L227R. $IC_{50}$ values (pM) for neutralizing human anti-EEEV mAbs against SINV/EEEV WT, M68T, G192R, and L227R are indicated in the table. Neutralizing human anti-EEEV mAbs are listed in order of increasing $IC_{50}$ value against SINV/EEEV WT. $IC_{50}$ value in pM is indicated by the shade gradient (<33 [dark], 33 to 333 [medium], 333.01 to 3,333 [light], <10,000 [lightest]). Fold difference in $IC_{50}$ value ratio of SINV/EEEV WT versus each escape mutant virus (M68T, G192R, or L227R) are indicated. Ratio of neutralization activity against SINV/EEEV WT versus each escape mutant virus (M68T, G192R, or L227R) is indicated as the fold difference of $IC_{50}$ values. Increasing depth of shading indicates greater fold differences (>15 or > [dark], 10-15 [medium], 5-10 [light], <5 [white]), suggesting reduction in neutralization activity of the mAb. Data in FIGS. 27A-C represent mean±SD of technical triplicates and are representative of two independent focus reduction neutralization test (FRNT) experiments.

FIGS. 28A-D. Related to FIGS. 21A-G and FIG. 22A-G. EEEV-33 or EEEV-143 Fab binding to the E2 trimeric spike of SINV/EEEV particles. Side view (FIG. 28A) or 40° top-view (FIG. 28B) of EEEV E2 trimeric spikes for side-by-side comparisons of native SINV/EEEV (left), SINV/EEEV: EEEV-33 Fab complex (right) and SINV/EEEV: EEEV-143 Fab complex (middle) showing binding of one Fab (EEEV-33; EEEV-143) per E2 protomer within the trimeric spike. Low pass map of published native SINV/EEEV structure (EMD-9280) used for the comparison. Side view (FIG. 28C) or 40° top-view (FIG. 28D) of EEEV-33 Fab and EEEV-143 Fab bound to SINV/EEEV or EEEV VLP, respectively. For the SINV/EEEV (PDB ID: 6MX4) and EEEV-143 Fab (mutated sequence of PDB ID: 6MWX) docked and rigid body refined model of SINV/EEEV: EEEV-33 Fab complex, the structural proteins are shaded. For the EEEV VLP:EEEV-143 Fab complex (EMD-22277; PDB ID: 6XOB), the structural proteins are shaded.

FIGS. 29A-I. Related to FIGS. 22A-B. Cryo-EM reconstruction of EEEV VLP in complex with EEEV-143 Fab molecules. Cryo-EM structure of the apo form of EEEV VLP (FIGS. 29A-C) and of EEEV VLP:EEEV-143 Fab complex (FIGS. 29D-F) showing radially colored surface representation of full (FIGS. 29A and 29D) and cross-section (FIGS. 29B and 29E) of the map. FIG. 29C and FIG. 29F. Roadmaps of the apo form of EEEV VLP and EEEV VLP:EEEV-143 Fab complex reconstructions to illustrate EEEV-143 Fab binding sites (in dark shade). EEEV-143 binds in a tangential orientation and makes contacts with neighboring spikes for inter-spike cross-linking of SINV/EEEV particles. FIGS. 29G-H. Asymmetric unit view of EEEV structural proteins of the apo form of EEEV VLP (FIG. 29G) or in complex with EEEV-143 Fab molecules (FIG. 29H) bound in a tangential orientation. Alignment of EEEV structural proteins of the EEEV VLP apo form to the EEEV VLP:EEEV-143 Fab complex to show stabilization of the E2 glycoprotein upon EEEV-143 Fab binding (FIG. 29I).

FIGS. 30A-H. Related to FIGS. 23A-D and FIGS. 24A-D. In vivo body weight change and clinical disease signs observed in EEEV-33 and EEEV-143 mAb administered lethal EEEV aerosol challenge model. (FIG. 30A) Percent body weight change of EEEV-33, EEEV-143, and rDENV-2D22 prophylactically treated CD-1 mice over the course of 14 days. Percent change in weight (y-axis) for EEEV-33 (n=11), EEEV-143 (n=5), and rDENV-2D22 (n=10) are indicated over the course of 14 days after EEEV challenge (1,631 to 1,825 PFU/mouse; x-axis). (FIG. 30B) Percent body weight change of EEEV-143 and rDENV-2D22 prophylactically treated CD-1 mice over the course of 14 days. Percent change in weight (y-axis) for EEEV-143 (n=5) and rDENV-2D22 (n=5) are indicated over the course of 14 days after EEEV challenge (2,739 PFU/mouse; x-axis). (FIG. 30C) Clinical scores of EEEV-33, EEEV-143, and rDENV-2D22 prophylactically treated CD-1 mice over the course of 14 days. The number of mice (y-axis) for EEEV-33 (n=11), EEEV-143 (n=5), and rDENV-2D22 (n=10) with defined clinical scores (dead, moribund, seizures/ataxia, hunched back/behavioral, ruffled fur, healthy) are indicated over the course of 14 days post EEEV challenge (1,631 to 1,825 PFU/mouse; x-axis). (FIG. 30D) Clinical scores of EEEV-143 and rDENV-2D22 prophylactically treated CD-1 mice over the course of 14 days. The number of mice (y-axis) for EEEV-143 (n=5) and rDENV-2D22 (n=5) with defined clinical scores (dead, moribund, seizures/ataxia, hunched back/behavioral, ruffled fur, healthy) are indicated over the course of 14 days after EEEV challenge (2,739 PFU/mouse; x-axis). (FIG. 30E) Percent body weight change of EEEV-33, EEEV-143, and rDENV-2D22 therapeutically treated CD-1 mice over the course of 14 days. Percent change in weight (y-axis) for EEEV-33 (n=11), EEEV-143 (n=5), and rDENV-2D22 (n=5) are indicated over the course of 14 days after EEEV challenge (1,631 to 1,825 PFU/mouse; x-axis). (FIG. 30F) Percent body weight change of EEEV-143 therapeutically treated CD-1 and BALB/c mice, respectively, over the course of 14 days. Percent change in weight (y-axis) for EEEV-143 (n=5) is indicated over the course of 14 days after EEEV challenge (2,739 PFU/mouse; x-axis). (FIG. 30G) Clinical scores of EEEV-33, EEEV-143, and rDENV-2D22 therapeutically treated CD-1 mice over the course of 14 days. The number of mice (y-axis) for EEEV-33 (n=11), EEEV-143 (n=5), and rDENV-2D22 (n=5) with defined clinical scores are indicated over the course of 14 days after EEEV challenge (1,631 to 1,825 PFU/mouse; x-axis). (FIG. 30H) Clinical scores of EEEV-143 therapeutically treated CD-1 and BALB/c mice, respectively, over the course of 14 days. The number of mice (y-axis) for EEEV-143 (n=5) with defined clinical scores are indicated over the course of 14 days after EEEV challenge (2,739 PFU/mouse; x-axis).

FIGS. 31A-D. Related to STAR Methods. Cryo-EM processing of SINV/EEEV complexes with either EEEV-33 or EEEV-143 Fabs. Flow chart of cryo-EM processing steps and Fourier shell correlation (FSCs) of the maps of SINV/EEEV: rEEEV-33 Fab complex (FIG. 31A), SINV/EEEV: rEEEV-143 Fab complex (FIG. 31B), EEEV VLP (FIG. 31C), and EEEV VLP: rEEEV-143 Fab complex (FIG. 31D). The FSCs of the refined models agree with each other, suggesting that the models are not over-refined.

DESCRIPTION OF ILLUSTRATIVE EMBODIMENTS

Figure 11C:
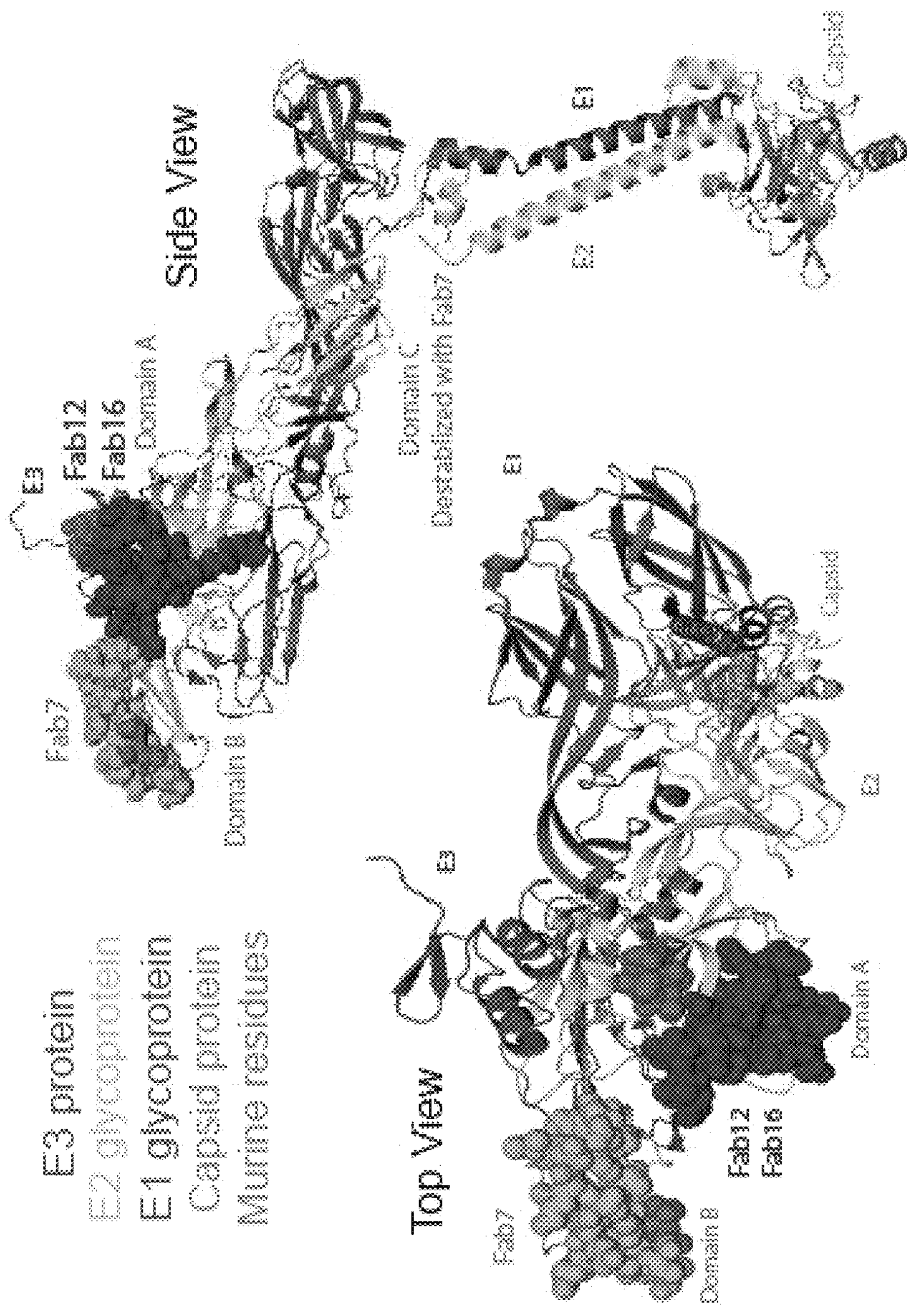
Figure 16:
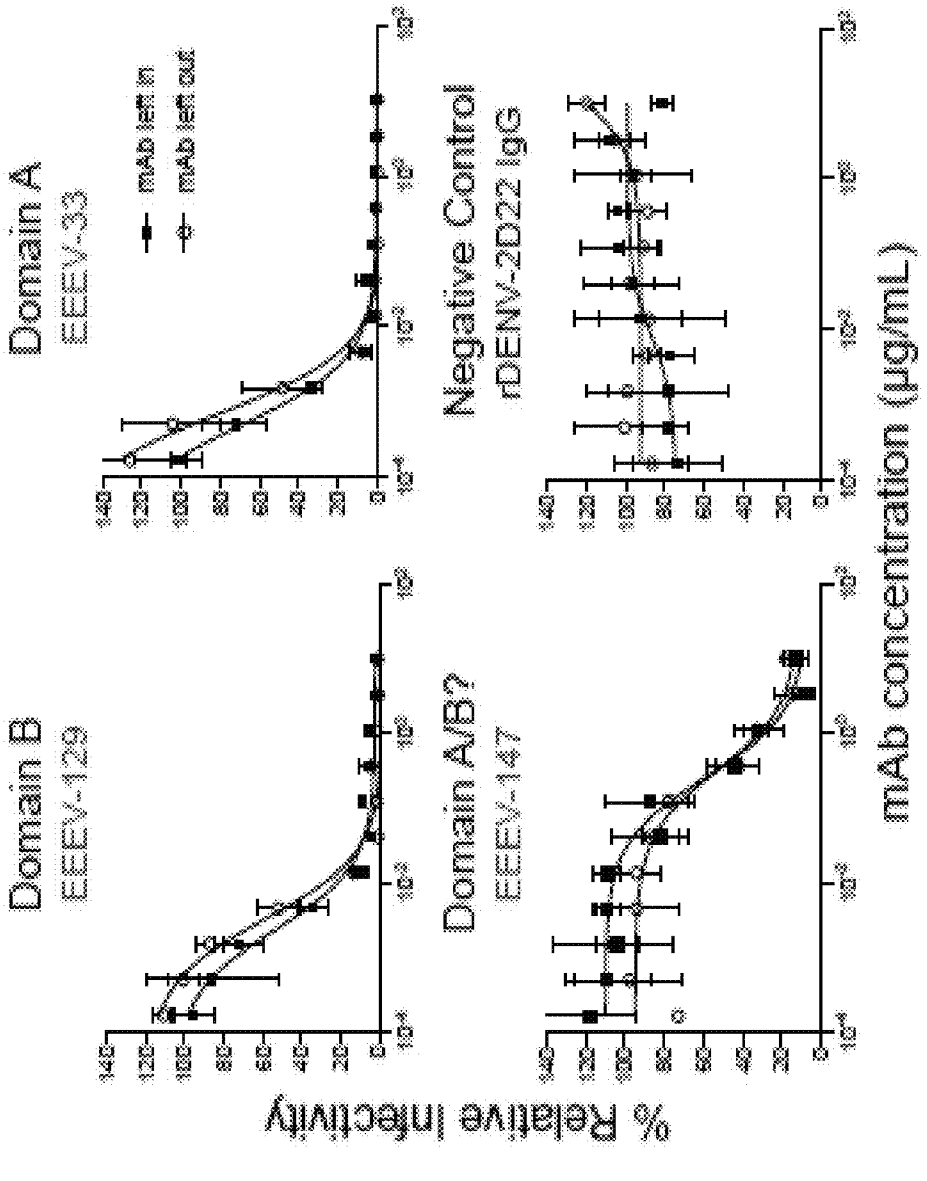
FIG. 16. Entry inhibition assay for representative mAbs that either recognize domains B, A, or A/B of the EEEV E2 glycoprotein. A negative control mAb, rDENV-2D22, was included. The difference between mAb left in (filled in circles) versus mAb removed via washing prior to addition of an overlay (open circles) helps indicate at which steps in the replication cycle the mAbs are able to neutralize SINV/EEEV. The similar neutralization potencies for these mAbs indicates that neutralization occurs at the early stages in the replication cycle, such as to prevent entry of SINV/EEEV into host cells.

As discussed above, there remains a need to better understand the protective immune response against alphaviruses. The objective of this the work described here was to address how human mAbs neutralize and interact with the encephalitic alphaviruses, with primary focus on EEEV. The inventors isolated human mAbs to Eastern equine encephalitis virus (EEEV), Venezuelan equine encephalitis virus (VEEV), and Western equine encephalitis virus (WEEV). The initial focus was on EEEV as the inventors isolated a large panel of human monoclonal antibodies (mAbs) from a naturally infected EEEV survivor. From this panel, they have elucidated the reactivity, breadth, basis of neutralization, and prophylactic and therapeutic capabilities of the human antibody repertoire towards EEEV. In addition, they made progress in the isolation and characterization of human mAbs against EEEV, VEEV, and WEEV with a primary focus on the cross-reactivity and potential cross-neutralization of these mAbs from donors vaccinated with all three viruses (Special Immunizations Program-SIP) or VEEV alone. These mAbs in particular helped in the identification of conserved targets of antibody recognition and neutralization towards the encephalitic alphaviruses.

From the first human EEEV mAb panel, the inventors identified the diversity of human mAb reactivity and breadth to EEEV and other clinically relevant alphaviruses: VEEV, WEEV and CHIKV. The inventors elucidated the basis of neutralization and identified an extremely potent neutralizing human mAb towards BSL-2 SINV/EEEV and BSL-3 EEEV. They found this mAb to exhibit prophylactic and therapeutic activity in a stringent aerosol challenge in vivo small animal model. Through epitope mapping, they determined the diverse epitopes and the distinct neutralizing antigenic determinants recognized by human mAbs on EEEV. Additionally, the inventors have begun to isolate human mAbs against EEEV, VEEV, and WEEV from SIP donors or those vaccinated with VEEV alone. Characterization of these mAbs will aim to determine the cross-reactive and potential cross-neutralization capabilities of human mAbs and identify potential correlates of protection against the encephalitic alphaviruses.

These and other aspects of the disclosure are described in detail below.

I. ALPHAVIRUSES

Alphavirus belongs to group IV of the Baltimore classification of the Togaviridae family of viruses, according to the system of classification based on viral genome composition introduced by David Baltimore in 1971. Alphaviruses, like all other group IV viruses, have a positive sense, single-stranded RNA genome. There are thirty alphaviruses able to infect various vertebrates such as humans, rodents, fish, birds, and larger mammals such as horses as well as invertebrates. Transmission between species and individuals occurs mainly via mosquitoes, making the alphaviruses a member of the collection of arboviruses- or arthropod-borne viruses. Alphavirus particles are enveloped, have a 70 nm diameter, tend to be spherical (although slightly pleomorphic), and have a 40 nm isometric nucleocapsid.

The alphaviruses are small, spherical, enveloped viruses with a genome of a single positive sense strand RNA. The total genome length ranges between 11,000 and 12,000 nucleotides, and has a 5' cap, and 3' poly-A tail. The four non-structural protein genes are encoded in the 5' two-thirds of the genome, while the three structural proteins are translated from a subgenomic mRNA colinear with the 3' one-third of the genome.

There are two open reading frames (ORF's) in the genome, non-structural and structural. The first is non-structural and encodes proteins (nsP1-nsP4) necessary for transcription and replication of viral RNA. The second encodes three structural proteins: the core nucleocapsid protein C, and the envelope proteins P62 and E1 that associate as a heterodimer. The viral membrane-anchored surface glycoproteins are responsible for receptor recognition and entry into target cells through membrane fusion.

The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the centre to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The structure of the Semliki Forest virus revealed a structure that is similar to that of flaviviral glycoprotein E, with three structural domains in the same primary sequence arrangement. The E2 glycoprotein functions to interact with the nucleocapsid through its cytoplasmic domain, while its ectodomain is responsible for binding a cellular receptor. Most alphaviruses lose the peripheral protein E3, but in Semliki viruses it remains associated with the viral surface.

Four nonstructural proteins (nsP1-4) which are produced as a single polyprotein constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved nsP3 creates a ring structure that encircles nsP2. These two proteins have an extensive interface.

Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn affects RNA infectivity altering viral RNA production levels.

The virus has a 60-70 nanometer diameter. It is enveloped, spherical and has a positive-strand RNA genome of ~12 kilobases. The genome encodes two polyproteins. The first polyprotein consists of four non-structural units: in order from the N terminal to the C terminal—nsP1, nsP2, nsP3, and nsP4. The second is a structural polyprotein composed of five expression units: from the N terminal to the C terminal—Capsid, E3, E2, 6K and E1. A sub genomic positive strand RNA—the 26S RNA—is replicated from a negative-stranded RNA intermediate. This serves as template for the synthesis of viral structural proteins. Most alphaviruses have conserved domains involved in regulation of viral RNA synthesis.

The nucleocapsid, 40 nanometers in diameter, contains 240 copies of the capsid protein and has a T=4 icosahedral symmetry. The E1 and E2 viral glycoproteins are embedded in the lipid bilayer. Single E1 and E2 molecules associate to form heterodimers. The E1-E2 heterodimers form one-toone contacts between the E2 protein and the nucleocapsid monomers. The E1 and E2 proteins mediate contact between the virus and the host cell.

Several receptors have been identified. These include prohibitin, phosphatidylserine, glycosaminoglycans and ATP synthase β subunit.

Replication occurs within the cytoplasm and virions mature by budding through the plasma membrane, where virus-encoded surface glycoproteins E2 and E1 are assimilated.

These two glycoproteins are the targets of numerous serologic reactions and tests including neutralization and hemagglutination inhibition. The alphaviruses show various degrees of antigenic cross-reactivity in these reactions and this forms the basis for the seven antigenic complexes, 30 species and many subtypes and varieties. The E2 protein is the site of most neutralizing epitopes, while the E1 protein contains more conserved, cross-reactive epitopes.

There are many alphaviruses distributed around the world with the ability to cause human disease. Infectious arthritis, encephalitis, rashes and fever are the most commonly observed symptoms. Larger mammals such as humans and horses are usually dead-end hosts or play a minor role in viral transmission; however, in the case of Venezuelan equine encephalitis the virus is mainly amplified in horses. In most other cases the virus is maintained in nature in mosquitoes, rodents and birds.

Alphavirus infections are spread by insect vectors such as mosquitoes. Once a human is bitten by the infected mosquito, the virus can gain entry into the bloodstream, causing viremia. The alphavirus can also get into the CNS where it is able to grow and multiply within the neurones. This can lead to encephalitis, which can be fatal.

When an individual is infected with this particular virus, its immune system can play a role in clearing away the virus particles. Alphaviruses are able to cause the production of interferons. Antibodies and T cells are also involved. The neutralizing antibodies also play an important role to prevent further infection and spread.

Diagnoses is based on clinical samples from which the virus can be easily isolated and identified. There are no alphavirus vaccines currently available. Vector control with repellents, protective clothing, breeding site destruction, and spraying are the preventive measures of choice.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}$H when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to alpahvirus will have several applications. These include the production of diagnostic kits for use in detecting and diagnosing alphavirus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce alphavirus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke, *Methods Mol. Biol.* 248:443-63, 2004), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer, *Prot. Sci.* 9:487-496, 2000). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267:252-259; Engen and Smith (2001) Anal. Chem. 73: 256A-265A. When the antibody neutralizes alphavirus, antibody escape mutant variant organisms can be isolated by propagating alphavirus in vitro or in animal models in the presence of high concentrations of the antibody. Sequence analysis of the alphavirus gene encoding the antigen targeted by the antibody, such as glycoprotein E1 or E2, reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-alphavirus antibody, the above-described binding methodology is performed in two orientations: In a first orientation, the reference antibody is allowed to bind to the alphavirus antigen under saturating conditions followed by assessment of binding of the test antibody to the alphavirus antigen. In a second orientation, the test antibody is allowed to bind to the alphavirus antigen under saturating conditions followed by assessment of binding of the reference antibody to the alphavirus antigen. If, in both orientations, only the first (saturating) antibody is capable of binding to the alphavirus, then it is concluded that the test antibody and the reference antibody compete for binding to the alphavirus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res, 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen, but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4):288-294). Methods of altering carbohydrate contents are known to those skilled in the art, see, e.g., Wallick, S. C. et al. (1988) "*Glycosylation Of A VH Residue Of A Monoclonal Antibody Against Alpha (1-6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the mAbs, or single-chain immunoglobulins producible, for example, via recombinant means. F(ab') antibody derivatives are monovalent, while $F(ab')_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG1 can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with GO, GIF, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.,* 22 (10), 1302-1306, 2004; Chennamsetty et al., *PNAS,* 106 (29), 11937-11942, 2009; Voynov et al., *Biocon. Chem.,* 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, Cp, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, CH2, and CH3 domains). Typically unfolding of the Fab domain produces the strongest peak. The DSC profiles and relative stability of the Fc portion show characteristic differences for the human IgG1, IgG2, IgG3, and IgG4 subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366:449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

Blood brain barrier. The blood brain barrier regulates the traverse of blood-circulating substances into the brain with selectivity. This barrier may reduce the entry of antibodies into the central nervous system necessary for diagnosis or therapy of central nervous system infection with alphaviruses. It may be possible to exploit the naturally occurring cellular trafficking systems and the receptor-mediated transfer machinery to move antibodies across the blood brain barrier safely to tissue site where the antibodies will be most effective. There have been a large number of studies of molecules that mediate active transport into the brain, including at least 20 receptors, including transferrin receptor, heparin-binding EGF, scavenger receptors AI, BI, EGF receptor, tumor necrosis factor, insulin and insulin-like growth factor receptors, apolipoprotein E receptor 2, leptin receptor, melanotransferrin receptor, or LDL receptors (Preston et al., *Adv. Pharmacol.* 71:147-163, 2014). Here, the inventors propose to use one or more of these active transport systems to deliver an alphavirus inhibiting antibody by making a chimeric or bispecific molecule that targets a transporting receptor and possesses a separate domain that targets an alphavirus protein.

pIgR. Encephalitic alphaviruses may enter the brain through the olfactory bulb, which is exposed in the nasal passages. The efficacy of antibody prevention or treatment for encephalitic alphaviruses may be enhanced by delivering a high concentration of the antibody to the nasal passage, especially around the area of the olfactory bulb. Serum immunoglobulins that circulate after parenteral administration may have limited access to the nasal passages because of the inefficiency of passive transudation across this mucosal barrier. Dimerized IgA and IgM can react with the polymeric immunoglobulin receptor (pIgR) produced by respiratory tract epithelial cells. Under normal conditions, the pIgR acts as a transport receptor for IgA and becomes part of the secreted IgA molecule. It renders the IgA molecule less susceptible to proteolytic digestion and more mucophilic, and it the ability of the IgA molecule to interact with potential pathogens and to prevent their attachment to cell surfaces. Here, the inventor proposes to use the pIgR active transport system to deliver an alphavirus inhibiting antibody by making a chimeric or bispecific molecule that targets a transporting receptor and possesses a separate domain that targets an alphavirus protein.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., $F(ab')_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175:217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579:3264; Wong and Scott, *Nat. Rev. Mol. Cell Biol.* 2004; 5:959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147:60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ζ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell-such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF ALPHAVIRUS INFECTION

A. Formulation and Administration

The present disclosure provides pharmaceutical compositions comprising anti-alphavirus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of alphavirus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine $^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99}$m and/or yttrium$^{90}$. 1$^{25}$I is often being preferred for use in certain embodiments, and technicium$^{99}$m and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99}$m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl) propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting alphavirus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of alphavirus in a subject. A wide variety of assay formats are contemplated, but specifically those that would be used to detect alphavirus in a fluid obtained from a subject, such as saliva, blood, plasma, sputum, semen or urine. In particular, semen has been demonstrated as a viable sample for detecting alphavirus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of alphavirus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing alphavirus and contacting the sample with a first antibody in accordance with the present disclosure, as the case may be, under conditions effective to allow the formation of immunocomplexes.

These methods include methods for purifying alphavirus or related antigens from a sample. The antibody will preferably be linked to a solid support, such as in the form of a column matrix, and the sample suspected of containing the alphavirus or antigenic component will be applied to the immobilized antibody. The unwanted components will be washed from the column, leaving the alphavirus antigen immunocomplexed to the immobilized antibody, which is then collected by removing the organism or antigen from the column.

The immunobinding methods also include methods for detecting and quantifying the amount of alphavirus or related components in a sample and the detection and quantification of any immune complexes formed during the binding process. Here, one would obtain a sample suspected of containing alphavirus or its antigens and contact the sample with an antibody that binds alphavirus or components thereof, followed by detecting and quantifying the amount of immune complexes formed under the specific conditions. In terms of antigen detection, the biological sample analyzed may be any sample that is suspected of containing alphavirus or alphavirus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to alphavirus or alphavirus antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histo-enzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the alphavirus or alphavirus antigen is added to the wells. After binding and washing to remove non-specifically bound immune complexes, the bound antigen may be detected. Detection may be achieved by the addition of another anti-alphavirus antibody that is linked to a detectable label. This type of ELISA is a simple "sandwich ELISA." Detection may also be achieved by the addition of a second anti-alphavirus antibody, followed by the addition of a third antibody that has binding affinity for the second antibody, with the third antibody being linked to a detectable label.

In another exemplary ELISA, the samples suspected of containing the alphavirus or alphavirus antigen are immobilized onto the well surface and then contacted with the anti-alphavirus antibodies of the disclosure. After binding and washing to remove non-specifically bound immune complexes, the bound anti-alphavirus antibodies are detected. Where the initial anti-alphavirus antibodies are linked to a detectable label, the immune complexes may be detected directly. Again, the immune complexes may be detected using a second antibody that has binding affinity for the first anti-alphavirus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of alphavirus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled alphavirus monoclonal antibodies to determine the amount of alphavirus antibodies in a sample. The basic format would include contacting a known amount of alphavirus monoclonal antibody (linked to a detectable label) with alphavirus antigen or particle. The alphavirus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect alphavirus or alphavirus antigens, the antibodies may be included in the kit. The immunodetection kits will thus comprise, in suitable container means, a first antibody that binds to alphavirus or alphavirus antigen, and optionally an immunodetection reagent.

In certain embodiments, the alphavirus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the alphavirus or alphavirus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones-malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective alphavirus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Results

Analysis of donor serum reactivity and neutralization activity to EEEV. To select donors for isolation of human mAbs, the inventors tested 13 donors for serum reactivity and neutralization activity to SINV/EEEV and recombinant EEEV structural proteins. From binding and neutralization assays, they observed interesting trends in response that were dependent on previous donor history. Donors with the greatest serum reactivity and neutralization activity to EEEV were those that survived natural infection and had endpoint titers of at least >1:4,096 (FIGS. 1A-B). In one case, however, the donor does not appear to seroconvert (endpoint titer <1:64). For donors vaccinated either against all three encephalitic viruses (EEEV, VEEV, and WEEV; SIP) to those only vaccinated against VEEV (FIGS. 1A-B), had a corresponding decrease in serum reactivity and neutralization activity to EEEV, with endpoint titers ranging from 1:4,096 to <1:64. Additionally, the inventors showed that donor serum reactivity differs in response to recombinant EEEV structural proteins. A similar trend was observed for serum reactivity to EEEV E2 glycoprotein as was observed to SINV/EEEV, with endpoint titers ranging from 1:4,096 to <1:64 (FIG. 1C). However, there was an increase in serum cross-reactivity (endpoint titer <1:256) from donors vaccinated with VEEV alone to the more conserved and less surface exposed EEEV E1 glycoprotein (FIG. 1D).

Analysis of donor serum reactivity to recombinant EEEV, VEEV, and WEEV virus-like particles (VLPs). To further characterize donor serum, the inventors determined donor serum reactivity to recombinant EEEV, VEEV, and WEEV VLPs. A similar trend based off of previous donor infection or vaccination history was observed for serum reactivity to the VLPs as was observed to SINV/EEEV and recombinant EEEV structural proteins. As expected, serum from donors that survived natural infection reacted primarily with EEEV VLPs (FIG. 2A). Additionally, donors vaccinated against all three encephalitic viruses (EEEV, VEEV, and WEEV; SIP) had greater serum cross-reactivity as determined by endpoint titer against EEEV, VEEV, and WEEV VLPs compared to those vaccinated with VEEV alone (FIGS. 2A-B).

Identification of human B-cell responses to the encephalitic alphaviruses. To generate human mAbs, the inventors used an established human hybridoma technique developed in the lab (Smith and Crowe, 2015; Yu et al., 2008). Briefly, from blood samples provided by donors, peripheral blood mononuclear cells (PBMCs) are isolated and transformed with Epstein-Barr virus (EBV). This generates lymphoblastoid cell lines (LCLs), in which antibody is produced. Through screening of the supernatant taken from these LCLs via binding assays, such as ELISA or cell surface display, provides an indication of whether there is antibody reactive to the antigen of interest present. The frequency of memory B cell population within PBMCs is approximately 0.1-1%. By taking into account the number of PBMCs, average number of LCLs, and reactivity of the LCLs, a relative B-cell frequency can be calculated. From EBV-transformation of several donors either naturally infected with EEEV or vaccinated against all three of the encephalitic alphaviruses (SIP), the inventors can compare the relative B-cell frequencies, for each donor. In the case of the naturally infected EEEV survivor (Donor 1069), all three EBV transformations from the same donor were relatively consistent and a high relative B-cell frequency (average 0.94%) to SINV/EEEV and recombinant EEEV structural proteins was observed (FIG. 3A). Additional EBV transformation of another naturally infected EEEV survivor (Donor 982), also had a high relative B-cell frequency (1.19%) to SINV/EEEV and recombinant EEEV structural proteins (FIG. 3A). In comparison of the relative B-cell frequencies between donors, the inventors showed that there is a decrease in the relative B-cell frequency (average 0.21%) of those vaccinated against EEEV (FIG. 3A). This may indicate the low immunogenicity of the formalin-inactivated EEEV vaccine. Additionally, from EBV transformation of SIP donors, the inventors show the relative B-cell frequency to other encephalitic alphaviruses, such as VEEV and WEEV (FIGS. 3B-C). Again, they observe low relative B-cell frequency from donors vaccinated against VEEV (average 0.26%) or WEEV (average 0.01%).

Current human hybridoma status of three EBV-transformed donors. To date, the inventors have EBV-transformed three donors for generation of human mAbs. Two of these donors were naturally infected with EEEV (Donors 982 and 1069) whereas one donor was vaccinated against all three encephalitic viruses as part of the SIP (Donor 1047). From Donor 1069, the inventors isolated 64 human mAbs. Of this panel, a majority of the human mAbs are reactive to recombinant EEEV E2 glycoprotein (×49), several are reactive to recombinant EEEV E1 glycoprotein (×10), and one is specific for a virus-dependent epitope (×1) (FIG. 4A and FIGS. 5A-C). The reactivity of four human mAbs have yet to be characterized. Three human mAbs are cross-reactive with the E2 or E1 glycoprotein of other encephalitic alphaviruses, VEEV and WEEV, and the arthritogenic alphavirus, CHIKV (FIG. 4A and FIGS. 6A-D). A majority of the human mAb panel are IgG (×49), several are IgA (×4), and one IgM (×1) (FIG. 4B). Fifteen out of the 64 human mAbs isolated from Donor 1069 exhibit neutralization activity towards SINV/EEEV with <2 μg/mL $IC_{50}$ values (FIG. 4A and FIG. 7A). To generate human mAbs against EEEV, the inventors EBV-transformed another donor naturally infected with EEEV (Donor 982). The primary reason for this is to look for possible convergence of the human antibody repertoire against EEEV. To date, they are in the human hybridoma process for the isolation of 40 human mAbs. Based off of reactivity of hybridoma supernatants, there is a diverse reactivity to SINV/EEEV (×11), recombinant EEEV structural proteins (×21), and EEEV, VEEV, and WEEV VLPs or structural proteins (×8) (FIG. 4C). Of these, 10 exhibit neutralization activity (>70% reduction) against SINV/EEEV and are reactive to either virus-specific epitopes or recombinant EEEV E2 glycoprotein (FIG. 4C). To identify potential cross-reactive and cross-neutralizing human mAbs against the encephalitic alphaviruses, the inventors EBV-transformed a SIP donor (Donor 1047). Several human mAbs were isolated and found to be specific for EEEV (×5) or VEEV (×1) (FIG. 4D and FIGS. 12A-C). None of the mAbs exhibited neutralization activity against SINV/EEEV (>5 μg/mL $IC_{50}$ value). The decrease in number of isolated human mAbs reflects the lower relative B-cell frequency of SIP donors compared to naturally infected EEEV survivors.

Characterization of human EEEV-reactive mAbs isolated from a naturally infected EEEV survivor to SINV/EEEV and recombinant EEEV structural proteins. From a donor naturally infected with EEEV (Donor 1069), the inventors isolated the first human EEEV mAb panel. The 64 mAbs isolated were selected for based off of reactivity to SINV/EEEV and recombinant EEEV structural proteins (E2 and E1 glycoproteins) via ELISA. Further characterization of the human EEEV mAb panel, revealed that most of the human mAbs (×49) are reactive to the EEEV E2 glycoprotein (FIG. 5A). As the less surface exposed structural protein, the E1 glycoprotein, it is less expected to identify mAbs that recognize this antigen. However, the inventors identified 10 human EEEV mAbs that recognize the EEEV E1 glycoprotein (FIG. 5B). In addition, 1 human EEEV mAb displayed recognition of a virus-specific epitope, in which this mAb may depend on a quaternary epitope (FIG. 5C).

Specific reactivity of four mAbs is yet to be determined. There is diverse binding affinity of human EEEV mAbs to SINV/EEEV and recombinant EEEV E2 and E1 glycoproteins with tight binders (<10 ng/ml half-maximal effective concentration ($EC_{50}$) values) to weaker binders (<2 μg/mL $EC_{50}$ values) as determined by ELISA (FIGS. 5A-C). There are also differences in binding affinities to SINV/EEEV versus recombinant EEEV structural proteins, in which some mAbs bind well to both protein and virus, some better to virus than protein, vice versa, and some that bind weakly to both. The ratio of protein/virus $EC_{50}$ values is indicated (FIGS. 5A-C) to display the difference in reactivity towards dependence on virus-specific epitopes compared to recombinant monomeric protein.

Characterization of cross-reactive human EEEV mAbs. For isolation of the first human EEEV mAb panel, initial screening was based off of reactivity to SINV/EEEV and recombinant EEEV structural proteins. However, by further characterization, the inventors identified several human EEEV mAbs that cross-react with the other encephalitic alphaviruses, VEEV and WEEV, and the arthritogenic alphavirus, CHIKV (FIG. 6A). The inventors confirmed a pan-alphavirus mAb, in which EEEV-138 binds EEEV, VEEV, and WEEV VLPs and CHIKV (FIG. 6B). Another human mAb, EEEV-179, cross-reacts with EEEV, VEEV, and WEEV VLPs (FIG. 6B). EEEV-107 is a cross-reactive human EEEV and VEEV mAb as it binds to EEEV and VEEV VLPs and recombinant EEEV and VEEV E2 glycoprotein (FIG. 6C). Two additional human EEEV and VEEV mAbs, EEEV-21 and EEEV-81, are also cross-reactive. However, these two human mAbs do not bind to VEEV VLP (FIG. 6C). It is interesting that some cross-reactive mAbs recognize the E2 glycoprotein as it is expected that the more conserved E1 glycoprotein would be the target for cross-reactive mAbs. EEEV-157 is a cross-reactive human EEEV and VEEV mAb as it binds to EEEV and VEEV VLPs and recombinant EEEV E1 glycoprotein (FIG. 6D). Cross-neutralization will soon be tested through focus reduction neutralization test (FRNT) as the inventors just received the chimeric alphaviruses (SINV/SA-EEEV, SINV/VEEV, SINV/WEEV, SINV/CHIKV, and SINV/MAYV) from collaborator (Dr. William Klimstra; Univ. of Pittsburgh). Additionally, they acquired multiple alphavirus full-length structural polyproteins (i.e., NA-EEEV, MADV, VEEV subtypes, WEEV, and CHIKV) to detect binding reactivity of human mAbs through cell surface display.

Determination of neutralization activity of human EEEV-reactive mAbs to SINV/EEEV and EEEV. To determine the neutralization activity of human EEEV mAbs, the inventors performed FRNTs against SINV/EEEV. They found 15 human EEEV mAbs with neutralization activity against SINV/EEEV (FIG. 7A). Of these mAbs, 6 human EEEV mAbs exhibited potent neutralization activity, with <10 ng/mL and <100 ng/mL half-maximal inhibitory concentration ($IC_{50}$) and $IC_{99}$ values, respectively. Additionally, 9 human EEEV mAbs exhibited moderate neutralizing antibody, with <2 μg/mL $IC_{50}$ values. By further characterization, 7 human EEEV mAbs the inventors found to exhibit neutralizing activity against BSL-3 EEEV as determined through a cytopathic effect (CPE) assay (FIG. 7B). The respective sensitivities of FRNT and CPE assays could account for differences in neutralization activity of human EEEV mAbs. The inventors identified an extremely potent human EEEV mAb, EEEV-33, with <10 ng/mL $IC_{50}$ value against BSL-3 EEEV. Another potent human EEEV mAb, EEEV-147, they found to neutralize BSL-3 EEEV with <1 g/mL $IC_{50}$ value. Additionally, five other human EEEV mAbs they found to moderately neutralize BSL-3 EEEV with <6 μg/mL $IC_{50}$ values.

Small animal model studies to determine the prophylactic or therapeutic efficacy of EEEV-33 in vivo. The inventors initiated small animal model studies in collaboration with Dr. William Klimstra to assess the potential prophylactic and therapeutic activity for EEEV-33 in vivo. They found EEEV-33 to exhibit prophylactic (83%) and therapeutic (33%) activity in vivo when mice were given 100 μg of EEEV-33 i.p. 24 hours prior or after, respectively, in a stringent aerosol challenge model (FIGS. 8A-E).

Small animal model studies to determine the prophylactic or therapeutic efficacy of EEEV-30 in vivo. As a non-neutralizing control human mAb for small animal model studies, EEEV-30 was found to possess prophylactic activity (50%) in an in vivo aerosol BSL-3 EEEV challenge model (FIGS. 9A-D). This indicates potential Fc-mediated effector functions may play a role in conferring protection and treatment against EEEV infection. Future directions involve the down selection of non-neutralizing human mAbs with potential Fc-mediated effector functions and assessment of Fc variants, such as LALA and NA, in vivo. Synergistic effects of non-neutralizing and neutralizing human mAbs may also be addressed to increase the efficacy of prophylaxis and treatment options against EEEV infection in vivo.

Characterization of the neutralization mechanism(s) of human neutralizing EEEV mAbs. Antibodies are able to neutralize viruses at multiple stages in the viral replication cycle from prevention of receptor attachment to viral egress (Klasse, 2014; Burton et al., 2002). Previous studies regarding the mechanism of neutralization for alphavirus antibodies suggest that through binding to the E2 glycoprotein inhibition of viral entry, fusion, or viral egress occurs (Sun et al., 2013; Porta et al., 2014; Fox et al., 2015; Long et al., 2015; Jin et al., 2015). To identify step(s) in the replication cycle in which human mAbs neutralize SINV/EEEV, the inventors sought to test different neutralization mechanistic assays. To assess inhibition of virus attachment and/or entry, they compared differences in neutralization activity of several human EEEV mAbs through pre- and post-attachment entry inhibition assays. In the pre-attachment entry inhibition assay, mAb and virus are mixed together and added to cells at 4° C. to allow for virus attachment but not entry. In the post-attachment entry inhibition assay, virus is added to cells at 4° C. followed by addition of the mAb. A shift to 37° C. for 15 minutes allows for the virus to enter the cell. Foci are stained to detect the presence of virus. Comparison between these two assays helps provide insight into whether the mAb is able to neutralize through prevention of receptor attachment and/or entry or whether the mAb neutralizes at a post-attachment step in the replication cycle. From initial characterization of several human neutralizing mAbs through these assays, it appears that most mAbs neutralize at a step post-attachment in the replication cycle (FIG. 10A). However, mAbs such as EEEV-7 appear to neutralize through prevention of receptor attachment and/or entry due to the decrease in neutralization activity of the mAb when virus is already attached to the cell. This suggests that multiple mechanisms of neutralization are utilized by human EEEV mAbs against SINV/EEEV. To determine inhibition of viral egress, cells are incubated with virus for 2 hours at 37° C. Following extensive washing, different concentrations of a human EEEV mAb are incubated with the cells in the presence of ammonium chloride to prevent de novo infection. The cells are incubated at 37° C. for 6 hours. Supernatant is then collected, used in a plaque assay, or viral RNA extracted. Through a plaque assay or qRT-PCR, a reduction in virus titer will be observed to determine the effect of mAb on viral egress. From this assay, 3 neutralizing mAbs were tested, EEEV-7, EEEV-27, and EEEV-33. From initial results, EEEV-27 does not reduce the presence of infectious virus, indicating that EEEV-27 does not neutralize the virus through inhibition of viral egress. EEEV-7 and EEEV-33, however, reduce the presence of infectious virus as determined through plaque assay (FIG. 10B). The limitation in measuring infectious virus through plaque assay is that mAb is present in the supernatant. Through qRT-PCR, there was viral RNA present suggesting that EEEV-33 does not inhibit viral egress (FIG. 10C). However, one difficulty through this method is that any RNA released from cells during the assay can interfere with the results. In order to approach these difficulties, the inventors plan on removing unencapsulated viral RNA through RNase A treatment of the supernatant. Another option is to remove the mAb through immunoprecipitation and collect the resulting supernatant.

Identification of human antigenic determinants on EEEV. The E2 glycoprotein consists of three domains: domain B at the apical surface, followed by domain A, which contains the putative receptor-binding site, and domain C that lies proximal to the viral membrane (Griffin, 2013; Voss et al., 2010). There are also three domains of the E1 glycoprotein: domain II at the apical end contains the fusion loop, followed by domain I, and domain III that lies proximal to the membrane-spanning region (Griffin, 2013; Voss et al., 2010). To epitopes recognized by human EEEV mAbs, the inventors performed competition-binding studies via biolayer interferometry. Binding of human EEEV mAbs in competition with murine EEEV mAbs with known epitopes provides an indication of which epitopes are recognized. For the human EEEV mAbs that recognize recombinant EEEV E2 glycoprotein, they observed several competition-binding groups (FIG. 11A). This suggests that there are multiple antigenic determinants on the EEEV E2 glycoprotein. In particular, of the neutralizing mAbs, there are at least 3 competition groups, or neutralizing antigenic determinants, present on the EEEV E2 glycoprotein (FIG. 11B). There is partial overlap for some of these groups indicating close proximity of the epitopes to each other. A majority of neutralizing human EEEV mAbs compete with murine EEEV mAbs that recognize residues 180-181 on the E2 glycoprotein, corresponding to domain B. This suggests that this neutralizing antigenic determinant is immunodominant.

To further determine the epitopes recognized by human EEEV mAbs, the inventors performed hydrogen-deuterium exchange mass spectrometry (HDX-MS). Through HDX-MS, differences in Fab bound versus unbound E2 glycoprotein can identify the residues in which the Fab binds. They determined that Fab7 binds to 242-257 and 271-281 residues on the E2 glycoprotein, which corresponds to domain B (FIG. 11C). There is also destabilization of domain C of the E2 glycoprotein, suggesting that Fab7 may cause a conformational change upon binding to the E2 glycoprotein. They also determined that Fab12 and Fab16 bind to 130-144 and 175-188 residues of the E2 glycoprotein, which corresponds to domain A (FIG. 11C). Through competition-binding analysis, the inventors show that EEEV-7 does not compete with EEEV-12 and EEEV-16, which do compete. This provides internal controls and confirms both the competition binding and the HDX-MS results.

Structural studies of human EEEV mAbs in complex with SINV/EEEV and recombinant EEEV structural proteins. To determine the structural basis of neutralization by human EEEV mAbs, the inventors initiated structural studies through X-ray crystallography and electron microscopy (EM). Optimization of crystallization conditions for X-ray crystallography of E2-E1 heterodimer in complex with Fab molecules is ongoing. They initiated EM studies with Dr. Melanie Ohi for structural analyses of SINV/EEEV in complex with Fab molecules.

Isolation of human mAbs from SIP donors. To identify human mAbs that target conserved regions amongst the encephalitic alphaviruses, the inventors began isolation of human mAbs from donors immunized against EEEV, VEEV, and WEEV as part of the Special Immunizations Program (SIP). The primary focus of this work is on the cross-reactivity and potential cross-neutralization of these mAb for the identification of conserved targets of antibody recognition and neutralization towards the encephalitic alphaviruses. However, isolation of mAbs to date from a SIP donor (Donor 1047) were characterized as either EEEV (×5) or VEEV-specific (×1) (FIGS. 12A-C). The decrease in number of isolated human mAbs reflects the lower relative B-cell frequency of SIP donors compared to naturally infected EEEV survivors. This is further reflected by the decrease in binding affinity (higher $EC_{50}$ values; 16.8-3,972 ng/mL) in comparison to mAbs isolated from a naturally infected EEEV survivor (0.1-2,299 ng/mL; FIGS. 5A-C). Further analysis of potential human mAbs isolated from SIP donors is needed and will be performed to identify VEEV-specific and potential cross-reactive/neutralizing human mAbs against the encephalitic alphaviruses.

Summary The studies conducted over the past year address many questions in the field relating to the human antibody repertoire against the encephalitic alphaviruses, with primary focus on Eastern equine encephalitis virus (EEEV). The inventors isolated and characterized the first human EEEV mAb panel to elucidate the diverse reactivity and breadth of the human antibody repertoire to SINV/EEEV and recombinant EEEV structural proteins. They identified several antigenic determinants on the EEEV E2 glycoprotein and revealed neutralizing antigenic sites. They characterized several potently neutralizing, protective, and therapeutic human EEEV mAbs to BSL-2 SINV/EEEV and BSL-3 EEEV that will aid in the revelation of the molecular and structural basis of neutralization against EEEV. These studies reveal the first human pan-alphavirus mAbs that can aid in the identification of conserved targets of antibody recognition and neutralization towards the encephalitic alphaviruses for potential diagnostic, vaccine, and therapeutic development.

Example 2—Discussion

The inventors identified three donors with natural EEEV infection, two of which were seropositive to the chimeric virus Sindbis/Eastern equine encephalitis virus (SINV/EEEV) as determined through serum reactivity and neutralization. They identified 10 donors with vaccination against the encephalitic alphaviruses-EEEV, VEEV and/or WEEV from the Special Immunizations Program (SIP; ×6) or VEEV vaccinated donors (×4). They determined that there is variation in donor reactivity to SINV/EEEV depending on prior vaccination history and found that those vaccinated against all three encephalitic alphaviruses have a corresponding increase in serum reactivity and neutralization activity to SINV/EEEV compared to those vaccinated against VEEV alone.

The inventors also showed that donor serum reactivity varied also in response to recombinant EEEV proteins. Donors naturally infected or vaccinated against EEEV reacted with varying degrees to the more surface exposed structural protein, the E2 glycoprotein. There was an increase in serum cross-reactivity from donors vaccinated with VEEV alone to the more conserved and less exposed structural protein, the E1 glycoprotein. Further, it was demonstrated that donor serum reactivity varies in response to virus-like particles (VLPs) for EEEV, VEEV, and WEEV. Again, the reactivity of serum corresponds with prior infection or vaccination history. Naturally infected EEEV survivors were primarily reactive to EEEV VLPs. Higher serum endpoint titers were observed for SIP donors vaccinated with EEEV, VEEV, and WEEV compared to VEEV vaccinees alone.

To further test donor serum reactivity and human mAb characterization, the inventors acquired multiple additional chimeric alphaviruses including SINV/MADV (formally SA-EEEV), SINV/VEEV, SINV/WEEV, SINV/CHIKV, and SINV/MAYV. They found the average relative B-cell frequency to be 1.0% for EEEV from two EBV-transformed naturally infected EEEV survivors. The inventors showed there is lower average relative B-cell frequencies to EEEV (0.21%), VEEV (0.26%), and WEEV (0.01%) from EBV-transformed SIP donors. Comparison between the average relative B-cell frequencies to EEEV may indicate low immunogenicity of the formalin-inactivated EEEV vaccine.

Using their established human hybridoma technology, the inventors isolated 64 human monoclonal antibodies (mAbs) from a naturally infected EEEV survivor (Donor 1069). The human mAbs were screened and selected for reactivity to recombinant EEEV structural proteins (E2 and E1 glycoproteins) and SINV/EEEV. Through characterization of this first human mAb panel to EEEV, they found that most of the human mAbs react to the EEEV E2 glycoprotein (×49). In addition, they showed that some human mAbs are reactive to the EEEV E1 glycoprotein (×10) and one is dependent on a virus-specific epitope (×1). Specific reactivity of four mAbs is yet to be determined. They also showed that there is diversity in reactivity to specified antigen from <10 ng/ml to <2 μg/mL half-maximal effective concentration ($EC_{50}$) values.

The inventors identified several human mAbs from the panel that are cross-reactive (×6) with other encephalitic (VEEV and/or WEEV) and arthritogenic alphaviruses (CHIKV). They acquired multiple alphavirus full-length structural polyproteins (i.e., NA-EEEV, MADV, VEEV subtypes, WEEV, and CHIKV) to detect binding reactivity of human mAbs through cell surface display. Through focus reduction neutralization tests (FRNTs), the inventors found 6 human mAbs with potent neutralization activity (<10 ng/mL half-maximal inhibitory concentration ($IC_{50}$) values) and 9 human mAbs with moderate neutralization activity (<2 μg/mL $IC_{50}$ values) against SINV/EEEV. By further characterization, they identified one extremely potent neutralizing mAb, EEEV-33, with <10 ng/mL $IC_{50}$ value against BSL-3 EEEV as determined through a CPE assay. Additionally, they identified one potent neutralizing mAb, EEEV-147, and 5 moderate neutralizing mAbs with <1 μg/mL and <6 μg/mL $IC_{50}$ values against BSL-33 EEEV, respectively. The inventors found EEEV-33 to exhibit prophylactic (83%) and therapeutic (33%) activity in an in vivo aerosol BSL-3 EEEV challenge model, while they found a non-neutralizing human mAbs, EEEV-30, to possess prophylactic activity (50%) in an in vivo aerosol BSL-3 EEEV challenge model.

To identify steps in the replication cycle in which human mAbs neutralize SINV/EEEV, the inventors sought to test different neutralization mechanistic assays. As this is still in progress, it is not entirely clear the precise mechanism(s) of neutralization. However, it appears that most neutralizing human mAbs inhibit SINV/EEEV at a step post-attachment in the replication cycle. Some mAbs were found to show differences in pre-versus post-attachment entry neutralization assays, indicating the contribution of neutralization by these mAbs at attachment and/or entry steps in the replication cycle. This suggests that multiple mechanisms of neutralization are involved against SINV/EEEV in this diverse human mAb panel.

The inventors identified distinct antigenic determinants through competition-binding analysis and hydrogen-deuterium exchange mass spectrometry (HDX-MS). They found diverse epitopes recognized by the panel of human EEEV mAbs present on recombinant EEEV E2 glycoprotein. This further suggests the diversity in recognition of human mAbs to EEEV. Of the neutralizing mAbs, at least 3 neutralizing antigenic determinants were exposed. They showed that one main neutralizing antigenic site corresponds to domain B at the tip of the EEEV E2 glycoprotein, whereas the other minor neutralizing antigenic sites correspond to domain A of the EEEV E2 glycoprotein.

The inventors identified 40 additional human clonal hybridomas reactive to SINV/EEEV, recombinant EEEV structural proteins, and VLPs from an additional naturally infected EEEV survivor (Donor 982). These mAbs will soon be isolated for complete characterization. From initial characterization of hybridoma supernatants, there appears to be diverse reactivity to SINV/EEEV (×11), recombinant EEEV structural proteins (×21), and EEEV, VEEV, and WEEV VLPs or structural proteins (×8). Of these hybridomas, 10 exhibit neutralization activity (>70% reduction) against SINV/EEEV.

Six additional human mAbs were identified that are EEEV-specific (×5), or VEEV-specific (×1) from SIP donor (Donor 1047). These mAbs do not exhibit neutralization activity against SINV/EEEV (>5 μg/mL $IC_{50}$ value). The VEEV-specific mAb will soon be characterized for neutralization activity against SINV/VEEV. The decrease in number of isolated human mAbs reflects the lower relative B-cell frequency of SIP donors compared to naturally infected EEEV survivors. Future isolation of human mAbs from SIP donors will be performed to identify VEEV-specific and potential cross-reactive/neutralizing human mAbs against the encephalitic alphaviruses.

Example 3—Results

Through the use of an established human hybridoma technique (described above), a large panel of human mAbs from a naturally-infected survivor of EEEV were isolated based on binding to a chimeric Sindbis virus expressing the EEEV surface proteins (SINV/EEEV). Specific binding and neutralization potency against SINV/EEEV were determined for the panel of human anti-EEEV mAbs. Of the panel of 57 human anti-EEEV mAbs isolated, 47 mAbs recognize the E2 glycoprotein. These mAbs recognize diverse epitopes on the E2 glycoprotein surface and display differences in affinity for virus-specific epitopes. From this panel, 12 exhibited neutralizing activity, 7 of which have very potent $IC_{50}$ values (under 10 ng/ml) for neutralization and recognize at least three neutralizing antigenic determinants on the EEEV E2 glycoprotein. The neutralizing mAbs utilize multiple molecular mechanisms of virus inhibition; however, most of the mAbs appear to inhibit virus entry into host cells. An extremely potent neutralizing mAb (EEEV-33) exhibited prophylactic and therapeutic activity against lethal aerosol challenge in mice with WT EEEV. Through comprehensive characterization of 57 human anti-EEEV mAbs, several potent neutralizing mAbs were identified. These mAbs appear to inhibit virus entry and recognize several neutralizing antigenic determinants on the EEEV E2 glycoprotein to do so. The understanding of how these mAbs neutralize and interact with EEEV will help to facilitate the design of efficient therapeutics and vaccines against this clinically relevant alphavirus. The supporting data are shown in FIGS. 13A-17B.

Example 4—Materials and Methods

SINV/EEEV production. BHK-21 cells were plated the day before using $3\times10^7$ cells per T-225 $cm^2$ flask (Corning). The following day, cells were inoculated with SINV/EEEV at a MOI of 0.2 in DMEM/2% FBS. After incubation at 37° C. in 5% $CO_2$ for 48 hours, SINV/EEEV was harvested by clarification of infected BHK-21 cell supernatants through a 0.2-μm pore size filter (Nalgene). Virus then was used fresh or stored at −80° C. until use. For cryo-EM studies, BHK-21 cells were inoculated with SINV/EEEV at a MOI of 5 in DMEM/2% FBS. After incubation at 37° C. in 5% $CO_2$ for 16 hours, SINV/EEEV was harvested by centrifugation at 2,000×g at 4° C. for 10 minutes. Virus supernatant was precipitated in 14% (w/v) PEG 6000 (Sigma-Aldrich) and 4.6% (w/v) NaCl (Corning) overnight at 4° C., followed by centrifugation at 2,500×g at 4° C. for 30 minutes. A linear, continuous 10 to 50% OptiPrep (Sigma-Aldrich) gradient was used to purify the SINV/EEEV particles further at 136,873×g ($r_{max}$) for 1.5 hours at 4° C. using an AH-650 swinging bucket rotor (Sorvall). SINV/EEEV particles were collected and buffer exchanged into TNE buffer (50 mM Tris-HCl pH 7.5 (Sigma), 100 mM NaCl, 0.1 mM EDTA (Corning)) via 100K MWCO Amicon® Ultra Centrifugal Filter Units (Millipore) to a concentration of ~0.1 mg/mL total protein content, as determined by a Bradford assay (Thermo Fisher Scientific) or BCA assay (Thermo Fisher Scientific). Virus then was used fresh or stored at 4° C. until use.

Recombinant EEEV E1 ectodomain expression. The EEEV E1 ectodomain was produced in Expi293F cells using the ExpiFectamine 293 transfection kit (Gibco) according to the manufacturer's protocol. Briefly, 1 μg/mL of pcDNA3.1 (+)-EEEV E1 ectodomain was diluted in Opti-MEM medium (Gibco) with ExpiFectamine 293 reagent (Gibco) for 15 to 20 minutes at room temperature before addition to the Expi293F cells. Cells were incubated at 37° C. in a humidified atmosphere of 8% $CO_2$ and supernatant was harvested by centrifugation and subsequent filtering through a 0.45-μm pore size filter (Nalgene) 2 to 6 days after transfection. Cell supernatant was purified through a His-Trap excel column (GE Healthcare Life Sciences) according to the manufacturer's protocol on an ÄKTA pure 25M chromatography system.

Human hybridoma generation. PBMCs previously cryopreserved were thawed rapidly and transformed with Epstein-Barr virus (EBV), as previously described (Yu et al., 2008a; Yu et al., 2008b). Briefly, in B cell growth medium (ClonaCell-HY Medium A (Stem Cell Technologies), CpG (Invitrogen), Chk2 inhibitor (Sigma-Aldrich), cyclosporin A (Sigma-Aldrich), and EBV filtrate from the B95.8 cell line), 5 to 7 million PBMCs were added at 50 μL/well to 384-well plates (Thermo Fisher Scientific) and incubated at 37° C. in a humidified atmosphere of 7% $CO_2$. After 7-10 days, cells were expanded to 96-well plates in B cell expansion medium (Medium A, CpG, Chk2 inhibitor, and irradiated heterologous human PBMCs (Nashville Red Cross) at a density of 10 million cells/mL). The plates were incubated at 37° C. in a humidified atmosphere of 7% $CO_2$ for an additional 4-5 days prior to screening by ELISA, as described below. Cells from wells containing reactive supernatants were fused with the non-secreting myeloma cell line, HMMA2.5, using an electrofusion protocol as previously described (Yu et al., 2008a). Fused hybridomas were selected by plating in HAT medium (Medium A, ClonaCell™-HY Medium E (Stem Cell Technologies), 50×HAT medium supplement (Sigma-Aldrich), ouabain octahydrate; Sigma-Aldrich) at 50 μL/well in 384-well plates. The plates were incubated for a total of 14 to 21 days at 37° C. in a humidified atmosphere of 7% $CO_2$ prior to screening by ELISA.

Human mAb generation. Wells containing reactive hybridomas were cloned by single-cell fluorescence-activated cell sorting. These hybridoma clones were expanded in Medium E serially into 48-well plates, 12-well plates, and T-75 $cm^2$ flasks, respectively. Hybridoma clones were expanded further into T-225 $cm^2$ flasks or G-Rex® devices (Wilson Wolf) in serum-free medium (Hybridoma SFM; Gibco). Supernatants were harvested after approximately 21 days, or in sets of 3 to 5 days, respectively, through a 0.2-μm pore size filter. Antibodies were purified from the filtrate using HiTrap Protein G (GE Healthcare Life Sciences), HiTrap MabSelect SuRe (GE Healthcare Life Sciences), HiTrap KappaSelect (GE Healthcare Life Sciences), HiTrap LambdaFabSelect (GE Healthcare Life Sciences), or CaptureSelect™ IgA affinity matrix (Thermo Fisher Scientific) columns on an ÄKTA pure 25M chromatography system. Antibodies were concentrated using 50K MWCO Amicon® Ultra centrifugal filter units (Millipore) followed by desalting and buffer exchange with 7K MWCO Zeba desalting columns (Thermo Fisher Scientific).

Hybridoma supernatant protein ELISA. Recombinant EEEV E2 glycoprotein (E3E2) (strain V105; IBT Bioservices) was diluted to 0.5 μg/mL in 1×D-PBS to coat 384-well ELISA plates (Thermo Fisher Scientific) at 25 μL/well and incubated at 4° C. overnight. The plates were washed 3× with D-PBS-T (1×D-PBS+0.05% Tween 20; Cell Signaling Technology) and blocked for 1 hour at room temperature with 25 L/well blocking solution (2% non-fat dry milk (Bio-Rad), 2% goat serum (Gibco) in D-PBS-T). After blocking, the plates then were washed 3× with D-PBS-T and a volume of 10 to 25 μL/well of supernatant from each well containing EBV-transformed B cells or hybridoma cell lines was added. Plates were incubated for 2 hours at room temperature or overnight at 4° C. Plates then were washed 3× with D-PBS-T and a suspension of secondary antibodies (goat anti-human IgG-AP (Meridian Life Science) and goat anti-human IgA-AP; Southern Biotech) at a 1:4,000 dilution in 1% blocking solution (1% non-fat dry milk, 1% goat serum) was added at 25 μL/well for 1 hour at room temperature. Alkaline phosphatase substrate solution (phosphatase substrate tablets (Sigma-Aldrich) in AP substrate buffer (1M Tris aminomethane (Fisher Scientific), 30 mM $MgCl_2$ (Sigma-Aldrich) was added at 25 μL/well following plate washing 4× with D-PBS-T. Plates were incubated at room temperature in the dark for 1-2 hours and then read at an optical density of 405 nm with a BioTek™ plate reader.

Hybridoma supernatant SINV/EEEV ELISA. A murine mAb (EEEV-66; MSD and ASK (Kim et al., 2019)) was diluted to 0.5 g/mL in 1×D-PBS to coat 384-well ELISA plates at 25 μL/well and incubated at 4° C. overnight. The remainder of the ELISA protocol follows as described above for the protein ELISA. However, after blocking, clarified SINV/EEEV supernatant diluted 1:10 in 1× D-PBS (approximately $1\times10^6$ to $1\times10^7$ FFU/mL as determined through focus reduction test (FRT) with BHK-21 cells) at 25 μL/well was added. After incubation for 1-2 hours at room temperature, the plates then were washed 6× with D-PBS-T (the first 2-3 washes were conducted under BSL-2 conditions in a laminar flow biosafety cabinet).

5' RACE nucleotide sequence analysis. Antibody heavy and light-chain variable region genes were sequenced from antigen-specific hybridoma lines that had been cloned biologically using single-cell flow cytometric sorting. Total RNA was extracted using the RNeasy Mini kit (Qiagen). A modified 5' RACE (Rapid Amplification of cDNA Ends) approach was similar to that previously reported (Turchaninova et al., 2016). Briefly, 5 μL of total RNA was mixed with cDNA synthesis primer mix (10 μM each) and incubated for 2 min at 70° C. and then the incubation temperature was decrease to 42° C. to anneal the synthesis primers (1 to 3 min). After incubation, a mix containing 5× first-strand buffer (Clontech), DTT (20 mM), 5' template switch oligo (10 μM), dNTP solution (10 mM each) and 10× SMART-Scribe Reverse Transcriptase (Clontech) was added to the primer-annealed total RNA reaction and incubated for 60 min at 42° C. The first-strand synthesis reaction was purified using the AMPure Size Select Magnetic Bead Kit at a ratio of 0.6× (Beckman Coulter). Following, a single PCR amplification reaction containing 5 μL first-strand cDNA, 2× Q5 High Fidelity Mastermix (NEB), dNTP (10 mM each), forward universal primer (10 μM) and reverse primer mix (0.2 μM each in heavy-chain mix, 0.2 μM each in light-chain mix) were subjected to thermal cycling with the following conditions: initial denaturation for 1 min 30 s followed by 30 cycles of denaturation at 98° C. for 10 s, annealing at 60° C. for 20 s, and extension at 72° C. for 40 s, followed by a final extension step at 72° C. for 4 min. The first PCR reaction was purified using the AMPure Size Select Magnetic Bead Kit at a ratio of 0.6× (Beckman Coulter). Amplicon libraries then were prepared according to the Pacific Biosciences Multiplex SMRT Sequencing protocol and sequenced on a Pacific Biosciences Sequel system platform. Raw sequencing data was demultiplexed and circular consensus sequences (Cardoso et al., 2019). were determined using the Pacific Biosciences SMRT Analysis tool suite. The identities of gene segments and mutations from germlines were determined by alignment using the ImMunoGenetics (IMGT) database (Brochet et al., 2008; Giudicelli and Lefranc, 2011).

Recombinant human Fab, IgG1, and IgA1 production. Recombinant human anti-EEEV mAb or Fab molecules were produced in Expi293F cells using the ExpiFectamine 293 transfection kit according to the manufacturer's protocol. Briefly, 1 μg/mL of DNA was diluted in Opti-MEM I medium with ExpiFectamine 293 reagent for 15 to 20 minutes at room temperature before addition to the Expi293F cells. Cells were incubated at 37° C. in a humidified atmosphere of 8% $CO_2$ and supernatant was harvested by centrifugation and subsequent filtering through a 0.45-μm pore size filter 6 to 7 days after transfection. For IgG1, IgA1, Fab molecules, cell supernatant was purified through a HiTrap MabSelect SuRe, CaptureSelect™ IgA affinity matrix, or CaptureSelect™ CH1-XL affinity column, respectively, according to the manufacturer's protocol on an ÄKTA pure 25M chromatography system. Antibodies were concentrated using 30K or 50K MWCO Amicon® Ultra Centrifugal Filter Units followed by desalting and buffer exchange with 7K MWCO Zeba desalting columns.

Protein $EC_{50}$ ELISA. Recombinant EEEV E2 glycoprotein (E3E2) (strain V105; IBT BioServices), EEEV E1 ectodomain (strain FL93-939), or CHIKV E1 protein (Meridian Life Science) was diluted to 0.5, 2, or 2 μg/mL, respectively, in 1× D-PBS to coat 384-well ELISA plates at 25 μL/well and incubated at 4° C. overnight. A protein screening ELISA was performed as previously described above. However, instead of hybridoma supernatant, purified mAb was diluted to 10 g/mL in blocking solution (1% non-fat dry milk, 1% goat serum) and added at 25 μL/well for 2 hours at room temperature. Additionally, plates were incubated at room temperature in the dark for 2 hours and then read at an optical density of 405 nm with a BioTek™ plate reader. For recombinant anti-EEEV mAbs and Fab molecules, a suspension of secondary antibodies (goat anti-human kappa-HRP (Southern Biotech) and goat anti-human lambda-HRP (Southern Biotech)) at a 1:4,000 dilution in 1% blocking solution (1% non-fat dry milk, 1% goat serum) was added at 25 μL/well for 1 hour at room temperature. 1-Step Ultra TMB-ELISA substrate solution (Thermo Fisher Scientific) was added at 25 μL/well following plate washing 4× with D-PBS-T. The reaction was stopped after 10 minutes at room temperature by addition of 25 μL/well of 1N HCl (Fisher Scientific). The plates then were read at an optical density of 450 nm with a BioTek™ plate reader. $EC_{50}$ values were determined after log transformation of concentration values and non-linear regression analysis using sigmoidal dose-response (variable slope) using GraphPad Prism software version 8.

SINV/EEEV $EC_{50}$ ELISA. A mouse anti-EEEV mAb (EEEV-66; MSD and ASK (Kim et al., 2019)) was coated onto 384-well plates and incubated at 4° C. overnight, as previously described above. After the blocking step, SINV/EEEV was diluted in 1× D-PBS to a titer of approximately $2.2\times10^7$ FFU/mL as determined through FRT with BHK-21 cells. After incubation for 2 hours at room temperature, the plates then were washed 6× with D-PBS-T (the first 2-3 washes were conducted under BSL-2 conditions in a laminar flow biosafety cabinet).

Focus reduction test (FRT). BHK-21 or Vero cells were plated at $2.5\times10^6$ cells/96-well plate in DMEM/5% FBS/10 mM HEPES (Corning) at 150 μL/well. Cells were incubated at 37° C. in 5% $CO_2$ overnight. Cells plated approximately 24 hours prior were washed 2× with 1× D-PBS. Serial three-fold dilutions of SINV/EEEV were diluted in DMEM/2% FBS/10 mM HEPES and added at 100 μL/well to the cells. The virus and cells were incubated at 37° C. in 5% $CO_2$ for 1.5 hours. A 2% methylcellulose (Sigma-Aldrich):

2×DMEM (Millipore): 4% FBS: 20 mM HEPES overlay then was added to the cells at 100 μL/well. Cells then were incubated at 37° C. in 5% $CO_2$ for 18 hours. Plates were fixed with 1% PFA (diluted in 1× D-PBS; Alfa Aesar) at 100 μL/well for 1 hour at room temperature. Plates then were washed 3× with 1× D-PBS followed by 1× Perm Wash (1× D-PBS, 0.1% saponin (Sigma-Aldrich), 0.1% BSA (Sigma-Aldrich)) at 200 μL/well. Immune EEEV ascites fluid (ATCC) at 1:6,000 dilution in 1× Perm Wash was then added at 50 μL/well. The plates were incubated either at room temperature for 2 hours with rocking or overnight at 4° C. Plates were washed 3× with 1× D-PBS-T followed by the addition of a suspension of secondary antibodies (goat anti-mouse IgG-Fc-specific-HRP (Jackson ImmunoResearch)) at 1:2,000 dilution in 1× Perm Wash. Plates were incubated for 1 hour at room temperature with rocking. Plates were washed 3× with 1× D-PBS-T followed by addition of TrueBlue™ peroxidase substrate solution (SeraCare) at 40 μL/well. Plates were incubated for ~15 minutes at room temperature followed by a rinse with MilliQ water. The plates then were air dried and imaged on an ImmunoSpot S6 Universal machine (CTL).

Focus reduction neutralization test (FRNT). Vero cells were plated at 2.5×10$^6$ cells/96-well plate in DMEM/5% FBS/10 mM HEPES at 150 μL/well. Cells were incubated at 37° C. in 5% $CO_2$ overnight. Purified mAb was diluted to 20 μg/mL (final concentration 10 μg/mL) in DMEM/2% FBS/10 mM HEPES. Serial three-fold dilutions of the mAb were performed. MAb-only dilutions were separated to serve as a negative control. SINV/EEEV was diluted to ~100 focus-forming units (ffu)/well in DMEM/2% FBS/10 mM HEPES and added to the mAb serial dilutions. The mAb: virus mixture was incubated at 37° C. in 5% $CO_2$ for 1 hour. Vero cells plated approximately 24 hours prior were washed 2× with 1× D-PBS. The mAb: virus mixture then was added at 100 μL/well to the cells and incubated at 37° C. in 5% $CO_2$ for 1.5 hours. A 2% methylcellulose: 2×DMEM/4% FBS/20 mM HEPES overlay then was added to the cells at 100 μL/well. Cells were incubated at 37° C. in 5% $CO_2$ for 18 hours.

Plates were fixed and immunostained as described for FRT.

Post-attachment neutralization assay. Vero cells were plated at 2.5×10$^6$ cells/96-well plate in DMEM/5% FBS/10 mM HEPES at 150 μL/well. Cells were incubated at 37° C. in 5% $CO_2$ overnight. Vero cells plated approximately 24 hours prior the media was replaced with chilled DMEM/2% FBS/10 mM HEPES and cells were chilled at 4° C. for 15 minutes. SINV/EEEV was diluted to ~100 ffu per well in chilled DMEM/2% FBS/10 mM HEPES and added to the cells at 4° C. for 1 hour. Purified mAb was diluted to 10 μg/mL in chilled DMEM/2% FBS/10 mM HEPES. Serial three-fold dilutions of the mAb were performed. MAb-only dilutions were separated to serve as a negative control. Cells were washed 3× with chilled DMEM/2% FBS/10 mM HEPES. mAb then was added at 100 μL/well to the cells and incubated at 4° C. for 1 hour. Cells were washed 3× with DMEM/2% FBS/10 mM HEPES and incubated at 37° C. for 15 minutes. A 2% methylcellulose: 2×DMEM/4% FBS/20 mM HEPES overlay then was added to the cells at 100 μL/well. Cells were incubated at 37° C. in 5% $CO_2$ for 18 hours. Plates were fixed and immunostained as described for FRT.

Entry inhibition assay. A FRNT was performed as previously described. However, prior to addition of overlay, the cells were washed 4× with DMEM/2% FBS/10 mM HEPES and incubated at 37° C. in 5% $CO_2$ for 15 minutes. A 2% methylcellulose: 2×DMEM/4% FBS/20 mM HEPES overlay then was added to the cells at 100 μL/well. Cells were incubated at 37° C. in 5% $CO_2$ for 18 hours. Plates were fixed and immunostained as described for FRT.

EEEV plaque reduction neutralization test. Antibody preparations were diluted serially (using 2-fold dilutions) and incubated with ~100 pfu of EEEV FL93-939 for 1 h at 37° C. Anti-EEEV ascites serum (ATCC) was used as a positive control. After incubation, Vero cell monolayer cultures in 6-well plates were inoculated and incubated for 1 h at 37° C. After overlay with agarose immunodiffusion grade (MP Biomedicals), plates were incubated for 2 days followed by overlay with neutral red for at least 6 h to count plaques. Percent neutralization was calculated based on the number of plaques in each serum dilution compared to the number of plaques in untreated control wells inoculated with virus.

Competition-binding analysis using biolayer interferometry. Anti-penta his (HIS1K) biosensor tips (FortéBio) on an Octet Red96 or HTX biolayer interferometry instrument (FortéBio) were soaked for 10 minutes in 1× kinetics buffer (FortéBio), followed by a baseline signal measurement for 60 seconds. Recombinant EEEV E2 glycoprotein (5 μg/mL; IBT BioServices) was immobilized onto the biosensor tips for 60 seconds. After a wash step in 1× kinetics buffer for 30 to 60 seconds, the first antibody (50 μg/mL) was incubated with the antigen-containing biosensor for 600 seconds. After a wash step in 1× kinetics buffer for 30 to 60 seconds, the biosensor tips then were immersed into the second antibody (50 μg/mL) for 180 seconds. Comparison between the maximal signal of each antibody compared to a buffer-only control was used to determine the percent binding of each antibody. A reduction in maximum signal to <33% of un-competed signal was considered full competition of binding for the second antibody in the presence of the first antibody. A reduction in maximum signal to between 33 to 67% of un-competed was considered intermediate competition of binding for the second antibody in the presence of the first antibody. Percent binding of the maximum signal >67% was considered absence of competition of binding for the second antibody in the presence of the first antibody.

Alanine-scanning mutagenesis analysis. WT EEEV (strain FL93-939) structural proteins (capsid-E3-E2-6K-E1) and E2 mutants were expressed on the surface of Expi293F cells using the ExpiFectamine 293 transfection kit according to the manufacturer's protocol as previously described. Cells were incubated at 37° C. in a humidified atmosphere of 8% $CO_2$, were harvested 24 hours after transfection, and fixed with 1% PFA/PBS. Cells were washed twice with 1×DPBS and stored at 4° C. in FACS buffer (1×DPBS, 2% FBS, 2 mM EDTA) until use or used immediately. Cells were plated at 40,000-50,000 cells/well in 96-well V-bottom plates (Corning). Anti-EEEV mAbs or the irrelevant mAb negative control, rDENV-2D22, were diluted to 1 μg/mL in FACS buffer and incubated with the cells for 1 hour at 4° C. Cells were washed with FACS buffer and then incubated with secondary antibodies (anti-human IgG-PE (Southern Biotech) and anti-human IgA-PE (Southern Biotech) or anti-mouse IgG-PE (Southern Biotech)) diluted 1:1,000 in FACS buffer for 1 hour at 4° C. Cells were washed with FACS buffer and resuspended in 25 μL/well of FACS buffer. Number of events were collected on an IntelliCyt® iQue Screener PLUS flow cytometer (Sartorius). For analysis, mock transfected Expi293F cells were included as a negative control and subtracted as background. The percent binding of each mAb to the alanine mutants was compared to the WT EEEV structural protein control. An initial screen of residues D1-L267 was performed to identify residues with <25% binding and at least two mAbs with >70% binding to control for expression. These residues were further assessed for loss-of-binding phenotype for at least two additional biological replicates. Critical residues were defined as at least two mAbs with >70% binding to control for expression and <25% binding relative to WT protein.

Cryo-EM sample preparation and data acquisition. Purified SINV/EEEV particles and recombinant anti-EEEV Fab (EEEV-33 or EEEV-143) (1:10 molar ratio) were incubated on ice for 30 minutes. 3 μL of mixture was applied on Lacy 400 mesh copper grids (TED PELLA) or carbon coated R2/2 copper Quantifoil holey grids (Electron Microscopy Sciences). The samples were vitrified in liquid ethane using a Vitrobot (Thermo Fisher Scientific) set at 4° C. and 100% relative humidity under BSL-2 containment conditions. Images for SINV/EEEV: EEEV-33 Fab were collected on a Titan Krios electron microscope (Thermo Fisher Scientific) equipped with a K2 Summit Direct Electron Detector (Gatan) operated at 300 kV and having a nominal pixel size of 1.64 Å per pixel. Images for SINV/EEEV: EEEV-143 Fab were collected on a Glacios electron microscope (Thermo Fisher Scientific) equipped with a K2 Summit Direct Electron Detector operated at 200 kV and having a nominal pixel size of 2.0 Å per pixel. Micrographs were acquired automatically using Leginon software (Carragher et al., 2000). The total exposure time for both samples was 10 sec and frames were recorded every 0.2 sec. Defocus values ranged from 1.0 to 2.5 μm. The total accumulated does was ~50 $e^{-}/Å^{2}$ for SINV/EEEV: EEEV-33 Fab and ~25 $e^{-}/Å^{2}$ for and SINV/EEEV: EEEV-143 Fab samples.

Cryo-EM data processing. Cryo-EM movies (50 frames, 200 msec exposure per frame) were corrected for beam-induced motion and dose-weighted using MotionCor2 (Zheng et al., 2017) resulting in global motion-corrected frame stacks and summed micrographs. Contrast transfer function (CTF) parameters was estimated using Gctf (Zhang, 2016). EEEV particles manually picked from selected micrographs in RELION 3.0 (Zivanov et al., 2018) using a box size of 800 pixels (1.64 Å) or 700 pixels (2.0 Å). Approximately 18,000 particles were picked from 2,111 micrographs of SINV/EEEV: EEEV-33 Fab and 10,000 particles were picked from 2,501 micrographs of SINV/EEEV: EEEV-143 Fab. The particles were subjected to reference-free 2D classification in RELION 3.0 and selected particles associated with good classes were exported to cisTEM (Grant et al., 2018). The de-novo initial model was generated without imposing any symmetry (C1 symmetry) which was subjected for 3D auto refinement (I1 symmetry) without mask in cisTEM. Further, the 3D model and associated particles obtained from cisTEM were exported to RELION 3.0 and used for the final masked 3D refinement (I1 symmetry) and postprocessing (FIG. 31A). The resolution of the maps was evaluated using the "gold standard" Fourier shell correlation (FSC) at 0.143 criterion (Henderson et al., 2012; Scheres and Chen, 2012) (FIG. 31B).

EEEV VLP negative stain grid preparation and imaging. For screening and imaging of negatively stained (NS) EEEV VLP (Ko et al., 2019) or EEEV VLP:EEEV-143 Fab samples, ~3 μL of the sample at concentrations of 10-15 μg/mL was applied to glow discharged grid with continuous carbon film on 400 square mesh copper EM grids (Electron Microscopy Sciences). The grids were stained with 0.75% uranyl formate (Ohi et al., 2004). Images were recorded on a 4k×4k CCD camera using an FEI TF20 transmission electron microscope (Thermo Fisher Scientific) operated at 200 keV and control with SerialEM (Mastronarde, 2005). All images were taken at 50,000× magnification with a pixel size of 2.18 A/pix in low-dose mode at a defocus of 1.5 to 1.8 μm. Image processing was performed using the Scipion software package (de la Rosa-Trevin et al., 2016). Images were import and particles were CTF estimated (Rohou and Grigorieff, 2015), then picked (Sorzano et al., 2013). 2D class averages were performed using Xmipp3.0 cl2d (de la Rosa-Trevin et al., 2013; Sorzano et al., 2013).

EEEV VLP cryo-EM sample preparation and data collection. For the EEEV VLP:EEEV-143 Fab complex, EEEV VLP at concentration of 0.2 mg/mL was mixed with EEEV-143 Fab in a molar ratio of 720:1 (Fab: VLP) and incubated on ice for 1 hour. Then, 2.2 μL of either EEEV VLP or EEEV VLP/EEEV-143 Fab was applied 2× to a 300 mesh Lacey grid that was glow discharged for 25 s at 25 milliamperes. The grid was blotted for 2 s before being plunged into liquid ethane using a FEI Vitrobot Mark4 (Thermo Fisher Scientific) at 8° C. and 100% humidity. The grids were imaged in Titan Krios (Thermo Fisher Scientific) operated at 300 keV equipped with Falcon 3EC Direct Electron Detector (Thermo Fisher Scientific) using counting mode. Movies collected at a nominal magnification of 96,000x, pixel size of 0.8608 A/pix for the EEEV VLP and at 75,000x, pixel size of 1.11 A/pix for the EEEV VLP:EEEV-143 Fab complex. Both data set were in a defocus range of 0.8 to 2.8 μm. Grids were exposed at 1e–/$Å^{2}$/frame over 30 frames resulting in a total dose of ~30 e–/$Å^{2}$ (see also Table S1).

EEEV VLP cryo-EM data processing. Movies were preprocessed on-the fly (MotionCor2 (Zheng, 2017 #89), Gctf (Zhang, 2016), using RELION (Scheres, 2012; Zivanov et al., 2018). Micrographs with low resolution, high astigmatism and defocus were removed from the data set. Further processing was done using RELION 3.1 beta. A small subset of micrographs were autopicked first by RELION LOG (Fernandez-Leiro and Scheres, 2017) and 2D class averages were determined. Representative classes were selected and used as templates for another round of autopicking. The particles were then subjected to multiple rounds of 2D class averages and 3D classification (with and without symmetry). The particles from the selected classes were re-extracted, 3D classified and subjected to 3D auto refinement. The data was processed further with Ctfrefine, polished and postprocessing was done (detailed statistics are provided in Table S1 and Figure S7).

EEEV VLP model building. For the EEEV VLP, a homology model of SINV/EEEV (PDB: 6MX4) was used for docking to the cryoEM map with PHENIX (Adams et al., 2010). To improve coordinate fitting, the model was subjected to iterative refinement of manual building in Coot (Emsley and Cowtan, 2004) and PHENIX real-space refine (Adams et al., 2010). The model was validated with Molprobity (Chen et al., 2010). For the EEEV VLP:EEEV-143 Fab complex, the refined model of the VLP was used as starting model and was docked to the EM map with UCSF Chimera (Pettersen et al., 2004). The model was then refined in PHENIX (phenix real-space refine) by rigid body and a homology model of EEEV-143 Fab (PDB: 6MWX) was mutated to the EEEV-143 Fab sequence, docked, and rigid body refined to the EM map.

Mouse aerosol challenge with EEEV. Mice were inoculated with EEEV strain FL93-939 by aerosol, as previously described (Trobaugh et al., 2019). Briefly, mice were challenged with ~10 $LD_{50}$ (~2,500 PFU) of 20% sucrose-purified WT EEEV FL93-nLuc TaV using the AeroMP exposure system (Biaera Technologies, Hagerstown, MD) inside a class III biological safety cabinet and either an Aeroneb nebulizer (Aerogen) or 3-jet Collison nebulizer (CH Technologies). All mice were monitored twice daily for morbidity and mortality.

In vivo imaging At different times after challenge, mice were injected with 10 mg of Nano-Glo substrate (Promega) subcutaneously in 500 mL PBS, as previously described (Gardner et al., 2017). Four minutes after substrate injection, the mice were imaged using the IVIS Spectrum CT Instrument (PerkinElmer) using the autoexposure setting. The total flux (photons per second) in the head region was calculated for each animal using Living Image Software 4.5.1, with all images set to the same scale.

Quantification and statistical analysis. Statistical details can be found in the figure legends. $EC_{50}$ values for binding and $IC_{50}$ values for neutralization were determined after log transformation of concentration values and non-linear regression analysis using sigmoidal dose-response (variable slope). Direct comparison of differences in mAb binding to virion particle-specific epitopes versus sites in recombinant E2 glycoprotein cannot be performed on a molar basis. The precise total number of epitopes present on SINV/EEEV particles is unknown in an antibody-based capture ELISA format and may be greater than that on the recombinant EEEV E2 glycoprotein. To describe the differences in mAb binding, a virus/protein $EC_{50}$ ratio was used. Survival curves were generated using the Kaplan-Meier method and curves compared the log-rank test with Bonferroni multiple comparison correction (n=number of mice, *=p<0.05, **=p<0.01, ns=not statistically significant). A one-way ANOVA with Dunnett's multiple comparison correction was used to compare luminescence intensity of IVIS images (*=p<0.01). All statistical analyses were performed using Prism software version 8 (GraphPad).

Human anti-EEEV mAbs isolated from a naturally infected EEEV survivor potently neutralize EEEV. The inventor isolated a panel of forty-eight human anti-EEEV mAbs from the B cells in a peripheral blood sample of a donor who had a prior documented, naturally-acquired EEEV infection. To down-select mAbs from this panel, the inventor focused on those that could efficiently neutralize Sindbis virus (SINV)/EEEV, a chimeric virus for use in BSL2 conditions containing the nonstructural proteins of SINV and displaying the structural proteins of EEEV strain FL93-939 (Kim et al., 2019). Twelve human anti-EEEV mAbs exhibited neutralization activity against SINV/EEEV (FIGS. 18A and 18D). All mAbs isolated were of the IgG1 subclass except for EEEV-143, which was isolated as an IgA1 (FIG. 18D). Of these, seven exhibited potent neutralization activity (defined as half-maximal inhibitory concentration ($IC_{50}$)<20 μM; <6 ng/mL) and five exhibited moderate neutralization activity (defined as mAbs with 20 μM-4 nM [6 ng/ml-1.2 μg/mL] $IC_{50}$ values) against SINV/EEEV.

The activity of human anti-EEEV mAbs also was tested against the pathogenic EEEV strain FL93-939 under BSL-3 conditions. Overall, the neutralization potency with EEEV was consistent with results obtained with SINV/EEEV, supporting the use of chimeric virus for functional analysis (FIG. 18C). Nine mAbs neutralized EEEV completely at 75 nM (22.5 μg/mL), such that a residual fraction of infectious virus was not observed (FIG. 18C). Several human anti-EEEV mAbs exhibited extremely potent neutralization activity against EEEV; three mAbs (EEEV-27, EEEV-33, and EEEV-106) achieved nearly 100% neutralization of EEEV even at the lowest concentration tested, 37 μM (11 ng/ml) (FIGS. 18C-D). Nine human anti-EEEV mAbs exhibited neutralization activity of <400 μM (120 ng/mL) $IC_{50}$ values against EEEV. Additionally, two human anti-EEEV mAbs exhibited weak neutralization activity with $IC_{50}$ values in a range of 400 μM-5 nM (120 ng/ml-1.5 μg/mL) against EEEV (FIG. 18D). EEEV-97 did not neutralize EEEV at any of the concentrations tested, which corresponded with its weak activity against SINV/EEEV.

Neutralizing human anti-EEEV mAbs bind to SINV/EEEV particles and/or recombinant EEEV E2 glycoprotein. To identify the antigen specificity of the neutralizing human anti-EEEV mAbs, the inventor assessed binding to SINV/EEEV particles and EEEV E2 or E1 glycoproteins (FIGS. 19A-C and FIGS. 25A-C). The neutralizing human anti-EEEV mAbs exhibited distinct patterns of reactivity to SINV/EEEV particles or recombinant EEEV E2 glycoprotein, with most mAbs binding to both protein and virus with equal strength; however, some mAbs bound better to SINV/EEEV whereas other recognized the E2 glycoprotein more avidly (FIGS. 19A-C and FIG. 25A-C). Binding to EEEV or CHIKV E1 glycoproteins was not detected. A majority of the mAbs bound strongly to either E2 antigen (isolated protein or SINV/EEEV particles) by ELISA (<100 μM [<30 ng/mL] half-maximal effective binding concentration [$EC_{50}$] values), whereas EEEV-33 bound weakly to recombinant E2 glycoprotein compared to SINV/EEEV particles (<4 nM vs 11 PM [<1.2 μg/mL vs 3.3 ng/mL] $EC_{50}$ values) (FIG. 19B). The ratio of virus/protein $EC_{50}$ values for binding was determined (FIG. 19B) to identify differences in reactivity of mAbs recognizing virion particle-specific epitopes versus those more accessible in recombinant E2 glycoprotein. Preferential binding to virion-specific epitopes suggests that some mAbs recognize quaternary epitopes on the virion or require bivalent binding with specific geometric orientation. This finding was observed for EEEV-33, as the binding strength to SINV/EEEV particles was much stronger than for EEEV E2 glycoprotein, indicated by a virus/protein $EC_{50}$ ratio of 0.003. Most neutralizing mAbs strongly bound both protein and virus, with a virus/protein $EC_{50}$ ratio of ~1. However, a few mAbs bound E2 protein better than SINV/EEEV particles, such as EEEV-147 (virus/protein $EC_{50}$ ratio=4.4), indicating that these mAbs may recognize an epitope that is less accessible on the virion surface under the conditions tested.

Optimal neutralization of SINV/EEEV requires bivalent interactions. The neutralization potency of Fab and IgG molecules has been compared previously for several alphaviruses (Hasan et al., 2018; Long et al., 2015). In some cases, the neutralizing activity of the Fab form of the mAb is substantially lower than the intact IgG (Hasan et al., 2018). However, the inventor found that the Fab forms for some neutralizing human anti-EEEV mAbs (EEEV-33, EEEV-94, EEEV-106, EEEV-129, EEEV-143) still neutralized SINV/EEEV efficiently with <1 nM (<300 ng/ml) $IC_{50}$ values (FIGS. 18B and 18D), indicating that the monovalent Fab molecules may achieve sufficient occupancy of binding for neutralization of EEEV. This finding of similar neutralization potency for mAbs and Fabs was consistent with the similar binding strength of mAb or Fab molecules to SINV/EEEV particles (FIGS. 25A-C). The neutralization potency of EEEV-94, EEEV-106, EEEV-129, and EEEV-143 as Fab molecules was still reduced (~10 [EEEV-94] to 276 [EEEV-143]-fold change in $IC_{50}$ values), suggesting bivalent or tetravalent interactions as an IgG (EEEV-94, EEEV-106, ad EEEV-129) or IgA (EEEV-143), respectively, may contribute to optimal neutralization of SINV/EEEV. EEEV-33 had comparable neutralization potency as a Fab or IgG molecule (~4-fold change), indicating that valency interactions are not necessary for neutralization of SINV/EEEV by EEEV-33.

In contrast, EEEV-27 and EEEV-93 exhibited greatly reduced neutralization potency when expressed as Fab molecules, compared to IgG, and showed a corresponding reduction in binding to SINV/EEEV particles (>1,000-fold reduction in $IC_{50}$ and $EC_{50}$ values) (FIGS. 25A-C). These findings suggest that for EEEV-27 and EEEV-93, the monovalent interaction of Fab with SINV/EEEV particles likely is of low affinity. Thus, the avidity benefits of interactions achieved though bivalent binding of EEEV-27 and EEEV-93 as an IgG molecule are required for optimal binding and neutralization of SINV/EEEV.

The $IC_{50}$ values of neutralization and $EC_{50}$ values for binding to SINV/EEEV did not correspond for all of the inhibitory human anti-EEEV mAbs or Fabs. EEEV-7, EEEV-12, EEEV-21, EEEV-97, and EEEV-147 bound SINV/EEEV particles with similar strength as Fab molecules, compared to IgG. However, a reduction in neutralization potency was observed for EEEV-7, EEEV-12, EEEV-21, EEEV-97, and EEEV-147 as Fab molecules, suggesting that the bivalent interactions as an IgG may enable cross-linking of two E2 protomers for optimal neutralization of SINV/EEEV.

Neutralizing human anti-EEEV mAbs recognize three antigenic determinants on the EEEV E2 glycoprotein. The E2 glycoprotein consists of three structural domains: 1) a flexible domain B at the apical surface that shields the fusion loop at the distal tip of the E1 glycoprotein, 2) domain A, which is suspected to contain the putative receptor binding site, and 3) domain C that lies proximal to the viral membrane and contains the transmembrane domain (Voss et al., 2010); Chen et al., 2020; Gardner et al., 2013; Gardner et al., 2011; Hasan et al., 2018; Zhang et al., 2011; (Fox et al., 2015). To determine the number of major antigenic sites recognized by neutralizing human anti-EEEV mAbs, the inventor performed competition-binding studies utilizing biolayer interferometry. Binding of human anti-EEEV mAbs was performed in competition with previously described domain B-specific murine anti-EEEV mAbs, including mEEEV-69 and mEEEV-86 (Kim et al., 2019). From this analysis, the inventor identified at least three competition-binding groups on the EEEV E2 glycoprotein corresponding to three neutralizing antigenic determinants (FIG. 20A). The inventor observed partial overlap for some of these competition groups, suggesting proximity of the epitopes to each other. A majority of the neutralizing human EEEV mAbs competed with murine anti-EEEV mAbs that recognize domain B on the E2 glycoprotein (mEEEV-69 or mEEEV-86) (Kim et al., 2019), showing that this antigenic determinant was most immunogenic in this individual for elicitation of neutralizing human anti-EEEV mAbs.

Figure 26:
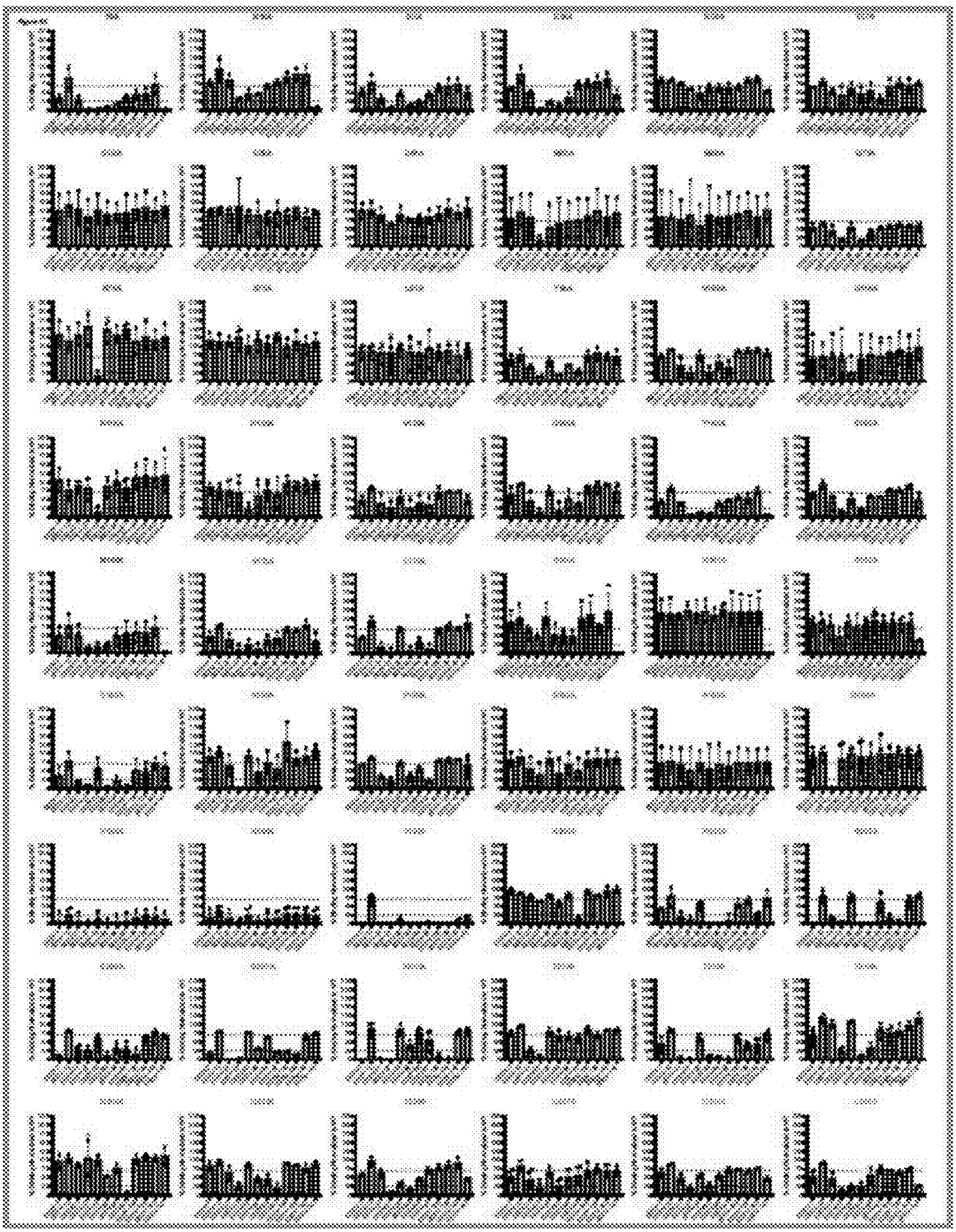
FIG. 26. Related to FIGS. 20A-D. Alanine-scanning mutagenesis library analysis. Bar graphs of neutralizing human anti-EEEV mAb binding to critical residues (<25% mAb binding with at least two other mAbs >70% to control for expression) or critical residues previously characterized for murine anti-EEEV mAbs (Kim et al., 2019) and the VEE-specific human mAb, F5 (Hunt et al., 2010; Porta et al., 2014). Each mAb is listed on the x-axis and percent binding relative to wildtype is on the y-axis. Data represent mean±SD of at least two independent experiments.

To identify critical interaction residues for neutralizing human anti-EEEV mAbs, the inventor generated an alanine-scanning mutagenesis library for the EEEV E2 glycoprotein. Each E2 protein residue was mutated to alanine, or alanine residues to serine, and the library was used to map residues for which a loss-of-binding phenotype of the antibody occurred. An initial screen (D1-L267) using this mutant E2 library was performed to identify residues with low level (<25%) of mAb binding either due to a loss-of-binding phenotype or reduced expression of the E2 glycoprotein (FIG. 20B and FIG. 26). At least one additional replicate was performed for residues identified in the initial screen and for key residues previously described for murine anti-EEEV mAbs (Kim et al., 2019) and the Venezuelan equine encephalitis virus (VEE)-specific human mAb F5, (Hunt et al., 2010; Porta et al., 2014). To control for expression, binding of at least two human anti-EEEV mAbs with >70% relative to wild-type (Emsley and Cowtan) was used. Similar to the competition-binding analysis, three groups of mAbs emerged from the loss-of-binding experiments for recognition of determinants on the EEEV E2 glycoprotein. Critical alanine residues identified in this analysis were mapped to the 4.2 Å cryo-EM three-dimensional model of EEEV virus-like particle (VLP) (EMD-22276; PDB ID: 6XO4; FIGS. 29A-C). The antigenic sites of the neutralizing human anti-EEEV mAbs correspond to epitopes on domains A (EEEV-33), B (EEEV-7, EEEV-21, EEEV-97, EEEV-106, EEEV-129, EEEV-143), or A/B (EEEV-27, EEEV-93, EEEV-94) of the E2 glycoprotein (FIG. 20D and Table S1). Variable gene sequence analysis revealed EEEV-7 and EEEV-106 belonged to a common lineage, which is supported by their recognition of similar residues for binding. Several mAbs (EEEV-27, EEEV-33, EEEV-93, EEEV-94, and EEEV-147) also recognized critical residues in the arch regions (arch 1 or arch 2), an acid-sensitive β-connecter region that connects domain A to domain B. Some E2 residues mutated to alanine were identified as critical that are not surface exposed (I33, E34, M65, Y98, V109, V128, G145, Y163, E165, M166, V172, V185, Y226, L227, L240), which may reflect allosteric effects on the epitope that impact antibody binding (Table S1). Although critical residues in the EEEV E2 domains were identified previously through alanine-scanning mutagenesis library analysis of murine anti-EEEV mAb (Kim et al., 2019); FIG. 20C and FIG. 26), some of the residues identified here are distinct (N-terminal linker: Y9, K10; Domain A: I33, E34, M65, Y98, V109, G116, N118, H120, V128; Arch 1: G145, Y163, E165, M166; Domain B: V172, L178, V185, K186, P190, K200, P202, R205, E206, G207, T216, D219, Q222, Y226; Arch 2: D229, L240), indicating that there may be differences in recognition by human and mouse anti-EEEV neutralizing antibodies.

SINV/EEEV neutralization escape mutant viruses with the mutations M68T, G192R, or L227R of the E2 glycoprotein were identified previously using domain A/B murine anti-EEEV mAbs. The mutated residues affected the neutralization potency of domain A and A/B specific murine anti-EEEV mAbs to SINV/EEEV. Domain B-specific murine anti-EEEV mAbs inhibited the escaped viruses as efficiently as WT SINV/EEEV (Kim et al., 2019). To assess whether viral escape also occurred for the neutralizing human anti-EEEV mAbs, the inventor tested activity of the mAbs against these viruses (FIGS. 27A-C). Similar to the murine anti-EEEV mAbs, mAbs that recognized domain B of the EEEV E2 glycoprotein still neutralized the G192R and L227R antibody escape mutant viruses with comparable potency to WT SINV/EEEV. The domain B-specific mAb EEEV-97, however, displayed reduced neutralization potency against all three escape mutant viruses. This finding may be due to the weak neutralization potency of EEEV-97 against SINV/EEEV. A number of domain B-specific mAbs (EEEV-7, EEEV-106, EEEV-129) displayed a >10-fold reduction in neutralization potency to SINV/EEEV (M68T). M68T may lead to an allosteric effect on the epitope for EEEV-7, EEEV-106, and EEEV-129, which all depend on the critical alanine residues R205, G207, and H213 for binding. Two other domain B-specific mAbs, EEEV-21 and EEEV-143, also displayed a >5-fold reduction in neutralization potency to SINV/EEEV (M68T). Again, this reduction may be due to an allosteric effect on the epitope for these mAbs. However, EEEV-21 and EEEV-143 depend on additional and/or different critical alanine residues for binding from those affecting EEEV-7, EEEV-106, and EEEV-129, such that M68T does not affect neutralization potency for EEEV-21 and EEEV-143 to the same extent. The domain A-specific EEEV-33 efficiently neutralized the G192R and L227R mutant viruses. However, a >5-fold reduction in neutralization potency was observed for SINV/EEEV (M68T). A loss-of-binding phenotype for clones in the EEEV E2 alanine mutant library was not observed for EEEV-12. However, EEEV-12 displayed a >10-fold or >5-fold reduction in neutralization potency to SINV/EEEV (M68T) or SINV/EEEV (L227R), respectively. Thus, EEEV-12 likely recognizes domain A on the E2 glycoprotein due to reduction of neutralization potency at these mutated residues and observed competition with EEEV-33 for binding to the E2 glycoprotein. Two mAbs, EEEV-94 (domain A/B) and EEEV-147 (N-link/arch 1), displayed comparable neutralization potency to the escaped viruses and WT SINV/EEEV, which correspond with the critical alanine residues identified for these mAbs. EEEV-27 and EEEV-93 (domain A/B) displayed reduced neutralization potency for M68T and L227R or comparable potency for the G192R escaped mutant viruses. Again, the observed mutated residues correspond with the epitope identified through alanine-scanning mutagenesis library analysis for EEEV-27 and EEEV-93. Thus, through complementary epitope mapping techniques, the inventor defined three major neutralizing antigenic determinants for human mAbs (domain A, B, and A/B) on the EEEV E2 glycoprotein.

EEEV-33 and EEEV-143 inhibit SINV/EEEV entry into cells. To begin to elucidate the mechanism of neutralization for human anti-EEEV mAbs, the inventor focused on two potently inhibitory mAbs, EEEV-33 (IgG1; domain A) and EEEV-143 (IgA1; domain B). Entry blockade was assessed by incubating mAbs with SINV/EEEV, allowing the virus to bind and internalize into cells at 37° C., and followed by extensive washing to remove unbound virus and mAb (FIGS. 21A and 22A). This approach limits exposure of virus to mAb at the attachment, entry and fusion steps of the infection cycle (Fox et al., 2015; Jin et al., 2015). A similar neutralization potency was observed compared to experiments in which the mAb was present at all stages, including egress. Thus, EEEV-33 and EEEV-143 likely act at one of the early entry stages of virus infection.

Next, to assess whether EEEV-33 or EEEV-143 block virus attachment to cells, a post-attachment neutralization assay was performed (FIGS. 21B and 22B). In this assay, virus was incubated with cells at 4° C. followed by addition of the mAb at 4° C. after attachment and removal of free virus. A reduction in neutralization potency of EEEV-33 and EEEV-143 was observed, which could indicate that EEEV-33 and EEEV-143 block virus attachment to cells to some degree or cannot reach full occupancy of virion binding sites for optimal neutralization due to epitopes blocked by the initial virus attachment to host cells. However, substantial inhibition still occurred post-attachment, indicating that EEEV-33 and EEEV-143 can inhibit virus entry into cells after adsorption to the cell surface.

EEEV-33 binds to a critical epitope within domain A of the E2 trimer of SINV/EEEV particles. The inventor characterized the structural basis for EEEV-33 recognition of SINV/EEEV using single particle cryo-electron microscopy (cryo-EM) and determined a three-dimensional structure of the complex at ~7.2 Å resolution (FIGS. 21C-G and FIGS. 31A-D). The competition-binding assay and E2 alanine library analysis showed that EEEV-33 recognizes domain A of the EEEV E2 glycoprotein (FIGS. 20A-D). Additionally, the observation that EEEV-33 preferentially recognizes virion particles and not recombinant monomeric EEEV E2 glycoprotein suggests that a quaternary interaction between the variable domain of the Fab and E2 protomers in the trimer facilitates binding (FIGS. 19A-C and FIGS. 25A-C). Thus, EEEV-33 may recognize a critical epitope within domain A of the E2 trimer for neutralization of SINV/EEEV. The structural analysis showed that three Fab molecules bound per E2 trimer in a radial orientation. Each E2 protomer was bound to one Fab molecule. The constant domains of each Fab within the trimer appear to make contacts with one another, such that occupancy might be reduced for the bulkier IgG form of EEEV-33 due to steric clashes of the Fc regions (FIGS. 21E-F). Additionally, the protomers within the E2 trimer do not move upon EEEV-33 Fab binding, when compared to the apo form of E2 (FIGS. 28A-D). This finding suggests EEEV-33 may stabilize or sterically hinder the E2 trimer upon binding as a Fab or IgG molecule or does not require significant conformational changes to inhibit viral entry or the conformational changes necessary for virus fusion with cells.

EEEV-143 binds to a critical epitope within domain B of the E2 trimer of SINV/EEEV particles and EEEV virus-like particles (VLPs). The inventor also characterized the structural basis of neutralization of EEEV-143 by studying the mAb in complex with SINV/EEEV particles using single particle cryo-EM. The inventor determined a three-dimensional structure at ~8.3 Å resolution (FIGS. 22C-G and FIGS. 31A-D). The inventor also characterized the structural basis for EEEV-143 in complex with EEEV VLPs (Ko et al., 2019) to ~8.5 Å resolution. Similar results to the SINV/EEEV complex reconstruction above were obtained, indicating the structural conformation of VLPs in development as a candidate vaccine is similar to that of SINV/EEEV (FIGS. 29A-H). The competition-binding assay and E2 alanine library analysis indicated that EEEV-143 recognizes an epitope in domain B of EEEV E2 glycoprotein. Similar to EEEV-33, the structure shows that three EEEV-143 Fab molecules associate with each E2 trimer with each E2 protomer bound to one Fab molecule, however, in a tangential orientation. The constant domains of Fabs bound between neighboring trimeric spikes across the two-fold axis appear to make contacts. In addition, Fabs bound to one q3 spike were ~11 Å apart from the constant domain of another Fab bound to the i3 spike across the three-fold axis (FIGS. 22E-F). Again, it is likely that occupancy might be reduced for the IgG form of EEEV-143, due to likely steric clashes of the Fc regions, and even more so with a polymeric IgA molecule, a model which is supported by the greater binding strength of EEEV-143 IgG1 and Fab molecules to SINV/EEEV (FIGS. 25A-C). As observed for EEEV-33, alignment of the structural protein asymmetric unit of the solved EEEV VLP (FIGS. 29A-C; ~4.2 Å) with the EEEV-Fab complex did not show movement of the E2 glycoprotein (FIGS. 28A-D and FIG. 29I). This finding suggests that EEEV-143 may stabilize or sterically hinder the E2 protein upon Fab binding or does not require significant conformational changes to neutralize SINV/EEEV. Furthermore, the tangential orientation of EEEV-143 Fab binding and Fab constant domain interactions suggests that EEEV-143 may neutralize SINV/EEEV through recognition of a critical epitope within domain B of the E2 trimer and cross-link two or four E2 protomers as an intact IgG or IgA molecule, respectively (FIG. 29F). As observed for EEEV-33, such a binding pattern could inhibit virus entry or prevent conformational changes necessary for virus fusion with host cells.

EEEV-33 protects against EEEV aerosol challenge in mice. The inventor next assessed the efficacy for EEEV-33 in vivo using an aerosol-challenge mouse model and a nanoLuciferase-expressing strain of EEEV FL93-939 (Sun et al., 2014). This model is more stringent than parenteral inoculation models, as aerosolization facilitates rapid entry into the brain via infection of epithelial cells and neurons in the cribriform plate and spread to the olfactory bulb (Phelps et al., 2019). In this model, prophylaxis with a 100-μg dose of EEEV-33 resulted in 91% survival, when administered by the intraperitoneal (i.p.) route 24 hours prior to virus exposure (FIG. 23A). Representative in vivo imaging (days 4 or 5 after virus inoculation) is shown in which EEEV replication was not observed in the brain, which differed from animals treated with the control antibody rDENV-2D22 (FIG. 23C). Survival was consistent with the body weight patterns of the mice over the course of 14 days (FIG. 30A). Additionally, clinical signs of disease (defined as ruffled fur, hunched back/behavioral, seizures/ataxia, moribund, or death) were not observed for the mice that survived. One mouse appeared moribund on day 4 and subsequently died by day 5 (FIG. 30C). Survival was reduced (27%) when the same dose of antibody was given 24 hours after exposure compared to rDENV-2D22 (FIG. 24A). This finding was expected, as once EEEV begins replicating in the brain parenchyma, it is more challenging to control with antibodies, which are generally excluded from the central nervous system due to the blood-brain barrier (Morens et al., 2019; Phelps et al., 2019). Representative in vivo imaging (days 4 or 5) is shown for mice that survived infection and reveal EEEV replication was not observed in the brain (FIG. 24C). Survival was consistent with the body weight patterns of the mice over the course of 14 days. A reduction in body weight was observed for the mice that died (FIG. 30E). Clinical signs of disease (ruffled fur, hunched back/behavioral, moribund, or death) were observed for the mice that died (FIG. 30G).

EEEV-143 protects and treats against WT EEEV aerosol challenge in mice. The mucosal IgA response is suspected to play a role in protection because mice with low IgG serum titers following vaccination with EEEV live attenuated virus candidates still were protected against lethal EEEV aerosol challenge (Trobaugh et al., 2019). Active transport of polymeric IgA into the lumen of mucosal respiratory tissue sites may increase the relative concentration of IgA antibodies in mucosal secretions and might enhance the therapeutic efficacy of a mAb for EEEV administered via the aerosol route. To assess this possibility, the inventor studied the treatment efficacy of the IgA isotype form of the neutralizing mAb EEEV-143. EEEV-143 mediated 100% survival when a 100-μg dose was administered i.p. route 24 hours prior to virus exposure compared to rDENV-2D22 (FIG. 23A). Remarkably, in one study (FIG. 24A), 4 of 5 (80%) mice inoculated survived when EEEV-143 was administered 24 hours after exposure (1,825 PFU/mouse) compared to rDENV-2D22. In a replicate study, EEEV-143 also mediated 100% survival when a 100-μg dose was administered i.p. route 24 hours prior to virus exposure (2,379 PFU/mouse) compared to rDENV-2D22 (FIG. 23B). However, in this cohort, only 20% of the EEEV-143-treated mice survived when mAbs were administered 24 hours after exposure (2,379 PFU/mouse) compared to rDENV-2D22 (FIG. 24B). The difference in therapeutic efficacy between these two studies may be attributed to the variability of infection efficiency in the aerosol model, as slightly different virus titers were administered according to results from back-titration of the inocula on the days of challenge. Representative in vivo imaging (days 4 or 5) is shown for mice that survived infection in which EEEV replication was not observed in the brain as compared to rDENV-2D22 (FIGS. 23C and 24C). Survival was consistent with body weight of the mice over the course of 14 days. A reduction in body weight was observed for the mice that died (FIGS. 30A-B and 30E-F). For the mice that died, all clinical signs of disease (ruffled fur, hunched back/behavioral, seizures/ataxia, moribund, and death) were observed (FIGS. 30C-D and 30G-H).

TABLE S1

Related to FIGS. 3, S2, and S3; summary table of EEEV E2 neutralizing antigenic determinants recognized by human anti-EEEV mAbs

| EEEV mAb | E2 Domain | Critical EEEV E2 alanine residues[a] | Allosteric EEEV E2 alanine residues[b] | Reduction in neutralization potency for SINV/EEEV escape mutant viruses[c] |
|---|---|---|---|---|
| EEEV-12 | A | No reduction | N/A | M68T (L227R) |
| EEEV-33 | A (N-link/A/Arch 1/B/Arch 2) | 9, 74, 116, 118, 120 | 34, 163, 166, 172, 240 | (M68T) |
| EEEV-147 | N-link/Arch 1 | 9, 10 | 163, 166 | Minimal reduction |
| EEEV-7 | B | 205, 206, 207, 213 | N/A | M68T |
| EEEV-106 | B | 205, 206, 207, 213 | N/A | M68T |
| EEEV-27 | A/B (N-link/A/ Arch 1/B/Arch 2) | 9, 73, 145, 178, 186, 190, 202, 205-207, 213-216, 222, 229 | 33-34, 65, 98, 109, 128, 163, 165-166, 172, 185, 226-227, 240 | M68T |
| EEEV-129 | B | 205, 207, 213 | N/A | M68T |
| EEEV-21 | B | 178, 194, 202, 205, 207, 213, 215 | 185 | (M68T) |
| EEEV-94 | A/B (N-link/A/B) | 9, 202, 205, 215 | 33, 185 | Minimal reduction |
| EEEV-143 | B | 202 | N/A | (M68T) |
| EEEV-93 | A/B (N-link/A/ Arch 1/B/Arch 2) | 9, 73, 178, 202, 205-206, 215-216 | 33-34, 98, 128, 145, 163, 165-166, 172, 185, 226, 240 | M68T, L227R |

TABLE S1-continued

Related to FIGS. 3, S2, and S3; summary table of EEEV E2 neutralizing antigenic determinants recognized by human anti-EEEV mAbs

| EEEV mAb | E2 Domain | Critical EEEV E2 alanine residues[a] | Allosteric EEEV E2 alanine residues[b] | Reduction in neutralization potency for SINV/EEEV escape mutant viruses[c] |
|---|---|---|---|---|
| EEEV-97 | B | 178, 190, 200, 202, 207, 215, 219, 222 | 185 | M68T, G192R, L227R |

[a]Surface-exposed critical alanine residues (<25% binding relative to WT) are identified as determined through alanine-scanning mutagenesis library analyses for each mAb. See FIG. 3B for a heat map representation of average percent binding of human anti-EEEV mAbs to critical residues and FIG. S2 for bar graph representation of human anti-EEEV mAb binding to critical residues.

[b]Critical alanine residues (<25% binding relative to WT) that are not surface exposed, as determined through alanine-scanning mutagenesis library analyses for each mAb are identified. The identified residues may result in a loss of binding phenotype due to allosteric effects on the epitope. N/A = not applicable

[c]Neutralization potency of human anti-EEEV mAbs for the SINV/EEEV escape mutant viruses (M68T, G192R, and L227R). Minimal reduction indicates that neutralization potency of respective human anti-EEEV mAb is similar to neutralization activity against WT SINV/EEEV. Escape mutants with a >10-fold reduction in neutralization potency are indicated for each mAb. Parentheses include escape mutants with >5-fold reduction in neutralization potency. See Figure S3 for neutralization curves of human anti-EEEV mAbs to SINV/EEEV escape mutant viruses (M68T, G192R, and L227R).

TABLE S2

Related to STAR Methods; parameters used for high-resolution data collection of SINV/EEEV: rEEEV-33 Fab, SINV/EEEV: rEEEV-143 Fab, EEEV VLP, and EEEV VLP: rEEEV-143 Fab

| | Parameters | SINV/EEEV: rEEEV-33 Fab | SINV/EEEV: rEEEV-143 Fab | EEEV VLP | EEEV VLP: rEEEV-143 Fab |
|---|---|---|---|---|---|
| Data Deposition | EMDB | 22223 | 22188 | 22276 | 22277 |
| | PDB | | | 6XO4 | 6XOB |
| Microscope setting | Microscope | Titan-Krios | Glacios | Titan Krios | Titan Krios |
| | Acceleration voltage (kV) | 300 | 200 | 300 | 300 |
| | Detector | | | Falcon 3EC | Falcon 3EC |
| | Magnification (x) | 18,000 | 22,000 | 96,000 | 75,000 |
| | Pixel size (Å) | 1.64 | 2.0 | 0.8608 | 1.11 |
| | Dose Exposure ($e^-/Å^2$) | 50 | 25 | 30 | 30 |
| | Defocus range (μm) | 1.0-2.5 | 1.0-2.5 | 0.8-2 | 1-2.5 |
| Data | # Micrographs | | | 1,745 | ~4,800 |
| | # particles | ~18,000 | ~10,000 | 3,935 | 3,600 |
| | # particle after 2D | ~12,900 | ~7,200 | 3,569 | 2,471 |
| | Final particles # | ~12,900 | ~7,200 | 3,469 | 1,300 |
| | Symmetry | icosahedral | icosahedral | icosahedral | icosahedral |
| | Resolution FSC = 0.143 (Å) | 7.2 | 8.3 | 4.2 | 8.5 |
| Model refinement and validation | Protein residues | — | — | 3,992 | 5,700 |
| | Map CC | — | — | 0.79 | 0.69 |
| | RMSD | — | — | | |
| | Bond lengths (Å) | — | — | 0.006 | 0.004 |
| | Bond angles | — | — | 0.671 | 0.816 |
| | Ramachandran | — | — | | |
| | Outliers (%) | — | — | 0 | 0 |
| | Allowed (%) | — | — | 10.93 | 21.64 |
| | Favored (%) | — | — | 89.07 | 78.36 |
| | Poor rotamers (%) | — | — | 5.41 | 21.99 |
| | MolProbity score | — | — | 2.9 | 3.98 |
| | Clash score | — | — | 18.8 | 53.27 |
| | CaBLAM score | — | — | 6.42 | 7.28 |

Example 5—Discussion

In this study, the inventor describes human mAbs isolated against EEEV from the B cells of an EEEV-immune individual with prior natural infection. Isolation of human anti-EEEV mAbs with moderate or potent neutralization activity against the chimeric virus Sindbis (SINV)/EEEV allowed for the characterization of the molecular and structural basis of neutralization against EEEV and addressed important questions relating to the human anti-EEEV antibody response. With identified a panel of 12 moderately and potently neutralizing human anti-EEEV mAbs to SINV/EEEV and WT EEEV. The inventor observed diverse patterns of reactivity and dependence on valency for binding and/or neutralization of SINV/EEEV. Potent mAbs neutralized SINV/EEEV as Fab molecules, suggesting bivalency or tetravalency is not necessary but may be required for optimal neutralization of SINV/EEEV. Two mAbs, EEEV-27 and EEEV-93, displayed reduced binding and neutralization potency as Fab molecules, indicating the requirement for bivalent interactions. Additionally, EEEV-7, EEEV-12, EEEV-21, EEEV-97, and EEEV-147 displayed reduced neutralization potency but not reduced binding as Fab molecules, indicating the neutralization mechanism for these mAbs may involve cross-linking of two E2 protomers as IgG molecules. Recognition of three neutralizing antigenic determinants (domains A, B, and A/B) was observed, with a majority of neutralizing mAbs isolated from this individual recognizing the E2 structural domain B. Further characterization of EEEV-33 and EEEV-143 identified the molecular and structural basis of neutralization, which enabled these mAbs to exhibit in vivo efficacy against highly pathogenic EEEV in an aerosol challenge model.

EEEV-33 is a potently neutralizing human anti-EEEV mAb, with 3.1 μM or <37 μM $IC_{50}$ values for neutralization against SINV/EEEV or EEEV, respectively. EEEV-33 preferentially binds SINV/EEEV particles compared to recombinant EEEV E2 glycoprotein, suggesting recognition of a quaternary epitope on the viral surface. A ~7.2 Å three-dimensional structure of SINV/EEEV bound to EEEV-33 Fab molecules helped elucidate the basis of neutralization by this antibody. The high neutralization potency of EEEV-33, which has similar potency as a Fab molecule, was consistent with the ability of three Fabs to bind each domain A binding site in the E2 trimer. The ability of three EEEV-33 Fabs to bind to each E2 trimer in the virus is unusual, compared to previous structural analyses of murine anti-EEEV mAbs in complex with SINV/EEEV particles (Hasan et al., 2018). From the murine antibody structural analysis, it was observed that steric clashes between Fab molecules, which target domain A of the E2 glycoprotein in a radial orientation, would limit the capacity for complete occupancy of the E2 trimer. However, EEEV-33 binds a unique epitope compared to the murine anti-EEEV mAbs, and the neutralization potency of EEEV-33 even as a Fab molecule is consistent with the occupancy observed in the cryo-EM model. Fab constant domain contacts were observed between Fabs bound within the trimeric spike, indicating that as an IgG molecule steric hindrance may limit occupancy. However, this feature may allow for intra-spike cross-linking to occur for neutralization. The inventor also observed that the protomers of the E2 trimer do not change conformation upon EEEV-33 Fab binding. Together, these data suggest that EEEV-33 recognizes a critical conformational epitope present on domain A of the E2 trimer of SINV/EEEV particles. Binding to this epitope, EEEV-33 may stabilize or sterically hinder the E2 trimer, in which inhibition of viral entry into cells or prevention of conformational changes necessary for virus fusion with cells could occur.

A neutralizing VEEV-specific human mAb similar to EEEV-33, designated F5, was characterized previously (Hunt et al., 2010; Porta et al., 2014). Antibody F5 was isolated using phage display from B cells of VEEV-immune donors. This antibody binds to residues 115-119 in domain A of the E2 glycoprotein, analogous to those recognized by EEEV-33. In contrast to EEEV-33, F5 Fab molecules bind this region of VEEV in a radial orientation and occupy one third of the binding sites. F5 was shown to stabilize the E2 trimer via intra-spike cross-linking (Porta et al., 2014). The similarity in binding and neutralization activity for two human mAbs (EEEV or VEEV) suggests a conserved antigenic site (residues 115-120) that may be targeted through unique mechanisms for neutralization of the encephalitic alphaviruses in humans.

EEEV-143 is another potently neutralizing human anti-EEEV mAb with 2.8 μM or 315 pM $IC_{50}$ values against SINV/EEEV or EEEV, respectively. EEEV-143 was isolated from a human B cell as an IgAQ1 antibody. In mice vaccinated with live-attenuated EEEV vaccine candidates, protection against aerosol challenge was observed even in some mice with low serum PRNT80 values (Trobaugh et al., 2019). This observation suggests that other immune responses may be involved, such as mucosal IgA for protection against aerosol challenge (Trobaugh et al., 2019). Strategies to prevent and/or treat EEEV through antibody-based methods that specifically target mucosal sites could be an important approach. Naturally occurring polymeric IgA (pIgA) molecules are transported actively across mucosal surfaces via the polymeric immunoglobulin receptor (pIgR) (Turula and Wobus, 2018). Transcytosis of neutralizing antibodies across the mucosa may block EEEV infection at or near the site of inoculation to prevent dissemination to the brain.

The structural basis of neutralization for EEEV-143 was determined using single particle cryo-EM of SINV/EEEV bound to EEEV-143 Fab molecules. The resulting ~8.3 Å structure showed that three Fabs also bound to each protomer in the E2 trimer. Fab constant domain contacts were observed around the two-fold axis and ~11 Å distance between Fabs bound to the q3 and i3 spikes across the three-fold axis. These contacts suggest that EEEV-143 forms inter-spike cross-links between adjacent E2 trimers as an IgG or IgA molecule. This inter-E2 trimer cross-linking could stabilize or sterically hinder the trimer to inhibit viral entry or prevent conformational changes necessary for virus fusion with host cells. Again, the binding of three EEEV-143 Fab molecules to each E2 trimer is unusual when compared to studies of neutralizing antibodies generated in mice, where steric clashes between Fab molecules that target domain B of the E2 glycoprotein in a tangential orientation limited the capacity for complete occupancy of the E2 trimer. However, the neutralization potency of EEEV-143 as Fab molecules is consistent with the inventor's structural analysis. The inventor suggests that steric clashes still will occur in the context of EEEV-143 expressed as a polymeric IgA molecule (dimeric IgA complex with joining [J] chain) as suggested by the reduction in the detected binding strength of this molecule compared to recombinant IgG1 or Fab molecules. The bulkiness of a polymeric IgA may reduce the occupancy of SINV/EEEV particle binding sites. Optimal in vitro neutralization of SINV/EEEV occurs as a polymeric IgA compared to Fab molecule, as there is >200-fold reduction in neutralization potency. Thus, the inter-spike cross-linking observed for EEEV-143 may require a bivalent (IgG) or tetravalent (IgA) antibody interaction for optimal neutralization of SINV/EEEV.

A neutralizing CHIKV mAb similar to EEEV-143, designated CHK-265, was characterized previously (Fox et al., 2015). CHK-265 is a broadly neutralizing and protective arthritogenic alphavirus mAb that inhibits viral entry and egress from cells. The ~16 Å cryo-EM reconstruction of CHIKV 181/25 particles in complex with CHKV-265 Fab molecules displays binding of three Fab molecules to each trimeric spike (q3 and i3). Inter-spike cross-linking was observed between two E2 protomers through recognition of domain B residues on one protomer and contacts domain A residues on an adjacent protomer. This binding leads to movement of domain B further over the E1 fusion loop and repositioning of domain A upon binding. CHK-265 Fab constant domain contacts also were observed across the two-fold axis further supporting the cross-liking mechanism of virus particles by CHK-265 as an IgG molecule. In contrast, EEEV-143 recognizes residues within domain B on one protomer and does not appear to induce conformational changes upon binding. Similarly, the constant domain Fab contacts observed for EEEV-143 around the 2-fold axis suggests that EEEV-143 may form inter-spike cross-links as an IgG or IgA molecule. The reduction in neutralization of EEEV-143 as a Fab molecule suggests that this mechanism is important for optimal neutralization of EEEV-143 at this site.

EEEV is classified as a USDA/CDC Select Agent due to potential for aerosolization and use as a bioterrorism agent. To mimic potential exposure of EEEV as a bioterrorism agent, aerosol challenge has been studied in mice and non-human primates (Phelps et al., 2019; Trobaugh et al., 2019; Wirawan et al., 2019). In this approach, mice were inoculated with EEEV via the aerosol route to assess the pre- or post-exposure treatment efficacy of EEEV-33 (IgG1) and EEEV-143 (IgA1). When given 24 hours before infection, EEEV-33 or EEEV-143 each protected mice with 91 or 100% survival compared to the control, respectively. When administered 24 hours after EEEV inoculation, EEEV-33 treated mice with 27% survival whereas EEEV-143 treated mice with 20 to 80% survival compared to the control. This experimental animal aerosol challenge model is stringent, since the rapid kinetics of viral replication in the central nervous system quickly decreases the likelihood of antibody-mediated protection. These studies suggest that there is need to study the in vivo efficacy in more detail, as multiple factors could affect efficacy including the timing for antibody administration, virus inoculation timing and concentration, route of virus infection, and antibody isotype and transcytosis across the mucosa and blood-brain barrier to achieve post-exposure treatment of EEEV via the aerosol route. As EEEV-33 and EEEV-143 recognize two different antigenic sites on the E2, a potential combination therapy with EEEV-33 and EEEV-143 might have greater efficacy and decrease the likelihood of viral escape mutant viruses generated in vivo.

Soon after EEEV aerosol challenge, virus-induced lesions are observed in the olfactory bulb (Phelps et al., 2019). The spread and course of EEEV infection within the brain parenchyma corresponds with the severity of olfactory bulb lesions (Phelps et al., 2019). Once virus entry into the brain occurs, it becomes challenging to neutralize the virus sufficiently to allow for control of spread and survival (Morens et al., 2019). One of the difficulties in treatment of EEEV is the requirement for antibodies to cross the blood-brain barrier (BBB) (Morens et al., 2019), which limits transport of molecules >400 Da (Neves V, 2016). During viral infection, disruption of the BBB occurs, allowing for infiltration of immune cells and larger molecules, such as antibodies (Metcalf et al., 2013; Metcalf and Griffin, 2011). However, with alphaviruses in the mouse model, the breakdown of the BBB is a late event in the disease course (Salimi et al., 2020) and the inflammatory consequences of viral replication result in neurological deterioration, making it difficult to recover after extensive infection (Griffin, 2016; Metcalf and Griffin, 2011). Developing molecules that cross this barrier more efficiently, such as through receptor-mediated transcytosis, might enhance the efficacy of therapeutic antibodies for EEEV infection (Pulgar, 2018).

Here, the inventor describes the isolation and characterization of a neutralizing human antibodies against EEEV. These studies provide molecular and structural bases of neutralization of EEEV by human mAbs and suggest several future research directions that could provide treatment options for patients. These include defining the importance of mucosal IgA and avidity interactions for optimal neutralization of EEEV, the correlates of antibody-mediated protection, and mechanisms for enhancing antibody transport across the BBB in vivo. Overall, the studies described here may help inform rationale structure-guided vaccine design and identify possible correlates of protection for lead therapeutic candidates against EEEV, and possibly other encephalitic alphaviruses.

Example 6—Efficacy of mAbs in a Lethal Mouse Model

Summary. Various monoclonal antibodies with specificity to eastern equine encephalitis virus (EEEV) were generated and some show protective activity after aerosol challenge of mice with EEEV. Neutralizing and non-neutralizing antibodies have been shown to be protective in mouse models. The purpose of this study is to evaluate these antibodies in an EEEV peripheral challenge model.

C57BL/6 mice, challenged s.c. with the FL93-939 strain of EEEV demonstrate morbidity and mortality. The mice succumb to disease by around 9 days post-virus injection and show various signs of neurological disease. This model has been used to identify effective intervention strategies to prevent or treat infection. Survival, weight change, viremia and viral titer in the brain are used as disease parameters to determine the efficacy of treatment with antiviral agents.

Animals. 115 C57BL/6 mice supplied by Jackson Laboratories were used. Mice were assigned by weight to experimental groups and individually marked with ear tags.

Virus. Eastern equine encephalitis virus (strain FL93-939). A challenge dose of $10^{3.3}$ $CCID_{50}$ was administered via bilateral s.c. injections in a total volume of 0.2 mL. Test agent: rEEEV-33, rEEEV-143, rEEEV-106, rEEEV-27, rEEEV-21, EEEV-373, EEEV-352, EEEV-346, EEEV-138, EEEV-109, and rDENV-2D22 were provided by Vanderbilt University Medical Center for testing in the mouse model.

Infectious cell culture assay. Virus titer was quantified using an infectious cell culture assay where a specific volume of either tissue homogenate or serum was added to the first tube of a series of dilution tubes. Serial dilutions were made and added to Vero cells. Three days later cytopathic effect (CPE) was used to identify the end-point of infection. Four replicates were used to calculate the 50% cell culture infectious doses ($CCID_{50}$) per mL of plasma or gram of tissues.

Experiment Design. Mice were challenged with EEEV via bilateral SC injections. Animals were treated with antibodies at doses of 10 mg/kg or 100 μg/kg via a single IP injection 24 hours post-virus challenge. Animals were monitored until 21 days post-virus inoculation (dpi) for disease signs and survival. Individual weights were recorded daily 0-10 dpi and on 14 and 18 dpi. Serum was collected from all mice 3 dpi for assessment of serum viremia.

Statistical analysis. Survival data were analyzed using the Wilcoxon log-rank survival analysis and all other statistical analyses were done using one-way ANOVA using a Bonferroni group comparison (Prism 5, GraphPad Software, Inc).

Ethics regulation of Laboratory animals. This study was conducted in accordance with the approval of the Institutional Animal Care and Use Committee of Utah State University (Protocol #10025). The work was done in the AAALAC-accredited Laboratory Animal Research Center of Utah State University. The U. S. Government (National Institutes of Health) approval was renewed 9 Mar. 2018 (PHS Assurance no. D16-00468) in accordance with the National Institutes of Health Guide for the Care and Use of Laboratory Animals (Revision; 2015).

Results and Discussion. Mice were infected with EEEV, followed by treatment 24 hours later. Ten antibodies were tested to verify in vivo efficacy. Animals were monitored for survival, weight change and viremia for 21 days after virus challenge.

Figure 32:
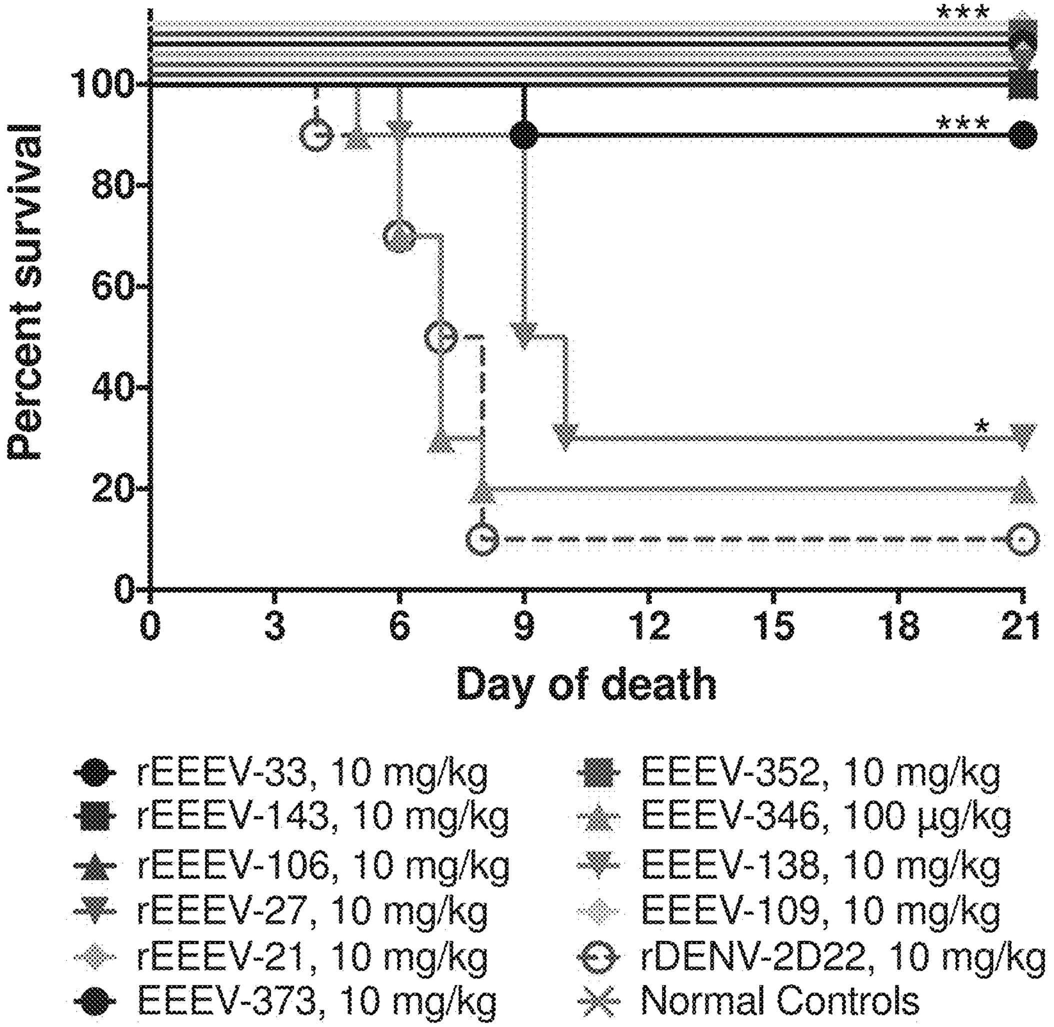
FIG. 32. Mortality curves of C57BL/6 mice after challenge with EEEV and treatment with various monoclonal antibodies (***P<0.001, *P<0.05 as compared to negative control rDENV-2D22 treatment).

Treatment with 7 of the 10 antibodies resulted in complete protection at a dose of 10 mg/kg administered as a single IP treatment 24 h after virus challenge (FIG. 32, Table A). Effective antibodies included rEEEV-143, rEEEV-106, rEEEV-27, rEEEV-21, EEEV-373, EEEV-352 and EEEV-109. A single death (90% survival) was observed in the group of mice treated with rEEEV-33, which was significantly improved (P<0.001) as compared with an isotype control (rDENV-2D22) (FIG. 32, Table A). There was appreciable mortality in groups treated with EEEV-346 (20% survival) and EEEV-138 (30% survival), suggesting these antibodies are less effective in this mouse model. A significant (P<0.05) improvement, however, was observed for the survival curve of the EEEV-138 treatment group as compared with the isotype control (FIG. 32, Table A). Overall, the majority of the tested antibodies (80%) were active in protecting mice from EEEV mortality.

Figure 33:
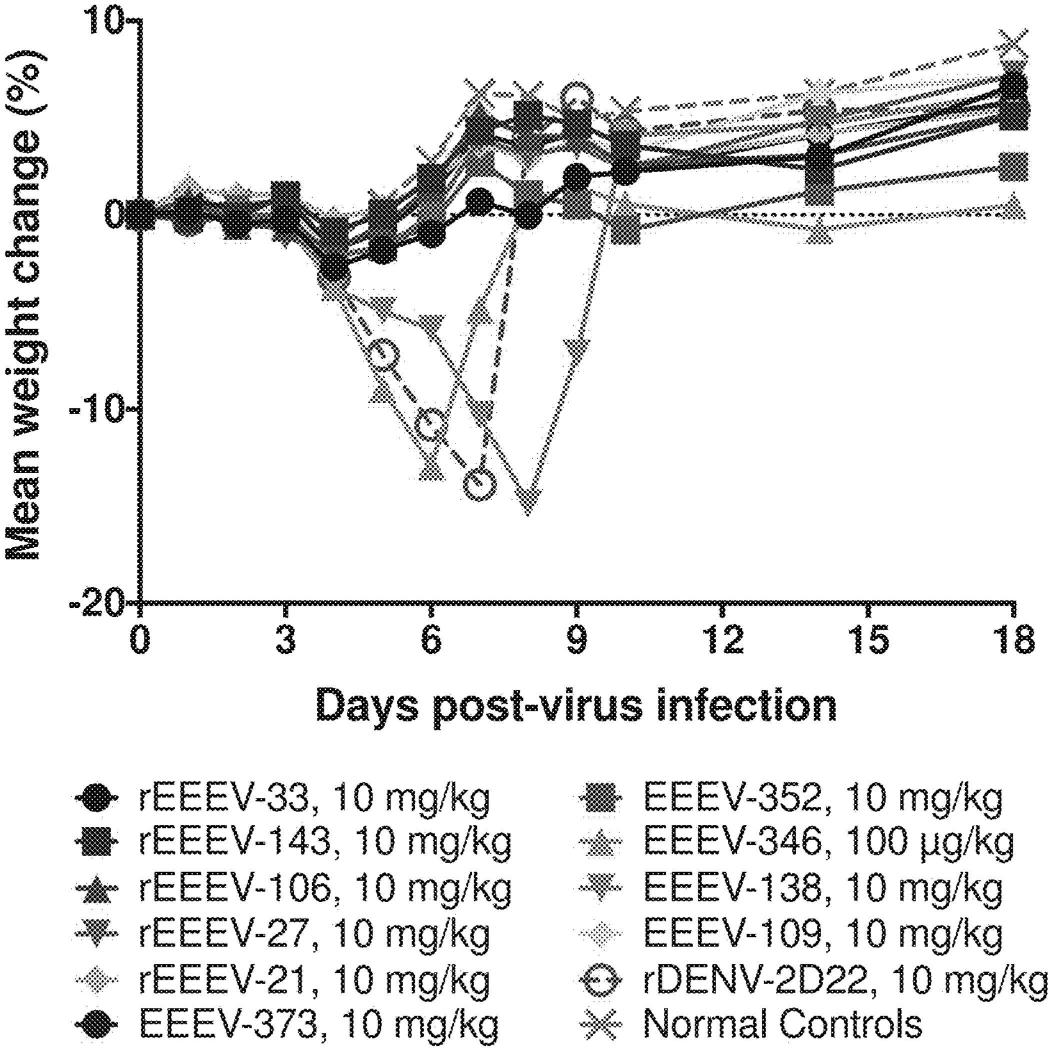
FIG. 33. Average percent weight change of animals inoculated with EEEV and treated with various mAbs.
Figure 34:
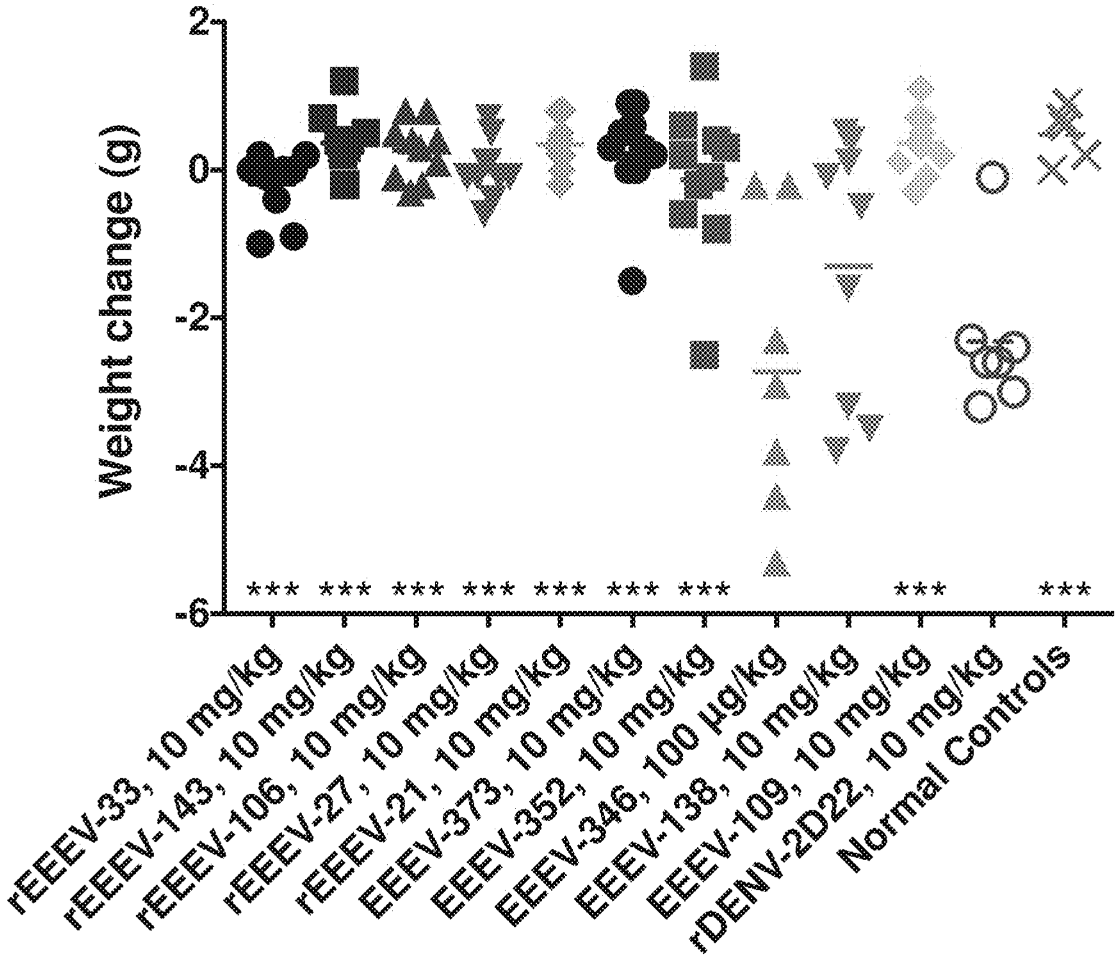
FIG. 34. Weight change between 0 and 6 dpi of animals inoculated with EEEV and treated with various mAbs (***P<0.001 as compared to negative control rDENV-2D22 treatment).

Weight change curves correlated with morality, where groups that had mortality greater than or equal to 70% had average weight curves similar to the isotype control-treated group (FIG. 33). All other averages were similar to that of the normal control group. Indeed, a significantly (P<0.001) improved weight change between 0 and 6 dpi was observed in groups that had 90-100% survival as compared with that of isotype control treated mice (FIG. 34, Table A). Similar weight loss was observed for groups treated with EEEV-346 and EEEV-138 with those treated with the Ab control rDENV-2D22 (FIG. 34, Table A).

Figure 35:
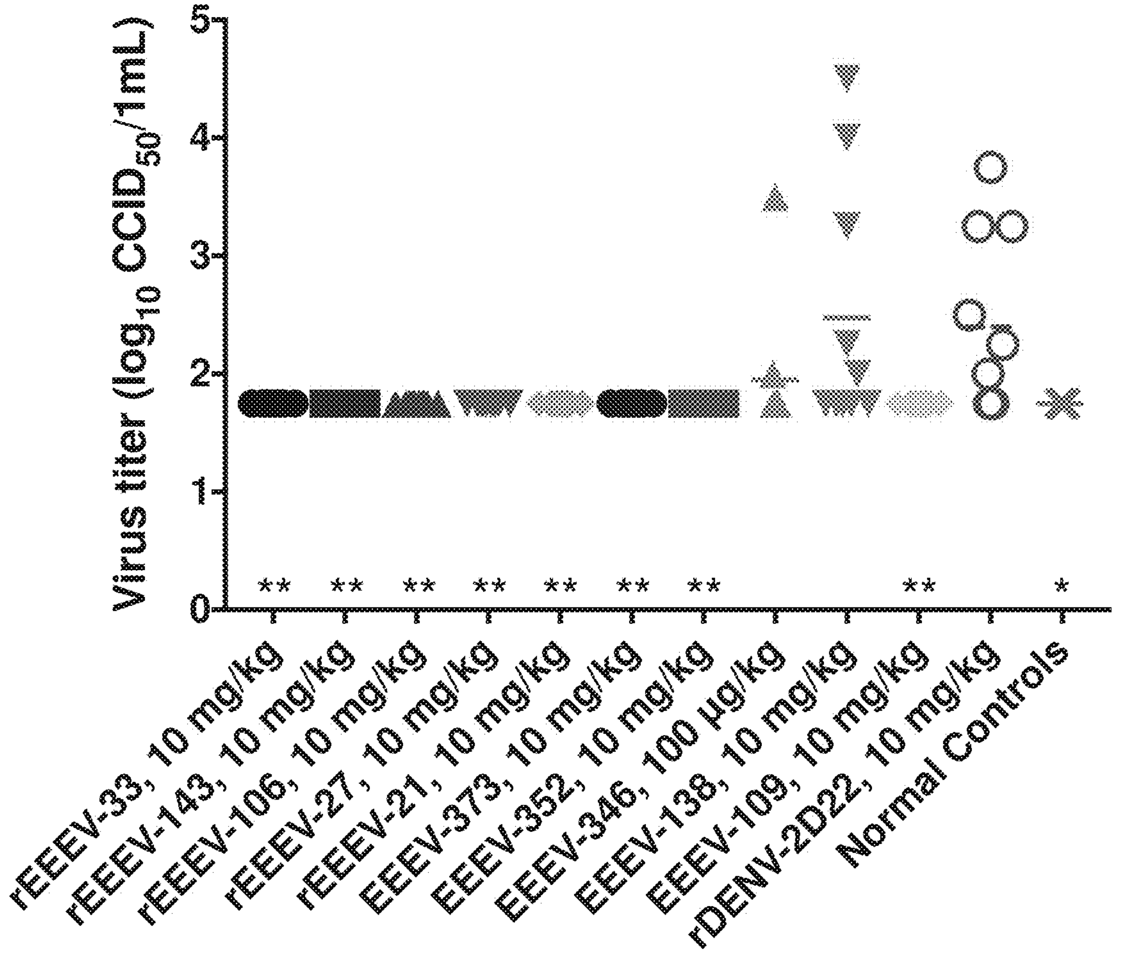
FIG. 35. Viral titers from serum collected 3 dpi from animals inoculated with EEEV and treated with various mAbs (**P<0.01, *P<0.05 as compared to negative control rDENV-2D22 treatment).

Virus titers were generally undetectable in groups treated with effective antibodies (FIG. 35, Table 1). The majority of mice treated with the isotype control Ab had detectable virus, although several mice had titers below the limit of detection (FIG. 35). A similar profile was observed in the group of mice treated with EEV-138, while mice treated with EEEV-346 generally had undetectable viremia on 3 dpi (FIG. 35). Overall, virus titers correlated with survival and weight change, which is similar to previous studies.

Conclusions. Treatment of EEEV-infected mice with rEEEV-33, rEEEV-143, rEEEV-106, rEEEV-27, rEEEV-21, EEEV-373, EEEV-352 and EEEV-109 resulted in significant improvement in all measured disease parameters and suggest these antibodies are effective in vivo against lethal EEEV. Further studies may investigate certain of these to determine minimal effective doses as well as efficacy of combination of antibodies that have different targets. Low or no efficacy was observed for EEEV-346 and EEEV-138, which in general were similar to treatment with the isotype control.

TABLE A

The effect of treatment with various monoclonal antibodies on a mouse model of EEEV disease
Animals: C57BL/6 mice
Duration of experiment: 21 days
Virus/route: FL93-939 EEEV/s.c.
Treatment vol./schedule: 0.1 mL, single injection 24 h post-virus inoculation

| Treatment | Virus | Alive/total | MDD[a] ± SD | Mean wt. change[b] (g) ± SD | Viremia[c] |
|---|---|---|---|---|---|
| rEEEV-33, 10 mg/kg | EEEV | 9/10 | 9.0*** | −0.2 ± 0.4*** | 1.8 ± 0.0** |
| rEEEV-143, 10 mg/kg | EEEV | 10/10 | 21.0 ± 0.0*** | 0.4 ± 0.4*** | 1.8 ± 0.0** |
| rEEEV-106, 10 mg/kg | EEEV | 10/10 | 21.0 ± 0.0*** | 0.3 ± 0.4*** | 1.8 ± 0.0** |
| rEEEV-27, 10 mg/kg | EEEV | 10/10 | 21.0 ± 0.0*** | 0.0 ± 0.4*** | 1.8 ± 0.0** |
| rEEEV-21, 10 mg/kg | EEEV | 10/10 | 21.0 ± 0.0*** | 0.3 ± 0.3*** | 1.8 ± 0.0** |
| EEEV-373, 10 mg/kg | EEEV | 10/10 | 21.0 ± 0.0*** | 0.2 ± 0.7*** | 1.8 ± 0.0** |
| EEEV-352, 10 mg/kg | EEEV | 10/10 | 21.0 ± 0.0*** | −0.1 ± 1.0*** | 1.8 ± 0.0** |
| EEEV-346, 100 μg/kg | EEEV | 2/10 | 6.6 ± 0.9 | −2.7 ± 2.0 | 2.0 ± 0.6 |
| EEEV-138, 10 mg/kg | EEEV | 3/10 | 8.9 ± 1.3* | −1.3 ± 1.8 | 2.5 ± 1.1 |
| EEEV-109, 10 mg/kg | EEEV | 10/10 | 21.0 ± 0.0*** | 0.4 ± 0.4*** | 1.8 ± 0.0** |
| rDENV-2D22, 10 mg/kg | EEEV | 1/10 | 6.9 ± 1.0 | −2.3 ± 1.0 | 2.4 ± 0.8 |
| Normal Controls | — | 5/5 | 21.0 ± 0.0** | 0.5 ± 0.4*** | 1.8 ± 0.0* |

[a]Mean day of death.
[b]Difference between weight on 0 and 6 days post-virus challenge representing maximal weight change within this study.
[c]Serum was collected 3 dpi. Values are mean virus titer ± SD.
***P < 0.001,
**P < 0.01,
*P < 0.05 as compared to rDENV-2D22 treatment.

TABLE 1

NUCLEOTIDE SEQUENCES FOR ANTIBODY VARIABLE REGIONS

| Clone | SEQ ID NO: | Chain | Variable Sequence Region |
|---|---|---|---|
| EEEV-103 | 1 | heavy | CAGGTGCAGCTGGTGGAGTCTGGGGGAGGCGTGGTCCAGCCTGGGAGGTCCCTGAGACTCTCTTGTGCAGCGTCTGGATT CCACTTCGGTAGTTATGGAATGCACTGGTTCCGCCAGGCTCCAGGCAAGGGACTGGAGTGGGTGGCAGTTACGTGGTATG ATGGAAGTAATAAAGACTATGTAGACTCCGTGAAGGGCCGATTCACCATCTCCAGAGACAATTCCGAGAACACATTGTATC TGCAAATGACCAGCCTGAGAGCCGAGGACACGGCTGTATATTACTGTGCGAGAGATGGAGGCAGTACCTGGCCCCCTGAT TATTGGGGCCAGGGAACCCTGGTCATCGTCTCCTCA |
| | 2 | light | CAGTCTCCAGCCACCCTGTCTGTGTCTCCGGGGGAAAGAGCCACCCTCTCCTGCAGGGCCAGTCAAAGTGTTAACAGAAAC TTAGCCTGGTACCAGCACAAACCTGGCCAGGCTCCCAGGCTCCTCATCTATGGTGCATCCACCAGGGTCACTGATATCCCAG CCAGGTTCAGTGGCAGTGGGTCTGGGACAGAGTTCACTCTCACCATCAGCAGCCTGCAGTCTGAAGATTTTGCAATTTATTA CTGTCAGCAGTATAATAACTGGCCTCGATTCACTTTCGGCCCTGGGACCAAAGTGGATATCAAA |

TABLE 1-continued

NUCLEOTIDE SEQUENCES FOR ANTIBODY VARIABLE REGIONS

| Clone | SEQ ID NO: | Chain | Variable Sequence Region |
| --- | --- | --- | --- |
| EEEV-104 | 3 | heavy | CAGGTGCAGCTGGTGCAGTCTGGGGCTGAGGTGAAGAAGCCTGGGGCCTCAGTGAAGGTCTCCTGCAAGGCTTCTGGATA<br>CACCTTCACCGACTACTATATGCACTGGGTGCGACAGGCCCCTGGACAAGGGCTTGAGTGGATGGGATGGATCAACCCTAA<br>CAGTGGTGGCACAAACTATGCACAGAAGTTTCAGGGCAGGGTCACCATGACCAGGGACACGTCCATCAGCACAGCCTACA<br>TGGAGCTGAGCAGGCTGAGATCTGACGACACGGCCGTGTATTACTGTGCGTGCGTGGATACAGCTATGGGCTGGGGCTTT<br>GACTACTGGGGCCAGGGAACCCTGGTCACCGTCTCCTCA |
| | 4 | light | GATGTTGTGATGACTCAGTCTCCACTCTCCCTGCCCGTCACCCTTGGACAGCCGGCCTCCATCTCCTGCAGGTCTAGTCAAA<br>GCCTCGTATACAGTGATGGAAACACCTACTTGAATTGGTTTCAGCAGAGGCCAGGCCAATCTCCAAGGCGCCTAATTTATA<br>AGGTTTCTAACCGGGACTCTGGGGTCCCAGACAGATTCAGCGGCAGTGGGTCAGGCACTGATTTCACACTGAAAATCAGCA<br>GGGTGGAGGCTGAGGATGTTGGGGTTTATTACTGCATGCAAGGTACACACTGGCCTCCGGCTTTCGGCGGAGGGACCAAG<br>GTGGAGATCAAA |
| EEEV-106 | 5 | heavy | CAGGTGCAGCTGCAGGAGTCGGGCCCAGGACTGGTGAAGCCTTCACAGACCCTGTCCCTCACCTGCACTGTCTCTGGTGGC<br>TCCGTCAGCAGTGGTGATTACTACTGGAATTGGATCCGCCAGCACCCACAGAAGGGCCTGGAGTGGATTGGGTACATCTTT<br>AACGGTGGGAGTACCAACTACAACCCGTCCGTCCAGAGTCGAGCCACCATATCGGTTGACACGTCTAAGAACGTGCTCTCC<br>CTGCAGCTGACTTCTGTGACTGCCGCGGACAGTGCCGTGTATTATTGTGCGAGAGATTGGGAACACTGTTTCAATGGTATA<br>TGCTACTACTACTTTGACTACTGGGGCCAGGGAACCCTGGTCACCGTCTCCTCC |
| | 6 | light | GACATCCAGATGACCCAGTCTCCATCCTCCCTGTCTGCATCTGTAGGAGACAGAGTCACCATCACTTGCCGGGCAAGTCAGA<br>GCATTAAGAACTATTTAAATTGGTATCAACAGAAACCAGGGACAGCCCCTAAGGTCCTGATCTTTGGTGCATCTAGTTTGCA<br>AAGTGGGGTCCCATCAAGGTTCAGTGGCAGTGGATCTGGGACAGATTTCACTCTCACCATCAGCAGTCTGCAACCTGAAGA<br>TTTTGCAACTTACTATTGTCAACAGAGTTACAGTACCCTCCGGACTTTCGGCGGAGGGACCAAGGTGAACATCAAA |
| EEEV-107 | 7 | heavy | CAGGTGCAGCTGGTGGAGTCTGGGGGAGGCGTGGTCCAGCCTGGGAGGTCCCTGAGACTCTCCTGTGCAGCGTCTGGCTT<br>CACCTTGAATAATTATGGCATTCACTGGGTCCGTCAGGCTCCAGGCAAGGGGCTGGAGTGGGTGGCACTTATATGGTTTGA<br>TGGGACTACCAAATACAACGGAGACTCCATGAAGGGCCGATTCACCATCTCCAGAGACAATTCCAAGAACACAGTTTATCT<br>GCAAATGAACAGCCTGAGAGCCGAGGACACGGCTGTGTATTATTGTGCGAGAGCCACATACGATTTTTGGAGTGGCGAGC<br>CCATTGGCCACTACTACATGGACGTCTGGGGCAAGGGGACCACGGTCACCGTCTCCTCA |
| | 8 | light | CAGACTGTGGTGACTCAGGAGCCCTCACTGACTGTGTCCCCAGGAGGGACAGTCACTCTCACCTGTGCTTCCAACACTGGA<br>GCAGTCACCAGTGATTTCTATCCAAACTGGTTCCAGCAGAAACCTGGACAAGCACCCAGGGCATTGATTTATAGTACAAAC<br>AACAAACACTCTTGGACCCCTGCCCGGTTCTCAGGCTCCCTCCTTGGGGGCAAAGCTGCCCTGACAGTGTCAGGTGTGCAG<br>CCTGAGGACGAGGCTGAGTATTACTGCCTGCTCTACTATGGTGGGGCTCAGGTCTATGTCTTCGGAACTGGGACCAAGGTC<br>ACCGTCCTA |
| EEEV-109 | 9 | heavy | GAGGTGCAGCTGTTGGAGTCTGGGGGAGGCTTGGTACAGCCTGGGGGGTCCCTGAGACTCTCCTGTGCAGCCTCTGGATT<br>CATCTTTGACATCTATGCCATGAACTGGGTCCGCCAGGCTCCAGGGAAGGGGCTGGAGTGGGTCTCGGCTATTAGTGGTA<br>GTGGTAGTACTACATACTATGCAGATTCTCTGAAGGGCCGATTCACCATTTCCAGAGACAATTCCAAGAACGCGGTGTATCT<br>ACAAATGAAGAGCCTGAGAGTCGACGACACGGCCGTATATTACTGTGCGAAAGGTTCTGGGGAGCAGCGCTATTACTTCT<br>ACCCCTTGGACTTCTGGGGCACAGGGACCACGGTCACCGTCTCCTCA |
| | 10 | light | TCATATGTGCTGACTCAGCCACCCTCGGTGTCAGTGGCCCCAGGACAGACGGCCAGGATAACCTGTGGGGAAGACAACAT<br>TGGAAGTAAAAGTGTGCACTGGTACCAGCAGAGGCCAGGCCAGGCCCCTGTTCTGGTCGTCTATGATGATAAGTATCGGC<br>CCTCAGGGATCCCTGAGCGATTCTCTGGCTCCAACTCTGGGAACACGGCCACCCTGACCATCAGCAGGATCGAAGCCGGGG<br>ATGAGGCCGACTATTACTGTCAGGTGTGGGATAGTCGTTATGATCGTCATGTGGTTTTCGGCGGAGGGACCAAGCTGACC<br>GTCCTA |
| EEEV-12 | 11 | heavy | CAGGTGCAGCTGGTGGAGTCTGGGGGAGGCGTGGTCCAGCCTGGGAGGTCCCTGAGACTCTCCTGTGAAGCGTCTGGATT<br>CTACTTCAATAGTTATGGCATGCACTGGGTCCGCCAGGCTCCAGGCAAGGGGCTGGAGTGGGTGGCAGTTATATGGTATG<br>ATGGAAGTACGAAGACCTATGTAGAGTCCGTGATGGGCCGATTCACCATCTCCAGAGACAATTCCAAGAACACGCTGTATC<br>TACAAATGAACAGCCTGAGAGTCGAGGACACGGCTGTGTATTACTGTGCGAGGGCCAGTGGCTGGGAGATTGACTACTGG<br>GGCCAGGGAACTCTGGTCACCGTCTACTCA |
| | 12 | light | CAGTCTGCCCTGACTCAGCCTGCCTCCGTGTCTGGGTCTCCTGGACAGTCGATCACCATCTCCTGCACTGGAACCAGCAGTG<br>ACGTTGGTGGTTATAATTATGTCTCCTGGTACCAACAGCACCCAGGCAAAGCCCCCAAACTCATCATTTTTGATGTCAATAAT<br>CGGCCCTCAGGGGTTTCTAATCGCTTCTCTGGCTCCAAGTCTGTCAACACGGCCTCCCTGACCATCTCTGGGCTCCGGGCTG<br>AGGACGAGGCTGATTATTACTGCAGCTCATATACAGCCAGCAGCACTCTCGTATTCGGCGGGGGGACCAAGCTGACCGTCC<br>TA |
| EEEV-126 | 13 | heavy | CAGGTGCAGCTGGTGCAGTCTGGGGCTGAGGTGAGGAAGCCGGGGTCCTCGGTGAAGGTCTCCTGCAAGGCTTCTGGAG<br>GCACCTTCAGCAATTATGATATCAACTGGGTGCGGCAGGCCCCTGGACAAGGGCTTGAGTGGATGGGAGGGATCATCCCT<br>ATCTTTGATACACCAAACTACGCACAGAAGTTCCAGGGCAGAGTCACCATTACCGCGGACGAGTCCACGACGAAAGCCTAC<br>ATGGAGCTGAGCAGCCTGAGATCTGAAGACACGGCCGTGTATTACTGTGCGAGAGGGGCGTCCCGATATTGTAATAGCAC<br>CAGCTGCTATAGAATTTTTGACTACTGGGGCCAGGGAAGCCTGGTCACCGTCTCCTCA |
| | 14 | light | GACATCCAGATGACCCAGTCTCCTTCCACCCTGTCTGCATCTGTAGGAGACAGAGTCACTATCACTTGCCGGGCCAGTCAGA<br>CTATTGGTGATTGGCTGGCCTGGTATCAGCAGAAACCAGGGAAAGCCCCTAAACTCCTGATCTATAAGGCGTCTTTTTAGA<br>AGGTGGGGTCCCATCAAGGTTCAGCGGCAGTGGATCTGGGACAACATTCACTCTCACCATCAGCAGCCTGCAGCCTGATGA<br>CTTTGCAACTTATTACTGCCAACACTATAACACCTATGCGTACAGTTTTGGCCAGGGGACCAAGCTGGAGATCAAA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EEEV-127 | 15 | heavy | CAGGTGCAGCTGGTGCAGTCGGGGGCTGAGGTGAAGAAGCCTGGGTCCTCGGTGAAGGTCTCCTGCAAGGCTTCTGGAG<br>GCACCTTCAGCGACTATAGTATCAACTGGGTGCGACAGGCCCCTGGACAAGGGCTTGAGTGGATGGGAGGGATCATCCCT<br>ATCGTTGGATCAGTCAACTACGCACAGAAGTTCCAGGGCAGAGTCACGATTACCGCGGACGACTCCACGAGCACAGCCTAC<br>ATGGAACTGAGCAGCCTGAGATCTGAAGACACGGCCGTATATTACTGTGCGACAGAAATAGGGATAGCAGTGGCTGGTAC<br>GATCTACTACGGTATGGACGTCTGGGGCCAAGGGACCACGGTCACCGTCTCCTCA |
| | 16 | light | GAAATTGTGTTGACACAGTCTCCAGCCACCCTGTCTTTGTCTCCAGGGGAAAGAGCCACCCTCTCCTGCAGGGCCAGTCAG<br>AGTGTTAGCAGCTACTTAGCCTGGTACCAACAGAAACCTGGCCAGGCTCCCAGGCTCCTCATCTATGATCCATCCAACAGG<br>GCCACTGGCATCCCAGCCAGGTTCAGTGGCAGTGGGTCTGGGACAGACTTCACTCTCACCATCAGCAGCCTAGAGCCTGAA<br>GATTTTGCAGTTTATTACTGTCAGCACCGTAGCAACTGGCCTCCGGGAACGTACACTTTTGGCCAGGGGACCAAGCTGGAG<br>ATCAAA |
| EEEV-129 | 17 | heavy | CAGGTGCAGCTGGTGGAGTCTGGGGGAGGCGTGGTCCAGCCTGGGAGGTCCCTGAGACTCTCCTGTGCAGCCTCTGGATT<br>CACCTTCAGTACCTATGCTATGCACTGGGTCCGCCAGGCTCCAGGCAAGGGGCTGGAGTGGGTGGCACTTCTATCATATGA<br>TGGAAGTAGTAAATACTACGCAGACTCCGTGAAGGGCCGATTCACCATCTCCAGAGACAATTCCAAGAACACGCTGTATCT<br>GCAAATGAGCAGCCTGAGAGCTGACGACACGGCTATATATTACTGTGCGAAAATACCTGTTAGTATGGTTCGGGGAGTTAT<br>GGAGTACGCTATGGACGTCTGGGGCCAAGGGACCACGGTCACCGTCTCCTCA |
| | 18 | light | TCCTATGTGCTGACTCAGCCACCCTCGGTGTCAGTGGCCCCAGGACAGACGGCCAGGATTACCTGTGGGGGAAACAACATT<br>GGAAGTAACACTGTGCACTGGTACCAGCAGAAGCCAGGCCAGGCCCCTGTGCTGGTCGTCTATGGTGATAGCGACCGGCC<br>CTCAGGGATCCCTGAGCGATTCTCTGGCTCCAACTCTGGGAACACGGCCACCCTGACCATCAGCAGGGTCGAAGCCGGGG<br>ATGAGGCCGACTATTACTGTCAGGTGTGGGATAGTAGTAGTGATCATGTGGTATTCGGCGGAGGGACCAAGCTGACCGTC<br>CTA |
| EEEV-138 | 19 | heavy | CAGGTTCAACTGGTGCAGTCTGGAACTGAGGTGAAGAAGCCTGGGGCCTCAGTGAAGGTCTCCTGCAAGGCCTCTGGTTA<br>CACTTTTACCAGTTATGGTTTCACCTGGGTGCGACAGGCCCCTGGGCAAGGGCTTGAGTGGATGGGGTGGATCAGTTCTTA<br>taataataacacaaactatgcacagaagttccagggcagagtcaccatgaccacagacacatccacgagcacagcctacat<br>GGAGCTGAGGAGCCTGAGATCTGACGACACGGCCGTCTTTTACTGTGCGAGAGATCGTTTTAGTGGCTACGATTTGGGCTA<br>CTGGGGCCAGGGAACCCTAGTCACCGTCTCCTCA |
| | 20 | light | CAGTCTGCCCTGACTCAGCCTGCCTCCGTGTCTGGGTCTCCTGGACAGTCGATCACCATCTCCTGCACTGGAACCAGCAGTG<br>ATGTTGGGAGTTATAACCTTGTCTCCTGGTACCAACAGCACCCAGGCAAAGCCCCCAAACTCATGATTTATGAGGTCACTAA<br>GCGGCCCTCAGGGGTTTCTAATCGCTTCTCTGGCTCCAAGTCTGGCAACACGGCCTCCCTGACAATCTCTGGGCTCCAGGCT<br>GAGGACGAGGCTGATTATTACTGCTGCTCATTTGCAGGTAGGAGCGCTCCATTCGGTACTGGGACCAAGGTCACCGTCCTA |
| EEEV-141 | 21 | heavy | CAGGTGCAGCTGGTGCAGTCTGGGGCTGAGGTGAAGAAGCCTGGATCCTCGGTGAAGGTCTCCTGCAAGGTTTCTGGGG<br>GCACCTTCAGTCACTTTGCCATCATCTGGGTGCGACAGGCCCCTGGACAGGGACTTGAGTGGATGGGAGGGATCATCCCA<br>GTCTTTGGCACAACAAACTACGTAGAGAAGTTCCAGGGGAGAGTCACGATTACCGCGGACGAGTCCAGGAGCACAGCCTA<br>CATGGAGTTGACTAGACTGACCTTTGAAGACACGGCCGTCTATTACTGTGCGAAAGGCTTTAGGGCGGGAGGAGCTAATA<br>CCGACTTCGACTACTGGGGCCAGGGAACCCTGGTCACCGTCTCCTCA |
| | 22 | light | CAGCTTGTAGTGACTCAATCGCCCTCTGCCTCTGCCTCCCTGGGAGCCTCGGTCAAGTTCACCTGCACTCTGAGCAGTGGGC<br>ACAGCACCTACTCCATCGCCTGGCATCAGCAACACCCAGCGAGGGGCCCTCGGTATTTGATGAGGGTTAACAGTGATGGCA<br>GCCACACCAAGGGGGACGGGATCCCTGATCGCTTCTCAGGCTCCAGCTCTGGGGCTGATCGCTTCCTCACCATCTCCAGACT<br>CCAGTCTGAGGATGAGGCTGACTATTACTGTCAGACCTGGGGCACTGGCATTCAAGTTGTTTTCGGCGGAGGAAGCAAGTT<br>GACCGTCCTA |
| EEEV-143 | 23 | heavy | CAGGTGCAGCTGGTGGAGTCTGGGGGAGGCGTGGTCCAGCCTGGGAGGTCCCTGAGACTCTCCTGTGCAGCCTCTGGATT<br>CACCTTCAGTAATTATGGCATCCACTGGGTCCGCCAGGCTCCAGGCAAGGGGCTGGAGTGGGTGGCAGTTATCTCATATGA<br>TGGAAGACATAAATACATAGCAGACCCCGTGAAGGGCCGATTCACCATCTCCAGAGACAATTCCAAGAACATGCTGTATCT<br>GCAAATGAACAGCCTGAGAACTGAGGACACGGCTGTCTATTACTGTGCGAAGGATACCAGTGGCTGGTACGAATTCTTTGA<br>CTCCTGGGGCCAGGGAATCCCGGTCACCGTCTCCTCA |
| | 24 | light | GAAATAGTGATGACGCAGTCTCCAGCCACCCTGTCTGTGTCTCCAGGGGAGAGAGCCACCCTCTCTTGTAGGGCCAGTCAG<br>AGTGTTGCCACCAACGTGGCCTGGTACCAGCAGAAACCTGGCCAGGCTCCCAGGCTCCTCATCTATGGTGCATCCACCAGG<br>GCCACTGGAATCCCGGCCAGGTTCAGTGGCAGTGGGTCTGGGACAGAGTTCACTCTCACCATCAGCAGCCTGCAGTCTGAG<br>GATTTTGCAGTTTATTATTGTCAGCAGTGCAATGACTGGCTGACGTTCGGCCAAGGGACCAAGGTGGAAATCAAA |
| EEEV-144 | 25 | heavy | CAGGTTCAGCTGGTGCAGTCTGGAGCTGAGGTGACGAAGCCTGGGGCCTCAGTGAAGGTCTCCTGCAAGACTTCTGGTTA<br>CACCTTTACCTACTATAATATCAGTTGGGTGCGACAGGCCCCTGGACAAGGGCTTGAGTGGATGGGATGGATCAGCGCTTA<br>CAGTGGTAACACACACTATGCACAGAAACTCCAGGGCAGAGTCACCATGACCATAGACACATCCACGAGCACAGCCTACAT<br>GGAGCTGAGGAGCCTGAGATCTGACGACACGGCCGTGTATTACTGTGCGAGAGATGGAGCCTCAGTACTACCACCTGCTT<br>CCGTCTACTACTCCTACATGGACGTCTGGGGCAAAGGGACCACGGTCACCGTCTCCTCA |
| | 26 | light | GACATCCAGATGACCCAGTCTCCATCCTCCCTGTCTGCATCTGTAGGAGACAGAGTCACCATCAGTTGTCGGGCAAGTCAG<br>AACATTAGCAGCTATTTAAATTGGTATCAGCAGAAACCAGGGAAAGCCCCTAAGGTCTTGATCTATGCTGCATCCAGTTTGC<br>AAAGAGGGGTCCCATCAAGGTTCAGTGGCAGTGGATCTGGGACAGATTTCACTCTCACCATCAGCAGTCTGCAACCTGAAG<br>ATTTTGCGACTTACTACTGTCAACAGAGTTACAGTACCCCTCGGACTTTTGGCCAGGGGACCAAGGTGGAGATCAAA |
| EEEV-145 | 27 | heavy | GAGGTGCAGCTGGTGGAGTCTGGGAGAGGCTTGGTCCAGCCTGGGGGGTCCCTGAGACTCTCCTGTGCAGCCTCTGGATT<br>CACCTTTAATATCTATTGGATGAGCTGGGTCCGCCAGGCTCCAGGGAAGGGGCTGGAGTGGGTGGCCAACATAAAACAAG<br>ACGGAAGTGAGAAATATTATGTGAATTCTGTGAAGGGCCGATTCACCATCTCCAGAGACAACGCCAAGTACTCACTGTATC<br>TGCAAATGAATAGCCTGAGAGCCGAGGACACGGCTGTGTATTACTGTGCGAGAGGATTCATAGGATATTGTAATAGTAAA<br>ACCTGCTCATATGACTTTGACTACTGGGGCCAGGGAGCCCTGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 28 | light | TCTTCTGAACTGACTCAGGACCCTGCTGTGTCTGTGGCCTTGGGACAGACAGTCAGGATCACATGCCAAGGAGACAGCCTCAGAAGTTTTTATGCAAGCTGGTACCAGCAGAAGCCAGGGCAGGCCCCTCTACTTGTCATCTACAATGAAAACAACCGGCCCTCAGGAATCCCAGACCGATTCTCTGGCTCCAGCTCAGGAAACACAGCTTCCTTGACCATCACTGGGACTCAGGCGGCAGATGACGCTGACTATTACTGTAGTTCCCGGGACAGCAGTGGTAACCATGTGCTCTTCGGCGGAGGGACCAAGCTGACCGTCCTA |
| EEEV-147 | 29 | heavy | CAGGTTCAGCTGGTGCAGTCTGGAGCTGAGGTGAAGAAGCCTGGGGCCTCAGTGAAGGTCTCCTGCAAGGCCTCTGGTTACACCTTTACCAACTATGGTATCACGTGGGTGCGACAGGCCCCTGGACAGGGGCTTGAGTGGATGGGATGGATCAGCGCTTACAATGGTAACACAGATTATGCGCAGAAGCTCCAGGGCAGAGTCACCATGACCACAGACACATCCACGAGCACAGCCTACATGGAACTGGGGAGCCTCAGATCTGACGACACGGCCGTGTATTACTGTGCGAGGGAACTATGGTTCGGGGACTTGGGCTACTGGGGCCAGGGAACCCTGGTCACCGTCTCCTCA |
| | 30 | light | GAAATTGTGTTGACGCAGTCTCCAGGCACCCTGTCTTTGTCTCCAGGGGAAAGAGCCACCCTCTCCTGCAGGGCCAGTCAGAGTGTGAGCCGCAGCAGCAGCAGCTACTTAGCCTGGTACCAGCAGAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTCACCATCAGCAGACTGGAGCCTGAAGATGTTGCAGTGTATTACTGTCAGCAGTATGGAAGTTCACCTCAGACTTTTGGCCAGGGGACCAAGCTGGAGATCAAA |
| EEEV-153 | 31 | heavy | GAAGTGCACCTGGTGGACTCTGGGGGAGGCTTGGAACAGCCTGGCAGGTCCCTGAGACTCTCCTGTGCAGCCTCTGGATTCACCTTTAGTGATTATGCCATGCACTGGGTCCGGCAAGCTCCAGGGAAGGGCCTGGAGTGGGTCTCAAGTATTAGTTGGAATAGTGGTAACATAGGCTATGCGGACTCTGTGAAGGGCCGATTCACCATCTCCAGAGACAACGCCAAGAACTCCCTGTATCTACAAATGAACACTCTGAAAACTGAGGACACGGCCTTCTATTACTGTGCAAGAGGCCCTTTTTTCAACTGGAATCCCACTAACTACTTTGACCACTGGGGCCAGGGAACCCTGGTCACCGTCTCCTCA |
| | 32 | light | GAAATTGTGTTGACGCAGTCTCCAGGCACCCTGTCTTTGTCTCCAGGGGAAAGAGCCACCCTCTCCTGCAGGGCCAGTCAGAGTGTTCCCAGCAGCTACTTAGCCTGGTACCAGCACAAACCTGGCCAGGCTCCCAGGCTCCTCATCTATGGTGCATCCAGCAGGGCCACTGGCATCCCAGACAGGTTCAGTGGCAGTGGGTCTGGGACAGACTTCACTCTAACCATCCGCAGACTGGAGCCTGAGGATTTTGCAGTGTACTACTGTCAGCAGTATGGTACGTCACCCCCCATGTACACTTTTGGCCAGGGGACCAAGCTGGAGATCAAA |
| EEEV-157 | 33 | heavy | CAGGTGCAAGTGGTGGAGTCTGGGGGAGGCGTGGTCCAGCCTGGGAGGTCCCTGAGACTCTCCTGTGCAGCCTCTGGATTCACCTTTACTAGTTATGGTATACACTGGGTCCGCCAGGCTCCAGGCAAGGGGCTGGAATGGGTGGCAGTTATATCGTATGATGGAAGTAATAGATTCTACGCAGACTCCGTGAAGGGCCGATTCACCATCTCCAGAGACAATTCTAAGAACACGTTGTATCTGCAAATGAACAGCCTGAGAGTTGAGGACACGGCTGTGTATTATTGTGCGAGAGGGAGGCTTTGTGTTGGTGATAGTTGCCACTCGGGGCCACTTGACTACTGGGGCCAGGGAACCCTGGTCACCGTCTCCTCA |
| | 34 | light | TCGTTTGAGCTGACGCAGCCACCCTCAATGTCCGTGTCCCCAGGACAGACAGCCAGGATCTCCTGCTCTGGAGATACATTGGGGAATAAATATGCTTACTGGTATCAACAGAAGCCAGGGCAGTCCCCTGTGCTGGTCATCTATCAAGATAACAAGCGGCCCTCAGGGATTCCTGAGCGATTCTCTGGCTCCAACTCTGGAAACACAGCCACTCTGACCATCAGCGGGACCCAGGCTATGGATTCGGCTGACTATTACTGTCAGGCGTGGGACAGCAGCGCTCATTATGTCTTCGGAACTGGGACCAAGGTCACCGTCCTA |
| EEEV-158 | 35 | heavy | CAGGTGCAGCTGGTGGAGTCTGGGGGAGGCGTGGTCCAGCCTGGGAGGTCCCTGAGACTCTCCTGTGCAGCCTCTGGATTCACCTTCAGTAGCTATGGCATGCACTGGGTCCGCCAGGCTCCAGGCAAGGGGCTGGAGTGGGTGGCAGTTATATCATATGATGAAAGTAATAAATACTATTCAGACTCCGTGAAGGGCCGATTCACCATCTCCAGAGACAATTCCAAGAACACGCTGTATCTGCAAATGAACAGCCTGAGAGCTGAGGACACGGCTGTGTATTACTGTGCGAAAAAGGGCTGTAGTGGTGGTAACTGTGACGAGGGCTTTGACTACTGGGGCCAGGGAACCCTGGTCACCGTCTCCTCA |
| | 36 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAGCACCCAGGCAAAGCCCCCAAACTCATGATTTATGAGGTCAGTAATCGGCCCTCAGGGGTTTCTCATCGCTTCTCTGGCTCCAAGTCTGGCAACACGGCCTCCCTGACCATCTCTGGGCTCCAGGCTGAGGACGAGGCTGATTATTACTGCATCTCATATAGAAGCAGCAGCACTCTTTATGTCTTCGGAACTGGGACCAAGGTCACCGTCCTA |
| EEEV-16 | 37 | heavy | CAGGTGCAGCTGGTGGAGTCTGGGGGAGGCGTGGTCCAGCCTGGGAGGTCCCTGAGACTCTCCTGTGCAGCGTCTGGATTCTACTTCAGTAGCTATGGCATGCACTGGGTCCGCCAGGCTCCAGGCAAGGGGCTGGAGTGGGTGGCAGTTATATGGTATGATGGAAGTAATAAATACTATGTAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGCGGATGGCTACAATTTTGACTACTGGGGCCAGGGAACCCTGGTCACCGTCTCCTCA |
| | 38 | light | TCTTCTGAGCTGACTCAGGACCCTGCTGTGTCTGTGGCCTTGGGACAGACAGTCAGGATCACATGCCAGGGAGACAGCCTCAGAAGCTATTTTGCAAGCTGGTACCAGCAGAAGCCAGGACAGGCCCCTGTAGTTGTCATCTTTGATAGAAACAACCGGCCCTCAGGGATCCCAGACCGATTCTCTGGCTCCAGCTCAGGAAGCACAGCTTCCTTGACCATCACTGGGGCTCAGGCGGAAGATGAGGCTGACTATTACTGTAACTCCCGGGACAGCAGTGGTAACCTTTATGTCTTCGGAACTGGGACCAAGGTCACCGTCCTA |
| EEEV-160 | 39 | heavy | CAGGTCACCTTGAAGGAGTCTGGTCCTGTGCTGGTGAAACCCACAGAGACCCTCACGCTGACCTGCAGCGTCTCTGGGTTCTCACTCAGCAGTGCTAGAATGGGTGTGAGCTGGATCCGTCAGCCCCCTGGGAAGGCCCTGGAGTGGCTTGCACACATTTTTTCGAGTGACGAAAAATCCTACAGCACATCTCTGAAGAGCAGGCTCTCCATCTCCAAGGACACCTCCAAAAGCCAGGTGGTCCTTACCTTGACCAACCTGGACCCTGTGGACACAGCCACATATTACTGTGCACGGATACGTGGCCCTAGTTATTACCACCAAAACTACTACTACTTCGGTATGGACGTCTGGGGCCAAGGGACCACGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 40 | light | GATATTGTGATGACTCAGTCTCCACTCTCCCTGCCCGTCACCCCTGGAGAGCCGGCCTCCATCTCCTGCAGGTCAAGTCAGAGCCTCCTACATAGTAATGGATACAACTATTTGGATTGGTACCTGCAGAAGCCAGGGCAGTCTCCACAGCTCCTGATCTATCTGGGTTCTAATCGGGCCTCCGGGGTCCCTGACAGGTTCAGTGGCAGTGGATCAGGCACAGATTTTACACTGCAAATTAGCAGAGTGGAGGCTGAGGATGTTGGAGTTTATTACTGCATGCAAGCTCTACAAGCTCCGTGGACGTTCGGCCAAGGGACCAAGGTGGAAATCAAA |
| EEEV-164 | 41 | heavy | CAGGTGCAGCTGCAGGAGTCGGGCCCAGGACTGGTGAAGCCTTCACAGACCCTGTCCCTCACCTGCGTAGTCTCTGGTGCCTCCATCAGCAGTGCTGATTCCTACTGGAGTTGGATCCGCCAGCACCCAGGGAAGGGCCTGGAGTGGATTGGGTACATCTATTACAGTGGGAGCACCTACTACAACCCGTCCCTCAAGAGTCGAGTTACCATATCAGTAGACACGTCTAAGAACCAGTTCTCCCTGAAGCTGACCTCTCTAACTGCCGCGGACACGGCCGTGTATTACTGTGCGAGAGGGGGACCTTATTGTGGTGGTGACTGCTATCGGTGGGGCCAGGGAACCCTGGTCACCGTCTCCTCA |
| | 42 | light | GACATCCAGCTGACCCAGTCTCCATCCTCCCTGTCTGCATCTGTAGGAGACAGAGTCACCATCACTTGCCAGGCGAGTCAGGACATTAGCAACTTTTTAAATTGGTATCAGCAGAAACCAGGGAAAGCCCCTAAGCTCCTGATCTACGATGCAGCCAATTTGGATACAGGGGTCCCATCAAGGTTCAGTGGAAGTGGATCTGAGACAGATTTTACTTTCACCATCAGCAGCCTGCAGCCTGAAGATATTGCAACATATTACTGTCAACAGTATGATAGTCTCCCTTGGACGTTCGGCCAAGGGACCAAGGTGGAAATCAAA |
| EEEV-168 | 43 | heavy | CAGGTGCAGCTGCGGGAGTCGGGCCCAGGACTGGTTAAGCCTTCGGAGACCCTGTCCCTCACCTGCACTGTCTCTAATGGCTCCATTAGTAGTTACTACTGGAGCTGGATCCGGCAGCCCGCCGGGAAGGGACTGGAGTGGATTGGGCGTATTTATAGTAGTGGGAGCACCAATTACAATCCCTCCCTCAAGAGTCGAGTCACCATGTCAGTAGACACGTCGAAGAACCAGTTCTCCCTGAGGCTGAGGTCTGTGACCGCCGCGGACACGGCCGTATATTATTGTGCGAGAGATTTGAGGGCGTGGATTCAGTTGCACAGGGCCAGTCTCTACTACTACTACATGGACGTCTGGGGCAAAGGGACCACGGTCACCGTCTCCTCA |
| | 44 | light | TCTTCTGAGCTGACTCAGGACCCTGCTGTGTCTGTGGCCTTGGGACAGACAGTCAGGATCACATGCCAAGGAGACAGCCTCAGAAGUTTTTATACAACCTGGTACCAGCAGAAGCCAGGACAGGCCCCTGTACTTGTCATCTATGGTACAAACAACCGGCCCTCAGGGATCCCAGAGCGATTCTCTGGCTCCAGTTCAGGAAACACAGCTTCCTTGACCATCACTGGGGCTCAGGCGGATGATGAGGCTGACTATTACTGTGACTCCCGGGACAGCAGTGGTGAACTTTGGCTGTTCGGCGGAGGGACCAAGCTGACCGTCCTA |
| EEEV-169 | 45 | heavy | GAGGTGCAGCTGTTGGAGTCTGGGGGAGGCTTGGTACAGCCGGGGGGGTCACTGAGACTCTCCTGTGTAGCCTCTGGATTCAGCTTTGGAAGCTATGGCATGAGCTGGGTCCGGCAGGCTCCAGGGAAGGGGCTGGAGTGGGTCTCAGGTATTGGTGGCAGGGGTGACAGCACATACTTCGCAGACTCCGTGAAGGGCCGATTCAGCATCTCCAGAGACAACTCCAAGAATACATTGTATCTACAAATGAACTTCCTGAGAGCCGAGGACACGGCCGTATATTATTGTGCGAAAGAAGGATTTGGTAGTGGTCATTTCCACGGGAGTAATGACTATTGGGGCCAGGGGACCCTGGTCACCGTGTCCTCA |
| | 46 | light | GACATCCAGATGACCCAATCTCCATCTTCCCTGTCTGCATCTGTAGGAGACAGAGTCACCATCGCTTGCCAGACGAGTCACGACATTAGCAACTATTTAAATTGGTATCAACAGAAACCAGGGAGAGCCCCTAAACTCCTGATCTACGATGCATCCAATTTGCAAACAGGGGTCCCATCTAGGTTCAGTGGAAGTGGCTCTGGGACAGATTTTACTCTCACCATCAGCAGCCTGCAGCCTGAAGATATTGCAACATATTACTGTCAACAGTTTGACAGTCTCCCACTCACTTTCGGCGGAGGGACCAAGGTGGGGGTCAAA |
| EEEV-17 | 47 | heavy | CAGGTGCAGCTGGTGCAGTCTGGGGCTGAGGTGAAGAAGCCTGGGGCCTCAGTGAAGGTCTCCTGCAAGGCTTCTGGATACACCTTCACCAGTTATGATATCAACTGGGTGCGACAGGCCACTGGACAAGGGCTTGAGTGGATGGGATGGATGAACCCTAACAGTGGTAACACAGGCTACGCACAGAAGTTCCAGGGCAGAGTCACCATGACCAGGAACACCTCCATAAGCACAGCCTACATGGAGCTGAGCAGCCTGAGATCTGATGACACGGCCGTATATTACTGTGCGAGATTTTACGATTTTTGGAGTGGTTTAGACATAGACGTCTGGGGCAAAGGGACCACGGTCACCGTCTTCTCA |
| | 48 | light | CAGTCTGCCCTGACTCAGCCTGCCTCCGTGTCTGGGTCTCCTGGACAGTCGATCACCATCTCCTGCACTGGAACCAGCAGTGACGTTGGTGGTTATAACTATGTCTCCTGGTACCAACAGCACCCAGGCAAAGCCCCCAAACTCATGATTTATGAGGTCAGTAATCGGCCCTCAGGGGTTTCTAATCGCTTCTCTGGCTCCAAGTCTGGCAACACGGCCTCCCTGACCATCTCTGGGCTCCAGGCTGAGGACGAGGCTGATTATTACTGCAGCTCATATACAAGCAGCATCACTCGAGTCTTCGGAACTGGGACCAAGGTCACCGTCCTA |
| EEEV-173 | 49 | heavy | CAGGTGCAGCTGGTGCAGTCTGGGGCTGAGGTGAAGAAGCCTGGGTCCTCGGTGAAGGTTTCCTGCAAGGCTTCTGGAGGCACCTTCAGCAACTATGGTATCAGCTGGGTGCGACAGGCCCCTGGACAAGGGCTTGAGTGGATGGGAGGGGTCATCCCCATCTTTGGAACAACAAAGTACGCAAAGAAGTTCCAGGGCAGAGTCACGGTTACCGCGGACAAATCCACGGGCACAGCCTACATGGAGCTGAGCAGCCTGATATCTGAGGACACGGCCGTGTATTACTGTGCGAGAGATGATGGAGCAGCAGCTGGCACGGGCTACTACGGCATGGCCGTCTGGGGCCAAGGGACCACGGTCACCGTCTCCTCA |
| | 50 | light | GAAATAGTGATGACGCAGTCTCCAGCCACCCTGTCTGTGTCTCCAGGGGAAAGAGCCACCCTCTCCTGCAGGGCCAGTCAGAGTGTTAGCAGCTACTTAGCCTGGTACCAGCAGAAGCCTGGCCAGGCTCCCAGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGGAGATTTTGCAGTTTATTACTGTCAGCAGTATGTTAACTGGCCCCAGTACACTTTTGGCCAGGGGACCAAGCTGGAGATCAAA |
| EEEV-179 | 51 | heavy | CAGGTGCAGCTTCTGCAGTCTGGGGCTGAGGTGAAGAAGCCTGGGTCCTCGGTGAAGGTCTCCTGCAAGGCTTCTGGAGGCACCTTCAGCAACATTGGTATCAGCTGGGTGCGACAGGCCCCTCGACAAGGGCTTGAGTGGATGGGAGGGATCATCCCTCTCTTTGCTACAACAAACTACGCACAGAACTTCCAGGGCAGACTCACTATTACCGCGGACAAGTCCACGACCACAGCCTACATGGAGCTGAACAGCCTGAGATCTGACGACACGGGCGTGTATTTCTGTGCGAGACAACTGGGGTGGGCATATTGTAATAGTAGCACCTGCTCCAAGGGCTGGTTCAACCCCTGGGGCCAGGGAACCCTGGTCACCGTCTCCTCA |
| | 52 | light | GATATTGTGATGACCCAGACTCCACTCTCCCTGCCCGTCACCCCTGGAGAGCCGGCCTCCATTTCCTGCAGGTCTAGTCAGAGCCTCTTGGATAGTGATGATGGAAACACCTATTTGGACTGGTACCTGCAGAAGCCAGGGCAGTCTCCACACCTCCTGATCTATACGGTTTCCTATCGGGCCTCTGGAGTCCCAGACAGGTTCAGTGGCAGTGGGTCAGGCACTGATTTCACACTGAAGATCAGCACGGTGGAGGCTGAGGATGTTGGAGTTTATTACTGCATGCAACGTACAGAGTTTCCTTACACTTTTGGCCAGGGGACCAAGCTGGAAATC |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EEEV-180 | 53 | heavy | CAGGTGCAGCTGCAGGAGTCGGGCCCAGGACTGGTGAAGCCTTCACAGACCCTGTCCCTCAGTTGCAGTGTCTCTGGTGG<br>CTCCATCAGCACTGGTGGATACTACTGGAGCTGGATCCGCCAGAAGTCAGGGAAGGGCCTGGAGTGGATTGGGTACATCT<br>CTAACATTGGGAACACCTACTACAACCCGTCGCTCAAGAGTCGAGTTGCCATTTCGTTAGACACGTCTAAGAATCAGTTCTC<br>CCTGAAGTTGAGCTCTGTGACTGCCGCGGACACGGCCGTGTATTACTGTGCGAAAGCCCCGCCCGATGCCTATGATTCGGG<br>GACTTATTATCTCGCCTACTACATGGACGTCTGGGGCAAAGGGACCACGGTCGCCGTCTCCTCA |
| | 54 | light | GACATCCAGATGACCCAGTTTCCCTCCACCCTGTCTGCATCTGTAGGAGACAGAGTCACCATCACTTGTCGGGCCAGTCAGA<br>GTATTAGTAGCTGGTTGGCCTGGTATCAGCAGAAACCAGGGAAAGCCCCTAACCTCCTGATCTATAAGGCGTCTAGTTTAG<br>AAAGTGGGGTCCCATCAAGGTTCAGCGGCAGTGGATCTGGGACAGAATTCACTCTCACCATCAGCAGCCTGCAGCCTGATG<br>ATTTTGCAAGTTATTACTGCCAACAGTATAATAGTTATCCGTACACTTTTGGCCAGGGGACCAAGTTGGAGATCAAA |
| EEEV-181 | 55 | heavy | CAGGTGCAGCTGGTGGAGTCTGGGGGAGGCGTGGTCCAGCCTGGGAGGTCCCTGAGACTCTCCTGTACAGCCTCTGGATT<br>CACCTTCAGTAACTATGGCATGCAGTGGGTCCGCCAGGCTCCAGGCAAGGGGCTGGAGTGGGTGGCAGTTATATCATATC<br>ATGGAAATAATAACTATACAGACTCCGTGAAGGGCCGATTCACCATCTCCAGAGACAATTCCAAGAACACGCTGTATCTGC<br>AAATGAACAGCCTGAGAGCTGAGGACACGGCTGTGTATTACTGTGCCACAGGTTTAGAGGGTGAATACTGGGGCCAGGG<br>AACCCTGGTCACCGTCTCCTCA |
| | 56 | light | TCCTATGAGCTGACACAGCCATCCTCAGTGTCAGTGTCTCCGGGACAGACAGCCAGGATCACCTGCTCAGGAGATTTACTG<br>GCAAAAATATATGCTCGGTGGTTCCAGCAGAAGCCAGGCCAGGCCCCTGAACTGGTGATTTATAAAGACAGTGAGCGGCC<br>CTCAGGGATCCCTGAGCGATTCTCCGGCTCCAGCTCAGGGACCACAGTCACCTTGACCATCAGCGGGGCCCAGGTTGAGGA<br>TGAGGCTGACTATTACTGTTACTCTGCGACTGACAACAATGGAGTGTTCGGCGGAGGGACCAAGCTGACCGTCCTA |
| EEEV-182 | 57 | heavy | CAGGTGCAGCTGCAGGAGTCGGGCCCAGGACTGGTGAAGCCTTCACAGACCCTGTCCCTCACCTGCACTGTCTCTGGTGGC<br>TCCATCAGCAGTGGTGATTACTACTGGAGCTGGATCCGCCAGCACCCAGGGAAGGGCCTAGAGTGGATTGGGTACATCTA<br>TTACAATGGGAACACCTACTCCAACCCGTCCCTCAAGAGTCGAGTTACCATATCAGTAGACACGTCTAAGAACCAGTTCTCC<br>CTGAGGCTGACCTCTGTGACTGCCGCGGACACGGCCGTGTATTACTGTGCGAGAGGGGGGAGGATACGATTTTTGGAGTG<br>GTATGACTACTGGGGCCAGGGAACCCTGGTCACCGTCTCCTCA |
| | 58 | light | GACATCCAGATGACCCAGTCTCCATCCTCCCTGTCTGCATCTGTAGGAGACAGAGTCACCATCACTTGCCGGGCAAGTCAGA<br>GCATTAGCAACTATTTAAATTGGTATCAGCAGAAACCAGGGAAAGCCCCTAAGCTCCTGATCTATGCTGCGTCCAGTTTGCA<br>AAGTGGGGTCCCATCAAGGTTCAGTGGCAGTGGATCTGGGACAGATTTCACTCTCACCATCAGCACTCTGCAACCTGAAGA<br>TTTTGCAACTTACTACTGTCAACAGAGTTACAGTTCCCCTCGAACTTTTGGCCTGGGGACCAAGCTGGAGATCAAA |
| EEEV-183 | 59 | heavy | CAGGTGCAGCTGGTGGAGTCTGGGGGAGGCGTGGTCCAGCCTGGGAGGTCCCTGAGACTCTCCTGTGCAGCGTCTGGATT<br>CAGTTTCAATAGCTATGGCATGCATTGGGTCCGCCAGGCTCCAGGCAAGGGGCTGGAGTGGGTGGCACTTACATGGTATG<br>ATGGAAGTAATAAATATTATGCAGAGTCCGTGAAGGGCCGATTCACCATCTCCAGAGACAATTCCAAGAACACGCTGTATC<br>TGCAAATGAACAGCCTGAGAGCCGAAGACACGGCTGTGTATTACTGTGCGAGAGATCAGGGATGTAGTGGTGGTAGCTGC<br>TACTCCGAGGGTTGGTTCGACCCCTGGGGCCAGGGAACCCTGGTCACCGTCTCCTCA |
| | 60 | light | CAGTCTGTGCTGACTCAGCCACCCTCAGCGTCTGGGACCCCCGGGCAGAGGGTCACCATCTCTTGTTCTGGAAGCAGCTCC<br>AATATCGGAGGTAATACTGTAAACTGGTACCAGCAGCTCCCAGGAACGGCCCCCAAACTCCTCATCTATAGTAATAATCAG<br>CGGCCCTCAGGGGTCCCTGACCGATTCTCTGGCTCCAAGTCTGGCACCTCAGCCTCCCTGGCCATCAGTGGGCTCCAGTCTG<br>AGGATGAGGCTGATTATTACTGTGCAGCATGGGATGACAGCCTGAATGCCGTGGTATTCGGCGGAGGGACCAAGCTGACC<br>GTCCTA |
| EEEV-184 | 61 | heavy | CAGATCACCTTGAAGGAGTCTGGTCCTACGCTGGTGAAACCCACACAGACCCTCACGCTGACCTGCACCTTTTCTGGGTTCT<br>CACTCAGTAGTAGTGGAGAGGGTCTGGGCTGGATCCGTCAGCCCCCAGGAAAGGCCCTGGAGTGGCTTGCTCTCATTTAT<br>GGGGATGATGATAAGCGCTACAGCCCTTCTCTGAAGAGTAGGCTCACCATCACCAAGGACACCTCCAAAAATCAGGTGGTC<br>CTTACAATGACCAACATGGACCCTGTGGACACAGCCACATATTACTGTGCACACAGGAGCGGATATTGTAGTGGTGGTGAT<br>TGCTACTCGAGATTAGGCTGGTTCGACCCCTGGGGCCTGGGAACCCTGGTCACCGTCTCCTCA |
| | 62 | light | GAAATTGTGTTGACGCAGTCTCCAGGCACCCTGTCTTTGTCTCCAGGGGAAAGAGCCACCCTCTCCTGCAGGGCCAGTCAG<br>AGTGTTAGCAACAACTACTTAGCCTGGTACCAGCAGAAACCTGGCCAGGCTCCCAGGCTCCTCATCTATGGTGCATCCAGC<br>AGGGCCACTGGCATCCCAGACAGGTTCAGTGGCAGTGGGTCTGGGACAGACTTCACTCTCACCATCAGCAGACTGGAGCC<br>TGAAGATTTTGCAGTGTATTACTGTCAGCAATATGGTAGGTCACTTTTCACTTTCGGCCCTGGGACCAAAGTGGATATCAAA |
| EEEV-21 | 63 | heavy | CAGGTGCAGCTGGTGGAGTCTGGGGGAGGCGTGGTCCAGCCTGGGAGGTCCCTGAGACTCTCCTGTGCAGCCTCTGGATT<br>CACCTTCAGGACCTATGCTCTGCACTGGGTCCGCCAGGCTCCAGGCAAGGGGCTGGAGTGGGTGGCAGTCATCTCATATGA<br>TGGAAGCAATAAATACTACGCAGACTCCGTGAAGGGCCGATTCACCATCTCCAGAGACAATTCCAAGAACACGCTGTTTGT<br>GCAAATGAATAGCCTGAGACCTGAGGACACGGCTGTGTATTACTGTACGAGAGTCGTTAATTTTGGAGTGGCTTTTATCCG<br>AGATGGGGTGTATGGGCACTACTACTACGGTATGGACGTCTGGGGCCAAGGGACCACGGTCACCGTCTCCTCA |
| | 64 | light | CAGTCTGTGTTGACGCAGCCGCCCTCAGTGTCTGCGGCCCCAGGACAGAAGGTCAGCATCTCCTGCTCTGGAAGCACCTCC<br>AACATTGGGAATAATTATGTATCCTGGTACCGGCAGTTCCCAGGAACAGCCCCCAAATTCCTCATTTATGACAATGATAAGC<br>GACCCTCAGGGATTCCTGACCGATTCTCTGGCTCCAAGTCTGGCACGTCAGCCACCCTGGGCATCACCGGACTCCAGACTG<br>GGGACGAGGCCGATTATTACTGCGGAACATGGGATAGCAGCCTGAGTGTTTGGGTGTTCGGCGGAGGGACCAAGCTGAC<br>CGTCCTA |
| EEEV-23 | 65 | heavy | CAGGTGCAAGTGCAGGAGTCGGGCCCAGGACTGGTGAAGACCTCGGAGACCCTGTCCCTCACCTGCACTGTCTCTGGTGG<br>ATCCATCAGTAGTTACTACTGGAGTTGGATCCGGCAGGCCGCCGGGAAGGGACTGGAGTGGATTGGGCGGACATATAGTG<br>GTGGGAGTCCCAATTACAACCCCTCCCTCAGGAGTCGAGTCACCGTGTCAGTGGACACGTCCAAGAACCAGTTCTCCCTGA<br>TCCTGACCTCTGTGACCGCCGCGGACACGGCCGTGTATTTCTGTGCGCGAGAAGACCACGGATTACGACAGAAATTTTACT<br>ACTACATGGACCTCTGGGGCAAAGGGACTGCGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 66 | light | TCCTATGTGCTGACTCAGCCACCCTCCGTGTCAGTGGCCCCAGGAAAGACGGCCAAGATTACCTGTGGGGGAAGCAACATTGGAAGTAAAAGTGTGCACTGGTACCAGCAGAAGCCAGGCCAGGCCCCTGTGTTGGTCATCTATTATGATAGTGACCGGCCCTCAGGGATCCCTGACCGATTCTCTGGCTCCAACTCTGGGAACACGGCCACCCTGACCATCAGCAGGGTCGAAGCCGGGGATGAGGCCGACTATTCCTGTCAGGTGTGGGATAGTTCTCCTGATCACTCCCCTGTGGTTTTTGGCGGAGGGACCAAGCTGACCGTCCTA |
| EEEV-26 | 67 | heavy | CAGGTGCAGCTGCAGGAGTCGGGCCCAGGACTGGTGAAGCCTTCGGAGACCCTGTCCCTCACTTGTATTGTCTCTGGTGGCTCCATCAATAGTTACTACTGGAGTTGGATCCGGCAGCCCGCCGGGAAGGCACTGGAGTGGATTGGGCGGATATATACCAGTGGGAGCACCAACTATAACCCCTCCCTCAAGAGTCGAGTCACCATGTCAGTAGACATGTCCAAGAACCAGTTCTCCCTGAAGCTGACCTCTGTGACCGCCGCGGACACGGCCGTGTATTACTGTGCGAGAGCCCCTCGTATACCAGTATCTGTAGAGGGTCATTACTACTACCACTACTACATGGACGTCTGGGGCAAAGGGACCACGGTCACCGTCTCCTC |
| | 68 | light | TCTTCTGTGCTGACTCAGGACCCTGCTGTGTCTGTGGCCTTGGGACAGACAGTCAGGATCACATGCCAAGGAGACAGCCTCAGAACCTATTATGCAAGCTGGTACCAGCAGAAGCCAGGACAGGCCCCTATACTTGTCATCTATGCTAAAAACCACCGGCCCTCAGGGATCCCAGACCGATTCTCTGGCTCCAGCTCAGGAAACACAGCTTCCTTGACCATCACTGGGGCTCAGGCGGAAGATGAGGCTGACTATTACTGTAACTCCCAGGACAGCAGTGGTAACCATCTAGGATTCGGCGGAGGGACCAAGCTGACCGTCCTAG |
| EEEV-27 | 69 | heavy | GAGGTGCAGCTGTTGGAGTCTGGGGGAGGCTTGGTACAGCCTGGGGGGTCCCTGAGACTCTCCTGTGCAGCCTCTGGATTCACCATTAGCAGATATGCCGTGACCTGGGTCCGCCAGGCTCCAGGGAAGGGGCTGGAGTGGGTCTCAACTATCACTGGTAGTGGTGGTAGGACATACTACGCAGACTCCGTGAAGGGCCGGTTCACCGTCTCCAGAGACAGTTCCAAGAACACACTGTATCTGCAAATGAACACCCTGAGAGCCGAAGACTCGGCCATATATTACTGTGCGAAAGGGATTGTAGTGGTCCTAGTGGGACCCCCCTACTTCGGTATGGACGTCTGGGGCCAAGGGACCACGGTCACCGTCTCCTCA |
| | 70 | light | TCCTATGTGCTGACTCAGCCACCCTCGGTGTCAGTGGCCCCAGGACAGACGGCCAGGATTCCCTGTGGGGGAAACAACATTGGAACTAAAACTGTACACTGGTACCAGCAGAAGCCAGGCCAGGCCCCTGTGCTGGTCGTCTATGATGATAGCGACCGGCCCTCAGGGATCCCTGAGCGATTCTCTGGCTCCAATTCTGGGAACACGGCCACCCTGACCATCAGCAGTGTCGAAGCCGGGGATGAGGCCGACTATCACTGTCAGGTGTGGGATAGTAGTAGTGATCTCGTGGTTTTCGGCGGAGGGACCAAGCTGACCGTCCTAG |
| EEEV-29 | 71 | heavy | CAGCTGCAGCTGCAGGAGTCCGGCTCAGGACTGGTGAAGCCTTCACAGACCCTGTCCCTCACCTGCGCTGTCTCTGGTGGTTCCATTAGTAGTGGTGTTTATTCCTGGAGCTGGATCCGGCAGCCACCAGGGAAGGGCCTGGAGTGGATTGGGTACATCTATCATAGTGGGAGCACCTACTACAACCCGTCCCTCAAGAGTCGAGTCACCATATCAGTAGACAGGTCCAAGAACCAGTTCTCCCTGAAGCTGAGCTCTGTGACCGCCGCGGACACGGCCGTGTATTACTGTGCCAGAGAGAGTGTAGCAAACTACTTTGACTACTGGGGCCAGGGAACCCTGGTCACCGTCTCCTCA |
| | 72 | light | GAAATTGTGTTGACACAGTCTCCAGCCACCCTGTCTTTGTCTCCAGGGGAAAGTGCCACCCTCTCCTGCAGGGCCAGTCAGAGTGTTGACAGCTACTTAGCCTGGTACCAACAGAAACCTGGCCAGGCTCCCAGGCTCCTCATCTATGATGCATCCAACAGGGCCTCTGGCATCCCAGCCAGGTTCAGTGGCAGTGGGTCTGGGACAGACTTCACTCTCACCATCAGCAGCCTAGAGCCTGAAGATTTTGCAGTTTATTACTGTCAGCAGCGTAGCGACTGGCCATTCACTTTCGGCCCTGGGACCAAAGTGGATATCAAAC |
| EEEV-30 | 73 | heavy | CAGGTGCAGCTGGTGGAGTCTGGGACTGAGGTGAAGAAGCCTGGGGCCTCAGTGAAGGTCTCCTGCAAGGCTTCTGAATACACCTTCACCGCCTACTATATACACTGGGTGCGGCAGGCCCCTGGACAAGGGCTTGAGTGGATGGGATGGATCAACCCTAACAGTGGTGGCACAAACTATGCACAGAAGTTTCAGGGCCGGGTCACCATGACCGGGGACACGTCCATCACCACAGCCTACATGGAGCTGAGCAGGCTGAGATCTGACGACACGGCCGTTTATTACTGTGCTTCGGATTACTTTGATAGTAGTGGTTATCATGACTACTGGGGCCAGGGAACTCTGGTCACCGTCTCCTCCG |
| | 74 | light | CAGTCTGCCCTGACTCAGCCTGCCTCCGTGTCTGGGTCTCCTGGACAGTCGATCACCATCTCCTGCACTGGAACCAGCAGTGATATTGGGAATTATAACCTTGTCTCCTGGTACCAACAACACCCAGGCAAAGCCCCCAAACTCATGATTTTTGAGGTCAGTAAGCGGCCCTCAGGGGTTTCTAATCGCTTCTCTGGCTCCAAGTCTGGCAACACGGCCTCCCTGACTATCTCTGGGCTCCAGGCTGAAGACGAGGCTCATTATTACTGCTGCTCATATGTGGATGATTGGGTATTCGGCGGAGGGACCAAACTGACCGTCCTG |
| EEEV-33 | 75 | heavy | CAGGTCACCTTGAAGGAGTCTGGTCCTGCGCTGGTGAAACCCACACAGACCCTCACACTGACCTGCACCTTCTCTGGGTTCTCACTCAGCACTAGTGGAATGCGTGTGAGCTGGATCCGTCAGCCCCCAGGGAAGGCCCTGGAGTGGCTTGCACGCATTGATTGGGATGATGATAAATTCTACAGCACATCTCTGAAGACCAGGCTCACCATCTCCAAGGACACCTCCAAAAACCAGGTGGTCCTTAGAATGACCAACATGGACCCTGTGGACACAGCCACGTATTACTGTGCACGGATACTCCCGGGATATTGTAGTGGAGGTAGCTGCTACTACAATTACCACTTTGACTACTGGGGCCAGGGAACTCTGGTCACCGTCTCCTCA |
| | 76 | light | TCCTATGTGCTGACTCAGCCACCCTCGGTGTCAGTGGCCCCAGGACAGACGGCCAGGATTACCTGTGGGGGAAACAACATTGGAAGTAAAAGTGTGCACTGGTACCAGCAGAAGCCAGGCCAGGCCCCTGTGCTGGTCGTCTATCATGATAGCGACCGGCCCTCAGGGATCCCTGAGCGATTCTCTGGCTCCAACTCTGGGAACACGGCCACCCTGACCATCAGCAGGGTCGAAGCCGGGGATGAGGCCGACTATTACTGTCAGGTGTGGGATAGTAGTAGTGACCCTTATGTCTTCGGAACTGGGACCAAGGTCACCGTCCTAG |
| EEEV-34 | 77 | heavy | CAGGTGCAGCTGGTGGAGTCTGGGGGAGGCGTGGTCCAGCCTGGGAGGTCCCTGAGACTCTCCTGTGCAGCGTCTGGATTCACCTTCAGTTCCTATGGCATGCACTGGGTCCGCCAGGCTCCAGGCAAGGGGCTGGAGTGGGTGGCAGTTATATGGTATGATGGAATAAATAAATACTATTCAGACTCCGTGAAGGGCCGATTCACCATCTCCAGAGACAATTCCAAGAACACGCTGTATCTGCAAATGAACAGCCTGAGAGCCGAGGACAAGGCTGTCTATTATTGTGCGAGAGAGGGGGGGGGCCAGCACGGTGACTATGCGAGCTGGTTCGACCCCTGGGGCCAGGGAACCCTGGTCACCGTGTCCTCAG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 78 | light | GACATCCAGATGACCCAGTCTCCATCCTCCCTGTCTGCATCTGTAGGAGACAGAGTCACCATCACTTGCCGGGCAAGTCAGA<br>GCATTAGCAGCTATTTAAATTGGTATCAGCAGAAACCAGGGAAAGCCCCTAAGCTCCTGATCTATACTGCATCCAGTTTGCA<br>AAGTGGGGTCCCATCAAGGTTCAGTGGCAGTGGATCTGGGACAGATTTCACTCTCACCATCAGCAGTCTGCAACCTGAAGA<br>TTTTGCAACTTACTACTGTCAACAGAGTTATAGTAAAGGGAGGACTTTCGGCCCTGGGACCAAAGTGGATATCAAAC |
| EEEV-35 | 79 | heavy | CAGGTGCAGCTGGTGCAGTCTGGGGCTGAGGTGAAGAAGCCTGGGTCCTCGGTGAAAGTCTCATGCAAGGCTTCTGGAG<br>GCTCCTTCAGAAGTTATGCTATCAGTTGGGTGCGACAGGCCCCTGGACAAGGGCTTGAGTGGATGGGAATGATCATCCCTA<br>TTTTTGACACGACAAACTACGCACAGAAGTTCCAGGGCAGAGTCACGATTACCGCGGACAAATCCACGAGCACAACGTACA<br>TGGAGCTGAACAGCCTAAAATCTGAGGACACGGCCGTATATTACTGTGCGAGAGATCTAAATCATTTCTATGCTAGTAGTG<br>GGCCAAATGACCTCTGGGGCCAGGGAACCCTGGTCACCGTGTCCTCAG |
| | 80 | light | GAAATTGTGTTGACGCAGTCTCCAGGCACCCTGTCTTTGTCTCCAGGGGAAAGAGCCACCCTCTCCTGCAGGGCCAGTCAG<br>AGTGTTAGCAGCAACTTCTTAGCCTGGTACCAGCAGAAACCTGGCCAGGCTCCCAGGCTCCTCATCTATGGTACATCTAGCA<br>GGGCCACTGGCATCCCAGACAGGTTCAGTGGCAGTGGGTCTGGGACAGATTTCACTCTCACCATCAGCAGACTGGAGCCT<br>GAAGATTTTGCAGTGTATTACTGTCAGCAGTATGGTGGCTCACCGGGGACGTTCGGCCAAGGGACCAAGGTGGAAATCAA<br>AC |
| EEEV-42 | 81 | heavy | CAGGTCACCTTGAAGGAGTCTGGTCCTGCGCTGGTGAGACCCACACAGACCCTCACACTGACCTGCACCTTCTCTGGGTTCT<br>CACTCACCACTAGTGGAATGCGTGTGAGCTGGATCCGTCAGCCCCCAGGGAAGGCCCTGGAGTGGCTTGCACGCATTGATT<br>GGGATGATGATAAATTCTACAGTACATCTCTGAAGACCAGGCTCACCATCTCCAAGGACACCTCCAAAAACCAGGTGGTCC<br>TTACACTGACCAACATGGACCCTGTGGACACAGCCACGTATTACTGTGCACGGTCCATGTATGATAGTAGTGGTTATTATCC<br>TCCGACTCCTTTTGATATCTGGGGCCAAGGGACAATGGTCACCGTCTCTTCAG |
| | 82 | light | GACATCCAGATGACCCAGTCTCCATCCTCCCTGTCTGCATCTGTAGGAGACAGAGTCACCATCACTTGCCGGGCAAGTCAGA<br>GCATTAGCAGGTACTTAAATTGGTATCAGCAGAAACCAGGGAAAGCCCCTAAGCTCCTGATCTATGCTGCATCCGCTTTGCA<br>AAGTGGGGTCCCATCAAGGTTCAGTGGCAGTGGATCTGGGACAGATTTCACTCTCACCATCAGCAGTCTGCAACCTGAAGA<br>TTTTGCAACTTACTCCTGTCAACAAAGTTTCAATACCCCATTCACTTTCGGCCCTGGGACCAAAGTGGATATCAAAC |
| EEEV-43 | 83 | heavy | GAGGTGCAGTTGTTGGAGTCTGGGGGAGGCTTGATACAGCCTGGGGGGTCCCTGAGACTCTCCTGTGCAGCCTCTGGATT<br>CACCTTTACCAACTATGCCATGAACTGGGTCCGCCAGGCTCCAGGGAAGGGGCTGGAGTGGGTCTCAGTTATTAGTGGTAG<br>TGGTGGTACCTCATATTACGCAGACTCCGTGAAGGGCCGGTTCACCATCTCCAGAGACAATTCCAAGAACACCCTGTATCTG<br>CAAATGAACAGCCTGAGAGCCGAGGACACGGCCGTATATTACTGTGCCAAAGGGGCTACTCTGATAGTGGTGGTTCTTCG<br>ACCGGATGTTTTTGATATCTGGGGCCAAGGCACAATGGTCACCGTCTCTTCA |
| | 84 | light | TCCTATGAGCTGACTCAGCCACCCTCAGTGTCCGTGTCCCCAGGACAGACAGCCAGCATCACCTGCTCTGGAGATAAATTG<br>GGGGATAAACATGCTTGCTGGTATCGACAGAAGCCAGGCCAGTCCCCTGTCCTGGTCATCTATCAAGATAGCAAGCGGCCC<br>TCAGGGATCCCTGAGCGATTCTCTGGCTCCAACTCTGGGAACACAGCCACTCTGACCATCAGCGGGACCCAGGCTATGGAT<br>GAGGCTGACTATTACTGTCAGGCGTGGGACAGCAACACTGCTCATTATGTCTTCGGAACTGGGACCAAGGTCACCGTCTTA |
| EEEV-47 | 85 | heavy | CAGGTGCAGCTGGTGGAGTCTGGGGGAGGCGTGGTCCAGCCTGGGAGGTCCCTGAGACTCTCCTGTGCAGCGTCTGGATT<br>CAGGTTCAGTAGCTATGGCATGCACTGGGTCCGCCAGGCTCCAGGCAAGGGGCTGGAGTGGGTGGGAGTTATATGGTAT<br>GATGGAAGTAATAAATACTACGCAGACTCCGTGAAGGGCCGATGCACCATCTCCAGAGACAATGCCAAGAACACTCTGTAT<br>CTGCAAATGAACAGCCTGAGAGCCGAGGACACGGCTATGTATTACTGTGCGAGAGTCTCCCGGGGAGCCGACGATTGGGA<br>CTACTACTACTACATGGACGTCTGGGGCAAAGGGACCACGGTCACCGTCTCCTCA |
| | 86 | light | GACATCGTGATGACCCAGTCTCCAGACTCCCTGGCTGTGTCTCTGGGCGAGAGGGCCACCATCAACTGCAAGTCCAGTCAC<br>AGTGTTTTATATTTCTCCAACAACAAGAACTGCTTAGCTTGGTATCAGCAGAAACCAGGACAGCCTCCTAAGTTGCTCATTTA<br>CTGGGCATCTACCCGGGAGTCCGGGGTCCCTGACCGATTCAGTGGCAGCGGGTCTGGGACAGATTTCACTCTCACCATCAG<br>CAGCCTGCAGGCTGAAGATGTGGCAGTTTATTACTGTCAGCAATATTATAGTACTCCTTTCACTTTCGGCCCTGGGACCAAA<br>GTGGATATCAGAC |
| EEEV-51 | 87 | heavy | CAGGTGCAGCTGGTGGAGTCTGGGGGAGGCGTGGTCCAGCCTGGGAGGTCCCTGAGACTCTCCTGTGCAGCGTCTGGATT<br>CATGTTCAGTAGCTATGGCATGCACTGGGTCCGCCAGGCTCCAGGCAAGGGGCTGGAGTGGGTGGCAGTTATATGGTATG<br>ATGGAAGTAATAAATACTATGCAGACTCCGTGAAGGGCCGATTCAGCATCTCCAGAGACAATTCCAAGAACACCCTGTATC<br>TGCAAATGAACAGTCTGAGAGCCGAGGACACGGCTGTGTATTACTGTGCGAGAGTAGTGGGGGGGGAGTTTGACTACTG<br>GGGCCAGGGAACCCTGGTCACCGTCTCCTCA |
| | 88 | light | AATTTTATGCTGACTCAGCCGCACTCTGTGTCGGAGTCTCCGGGGAAGACGGTAACCATCTCCTGCACCCGCAGCAGTGGC<br>AGCATTGCCAGCAACTATGTGCAGTGGTACCAACAGCGCCCGGGCAGTGCCCCCACCACTGTGATCTATGAGGATAACCAA<br>AGACCCTCTGGGGTCCCTGATCGGTTCTCTGGCTCCAGCGACAGCTCCTCCAACTCTGCCTCCCTCACCATCTCTGGACTGAA<br>GACTGAGGACGAGGCTGACTACTACTGTCAGTCTTATAATAGCAGCAATTGGGTGTTCGGCGGAGGGACCAAGCTGACCG<br>TCCTAG |
| EEEV-53 | 89 | heavy | CAGGTGCAGCTGGTGGAGTCTGGGGGAGGCGTGGTCCAGCCTGGGAGGTCCCTGAGACTCTCCTGTACAGCGTCTGGATT<br>CACATTCAGTAGCTATGGCATGCACTGGGTCCGCCAGACTCCAGACAAGGGGCTGGAGTGGGTGGCACTTATATGGTATG<br>ATGGAAGTAATAAATATTATGCAGACTCCGTGAAGGGCCGCTTCACCATCTCCAGAGACAATTCCAAGAACACACTGTATCT<br>GCAAATGGAGACCCTGAGAGCCGAGGACACGGCCGTTTATTACTGTGCGAGAGTTGGGGGAGTTGGATGGGAAGGGGAC<br>TTCTGGGGCCAGGGAACCTTGGTCACCGTCTCCTCAG |
| | 90 | light | CAGTCTGCCCTGACTCAGCCTGCCTCCGTGTCTGGGTCTCCTGGACAGTCGATCACCATCTCCTGCGCTGGATCCAGCAGTG<br>ACGTTGGTGCTAATAACTATGTCTCCTGGTACCAACAGGACCCAGGCCAAGCCCCCAAACTCATGATTTATGAGGTCAATTA<br>TCGGCCCTCAGGGGTTCCTAATCGCTTCTCTGGCTCCAAGTCTGGCAACACGGCCTACCTGACCATCTCTGGGCTCCAGGCT<br>GAGGACGAGGCTAATTATTTCTGCAGCTCATATTCAAGCGCCACCACTCTCCGATTCGGCGGAGGGACCAAACTGACCGTC<br>CTAG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| EEEV-54 | 91 | heavy | CAGGTTCAGTTGGTCCAGTCTGGAGCTGAGGTGAAGAAGCCAGGGGCCTCAGTGAAGGTCTCCTGCAAGACTTCTGGTTA<br>CATCTTTTCCAACTATGATATTAGTTGGGTGCGACAGGCCCCTGGCCAGGGGCTTGAGTGGATGGGATGGATCAGCGCTTA<br>CAGTGGTGAAAAAAAGTATTCACAGAAGTTCCAGGTCAGACTCACCATGACCGCAGACACTGCCACGAGCACAGCCTACAT<br>GGAACTGAGGAGCCTGAGATCTGACGACACGGCCGTGTATTATTGTGCGCGAGACCCTACTGTGGTCCATGCTTTGGATAT<br>CTGGGGCCAGGGGACAATGGTCACCGTCTCTTCAG |
| | 92 | light | GACATCCAGATGACCCAGTCTCCATCCTCCCTGTCTGCATCTGTAGGAGACAGAGTCACCATCACTTGCCAGGCGAGTCACG<br>ACATTAGTAAC7TTTTTAAATTGGTATCAACAGAAACCAGGGAAAGCCCCTAAACTCCTGATCTTCGATGCATCCAATTTGGA<br>ACCAGGGGTCCCATCAAGGTTCAGTGGAAGTGGATCTGGGACAGATTTCACTTTCACCATCAACAGCCTGCAGCCTGAAGA<br>TATTGCAACATACTACTGTCAACAGTATGATGATCTCGTGTACACTTTTGGCCAGGGGACCAAGCTGGAGATCAAAC |
| EEEV-55 | 93 | heavy | GAGGTGCAGCTGGTGGAGTCTGGGGGAGGCTTGGTACAGCCGGGGGGGTCCCTGAGACTCTCCTGTGCAGCCTCTGGATT<br>CACCTTCAGTAGCTATACCATGAATTGGGTCCGCCAGGCTCCAGGGAAGGGGCTGGAATGGGTTTCATATATTACTAATAG<br>TAGTAGTGCCATATACTACGCAGACTCTGTGAAGGGCCGATTCACCATCTCCAGAGACAATGCCAAGAACTCACTGTATCTA<br>CAAATGAACAGCCTGAGAGACGAGGACACGGCTGTGTATTACTGTGCGAGAGATCTTGCTCGGCCCCATCGGTACTATGAT<br>AATAGTGCTTATTTTGAGGTGTTTGACTCCTGGGGCCAGGGAACCCTGGTCACCGTCTCCTCA |
| | 94 | light | TCTTCTGAGCTGACTCAGGACCCTGCTGTGTCTGTGGCCTTGGGACAGACAGTCAGGATCACATGCCAAGGAGACAGCCTC<br>AGAAACTATTATGCAAGCTGGTACCAGCAGAAGCCAGGACAGGCCCCTGTTCTTGTCATCTATGGTAAAAATAACCGGCCC<br>TCAGGGATCCCAGACCGATTCTCTGGCTCCAACTCAGGAAACACAGCTTCCTTGACCATCACTGGGGCTCAGGCGGAAGAT<br>GAGGGTGACTATTACTGTAGCTCCCGGGACAGCAGTGGTAACTATCTGAGAGTCTTCGGAACTGGGACCAAGGTCACCGT<br>CCTAG |
| EEEV-58 | 95 | heavy | CAGGTGCAGCTGGTGGAGTCTGGGGGAGGCGTGGTCCAGCCTGGGAGGTCCCTGAGACTCTCCTGTGCAGCGTCTGGATT<br>CACCTTCAATAGCTATGGCATGCACTGGGTCCGCCAGACTCCAGGCAAGGGGCTGGAGTGGGTGGCAATTATATGGTATG<br>ATGGAAGTCAAAAATACTATGCAGACTCCGTGAAGGGCCGATTCACCATCTCCAGAGACAATTCCAAGAACACGCTGTATC<br>TGCAAATGAACAGCCTGAGAGCCGAGGACACGGCTGTGTATTACTGTGCGAGAGACGAGGGGAGCTATGACTTAGACTAC<br>TGGGGCCAGGGAACCCTGGTCACCGTCTCCTCA |
| | 96 | light | CAGTCTGCCCTGATTCAGCCTGCCTCCGTGTCTGGGTCTCCTGGACAGTCGATCACCATCTCCTGCACTGGAACCAAAAGTG<br>ACGTTGGTGGTTATAACTATGTCTCCTGGTACCAACAATACCCAGGCAAAACACCCAAACGCATGATTTTCGAGGTCAGTAA<br>TCGGCCCTCAGGGGCTTCTAATCGCTTCTCTGGCTCCAAGTCTGGCAACACGGCCTCCCTGACCATCTCTGGGCTCCAGGCT<br>GAGGACGAGGCTGATTATTATTGCACCTCATATACAAGTAGCAGCACTCTGGTCTTCGGCGGAGGGACCAAGCTGACCGTC<br>CTA |
| EEEV-66 | 97 | heavy | CAGGTGCAGCTGGTGGAGTCTGGGGGAGGCGTGGTCCAGCCTGGGAGGTCCCTGAGACTCTCCTGTGCAGCGTCTGGATT<br>CACCTTCAGTAGCTATGGCATGCACTGGGTCCGCCAGGCTCCAGGCAAGGGGCTGGAGTGGGTGGCAGTTATATGGCATG<br>ACGGCAGTAATAAATACTATGGAGACTCCGTGAAGGGCCGATTCACCATCTCCAGAGACAACTCCAAGAACACGCTATATT<br>TGCAAATGAACGGCCTGAGAGCCGAGGACACGGCTGTGTATTACTGTGCGAGAGTAGAAGGTGGGAGCTACTCAGGTGA<br>CTACTGGGGCCAGGGAACCCTGGTCACCGTCTCCTCA |
| | 98 | light | CAGTCTGCCCTGACTCAGCCTGCCTCCGTGTCTGGGTCTCCTGGACAGTCGATCACCATCTCCTGCACTGGAACCAGCAGTG<br>ACATTGGTGCTTATAACTCTGTCTCCTGGTACCAACAGCACCCAGGCAAAGCCCCCAAACTCATGATTTATGATGTCAGTAA<br>TCGGCCCTCAGGGGTTTCTAATCGCTTCTCTGGCTCCAAGTCTGGCAACACGGCCTCCCTGACCATCTCTGGGCTCCAGGCT<br>GAGGACGAGGCTGATTATTACTGCAGTTCCTTTACAAACACCGTCTCTGTGGTGTTCGGCGGAGGGACCAAGCTGACCGTC<br>CTA |
| EEEV-67a | 99 | heavy | CAGGTGCAACTGGTGGAGTCTGGGGGAGGCTTGGTCAAGCCTGGAGGGTCCCTGAGACTCTCCTGTGCAGCCTCTGGGTT<br>CATCTTCAGTGACTACTCCATGAATTGGATCCGCCAGGCTCCAGGGAAGGGTCTGGAGTGGATTTCATCAATTAGTCATAGT<br>GAGACTTACACATACTACGCAGACTCTGTGAAGGGCCGATTCACCATCTCCAGAGACAACGCCAAGAACTCACTTTATCTGC<br>AAATGCACAGCCTGAGAGCCGAAGACACGGGTGTCTATTACTGTGCGAGACCTCTAGAGGCAATGATGTGGGAGGAATTT<br>CACTTCTGGGGCCAGGGAATCCTGGTCAGCGTCTCCTCA |
| | 100 | light | CAGTCTGTGCTGACTCAGCCACCCTCCGCGTCTGGGACCCCCGGGCAGAGGGTCACCATCTCTTGTTCTGGAAGCACCTCCA<br>ACATCGGGACTAATTATGTCTACTGGTACCACCACCTCCCAGGAACGGCCCCCAAACTCCTCATCTATAGGACTAATCAGCG<br>GCCCTCAGGGGTCCCTGACCGATTCTCTGGCTCCAAGTCTGGCACCTCAGCCTCCCTGGTCATCAGTGGGCTCCGGTCCGAG<br>GATGAGGCTGATTATTACTGTGCGTCATGGGATGGCAGCCTGAGTGGGGTGCTATTCGGCGGAGGGACCAAGCTGACCGT<br>CCTAG |
| EEEV-67b | 101 | heavy | CAGGTGCAGCTGGTGCAGTCTGGGGCTGAGGTGAGGAAGCCGGGGTCCTCGGTGAAGGTCTCCTGCAAGGCTTCTGGAG<br>GCACCTTCAGCAATTATGATATCAACTGGGTGCGGCAGGCCCCTGGACAAGGGCTTGAGTGGATGGGAGGGATCATCCCT<br>ATCTTTGATACACCAAACTACGCACAGAAGTTCCAGGGCAGAGTCACCATTACCGCGGACGAGTCCACGACGAAAGCCTAC<br>ATGGAGCTGAGCAGCCTGAGATCTGAAGACACGGCCGTGTATTACTGTGCGAGAGGGGCGTCCCGATATTGTAATAGCAC<br>CAGCTGCTATAGAATTTTTGACTACTGGGGCCAGGGAAGCCTGGTCACCGTCTCCTCA |
| | 102 | light | CAGTCTGTGCTGACTCAGCCACCCTCCGCGTCTGGGACCCCCGGGCAGAGGGTCACCATCTCTTGTTCTGGAAGCACCTCCA<br>ACATCGGGACTAATTATGTCTACTGGTACCACCACCTCCCAGGAACGGCCCCCAAACTCCTCATCTATAGGACTAATCAGCG<br>GCCCTCAGGGGTCCCTGACCGATTCTCTGGCTCCAAGTCTGGCACCTCAGCCTCCCTGGTCATCAGTGGGCTCCGGTCCGAG<br>GATGAGGCTGATTATTACTGTGCGTCATGGGATGGCAGCCTGAGTGGGGTGCTATTCGGCGGAGGGACCAAGCTGACCGT<br>CCTAG |
| EEEV-68a | 103 | heavy | CAGGTGCAGCTGCAGGAGTCGGGCCCAGGACTGGTGAAGCCTTCGGAGACCCTGTCCCTCACCTGCACTGTCTCTGGTTAC<br>TCCATCAGCAGTGGTTACTACTGGGGCTGGATCCGGCAGCCCCCAGGGAAGGGCCTGGAGTGGATTGGGAGTGTCTATCA |

TABLE 1-continued

NUCLEOTIDE SEQUENCES FOR ANTIBODY VARIABLE REGIONS

| Clone | SEQ ID NO: | Chain | Variable Sequence Region |
| --- | --- | --- | --- |
| | | | TAGTGGGACCACTTACTACAACCCGTCCCTCAGGAGTCGAGTCACCATATCATCAGACACGTCCAAGAACCAGTTCTCCCTG<br>AGGCTGAGCTCTGTGACCGCCGCAGACACGGCCGTGTATTACTGTGCGGGCTCTCGGTTGGTTTCCGATATATGGCCCCTC<br>GTGGACGTCTGGGGCACAGGGACCACGGTCACCGTCTCCTCA |
| | 104 | light | GAAATTGTGTTGACGCAGTCTCCAGGCACCCTGTCTTTGTCTCCAGGTGAAAGAGCCACCCTCTCCTGCAGGGCCAGTCAG<br>AGTGTTAGCAGCAGCTACTTAGCCTGGTACCAGCAGAAACCTGGCCAGGCTCCCAGGCTCCTCATCTATGGTGCATCCAGC<br>AGGGCCACTGGCATCCCAGACAGGTTCAGTGGCAGTGGGTCTGGGACAGACTTCACTCTCACCTTCAGCAGACTGGAGCCT<br>GAAGATTTTGCCGTGTATTACTGTCAGCAGTATGGTAGCTCACCGTGGACGTTCGGCCAAGGGACCAAGGTGGAAATCAA<br>A |
| EEEV-68b | 105 | heavy | GAGGTGCAGCTGGTGGAGTCTGGGGGAGGCTTGGTAAAGCCTGGGGGGTCCCTTAGACTCTCCTGTGCAGCCTCTGGATT<br>CACTTTCAGTAACGTCTGGATGAGCTGGGTCCGCCAGGCTCCAGGGAAGGGGCTGGAGTGGGTTGGCCGTATTAAAAGCA<br>AAATTGATGGTGGGACAACAGACTACGCTGTATTCGTGAAAGGCAGATTCATCATCTCAAGAGATGATTCAAAAAATATGT<br>TGTATCTGCAAATGAACAGCCTGAAAACCGAGGACACAGCCGTGTATTACTGTACCACAGAGGATTATAATTACGTTTGGG<br>GGGGTCTCCCGGCGCCGTACGGTTTGGACGTCTGGGGCCAAGGGACCACGGTCACCGTCTCCTCA |
| | 106 | light | GAAATTGTGTTGACGCAGTCTCCAGGCACCCTGTCTTTGTCTCCAGGTGAAAGAGCCACCCTCTCCTGCAGGGCCAGTCAG<br>AGTGTTAGCAGCAGCTACTTAGCCTGGTACCAGCAGAAACCTGGCCAGGCTCCCAGGCTCCTCATCTATGGTGCATCCAGC<br>AGGGCCACTGGCATCCCAGACAGGTTCAGTGGCAGTGGGTCTGGGACAGACTTCACTCTCACCTTCAGCAGACTGGAGCCT<br>GAAGATTTTGCCGTGTATTACTGTCAGCAGTATGGTAGCTCACCGTGGACGTTCGGCCAAGGGACCAAGGTGGAAATCAA<br>A |
| EEEV-7 | 107 | heavy | CAGGTGCAGCTGCAGGAGTCGGGCCCAGGACTGGTGAAGACTTCACAGACCCTGTCCCTCACCTGCACTGTCTCTGGTGGC<br>TCCGTCATAAGTGGTGATTACTACTGGAGTTGGATCCGCCAGCCCCCAGGGAAGGGCCTGGAGTGGATTGGGTACATCTTT<br>AATAGTGGGAGCACCAACTACAACCCGTCCCTCAAGAGTCGAGTCACCATTTCAGCAGATAAGTCCAAGAAGCAGCTCTCC<br>CTTAAGCTGACCTCTGTGACTGCCGCAGACACGGCCGTGTATTACTGTGCCAGAGACTATGAGGGATGTACTAATGGTGTA<br>TGCTATACGTACTTAGACTTCTGGGGCCAGGGAACCCTGGTCACCGTCTCCTCAG |
| | 108 | light | GACATCCAGATGACCCAGTCTCCATCCTCCCTGTCTGCATCTGTAGGAGACAGAGTCATGATCACTTGCCGGGCAAGTCAG<br>AACATTAAAAACTATTTAAATTGGTATCAGCAGAAATCAGCGACAGCCCCTGAGCTCCTGATATATGGTGCTTCCAGTGTGC<br>AAAGTGGGGTCCCATCAAGGTTCAGTGGCAGTGGATCTGGGACAGAATTCACTCTCACCATCAGCAGTCTGCAACCCGAAG<br>ATTTTGCAACTTACTACTGTCAACAGAGTTACAGTACCCTCCGGACTTTCGGCGGAGGGACCAAGGTGGAGATCAAAC |
| EEEV-76 | 109 | heavy | CAGGTGCAGCTGGTGCAGTCTGGGGCTGAGGTGAAGAAGCCTGGGGCCTCAATGAAGGTCTCCTGCAAGACTTCTGGATA<br>CACCTTCACCGACTACTATATGCACTGGGTGCGACAGGCCCCTGGACAAGGGCGTGAGTGGATGGGATGGATCAACCCTA<br>AAAGTGGTGTCGCAAACTATGCACAGAAATTTCAGGACAGGGTCACCATGACCAGGGACACGTCCATCACCACAGCCTACA<br>TGGAGGTGACCAGGCTGAGATCTGACGACACGGCCGTGTATTACTGTGCGAGAGATCGGGGGATTTTTGGAGGTTACTAC<br>GGTTTGGACGTCTGGGGCCAAGGGACCACGGTCACCGTCTCCTCA |
| | 110 | light | CAGTCTGTGTTGACGCAGCCGCCCTCAGTGTCTGCGGCCCCAGGACAGAAGGTCACCATCTCCTGCTCTGGAAGCAGCTCC<br>AACATTGTGAATAATTATGTATCCTGGTACCGGCAGCTCCCAGGAACAGCCCCCAAACTCCTCATTTATGACAATAATAAGC<br>GACCCTCAGGGATTCCTGACCGATTCTCTGGCTCCAAGTCTGGCGCGTCAGCCACCCTGGGCATCACCGGACTCCAGACTG<br>GGGACGAGGCCGATTATTACTGCGGAACATGGGATAGCAGCCTGAGTGCTGTGGTCTTCGGCGAAGGGACCAAGGTGAC<br>CGTCCTA |
| EEEV-81a | 111 | heavy | CAGGTGCAACTGGTGGAGTCTGGGGGAGGCGTGGTCCAGCCTGGGAGGTCCCTGAGACTCTCCTGTGCAGCGTCTGGATT<br>CAGCTTCAGTGACTATGGCATGCACTGGGTCCGCCAGGCTCCAGGCAAGGGGCTGGAGTGGGTGGCAATTGTATGGTTTG<br>ATGGAAGTAATAAATACTATGCAGACTCCGTGAAGGGCCGATTCACCATCTCCAGAGACAATTCCAGGAACACACTGTATC<br>TGCAAATGAACAGCCTGAGAGGCGAGGACACGGCTGTGTATCACTGTGCGAGAGATTTTACCCCAACGGCGGTAGCTCTT<br>GACTACTGGGGCCAGGGAACCCTGGTCACCGTCTCCTCA |
| | 112 | light | CAGTCTGTGCTGACGCAGCCCCACTCTGTGTCGGAGTCTCCGGGGAAGACGGTAACCATCTCCTGCACCCGCAGCAGTGGC<br>AGCATTTCCCGCAACTATGTGCAGTGGTACCAGCAGCGCCCGGGCAGTGCCCCCACCACTGTGATCTATGAGGATAACCAA<br>AGGCCCTCTGGGGTCCCTGATCGGTTCTCTGGCTCCATCGACAGCTCCTCCAACTCTGCCTCCCTCACCATCTCTGGACTGAA<br>GACTGAGGACGAGGCTGACTACTACTGTCAGTCTTATGATAGCAGCCCTACCTGGGTGTTCGGCGGAGGGACCAAGCTGA<br>CCGTCCTA |
| EEEV-81b | 113 | heavy | CAGGTGCAACTGGTGGAGTCTGGGGGAGGCGTGGTCCAGCCTGGGAGGTCCCTGAGACTCTCCTGTGCAGCGTCTGGATT<br>CAGCTTCAGTGACTATGGCATGCACTGGGTCCGCCAGGCTCCAGGCAAGGGGCTGGAGTGGGTGGCAATTGTATGGTTTG<br>ATGGAAGTAATAAATACTATGCAGACTCCGTGAAGGGCCGATTCACCATCTCCAGAGACAATTCCAGGAACACACTGTATC<br>TGCAAATGAACAGCCTGAGAGGCGAGGACACGGCTGTGTATCACTGTGCGAGAGATTTTACCCCAACGGCGGTAGCTCTT<br>GACTACTGGGGCCAGGGAACCCTGGTCACCGTCTCCTCA |
| | 114 | light | AATTTTATGCTGACTCAGCCCCACTCTGTGTCGGAGTCTCCGGGGAAGACGGTAACCATCTCCTGCACCCGCAGCAGTGGC<br>AGCATTTCCCGCAACTATGTGCAGTGGTACCAGCAGCGCCCGGGCAGTGCCCCCACCACTGTGATCTATGAGGATAACCAA<br>AGGCCCTCTGGGGTCCCTGATCGGTTCTCTGGCTCCATCGACAGCTCCTCCAACTCTGCCTCCCTCACCATCTCTGGACTGAA<br>GACTGAGGACGAGGCTGACTACTACTGTCAGTCTTATGATAGCAGCCCTACCTGGGTGTTCGGCGGAGGGACCAAGCTGA<br>CCGTCCTA |
| EEEV-84 | 115 | heavy | CAGGTGCAGCTGCAGGAGTCGGGCCCAGGACTGGTGAAGCCTTCGGAGACCCTGTCCCTCACCTGCGCTGTCTCTGGTTAC<br>TCCATCAACAGTGGTTACTACTGGGCCTGGATCCGGCAGCCCCCAGGGAAGGGGCTAGAGTGGATTGGAAATATCTATCA<br>AAGTGGGAGCACCTACTACAACCCGTCCCTCATGAGTCGAGTCACCATATCAGTAGACGCGTCCAAGAACCAGTTATTCCT<br>GAACCTGAGCTCTGTGACCGCCGCAGAGACGGCCGTGTATTACTGTGCGACCTGTCACTCGTTGGGAACAAGTGCCTGGCC<br>GCTCCCGGACTACTGGGGCCAGGGAACCCTTGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 116 | light | GAAATTGTGTTGACGCAGTCTCCAGGCACCCTGTCTTTGTCTCCAGGGGAAAGAGCCACCCTCTCCTGCAAGACCAGTCAG<br>AGTATTAGCAGCGACTACTTAGCCTGGTACCAGCAGAGACCTGGCCAGGCTCCCTGGCTCCTCATCTTTGGTGCATCGAGC<br>AGGGCCACTGGTACCCCAGACAGGTTCAGTGGCAGTGGGTCTGGGACAGACTTCACTCTCACCATCAGCAGACTGGAGCC<br>TGAAGATTTTGCAGTGTATTTCTGTCAGCAGTATGGTAGTTCACCGTTCACTTTTGGCCAGGGGACCAACCTGGAGATCAAA |
| EEEV-88 | 117 | heavy | GAGGTGCAGCTGGTGGAGTCTGGGGGAGGCTTGGTAAAGCCTGGGGGGTCCCTTAGACTCTCCTGTGCAGCCTCTGGATT<br>CACTTTCAGTAACGTCTGGATGAGCTGGGTCCGCCAGGCTCCAGGGAAGGGGCTGGAGTGGGTTGGCCGTATTAAAAGCA<br>AAATTGATGGTGGGACAACAGACTACGCTGTATTCGTGAAAGGCAGATTCATCATCTCAAGAGATGATTCAAAAAATATGT<br>TGTATCTGCAAATGAACAGCCTGAAAACCGAGGACACAGCCGTGTATTACTGTACCACAGAGGATTATAATTACGTTTGGG<br>GGGGTCTCCCGGCGCCGTACGGTTTGGACGTCTGGGGCCAAGGGACCACGGTCACCGTCTCCTCA |
| | 118 | light | CAGTCTGCCCTGACTCAGCCTCCCTCCGTGTCCGGGTCTCCTGGACAGTCAGTCACCATCTCCTGCACTGGAACCAGCAGTG<br>ACGTTGGTAGTTATAACCGTGTCTCCTGGTACCAGCAGCCCCCAGGCACAGCCCCCAAACTCATGATTTATGAGGTCAGTAA<br>TCGGCCCTCAGGGGTCCCTGATCGCTTCTCTGGGTCCAAGTCTGGCAACACGGCCTCCCTGACCATCTCTGGGCTCCAGGCT<br>GAGGACGAGGCTGATTATTACTGCAGCTTATATACAGTCAGCAGCAATGTGGTATTCGGCGGAGGGACCAAGCTGACCGT<br>CCTG |
| EEEV-93 | 119 | heavy | CAGGTGCAGCTGCAGGAGTCGGGCCCAGGACTGGTGAAGCCTTCACAGACCCTGTCCCTCACCTGCACTGTCTCTGGTGGC<br>TCCATCAGCAGTGGTGGTTACTACTGGAGCTGGATCCGCCAGCACCCAGGGAAGGGCCTGGAGTGGATTGGGCACATCTA<br>TTACAGTGGGAACACCTACTACAACCCGTCCCTCAAGAGTCGAGTAACCATATCAGTAGACACGTCTAAGAACCAGTTCTCC<br>CTGAAGCTGAGCTCTGTGACTGCCGCGGACACGGCCGTGTATTACTGTGCGAGAGAAACCCATAGTGGGAGCTACGGCTA<br>CTGGGGCCAGGGAACCCTGGTCACCGTCTCCTCA |
| | 120 | light | CAGTCTGCCCTGACTCAGCCTCCCTCCGCGTCCGGGTCTCCTGGACAGTCAGTAACCATCTCCTGCACTGGAACCAGCAGTG<br>ACGTTGGTGGTTATAACTATGTCTCCTGGTACCAACAGCACCCAGGCAAAGCCCCCAAACTCATGATTTATGAGGTCAGTAA<br>GCGGCCCTCAGGTGTCCCTGATCGCTTCTCTGGCTCCAAGTCTGGCAACACGGCCTCCCTGACCGTCTCTGGGCTCCAGGCT<br>GAGGATGAGGCTGATTATTACTGCAGCTCATATGCAGGCAGCAACGTTTGGGTGTTCGGCGGAGGGACCAAGCTGACCGT<br>CCTA |
| EEEV-94 | 121 | heavy | CAGGTGCAGCTGGTGGAGTCTGGGGGAGGCGTGGTCCAGCCTGGGAGGTCCCTGAGACTCTCCTGTGCAGCCTCTGGGTT<br>CGTCTTCACTAATTATGTTATGCACTGGGTCCGCCAGGCTCCAGGCAAGGCGCTGGAGTGGGTGACACTTATATCATATGA<br>TGGAAACAATAAATACTACACAGACTCCGTGAAGGGCCGATTCACCATCTCCAGAGACAATTCCAAGAACACGCTGTATCT<br>GCAAATGAACAGCCTGAGAGCTGAGGACACGGCTTTATATTACTGTGCGAGATCTCCGCACGGTGACGTCCCTGACTACTA<br>CTTCGATCTCTGGGGCCGTGGCACCCTGGTCACTGTCTCCTCA |
| | 122 | light | GACATCCAGATGACCCAGTCTCCTTCCACCCTGTCTGCATCTGTAGGAGACAGAGTCACCATCACTTGCCGGGCCAGTCAGA<br>GTATTAGTAGCTGGTTGGCCTGGTATCAGCACAAACCAGGGAAACCCCCTAAGCTCCTGATCTATAAGGCGTCTAGTTTACA<br>AAGTGGGGTCCCATCAAGGTTCAGCGGCAGTGGATCTGGGACAGAATTCACTCTCACCATCAGCAGCCTGCAGCCTGATGA<br>TTTTGCAACTTATTACTGCCAACAGTATAATACTTATCGGGCGTTCGGCCTAGGGACCAAGGTGGAGATCAAA |
| EEEV-97 | 123 | heavy | CAGGTGCAGCTGGTGCAGTCAGGGGCTGAGGTGAGGAAGCCTGGGTCCTCGGTGAAGGTCTCCTGCGTGGCTTCTGGAG<br>GCACCTTCAGGAACTATGCTATCAGCTGGGTGCGACGGGCCCCTGGACAAGGGCTTGAGTGGATGGGAGGGATCATCCCT<br>ATCTTTGGTACAACAAACTACGCACAGAAGTTCCAGGGCAGAGTCACGATTTCCGCGGACGAGTCCACGAGCACAGCCTAC<br>ATGGAGCTGAGCAGCCTGAGATCTGAGGACACGGCCGTCTATTACTGTGCGAGAGATTACTATGAGAGGACTGATTATTAC<br>ACCCCGGGCTACTGGGGCCAGGGAACCCTGGTCACCGTCTCCTCA |
| | 124 | light | TCCTATGTGCTGACTCAGCCACCCTCAGTGTCAGTGGCCCCAGGAAAGACGGCCAGGATTACCTGTGGGGGAAACAACATT<br>GAAAGTACAAGTGTTCACTGGTACCAGCAGAAGCCAGGCCAGGCCCCTGTGCTGGTCATCTATTTTGATAGCGACCGGCCC<br>TCAGGGATCCCTGAGCGATTCTCTGGCTCCAACTCTGGAAACACGGCCACCCTGACCCTCAGCAGGGTCGAAGCCGGGGAT<br>GAGGCCGACTATTACTGTCAGGTGTGGGATAGTAGTAGTGATCATGTGGTATTCGGCGGAGGGACCAAGCTGACCGTCCT<br>A |
| EEEV-98 | 125 | heavy | CAGGTGCAGCTGCAGGAGTCGGGCCCAGGACTGGTGAAGCCATCGGAGACCCTGTCCCTCACCTGCTCTGTCTCTAATTAC<br>TCCATTACCAGTACTTACTACTGGGGGTGGATCCGGCAGCCCCCAGGGAAGGGGCTGGAGTGGATTGGGAGTGTTTATCA<br>TACTGGGAGCACTTATTACAACCCGTCCCTCAAGAGTCGAGTCACCATATCAGTAGACACGTCCAAGAACCGGTTCTCCCTG<br>AGGCTGCGCTCTGTGACCGCCGCAGACACGGCCGTTTATTACTGTGCGAGAGAGATACCGGCATGGATTTACTACTTGGAC<br>GTCTGGGGCAAAGGGGCCACGGTCACCGTCTCCTCG |
| | 126 | light | CAGTCTGTGTTGACGCAGCCGCCCTCAGTGTCTGCGGCCCCTGGGCAGCAGGTCACCATCTCCTGCTCTGTAAGCAGCTCCA<br>ACATTGGGACCACTTATGTATCCTGGTACCAGCAACTCCCAGGAACAGCCCCCAAACTCCTCATTTATGACAACAATAGGCG<br>ACCCTCAGGGATTCCTGACCGATTCTCTGGCTCCAAGTCTGGCACGTCAGCCACCCTGGGCATCACCGGACTCCAGACTGG<br>GGACGAGGCCGATTATTACTGCGGAGCATGGGATAGCAGCCTGAGTGCTGGGGTGTTCGGCGGGGGGACCAAGCTGACC<br>GTCCTA |

TABLE 2

PROTEIN SEQUENCES FOR ANTIBODY VARIABLE REGIONS

| Clone | SEQ ID NO: | Chain | Variable Sequence |
|---|---|---|---|
| EEEV-103 | 127 | heavy | QVQLVESGGGVVQPGRSLRLSCAASGFHFGSYGMHWFRQAPGKGLEWVAVTWYDGSNKDYVDSVKGRFTISRDNSENTLYLQMTSLRAEDTAVYYCARDGGSTWPPDYWGQGTLVIVSS |
| | 128 | light | QSPATLSVSPGERATLSCRASQSVNRNLAWYQHKPGQAPRLLIYGASTRVTDIPARFSGSGSGTEFTLTISSLQSEDFAIYYCQQYNNWPRFTFGPGTKVDIK |
| EEEV-104 | 129 | heavy | QVQLVQSGAEVKKPGASVKVSCKASGYTFTDYYMHWVRQAPGQGLEWMGWINPNSGGTNYAQKFQGRVTMTRDTSISTAYMELSRLRSDDTAVYYCACVDTAMGWGFDYWGQGTLVTVSS |
| | 130 | light | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPPAFGGGTKVEIK |
| EEEV-106 | 131 | heavy | QVQLQESGPGLVKPSQTLSLTCTVSGGSVSSGDYYWNWIRQHPQKGLEWIGYIFNGGSTNYNPSVQSRATISVDTSKNVLSLQLTSVTAADSAVYYCARDWEHCFNGICYYYFDYWGQGTLVTVSS |
| | 132 | light | DIQMTQSPSSLSASVGDRVTITCRASQSIKNYLNWYQQKPGTAPKVLIFGASSLQSGVPSRFSGSGSGTDFTLTISSLQPEDFATYYCQQSYSTLRTFGGGTKVNIK |
| EEEV-107 | 133 | heavy | QVQLVESGGGVVQPGRSLRLSCAASGFTLNNYGIHWVRQAPGKGLEWVALIWFDGTTKYNGDSMKGRFTISRDNSKNTVYLQMNSLRAEDTAVYYCARATYDFWSGEPIGHYYMDVWGKGTTVTVSS |
| | 134 | light | QTVVTQEPSLTVSPGGTVTLTCASNTGAVTSDFYPNWFQQKPGQAPRALIYSTNNKHSWTPARFSGSLLGGKAALTVSGVQPEDEAEYYCLLYYGGAQVYVFGTGTKVTVL |
| EEEV-109 | 135 | heavy | EVQLLESGGGLVQPGGSLRLSCAASGFIFDIYAMNWVRQAPGKGLEWVSAISGSGSTTYYADSLKGRFTISRDNSKNAVYLQMKSLRVDDTAVYYCAKGSGEQRYYFYPLDFWGTGTTVTVSS |
| | 136 | light | SYVLTQPPSVSVAPGQTARITCGEDNIGSKSVHWYQQRPGQAPVLVVYDDKYRPSGIPERFSGSNSGNTATLTISRIEAGDEADYYCQVWDSRYDRHVVFGGGTKLTVL |
| EEEV-12 | 137 | heavy | QVQLVESGGGVVQPGRSLRLSCEASGFYFNSYGMHWVRQAPGKGLEWVAVIWYDGSTKTYVESVMGRFTISRDNSKNTLYLQMNSLRVEDTAVYYCARASGWEIDYWGQGTLVTVYS |
| | 138 | light | QSALTQPASVSGSPGQSITISCTGTSSDVGGYNYVSWYQQHPGKAPKLIIFDVNNRPSGVSNRFSGSKSVNTASLTISGLRAEDEADYYCSSYTASSTLVFGGGTKLTVL |
| EEEV-126 | 139 | heavy | QVQLVQSGAEVRKPGSSVKVSCKASGGTFSNYDINWVRQAPGQGLEWMGGIIPIFDTPNYAQKFQGRVTITADESTTKAYMELSSLRSEDTAVYYCARGASRYCNSTSCYRIFDYWGQGSLVTVSS |
| | 140 | light | DIQMTQSPSTLSASVGDRVTITCRASQTIGDWLAWYQQKPGKAPKLLIYKASFLEGGVPSRFSGSGSGTTFTLTISSLQPDDFATYYCQHYNTYAYSFGQGTKLEIK |
| EEEV-127 | 141 | heavy | QVQLVQSGAEVKKPGSSVKVSCKASGGTFSDYSINWVRQAPGQGLEWMGGIIPIVGSVNYAQKFQGRVTITADDSTSTAYMELSSLRSEDTAVYYCATEIGIAVAGTIYYGMDVWGQGTTVTVSS |
| | 142 | light | EIVLTQSPATLSLSPGERATLSCRASQSVSSYLAWYQQKPGQAPRLLIYDPSNRATGIPARFSGSGSGTDFTLTISSLEPEDFAVYYCQHRSNWPPGTYTFGQGTKLEIK |
| EEEV-129 | 143 | heavy | QVQLVESGGGVVQPGRSLRLSCAASGFTFSTYAMHWVRQAPGKGLEWVALLSYDGSSKYYADSVKGRFTISRDNSKNTLYLQMSSLRADDTAIYYCAKIPVSMVRGVMEYAMDVWGQGTTVTVSS |
| | 144 | light | SYVLTQPPSVSVAPGQTARITCGGNNIGSNTVHWYQQKPGQAPVLVVYGDSDRPSGIPERFSGSNSGNTATLTISRVEAGDEADYYCQVWDSSSDHVVFGGGTKLTVL |
| EEEV-138 | 145 | heavy | QVQLVQSGTEVKKPGASVKVSCKASGYTFTSYGFTWVRQAPGQGLEWMGWISSYNNNTNYAQKFQGRVTMTTDTSTSTAYMELRSLRSDDTAVFYCARDRFSGYDLGYWGQGTLVTVSS |
| | 146 | light | QSALTQPASVSGSPGQSITISCTGTSSDVGSYNLVSWYQQHPGKAPKLMIYEVTKRPSGVSNRFSGSKSGNTASLTISGLQAEDEADYYCCSFAGRSAPFGTGTKVTVL |
| EEEV-141 | 147 | heavy | QVQLVQSGAEVKKPGSSVKVSCKVSGGTFSHFAIIWVRQAPGQGLEWMGGIIPVFGTTNYVEKFQGRVTITADESRSTAYMELTRLTFEDTAVYYCAKGFRAGGANTDFDYWGQGTLVTVSS |
| | 148 | light | QLVVTQSPSASASLGASVKFTCTLSSGHSTYSIAWHQQHPARGPRYLMRVNSDGSHTKGDGIPDRFSGSSSGADRFLTISRLQSEDEADYYCQTWGTGIQVVFGGGSKLTVL |

TABLE 2-continued

| PROTEIN SEQUENCES FOR ANTIBODY VARIABLE REGIONS | | | |
|---|---|---|---|
| Clone | SEQ ID NO: | Chain | Variable Sequence |
| EEEV-143 | 149 | heavy | QVQLVESGGGVVQPGRSLRLSCAASGFTFSNYGIHWVRQAPGKGLEWVAVISYDGRHKYIADPVKGRFTISRDNSKNMLYLQMNSLRTEDTAVYYCAKDTSGWYEFFDSWGQGIPVTVSS |
| | 150 | light | EIVMTQSPATLSVSPGERATLSCRASQSVATNVAWYQQKPGQAPRLLIYGASTRATGIPARFSGSGSGTEFTLTISSLQSEDFAVYYCQQCNDWLTFGQGTKVEIK |
| EEEV-144 | 151 | heavy | QVQLVQSGAEVTKPGASVKVSCKTSGYTFTYYNISWVRQAPGQGLEWMGWISAYSGNTHYAQKLQGRVTMTIDTSTSTAYMELRSLRSDDTAVYYCARDGASVLPPASVYYSYMDVWGKGTTVTVSS |
| | 152 | light | DIQMTQSPSSLSASVGDRVTISCRASQNISSYLNWYQQKPGKAPKVLIYAASSLQRGVPSRFSGSGSGTDFTLTISSLQPEDFATYYCQQSYSTPRTFGQGTKVEIK |
| EEEV-145 | 153 | heavy | EVQLVESGRGLVQPGGSLRLSCAASGFTFNIYWMSWVRQAPGKGLEWVANIKQDGSEKYYVNSVKGRFTISRDNAKYSLYLQMNSLRAEDTAVYYCARGFIGYCNSKTCSYDFDYWGQGALVTVSS |
| | 154 | light | SSELTQDPAVSVALGQTVRITCQGDSLRSFYASWYQQKPGQAPLLVIYNENNRPSGIPDRFSGSSSGNTASLTITGTQAADDADYYCSSRDSSGNHVLFGGGTKLTVL |
| EEEV-147 | 155 | heavy | QVQLVQSGAEVKKPGASVKVSCKASGYTFTNYGITWVRQAPGQGLEWMGWISAYNGNTDYAQKLQGRVTMTTDTSTSTAYMELGSLRSDDTAVYYCARELWFGDLGYWGQGTLVTVSS |
| | 156 | light | EIVLTQSPGTLSLSPGERATLSCRASQSVSRSSSSYLAWYQQKPGQAPRLLIYGASSRATGIPDRFSGSGSGTDFTLTISRLEPEDVAVYYCQQYGSSPQTFGQGTKLEIK |
| EEEV-153 | 157 | heavy | EVHLVDSGGGLEQPGRSLRLSCAASGFTFSDYAMHWVRQAPGKGLEWVSSISWNSGNIGYADSVKGRFTISRDNAKNSLYLQMNTLKTEDTAFYYCARGPFFNWNPTNYFDHWGQGTLVTVSS |
| | 158 | light | EIVLTQSPGTLSLSPGERATLSCRASQSVPSSYLAWYQHKPGQAPRLLIYGASSRATGIPDRFSGSGSGTDFTLTIRRLEPEDFAVYYCQQYGTSPPMYTFGQGTKLEIK |
| EEEV-157 | 159 | heavy | QVQVVESGGGVVQPGRSLRLSCAASGFTFTSYGIHWVRQAPGKGLEWVAVISYDGSNRFYADSVKGRFTISRDNSKNTLYLQMNSLRVEDTAVYYCARGRLCVGDSCHSGPLDYWGQGTLVTVSS |
| | 160 | light | SFELTQPPSMSVSPGQTARISCSGDTLGNKYAYWYQQKPGQSPVLVIYQDNKRPSGIPERFSGSNSGNTATLTISGTQAMDSADYYCQAWDSSAHYVFGTGTKVTVL |
| EEEV-158 | 161 | heavy | QVQLVESGGGVVQPGRSLRLSCAASGFTFSSYGMHWVRQAPGKGLEWVAVISYDESNKYYSDSVKGRFTISRDNSKNTLYLQMNSLRAEDTAVYYCAKKGCSGGNCDEGFDYWGQGTLVTVSS |
| | 162 | light | QSALTQPASVSGSPGQSITISCTGTSSDVGGYNYVSWYQQHPGKAPKLMIYEVSNRPSGVSHRFSGSKSGNTASLTISGLQAEDEADYYCISYRSSSTLYVFGTGTKVTVL |
| EEEV-16 | 163 | heavy | QVQLVESGGGVVQPGRSLRLSCAASGFYFSSYGMHWVRQAPGKGLEWVAVIWYDGSNKYYVDSVKGRFTISRDNSKNTLYLQMNSLRAEDTAVYYCARADGYNFDYWGQGTLVTVSS |
| | 164 | light | SSELTQDPAVSVALGQTVRITCQGDSLRSYFASWYQQKPGQAPVVVIFDRNNRPSGIPDRFSGSSSGSTASLTITGAQAEDEADYYCNSRDSSGNLYVFGTGTKVTVL |
| EEEV-160 | 165 | heavy | QVTLKESGPVLVKPTETLTLTCSVSGFSLSSARMGVSWIRQPPGKALEWLAH1FSSDEKSYSTSLKSRLSISKDTSKSQVVLTLTNLDPVDTATYYCARIRGPSYYHQNYYYFGMDVWGQGTTVTVSS |
| | 166 | light | DIVMTQSPLSLPVTPGEPASISCRSSQSLLHSNGYNYLDWYLQKPGQSPQLLIYLGSNRASGVPDRFSGSGSGTDFTLQISRVEAEDVGVYYCMQALQAPWTFGQGTKVEIK |
| EEEV-164 | 167 | heavy | QVQLQESGPGLVKPSQTLSLTCVVSGASISSADSYWSWIRQHPGKGLEWIGYIYYSGSTYYNPSLKSRVTISVDTSKNQFSLKLTSLTAADTAVYYCARGGPYCGGDCYRWGQGTLVTVSS |
| | 168 | light | DIQLTQSPSSLSASVGDRVTITCQASQDISNFLNWYQQKPGKAPKLLIYDAANLDTGVPSRFSGSGSETDFTFTISSLQPEDIATYYCQQYDSLPWTFGQGTKVEIK |
| EEEV-168 | 169 | heavy | QVQLRESGPGLVKPSETLSLTCTVSNGSISSYYWSWIRQPAGKGLEWIGRIYSSGSTNYNPSLKSRVTMSVDTSKNQFSLRLRSVTAADTAVYYCARDLRAWIQLHRASLYYYYMDVWGKGTTVTVSS |
| | 170 | light | SSELTQDPAVSVALGQTVRITCQGDSLRSFYTTWYQQKPGQAPVLVIYGTNNRPSGIPERFSGSSSGNTASLTITGAQADDEADYYCDSRDSSGELWLFGGGTKLTVL |
| EEEV-169 | 171 | heavy | EVQLLESGGGLVQPGGSLRLSCVASGFSFGSYGMSWVRQAPGKGLEWVSGIGGRGDSTYFADSVKGRFSISRDNSKNTLYLQMNFLRAEDTAVYYCAKEGFGSGHFHGSNDYWGQGTLVTVSS |
| | 172 | light | DIQMTQSPSSLSASVGDRVTIACQTSHDISNYLNWYQQKPGRAPKLLIYDASNLQTGVPSRFSGSGSGTDFTLTISSLQPEDIATYYCQQFDSLPLTFGGGTKVGVK |

TABLE 2-continued

PROTEIN SEQUENCES FOR ANTIBODY VARIABLE REGIONS

| Clone | SEQ ID NO: | Chain | Variable Sequence |
|---|---|---|---|
| EEEV-17 | 173 | heavy | QVQLVQSGAEVKKPGASVKVSCKASGYTFTSYDINWVRQATGQGLEWMGWMNPNSGNTGYAQKFQGRVTMTRNTSISTAYMELSSLRSDDTAVYYCARFYDFWSGLDIDVWGKGTTVTVFS |
| | 174 | light | QSALTQPASVSGSPGQSITISCTGTSSDVGGYNYVSWYQQHPGKAPKLMIYEVSNRPSGVSNRFSGSKSGNTASLTISGLQAEDEADYYCSSYTSSITRVFGTGTKVTVL |
| EEEV-173 | 175 | heavy | QVQLVQSGAEVKKPGSSVKVSCKASGGTFSNYGISWVRQAPGQGLEWMGGVIPIFGTTKYAKKFQGRVTVTADKSTGTAYMELSSLISEDTAVYYCARDDGAAAGTGYYGMAVWGQGTTVTVSS |
| | 176 | light | EIVMTQSPATLSVSPGERATLSCRASQSVSSYLAWYQQKPGQAPRLLIYGASTRATGIPARFSGSGSGTEFTLTISSLQSGDFAVYYCQQYVNWPQYTFGQGTKLEIK |
| EEEV-179 | 177 | heavy | QVQLLQSGAEVKKPGSSVKVSCKASGGTFSNIGISWVRQAPRQGLEWMGGIIPLFATTNYAQNFQGRLTITADKSTTTAYMELNSLRSDDTGVYFCARQLGWAYCNSSTCSKGWFNPWGQGTLVTVSS |
| | 178 | light | DIVMTQTPLSLPVTPGEPASISCRSSQSLLDSDDGNTYLDWYLQKPGQSPHLLIYTVSYRASGVPDRFSGSGSGTDFTLKISTVEAEDVGVYYCMQRTEFPYTFGQGTKLEI |
| EEEV-180 | 179 | heavy | QVQLQESGPGLVKPSQTLSLSCSVSGGSISTGGYYWSWIRQKSGKGLEWIGYISNIGNTYYNPSLKSRVAISLDTSKNQFSLKLSSVTAADTAVYYCAKAPPDAYDSGTYYLAYYMDVWGKGTTVAVSS |
| | 180 | light | DIQMTQFPSTLSASVGDRVTITCRASQSISSWLAWYQQKPGKAPNLLIYKASSLESGVPSRFSGSGSGTEFTLTISSLQPDDFASYYCQQYNSYPYTFGQGTKLEIK |
| EEEV-181 | 181 | heavy | QVQLVESGGGVVQPGRSLRLSCTASGFTFSNYGMQWVRQAPGKGLEWVAVISYHGNNNYTDSVKGRFTISRDNSKNTLYLQMNSLRAEDTAVYYCATGLEGEYWGQGTLVTVSS |
| | 182 | light | SYELTQPSSVSVSPGQTARITCSGDLLAKIYARWFQQKPGQAPELVIYKDSERPSGIPERFSGSSSGTTVTLTISGAQVEDEADYYCYSATDNNGVFGGGTKLTVL |
| EEEV-182 | 183 | heavy | QVQLQESGPGLVKPSQTLSLTCTVSGGSISSGDYYWSWIRQHPGKGLEWIGYIYYNGNTYSNPSLKSRVTISVDTSKNQFSLRLTSVTAADTAVYYCARGGRIRFLEWYDYWGQGTLVTVSS |
| | 184 | light | DIQMTQSPSSLSASVGDRVTITCRASQSISNYLNWYQQKPGKAPKLLIYAASSLQSGVPSRFSGSGSGTDFTLTISTLQPEDFATYYCQQSYSSPRTFGLGTKLEIK |
| EEEV-183 | 185 | heavy | QVQLVESGGGVVQPGRSLRLSCAASGFSFNSYGMHWVRQAPGKGLEWVALTWYDGSNKYYAESVKGRFTISRDNSKNTLYLQMNSLRAEDTAVYYCARDQGCSGGSCYSEGWFDPWGQGTLVTVSS |
| | 186 | light | QSVLTQPPSASGTPGQRVTISCSGSSSNIGGNTVNWYQQLPGTAPKLLIYSNNQRPSGVPDRFSGSKSGTSASLAISGLQSEDEADYYCAAWDDSLNAVVFGGGTKLTVL |
| EEEV-184 | 187 | heavy | QITLKESGPTLVKPTQTLTLTCTFSGFSLSSSGEGLGWIRQPPGKALEWLALIYGDDDKRYSPSLKSRLTITKDTSKNQVVLTMTNMDPVDTATYYCAHRSGYCSGGDCYSRLGWFDPWGLGTLVTVSS |
| | 188 | light | EIVLTQSPGTLSLSPGERATLSCRASQSVSNNYLAWYQQKPGQAPRLLIYGASSRATGIPDRFSGSGSGTDFTLTISRLEPEDFAVYYCQQYGRSLFTFGPGTKVD1K |
| EEEV-21 | 189 | heavy | QVQLVESGGGVVQPGRSLRLSCAASGFTFRTYALHWVRQAPGKGLEWVAVISYDGSNKYYADSVKGRFTISRDNSKNTLFVQMNSLRPEDTAVYYCTRVVNFGVAFIRDGVYGHYYYGMDVWGQGTTVTVSS |
| | 190 | light | QSVLTQPPSVSAAPGQKVSISCSGSTSNIGNNYVSWYRQFPGTAPKFLIYDNDKRPSGIPDRFSGSKSGTSATLGITGLQTGDEADYYCGTWDSSLSVWVFGGGTKLTVL |
| EEEV-23 | 191 | heavy | QVQVQESGPGLVKTSETLSLTCTVSGGSISSYYWSWIRQAAGKGLEWIGRTYSGGSPNYNPSLRSRVTVSVDTSKNQFSLILTSVTAADTAVYFCAREDHGLRQKFYYYMDLWGKGTAVTVSS |
| | 192 | light | SYVLTQPPSVSVAPGKTAKITCGGSNIGSKSVHWYQQKPGQAPVLVIYYDSDRPSGIPDRFSGSNSGNTATLTISRVEAGDEADYSCQVWDSSPDHSPVVFGGGTKLTVL |
| EEEV-26 | 193 | heavy | QVQLQESGPGLVKPSETLSLTCIVSGGSINSYYWSWIRQPAGKALEWIGRIYTSGSTNYNPSLKSRVTMSVDMSKNQFSLKLTSVTAADTAVYYCARAPRIPVSVEGHYYYHYYMDVWGKGTTVTVS |
| | 194 | light | SSVLTQDPAVSVALGQTVRITCQGDSLRTYYASWYQQKPGQAPILVIYAKNHRPSGIPDRFSGSSSGNTASLTITGAQAEDEADYYCNSQDSSGNHLGFGGGTKLTVL |
| EEEV-27 | 195 | heavy | EVQLLESGGGLVQPGGSLRLSCAASGFTISRYAVTWVRQAPGKGLEWVSTITGSGGRTYYADSVKGRFTVSRDSSKNTLYLQMNTLRAEDSAIYYCAKGIVVVLVGPPYFGMDVWGQGTTVTVSS |
| | 196 | light | SYVLTQPPSVSVAPGQTARIPCGGNNIGTKTVHWYQQKPGQAPVLVVYDDSDRPSGIPERFSGSNSGNTATLTISSVEAGDEADYHCQVWDSSSDLVVFGGGTKLTVL |

TABLE 2-continued

PROTEIN SEQUENCES FOR ANTIBODY VARIABLE REGIONS

| Clone | SEQ ID NO: | Chain | Variable Sequence |
|---|---|---|---|
| EEEV-29 | 197 | heavy | QLQLQESGSGLVKPSQTLSLTCAVSGGSISSGVYSWSWIRQPPGKGLEWIGYIYH SGSTYYNPSLKSRVTISVDRSKNQFSLKLSSVTAADTAVYYCARESVANYFDYWG QGTLVTVSS |
| | 198 | light | EIVLTQSPATLSLSPGESATLSCRASQSVDSYLAWYQQKPGQAPRLLIYDASNRAS GIPARFSGSGSGTDFTLTISSLEPEDFAVYYCQQRSDWPFTFGPGTKVDIK |
| EEEV-30 | 199 | heavy | QVQLVESGTEVKKPGASVKVSCKASEYTFTAYYIHWVRQAPGQGLEWMGWIN PNSGGTNYAQKFQGRVTMTGDTSITTAYMELSRLRSDDTAVYYCASDYFDSSGY HDYWGQGTLVTVSS |
| | 200 | light | QSALTQPASVSGSPGQSITISCTGTSSDIGNYNLVSWYQQHPGKAPKLMIFEVSK RPSGVSNRFSGSKSGNTASLTISGLQAEDEAHYYCCSYVDDWVFGGGTKLTVL |
| EEEV-33 | 201 | heavy | QVTLKESGPALVKPTQTLTLTCTFSGFSLSTSGMRVSWIRQPPGKALEWLARID WDDDKFYSTSLKTRLTISKDTSKNQVVLRMTNMDPVDTATYYCARILPGYCSGG SCYYNYHFDYWGQGTLVTVSS |
| | 202 | light | SYVLTQPPSVSVAPGQTARITCGGNNIGSKSVHWYQQKPGQAPVLVVYHDSDR PSGIPERFSGSNSGNTATLTISRVEAGDEADYYCQVWDSSSDPYVFGTGTKVTVL |
| EEEV-34 | 203 | heavy | QVQLVESGGGVVQPGRSLRLSCAASGFTFSSYGMHWVRQAPGKGLEWVAVI WYDGINKYYSDSVKGRFTISRDNSKNTLYLQMNSLRAEDKAVYYCAREGGGQH GDYASWFDPWGQGTLVTVSS |
| | 204 | light | DIQMTQSPSSLSASVGDRVTITCRASQSISSYLNWYQQKPGKAPKLLIYTASSLQS GVPSRFSGSGSGTDFTLTISSLQPEDFATYYCQQSYSKGRTFGPGTKVDIK |
| EEEV-35 | 205 | heavy | QVQLVQSGAEVKKPGSSVKVSCKASGGSFRSYAISWVRQAPGQGLEWMGMII PIFDTTNYAQKFQGRVTITADKSTSTTYMELNSLKSEDTAVYYCARDLNHFYASS GPNDLWGQGTLVTVSS |
| | 206 | light | EIVLTQSPGTLSLSPGERATLSCRASQSVSSNFLAWYQQKPGQAPRLLIYGTSSRA TGIPDRFSGSGSGTDFTLTISRLEPEDFAVYYCQQYGGSPGTFGQGTKVEIK |
| EEEV-42 | 207 | heavy | QVTLKESGPALVRPTQTLTLTCTFSGFSLTTSGMRVSWIRQPPGKALEWLARID WDDDKFYSTSLKTRLTISKDTSKNQVVLTLTNMDPVDTATYYCARSMYDSSGYY PPTPFDIWGQGTMVTVSS |
| | 208 | light | DIQMTQSPSSLSASVGDRVTITCRASQSISRYLNWYQQKPGKAPKLLIYAASALQ SGVPSRFSGSGSGTDFTLTISSLQPEDFATYSCQQSFNTPFTFGPGTKVDIK |
| EEEV-43 | 209 | heavy | EVQLLESGGGLIQPGGSLRLSCAASGFTFTNYAMNWVRQAPGKGLEWVSVISG SGGTSYYADSVKGRFTISRDNSKNTLYLQMNSLRAEDTAVYYCAKGATLIVVVLR PDVFDIWGQGTMVTVSS |
| | 210 | light | SYELTQPPSVSVSPGQTASITCSGDKLGDKHACWYRQKPGQSPVLVIYQDSKRP SGIPERFSGSNSGNTATLTISGTQAMDEADYYCQAWDSNTAHYVFGTGTKVTV L |
| EEEV-47 | 211 | heavy | QVQLVESGGGVVQPGRSLRLSCAASGFRFSSYGMHWVRQAPGKGLEWVGVI WYDGSNKYYADSVKGRCTISRDNAKNTLYLQMNSLRAEDTAMYYCARVSRGA DDWDYYYYMDVWGKGTTVTVSS |
| | 212 | light | DIVMTQSPDSLAVSLGERATINCKSSHSVLYFSNNKNCLAWYQQKPGQPPKLLIY WASTRESGVPDRFSGSGSGTDFTLTISSLQAEDVAVYYCQQYYSTPFTFGPGTKV DIR |
| EEEV-51 | 213 | heavy | QVQLVESGGGVVOPGRSLRLSCAASGFMFSSYGMHWVRQAPGKGLEWVAVI WYDGSNKYYADSVKGRFSISRDNSKNTLYLQMNSLRAEDTAVYYCARVVGGEF DYWGQGTLVTVSS |
| | 214 | light | NFMLTQPHSVSESPGKTVTISCTRSSGSIASNYVQWYQQRPGSAPTTVIYEDNQ RPSGVPDRFSGSSDSSSNSASLTISGLKTEDEADYYCQSYNSSNWVFGGGTKLTV L |
| EEEV-53 | 215 | heavy | QVQLVESGGGVVQPGRSLRLSCTASGFTFSSYGMHWVRQTPDKGLEWVALIW YDGSNKYYADSVKGRFTISRDNSKNTLYLQMETLRAEDTAVYYCARVGGVGWE GDFWGQGTLVTVSS |
| | 216 | light | QSALTQPASVSGSPGQSITISCAGSSSDVGANNYVSWYQQDPGQAPKLMIYEV NYRPSGVPNRFSGSKSGNTAYLTISGLQAEDEANYFCSSYSSATTLRFGGGTKLTV L |
| EEEV-54 | 217 | heavy | QVQLVQSGAEVKKPGASVKVSCKTSGYIFSNYDISWVRQAPGQGLEWMGWIS AYSGEKKYSQKFQVRLTMTADTATSTAYMELRSLRSDDTAVYYCARDPTVVHAL DIWGQGTMVTVSS |
| | 218 | light | DIQMTQSPSSLSASVGDRVTITCQASHDISNFLNWYQQKPGKAPKLLIFDASNLE PGVPSRFSGSGSGTDFTFTINSLQPEDIATYYCQQYDDLVYTFGQGTKLEIK |

TABLE 2-continued

PROTEIN SEQUENCES FOR ANTIBODY VARIABLE REGIONS

| Clone | SEQ ID NO: | Chain | Variable Sequence |
|---|---|---|---|
| EEEV-55 | 219 | heavy | EVQLVESGGGLVQPGGSLRLSCAASGFTFSSYTMNWVRQAPGKGLEWVSYITNSSSAIYYADSVKGRFTISRDNAKNSLYLQMNSLRDEDTAVYYCARDLARPHRYYDNSAYFEVFDSWGQGTLVTVSS |
| | 220 | light | SSELTQDPAVSVALGQTVRITCQGDSLRNYYASWYQQKPGQAPVLVIYGKNNRPSGIPDRFSGSNSGNTASLTITGAQAEDEGDYYCSSRDSSGNYLRVFGTGTKVTVL |
| EEEV-58 | 221 | heavy | QVQLVESGGGVVQPGRSLRLSCAASGFTFNSYGMHWVRQTPGKGLEWVAIIWYDGSQKYYADSVKGRFTISRDNSKNTLYLQMNSLRAEDTAVYYCARDEGSYDLDYWGQGTLVTVSS |
| | 222 | light | QSALIQPASVSGSPGQSITISCTGTKSDVGGYNYVSWYQQYPGKTPKRMIFEVSNRPSGASNRFSGSKSGNTASLTISGLQAEDEADYYCTSYTSSSTLVFGGGTKLTVL |
| EEEV-66 | 223 | heavy | QVQLVESGGGVVQPGRSLRLSCAASGFTFSSYGMHWVRQAPGKGLEWVAVIWHDGSNKYYGDSVKGRFTISRDNSKNTLYLQMNGLRAEDTAVYYCARVEGGSYSGDYWGQGTLVTVSS |
| | 224 | light | QSALTQPASVSGSPGQSITISCTGTSSDIGAYNSVSWYQQHPGKAPKLMIYDVSNRPSGVSNRFSGSKSGNTASLTISGLQAEDEADYYCSSFTNTVSVVFGGGTKLTVL |
| EEEV-67a | 225 | heavy | QVQLVESGGGLVKPGGSLRLSCAASGFIFSDYSMNWIRQAPGKGLEWISSISHSETYTYYADSVKGRFTISRDNAKNSLYLQMHSLRAEDTGVYYCARPLEAMMWEEFHFWGQGILVSVSS |
| | 226 | light | QSVLTQPPSASGTPGQRVTISCSGSTSNIGTNYVYWYHHLPGTAPKLLIYRTNQRPSGVPDRFSGSKSGTSASLVISGLRSEDEADYYCASWDGSLSGVLFGGGTKLTVL |
| EEEV-67b | 227 | heavy | QVQLVQSGAEVRKPGSSVKVSCKASGGTFSNYDINWVRQAPGQGLEWMGGIIPIFDTPNYAQKFQGRVTITADESTTKAYMELSSLRSEDTAVYYCARGASRYCNSTSCYRIFDYWGQGSLVTVSS |
| | 228 | light | QSVLTQPPSASGTPGQRVTISCSGSTSNIGTNYVYWYHHLPGTAPKLLIYRTNQRPSGVPDRFSGSKSGTSASLVISGLRSEDEADYYCASWDGSLSGVLFGGGTKLTVL |
| EEEV-68a | 229 | heavy | QVQLQESGPGLVKPSETLSLTCTVSGYSISSGYYWGWIRQPPGKGLEWIGSVYHSGTTYYNPSLRSRVTISSDTSKNQFSLRLSSVTAADTAVYYCAGSRLVSDIWPLVDVWGTGTTVTVSS |
| | 230 | light | EIVLTQSPGTLSLSPGERATLSCRASQSVSSSYLAWYQQKPGQAPRLLIYGASSRATGIPDRFSGSGSGTDFTLTFSRLEPEDFAVYYCQQYGSSPWTFGQGTKVEIK |
| EEEV-68b | 231 | heavy | EVQLVESGGGLVKPGGSLRLSCAASGFTFSNVWMSWVRQAPGKGLEWVGRIKSKIDGGTTDYAVFVKGRFIISRDDSKNMLYLQMNSLKTEDTAVYYCTTEDYNYVWGGLPAPYGLDVWGQGTTVTVSS |
| | 232 | light | EIVLTQSPGTLSLSPGERATLSCRASQSVSSSYLAWYQQKPGQAPRLLIYGASSRATGIPDRFSGSGSGTDFTLTFSRLEPEDFAVYYCQQYGSSPWTFGQGTKVEIK |
| EEEV-7 | 233 | heavy | QVQLQESGPGLVKTSQTLSLTCTVSGGSVISGDYYWSWIRQPPGKGLEWIGYIFNSGSTNYNPSLKSRVTISADKSKKQLSLKLTSVTAADTAVYYCARDYEGCTNGVCYTYLDFWGQGTLVTVSS |
| | 234 | light | DIQMTQSPSSLSASVGDRVMITCRASQNIKNYLNWYQQKSATAPELLIYGASSVQSGVPSRFSGSGSGTEFTLTISSLQPEDFATYYCQQSYSTLRTFGGGTKVEIK |
| EEEV-76 | 235 | heavy | QVQLVQSGAEVKKPGASMKVSCKTSGYTFTDYYMHWVRQAPGQGREWMGWINPKSGVANYAQKFQDRVTMTRDTSITTAYMEVTRLRSDDTAVYYCARDRGIFGGYYGLDVWGQGTTVTVSS |
| | 236 | light | QSVLTQPPSVSAAPGQKVTISCSGSSSNIVNNYVSWYRQLPGTAPKLLIYDNNKRPSGIPDRFSGSKSGASATLGITGLQTGDEADYYCGTWDSSLSAVVFGEGTKVTVL |
| EEEV-81a | 237 | heavy | QVQLVESGGGVVQPGRSLRLSCAASGFSFSDYGMHWVRQAPGKGLEWVAIVWFDGSNKYYADSVKGRFTISRDNSRNTLYLQMNSLRGEDTAVYHCARDFTPTAVALDYWGQGTLVTVSS |
| | 238 | light | QSVLTQPHSVSESPGKTVTISCTRSSGSISRNYVQWYQQRPGSAPTTVIYEDNQRPSGVPDRFSGSIDSSSNSASLTISGLKTEDEADYYCQSYDSSPTWVFGGGTKLTVL |
| EEEV-81b | 239 | heavy | QVQLVESGGGVVQPGRSLRLSCAASGFSFSDYGMHWVRQAPGKGLEWVAIVWFDGSNKYYADSVKGRFTISRDNSRNTLYLQMNSLRGEDTAVYHCARDFTPTAVALDYWGQGTLVTVSS |
| | 240 | light | NFMLTQPHSVSESPGKTVTISCTRSSGSISRNYVQWYQQRPGSAPTTVIYEDNQRPSGVPDRFSGSIDSSSNSASLTISGLKTEDEADYYCQSYDSSPTWVFGGGTKLTVL |
| EEEV-84 | 241 | heavy | QVQLQESGPGLVKPSETLSLTCAVSGYSINSGYYWAWIRQPPGKGLEWIGNIYQSGSTYYNPSLMSRVTISVDASKNQLFLNLSSVTAAETAVYYCATCHSLGTSAWPLPDYWGQGTLVTVSS |
| | 242 | light | EIVLTQSPGTLSLSPGERATLSCKTSQSISSDYLAWYQQRPGQAPWLLIFGASSRATGTPDRFSGSGSGTDFTLTISRLEPEDFAVYFCQQYGSSPFTFGQGTNLEIK |

TABLE 2-continued

PROTEIN SEQUENCES FOR ANTIBODY VARIABLE REGIONS

| Clone | SEQ ID NO: | Chain | Variable Sequence |
|---|---|---|---|
| EEEV-88 | 243 | heavy | EVQLVESGGGLVKPGGSLRLSCAASGFTFSNVWMSWVRQAPGKGLEWVGRIKSKIDGGTTDYAVFVKGRFIISRDDSKNMLYLQMNSLKTEDTAVYYCTTEDYNYVWGGLPAPYGLDVWGQGTTVTVSS |
| | 244 | light | QSALTQPPSVSGSPGQSVTISCTGTSSDVGSYNRVSWYQQPPGTAPKLMIYEVSNRPSGVPDRFSGSKSGNTASLTISGLQAEDEADYYCSLYTVSSNVVFGGGTKLTVL |
| EEEV-93 | 245 | heavy | QVQLQESGPGLVKPSQTLSLTCTVSGGSISSGGYYWSWIRQHPGKGLEWIGHIYYSGNTYYNPSLKSRVTISVDTSKNQFSLKLSSVTAADTAVYYCARETHSGSYGYWGQGTLVTVSS |
| | 246 | light | QSALTQPPSASGSPGQSVTISCTGTSSDVGGYNYVSWYQQHPGKAPKLMIYEVSKRPSGVPDRFSGSKSGNTASLTVSGLQAEDEADYYCSSYAGSNVWVFGGGTKLTVL |
| EEEV-94 | 247 | heavy | QVQLVESGGGVVQPGRSLRLSCAASGFVFTNYVMHWVRQAPGKALEWVTLISYDGNNKYYTDSVKGRFTISRDNSKNTLYLQMNSLRAEDTALYYCARSPHGDVPDYYFDLWGRGTLVTVSS |
| | 248 | light | DIQMTQSPSTLSASVGDRVTITCRASQSISSWLAWYQHKPGKPPKLLIYKASSLQSGVPSRFSGSGSGTEFTLTISSLQPDDFATYYCQQYNTYRAFGLGTKVEIK |
| EEEV-97 | 249 | heavy | QVQLVQSGAEVRKPGSSVKVSCVASGGTFRNYAISWVRRAPGQGLEWMGGIIPIFGTTNYAQKFQGRVTISADESTSTAYMELSSLRSEDTAVYYCARDYYERTDYYTPGYWGQGTLVTVSS |
| | 250 | light | SYVLTQPPSVSVAPGKTARITCGGNNIESTSVHWYQQKPGQAPVLVIYFDSDRPSGIPERFSGSNSGNTATLTLSRVEAGDEADYYCQVWDSSSDHVVFGGGTKLTVL |
| EEEV-98 | 251 | heavy | QVQLQESGPGLVKPSETLSLTCSVSNYSITSTYYWGWIRQPPGKGLEWIGSVYHTGSTYYNPSLKSRVTISVDTSKNRFSLRLRSVTAADTAVYYCAREIPAWIYYLDVWGKGATVTVSS |
| | 252 | light | QSVLTQPPSVSAAPGQQVTISCSVSSSNIGTTYVSWYQQLPGTAPKLLIYDNNRRPSGIPDRFSGSKSGTSATLGITGLQTGDEADYYCGAWDSSLSAGVFGGGTKLTVL |

TABLE 3

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EEEV-103 | GFHFGSYG (253) | TWYDGSNK (254) | ARDGGSTWPPDY (255) |
| EEEV-104 | GYTFTDYY (256) | INPNSGGT (257) | ACVDTAMGWGFDY (258) |
| EEEV-106 | GGSVSSGDYY (259) | IFNGGST (260) | ARDWEHCFNGICYYYF (261) |
| EEEV-107 | GFTLNNYG (262) | IWFDGTTK (263) | ARATYDFWSGEPIGHYYMDV (264) |
| EEEV-109 | GFIFDIYA (265) | ISGSGSTT (266) | AKGSGEQRYYFYPLDF (267) |
| EEEV-12 | GFYFNSYG (268) | IWYDGSTK (269) | ARASGWEIDY (270) |
| EEEV-126 | GGTFSNYD (271) | HPIFDTP (272) | ARGASRYCNSTSCYRIFDY (273) |
| EEEV-127 | GGTFSDYS (274) | IIPIVGSV (275) | ATEIGIAVAGTIYYGMDV (276) |
| EEEV-129 | GFTFSTYA (277) | LSYDGSSK (278) | AKIPVSMVRGVMEYAMDV (279) |
| EEEV-138 | GYTFTSYG (280) | ISSYNNNT (281) | ARDRFSGYDLGY (282) |
| EEEV-141 | GGTFSHFA (283) | IIPVFGTT (284) | AKGFRAGGANTDFDY (285) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EEEV-143 | GFTFSNYG (286) | ISYDGRHK (287) | AKDTSGWYEFFDS (288) |
| EEEV-144 | GYTFTYYN (289) | ISAYSGNT (290) | ARDGASVLPPASVYYSYMDV (291) |
| EEEV-145 | GFTFNIYW (292) | IKQDGSEK (293) | ARGFIGYCNSKTCSYDFDY (294) |
| EEEV-147 | GYTFTNYG (295) | ISAYNGNT (296) | ARELWFGDLGY (297) |
| EEEV-153 | GFTFSDYA (298) | ISWNSGNI (299) | ARGPFFNWNPTNYFDH (300) |
| EEEV-157 | GFTFTSYG (301) | ISYDGSNR (302) | ARGRLCVGDSCHSGPLDY (303) |
| EEEV-158 | GFTFSSYG (304) | ISYDESNK (305) | AKKGCSGGNCDEGFDY (306) |
| EEEV-16 | GFYFSSYG (307) | IWYDGSNK (308) | ARADGYNFDY (309) |
| EEEV-160 | GFSLSSARMG (310) | IFSSDEK (311) | ARIRGPSYYHQNYYYFGMDV (312) |
| EEEV-164 | GASISSADSY (313) | IYYSGST (314) | ARGGPYCGGDCYR (315) |
| EEEV-168 | NGSISSYY (316) | IYSSGST (317) | ARDLRAWIQLHRASLYYYYMDV (318) |
| EEEV-169 | GFSFGSYG (319) | IGGRGDST (320) | AKEGFGSGHFHGSNDY (321) |
| EEEV-17 | GYTFTSYD (322) | MNPNSGNT (323) | ARFYDFWSGLDIDV (324) |
| EEEV-173 | GGTFSNYG (325) | VIPIFGTT (326) | ARDDGAAAGTGYYGMAV (327) |
| EEEV-179 | GGTFSNIG (328) | IIPLFATT (329) | ARQLGWAYCNSSTCSKGWFNP (330) |
| EEEV-180 | GGSISTGGYY (331) | ISNIGNT (332) | AKAPPDAYDSGTYYLAYYMDV (333) |
| EEEV-181 | GFTFSNYG (334) | ISYHGNNN (335) | ATGLEGEY (336) |
| EEEV-182 | GGSISSGDYY (337) | IYYNGNT (338) | ARGGRIRFLEWYDY (339) |
| EEEV-183 | GFSFNSYG (340) | TWYDGSNK (341) | ARDQGCSGGSCYSEGWFDP (342) |
| EEEV-184 | GFSLSSSGEG (343) | IYGDDDK (344) | AHRSGYCSGGDCYSRLGWFDP (345) |
| EEEV-21 | GFTFRTYA (346) | ISYDGSNK (347) | TRWNFGVAFIRDGVYGHYYYGMDV (348) |
| EEEV-23 | GGSISSYY (349) | TYSGGSP (350) | AREDHGLRQKFYYYMDL (351) |
| EEEV-26 | GGSINSYY (352) | IYTSGST (353) | ARAPRIPVSVEGHYYYHYYMDV (354) |
| EEEV-27 | GFTISRYA (355) | ITGSGGRT (356) | AKGIVVVLVGPPYFGMDV (357) |
| EEEV-29 | GGSISSGVYS (358) | IYHSGST (359) | ARESVANYFDY (360) |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| EEEV-30 | EYTFTAYY (361) | INPNSGGT (362) | ASDYFDSSGYHDY (363) |
| EEEV-33 | GFSLSTSGMR (364) | IDWDDDK (365) | ARILPGYCSGGSCYYNYHFDY (366) |
| EEEV-34 | GFTFSSYG (367) | IWYDGINK (368) | AREGGGQHGDYASWFDP (369) |
| EEEV-35 | GGSFRSYA (370) | HPIFDTT (371) | ARDLNHFYASSGPNDL (372) |
| EEEV-42 | GFSLTTSGMR (373) | IDWDDDK (374) | ARSMYDSSGYYPPTPFDI (375) |
| EEEV-43 | GFTFTNYA (376) | ISGSGGTS (377) | AKGATLIVVVLRPDVFDI (378) |
| EEEV-47 | GFRFSSYG (379) | IWYDGSNK (380) | ARVSRGADDWDYYYYMDV (381) |
| EEEV-51 | GFMFSSYG (382) | IWYDGSNK (383) | ARVVGGEFDY (384) |
| EEEV-53 | GFTFSSYG (385) | IWYDGSNK (386) | ARVGGVGWEGDF (387) |
| EEEV-54 | GYIFSNYD (388) | ISAYSGEK (389) | ARDPTVVHALDI (390) |
| EEEV-55 | GFTFSSYT (391) | ITNSSSAI (392) | ARDLARPHRYYDNSAYFEVFDS (393) |
| EEEV-58 | GFTFNSYG (394) | IWYDGSQK (395) | ARDEGSYDLDY (396) |
| EEEV-66 | GFTFSSYG (397) | IWHDGSNK (398) | ARVEGGSYSGDY (399) |
| EEEV-67a | GFIFSDYS (400) | ISHSETYT (401) | ARPLEAMMWEEFHF (402) |
| EEEV-67b | GGTFSNYD (403) | HPIFDTP (404) | ARGASRYCNSTSCYRIFDY (405) |
| EEEV-68a | GYSISSGYY (406) | VYHSGTT (407) | AGSRLVSDIWPLVDV (408) |
| EEEV-68b | GFTFSNVW (409) | IKSKIDGGTT (410) | TTEDYNYVWGGLPAPYGLDV (411) |
| EEEV-7 | GGSVISGDYY (412) | IFNSGST (413) | ARDYEGCTNGVCYTYLDF (414) |
| EEEV-76 | GYTFTDYY (415) | INPKSGVA (416) | ARDRGIFGGYYGLDV (417) |
| EEEV-81a | GFSFSDYG (418) | VWFDGSNK (419) | ARDFTPTAVALDY (420) |
| EEEV-81b | GFSFSDYG (421) | VWFDGSNK (422) | ARDFTPTAVALDY (423) |
| EEEV-84 | GYSINSGYY (424) | IYQSGST (425) | ATCHSLGTSAWPLPDY (426) |
| EEEV-88 | GFTFSNVW (427) | IKSKIDGGTT (428) | TTEDYNYVWGGLPAPYGLDV (429) |
| EEEV-93 | GGSISSGGYY (430) | IYYSGNT (431) | ARETHSGSYGY (432) |
| EEEV-94 | GFVFTNYV (433) | ISYDGNNK (434) | ARSPHGDVPDYYFDL (435) |

TABLE 3-continued

| CDR HEAVY CHAIN SEQUENCES | | | |
|---|---|---|---|
| Clone | CDRH1 (SEQ ID NO:) | CDRH2 (SEQ ID NO:) | CDRH3 (SEQ ID NO:) |
| EEEV-97 | GGTFRNYA (436) | HPIFGTT (437) | ARDYYERTDYYTPGY (438) |
| EEEV-98 | NYSITSTYY (439) | VYHTGST (440) | AREIPAWIYYLDV (441) |

TABLE 4

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| EEEV-103 | QSVNRN (442) | GAS (443) | QQYNNWPRFT (444) |
| EEEV-104 | QSLVYSDGNTY (445) | KVS (446) | MQGTHWPPA (447) |
| EEEV-106 | QSIKNY (448) | GAS (449) | QQSYSTLRT (450) |
| EEEV-107 | TGAVTSDFY (451) | STN (452) | LLYYGGAQVYV (453) |
| EEEV-109 | NIGSKS (454) | DDK (455) | QVWDSRYDRHVV (456) |
| EEEV-12 | SSDVGGYNY (457) | DVN (458) | SSYTASSTLV (459) |
| EEEV-126 | QTIGDW (460) | KAS (461) | QHYNTYAYS (462) |
| EEEV-127 | QSVSSY (463) | DPS (464) | QHRSNWPPGTYT (465) |
| EEEV-129 | NIGSNT (466) | GDS (467) | QVWDSSSDHVV (468) |
| EEEV-138 | SSDVGSYNL (469) | EVT (470) | CSFAGRSAP (471) |
| EEEV-141 | SGHSTYS (472) | VNSDGSH (473) | QTWGTGIQVV (474) |
| EEEV-143 | QSVATN (475) | GAS (476) | QQCNDWLT (477) |
| EEEV-144 | QNISSY (478) | AAS (479) | QQSYSTPRT (480) |
| EEEV-145 | SLRSFY (481) | NEN (482) | SSRDSSGNHVL (483) |
| EEEV-147 | QSVSRSSSSY (484) | GAS (485) | QQYGSSPQT (486) |
| EEEV-153 | QSVPSSY (487) | GAS (488) | QQYGTSPPMYT (489) |
| EEEV-157 | TLGNKY (490) | QDN (491) | QAWDSSAHYV (492) |
| EEEV-158 | SSDVGGYNY (493) | EVS (494) | ISYRSSSTLYV (495) |
| EEEV-16 | SLRSYF (496) | DRN (497) | NSRDSSGNLYV (498) |
| EEEV-160 | QSLLHSNGYNY (499) | LGS (500) | MQALQAPWT (501) |

TABLE 4-continued

| CDR LIGHT CHAIN SEQUENCES | | | |
|---|---|---|---|
| Clone | CDRL1 (SEQ ID NO:) | CDRL2 (SEQ ID NO:) | CDRL3 (SEQ ID NO:) |
| EEEV-164 | QDISNF (502) | DAA (503) | QQYDSLPWT (504) |
| EEEV-168 | SLRSFY (505) | GTN (506) | DSRDSSGELWL (507) |
| EEEV-169 | HDISNY (508) | DAS (509) | QQFDSLPLT (510) |
| EEEV-17 | SSDVGGYNY (511) | EVS (512) | SSYTSSITRV (513) |
| EEEV-173 | QSVSSY (514) | GAS (515) | QQYVNWPQYT (516) |
| EEEV-179 | QSLLDSDDGNTY (517) | TVS (518) | MQRTEFPYT (519) |
| EEEV-180 | QSISSW (520) | KAS (521) | QQYNSYPYT (522) |
| EEEV-181 | LLAKIY (523) | KDS (524) | YSATDNNGV (525) |
| EEEV-182 | QSISNY (526) | AAS (527) | QQSYSSPRT (528) |
| EEEV-183 | SSNIGGNT (529) | SNN (530) | AAWDDSLNAVV (531) |
| EEEV-184 | QSVSNNY (532) | GAS (533) | QQYGRSLFT (534) |
| EEEV-21 | TSNIGNNY (535) | DND (536) | GTWDSSLSVWV (537) |
| EEEV-23 | NIGSKS (538) | YDS (539) | QVWDSSPDHSPVV (540) |
| EEEV-26 | SLRTYY (541) | AKN (542) | NSQDSSGNHLG (543) |
| EEEV-27 | NIGTKT (544) | DDS (545) | QVWDSSSDLVV (546) |
| EEEV-29 | QSVDSY (547) | DAS (548) | QQRSDWPFT (549) |
| EEEV-30 | SSDIGNYNL (550) | EVS (551) | CSYVDDWV (552) |
| EEEV-33 | NIGSKS (553) | HDS (554) | QVWDSSSDPYV (555) |
| EEEV-34 | QSISSY (556) | TAS (557) | QQSYSKGRT (558) |

TABLE 4-continued

CDR LIGHT CHAIN SEQUENCES

| Clone | CDRL1 (SEQ ID NO:) | CDRL2 (SEQ ID NO:) | CDRL3 (SEQ ID NO:) |
|---|---|---|---|
| EEEV-35 | QSVSSNF (559) | GTS (560) | QQYGGSPGT (561) |
| EEEV-42 | QSISRY (562) | AAS (563) | QQSFNTPFT (564) |
| EEEV-43 | KLGDKH (565) | QDS (566) | QAWDSNTAHYV (567) |
| EEEV-47 | HSVLYFSNNKNC (568) | WAS (569) | QQYYSTPFT (570) |
| EEEV-51 | SGSIASNY (571) | EDN (572) | QSYNSSNWV (573) |
| EEEV-53 | SSDVGANNY (574) | EVN (575) | SSYSSATTLR (576) |
| EEEV-54 | HDISNF (577) | DAS (578) | QQYDDLVYT (579) |
| EEEV-55 | SLRNYY (580) | GKN (581) | SSRDSSGNYLRV (582) |
| EEEV-58 | KSDVGGYNY (583) | EVS (584) | TSYTSSSTLV (585) |
| EEEV-66 | SSDIGAYNS (586) | DVS (587) | SSFTNTVSVV (588) |
| EEEV-67a | TSNIGTNY (589) | RTN (590) | ASWDGSLSGVL (591) |
| EEEV-67b | TSNIGTNY (592) | RTN (593) | ASWDGSLSGVL (594) |
| EEEV-68a | QSVSSSY (595) | GAS (596) | QQYGSSPWT (597) |
| EEEV-68b | QSVSSSY (598) | GAS (599) | QQYGSSPWT (600) |
| EEEV-7 | QNIKNY (601) | GAS (602) | QQSYSTLRT (603) |
| EEEV-76 | SSNIVNNY (604) | DNN (605) | GTWDSSLSAVV (606) |
| EEEV-81a | SGSISRNY (607) | EDN (608) | QSYDSSPTWV (609) |
| EEEV-81b | SGSISRNY (610) | EDN (611) | QSYDSSPTWV (612) |
| EEEV-84 | QSISSDY (613) | GAS (614) | QQYGSSPFT (615) |
| EEEV-88 | SSDVGSYNR (616) | EVS (617) | SLYTVSSNVV (618) |
| EEEV-93 | SSDVGGYNY (619) | EVS (620) | SSYAGSNVWV (621) |
| EEEV-94 | QSISSW (622) | KAS (623) | QQYNTYRA (624) |
| EEEV-97 | NIESTS (625) | FDS (626) | QVWDSSSDHVV (627) |
| EEEV-98 | SSNIGTTY (628) | DNN (629) | GAWDSSLSAGV (630) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., *Am. J. Pediatr. Hematol. Oncol.,* 12(4), 480-489, 1990.
Allred et al., *Arch. Surg.,* 125(1), 107-113, 1990.
Atherton et al., *Biol. of Reproduction,* 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.,* 12; 130(1):111-121, 1990.
Campbell, *In: Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.,* 74(2):425-433, 1977.
De Jager et al., *Semin. Nucl. Med.* 23(2), 165-179, 1993.
Dholakia et al., *J. Biol. Chem.,* 264, 20638-20642, 1989.
Diamond et al., *J Virol* 77, 2578-2586, 2003.
Doolittle and Ben-Zeev, *Methods Mol. Biol.,* 109:215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.

Gefter et al., *Somatic Cell Genet.,* 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLOS ONE* 2010; 5(5) e10569
Hessell et al., *Nature* 449, 101-4, 2007.
Khatoon et al., *Ann. of Neurology,* 26, 210-219, 1989.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Kyte and Doolittle, *J. Mol. Biol.,* 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.,* 99, 153-161, 1987.
Persic et al., *Gene* 187:1, 1997
Potter and Haley, *Meth. Enzymol.,* 91, 613-633, 1983.
Purpura et al., *Lancet Infect Dis.* 2016 October; 16(10): 1107-8. Epub 2016 Sep. 19.
Remington's Pharmaceutical Sciences, 15th Ed., 3:624-652, 1990.
Tang et al., *J. Biol. Chem.,* 271:28324-28330, 1996.
Wawrzynczak & Thorpe, In: *Immunoconjugates, Antibody Conuugates In Radioimaging And Therapy Of Cancer*, Vogel (Ed.), N Y, Oxford University Press, 28, 1987.
Yu et al., *J Immunol Methods* 336, 142-151, doi:10.1016/j.jim.2008.04.008, 2008.
Griffin D E. 2013. *Alphaviruses. Fields Virology.* $6^{th}$ edition.
Griffin D E. 2016. Neurotropic alphaviruses. *Neurotropic Viral Infections*. Volume 1: Neurotropic RNA Viruses. 175-204.
Sidwell R W, and Smee D F. 2003. Viruses of the Bunya- and Togavridiae families: potential as bioterrorism agents and means of control. *Antiviral Res.* 57:101-111.
Reichert et al., 2009. Alphavirus antiviral drug development: scientific gap analysis and prospective research areas. *Biosecur Bioterror.* 7:413-427.
Mathews J H, and Roehrig J T. 1982. Determination of the protective epitopes on the glycoproteins of Venezuelan equine encephalomyelitis virus by passive transfer of monoclonal antibodies. *The Journal of Immunology.* 129: 2763-2767.
Griffin D E. 1995. Roles and reactivates of antibodies to alphaviruses. *Seminars in Virology.* 6:249-255.
Zhang, W. et al., 2002. Placement of the structural proteins in Sindbis virus. *J. Virol.* 76, 11645-58(2002).
Mukhopadhyay, et al., 2006. Mapping the Structure and Function of the E1 and E2 Glycoproteins in Alphaviruses. *Structure* 14, 63-73.
Klasse P J. 2014. Neutralization of virus infectivity by antibodies: old problems in new perspectives. *Advances in Biology.* 2014:157895.
Burton D R. 2002. Antibodies, viruses and vaccines. Nature Reviews Immunology. 2:706-713.
Voss et al., 2010. Glycoprotein organization of Chikungunya virus particles revealed by X-ray crystallography.
Sun et al., 2013. Structural analyses at pseudo atomic resolution of Chikungunya virus and antibodies show mechanisms of neutralization. *eLife.* 2: e00435.
Selvarajah et al., 2013. A neutralizing monoclonal antibody targeting the acid-sensitive region in chikungunya virus E2 protects from disease. *PLOS Neglected Tropical Diseases.* 7(9):e2423.
Porta et al., 2014. Locking and blocking the viral landscape of an alphavirus with neutralizing antibodies. *Journal of Virology.* 88(17):9616-9623.
Fox et al., 2015. Broadly neutralizing alphavirus antibodies bind an epitope on E2 and inhibit entry and egress. *Cell.* 163:1095-1107.
Long et al., 2015. Cryo-E M structures elucidate neutralizing mechanisms of anti-chikungunya human monoclonal antibodies with therapeutic activity. *PNAS.* 112(45): 13898-13903.
Jin et al., 2015. *Cell Rep.* 13(11):2553-2564.
Calisher C H. 1994. Medically important arboviruses of the United States and Canada. *Clinical Microbiology Reviews.* 7(1):89-116.
Go et al., 2014. Zoonotic encephalitides caused by arboviruses: transmission and epidemiology of alphaviruses and flaviviruses. *Clin Exp Vaccine Res.* 3(1):58-77.
Markoff L. 2015. *Alphaviruses. Mandell, Douglas, and Bennett's Principles and Practice of Infectious Diseases.* 153:1865-1874.
Hunt et al., 2011. Treatment of mice with human monoclonal antibody 24 h after lethal aerosol challenge with virulent Venezuelan equine encephalitis virus prevents disease but not infection. *Virology.* 414:146-152.
Levine et al., 1991. Antibody-mediated clearance of alphavirus infection from neurons. *Science.* 254:856-860.
Griffin et al., 1997. The role of antibody in recovery from alphavirus encephalitis. *Immunological Reviews.* 159: 155-161.
Li et al., 2010. Structural changes of envelope proteins during alphaivrus fusion. *Nature.* 468(7324):705-708.
Kielian et al., 2010. Alphavirus entry and membrane fusion. *Viruses.* 2:796-825.
Zhang et al., 2011. 4.4 angstrom cyro-EM structure of an enveloped alphavirus Venezuelan equine encephalitis virus. *The EMBO Journal.* 30:3854-3863.
Roehrig et al., 1982. Antigenic analysis of the surface glycoproteins of a Venezuelan equine encephalomyelitis virus (TC-83) using monoclonal antibodies. *Virology.* 118:269-278.
Roehrig J T, and Mathews J H. 1985. The neutralization site on the E2 glycoprotein of Venezuelan equine encephalomyelitis (TC-83) is composed of multiple conformationally stable epitopes. *Virology.* 142:347-356.
Rico-Hesse et al., 1988. Monoclonal antibodies define antigenic variation in the ID variety of Venezuelan equine encephalitis virus. *Am J. Trop. Med. Hyg.* 38(1):187-194.
Roehrig, et al., 1988. In vitro mechanisms of monoclonal antibody neutralization of alphaviruses. *Virology.* 165:66-73.
Johnson et al., 1990. Variants of Venezuelan equine encephalitis virus that resist neutralization define a domain of the E2 glycoprotein. *Virology.* 177:676-683.
Hunt et al., 1990. Synthetic peptides of Venezuelan equine encephalomyelitis virus E2 glycoprotein. I. Immunogenic analysis and identification of a protective epitope. *Virology.* 179:701-711.
Hunt et al., 1991. Synthetic peptides of the E2 glycoprotein of Venezuelan equine encephalomyelitis virus. II. Antibody to the amino terminus protects animals by limiting viral replication. *Virology.* 185(1):281-290.
Agapov et al., 1994. Localization of four antigenic sites involved in Venezuelan equine encephalomyelitis virus protection. *Archives of Virology.* 139:173-181.
Hunt A R, and Roehrig J T. 1995. Localization of a protective epitope on a Venezuelan equine encephalomyelitis (VEE) virus peptide that protects mice from both epizootic and enzootic VEE virus challenge and is immunogenic in horses. Vaccine. 13(3):281-288.

Hunt et al., 2010. The first human epitope map of the alphaviral E1 and E2 proteins reveals a new E2 epitope with significant virus neutralizing activity. *PLOS Negl Trp Dis.* 4(7): e739.

Calisher et al., 1986. Specificity of immunoglobulin M and G antibody responses in humans infected with eastern and western equine encephalitis viruses: application to rapid serodiagnosis. *Journal of Clinical Microbiology.* 23(2): 369-372.

Pereboev et al., 1996. Glycoproteins E2 of the Venezuelan and eastern equine encephalomyelitis viruses contain multiple cross-reactive epitopes. *Arch Virol.* (141): 2191-2205.

Zhao et al., 2012. Phage display identifies an eastern equine encephalitis virus glycoprotein E2-specific B cell epitope. *Veterinary Immunology and Immunopathology.* (148): 364-368.

EnCheng et al., 2013a. Analysis of murine B-cell epitopes on eastern equine encephalitis virus glycoprotein E2. *Appl Microbiol Biotechnol.* (97):6359-6372.

EnCheng et al., 2013b. Comprehensive mapping of common immunodominant epitopes in the eastern equine encephalitis virus E2 protein recognized by avian antibody responses. *PLOS One.* (8): e69349.

Smith S A, and Crowe J E. 2015. Use of human hybridoma technology to isolate human monoclonal antibodies. *Microbiology Spectrum.* 3:1-12.

Yu et al., 2008. An optimized electrofusion-based protocol for generating virus-specific human monoclonal antibodies. *J Immunol Methods.* 336(2):142-151.

Hunt, A R and Roehrig, J T. 1985. Biochemical and biological characteristics of epitopes on the E1 glycoprotein of western equine encephalitis virus. *Virology.*

Calisher et al., 1980. Proposed antigenic classification of registered arboviruses I. Togaviridae, *Alphavirus. Intervirology.* 14:229-232.

Smith et al., 2015. Isolation and characterization of broad and ultrapotent human monoclonal antibodies with therapeutic activity against Chikungunya virus. *Cell Host and Microbe.* 18:86-95.

Hunt et al., 2006. A humanized murine monoclonal antibody protects mice either before or after challenge with virulent Venezuelan equine encephalomyelitis virus. *The Journal of General Virology.* 87:2467-2476.

Hulseweh, et al., 2014. Human-like antibodies neutralizing Western equine encephalitis virus. *mAbs.* 6:718-727.

Pal et al., 2013. Development of a highly protective combination monoclonal antibody therapy against Chikungunya virus. *PLOS pathogens.* 9: e1003312.

Jin et al., 2015. Neutralizing Monoclonal Antibodies Block Chikungunya Virus Entry and Release by Targeting an Epitope Critical to Viral Pathogenesis. *Cell reports.* 13:2553-2564.

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213-221.

Brochet, X., Lefranc, M. P., and Giudicelli, V. (2008). IMGT/V-QUEST: the highly customized and integrated system for IG and TR standardized V-J and V-D-J sequence analysis. Nucleic Acids Res 36, W503-508.

Cardoso, F. D., Rezende, I. M., Barros, E. L. T., Sacchetto, L., Garces, T., Silva, N. I. O., Alves, P. A., Soares, J. O., Kroon, E. G., Pereira, A., et al. (2019). Circulation of Chikungunya virus East-Central-South Africa genotype during an outbreak in 2016-17 in Piaui State, Northeast Brazil. Rev Inst Med Trop Sao Paulo 61, e57.

Carragher, B., Kisseberth, N., Kriegman, D., Milligan, R. A., Potter, C. S., Pulokas, J., and Reilein, A. (2000). Leginon: an automated system for acquisition of images from vitreous ice specimens. J Struct Biol 132, 33-45.

Centers for Disease Control and Prevention (CDC) website, cdc dot gov backslash easternequineencephalitis backslash tech backslash epi dot html, accessed on Jul. 5, 2020.

Chen, C. L., Hasan, S. S., Klose, T., Sun, Y., Buda, G., Sun, C., Klimstra, W. B., and Rossmann, M. G. (2020). Cryo-EM structure of eastern equine encephalitis virus in complex with heparan sulfate analogues. Proc Natl Acad Sci USA 117, 8890-8899.

Chen, V. B., Arendall, W. B., 3rd, Headd, J. J., Keedy, D. A., Immormino, R. M., Kapral, G. J., Murray, L. W., Richardson, J. S., and Richardson, D. C. (2010). MolProbity: all-atom structure validation for macromolecular crystallography. Acta Crystallogr D Biol Crystallogr 66, 12-21.

de la Rosa-Trevin, J. M., Oton, J., Marabini, R., Zaldivar, A., Vargas, J., Carazo, J. M., and Sorzano, C. O. (2013). Xmipp 3.0: an improved software suite for image processing in electron microscopy. J Struct Biol 184, 321-328.

de la Rosa-Trevin, J. M., Quintana, A., Del Cano, L., Zaldivar, A., Foche, I., Gutierrez, J., Gomez-Blanco, J., Burguet-Castell, J., Cuenca-Alba, J., Abrishami, V., et al. (2016). Scipion: A software framework toward integration, reproducibility and validation in 3D electron microscopy. J Struct Biol 195, 93-99.

Emsley, P., and Cowtan, K. (2004). Coot: model-building tools for molecular graphics. Acta Crystallogr D Biol Crystallogr 60, 2126-2132.

Fernandez-Leiro, R., and Scheres, S. H. W. (2017). A pipeline approach to single-particle processing in RELION. Acta Crystallogr D Struct Biol 73, 496-502.

Fibriansah, G., Ibarra, K. D., Ng, T. S., Smith, S. A., Tan, J. L., Lim, X. N., Ooi, J. S., Kostyuchenko, V. A., Wang, J., de Silva, A. M., et al. (2015). DENGUE VIRUS. Cryo-EM structure of an antibody that neutralizes dengue virus type 2 by locking E protein dimers. Science 349, 88-91.

Fox, J. M., Long, F., Edeling, M. A., Lin, H., van Duijl-Richter, M. K. S., Fong, R. H., Kahle, K. M., Smit, J. M., Jin, J., Simmons, G., et al. (2015). Broadly neutralizing alphavirus antibodies bind an epitope on E2 and inhibit entry and egress. Cell 163, 1095-1107.

Gardner, C. L., Ebel, G. D., Ryman, K. D., and Klimstra, W. B. (2011). Heparan sulfate binding by natural eastern equine encephalitis viruses promotes neurovirulence. Proc Natl Acad Sci USA 108, 16026-16031.

Giudicelli, V., and Lefranc, M. P. (2011). IMGT/junctionanalysis: IMGT standardized analysis of the V-J and V-D-J junctions of the rearranged immunoglobulins (IG) and T cell receptors (TR). Cold Spring Harb Protoc 2011, 716-725.

Grant, T., Rohou, A., and Grigorieff, N. (2018). cisTEM, user-friendly software for single-particle image processing. Elife 7, e35383.

Hasan, S. S., Sun, C., Kim, A. S., Watanabe, Y., Chen, C. L., Klose, T., Buda, G., Crispin, M., Diamond, M. S., Klimstra, W. B., et al. (2018). Cryo-EM structures of Eastern equine encephalitis virus reveal mechanisms of virus disassembly and antibody neutralization. Cell Rep 25, 3136-3147 e3135.

Henderson, R., Sali, A., Baker, M. L., Carragher, B., Devkota, B., Downing, K. H., Egelman, E. H., Feng, Z., Frank, J., Grigorieff, N., et al. (2012). Outcome of the first electron microscopy validation task force meeting. Structure 20, 205-214.
Hunt, A. R., and Roehrig, J. T. (1985). Biochemical and biological characteristics of epitopes on the E1 glycoprotein of western equine encephalitis virus. Virology 142, 334-346.
Kim, A. S., Austin, S. K., Gardner, C. L., Zuiani, A., Reed, D. S., Trobaugh, D. W., Sun, C., Basore, K., Williamson, L. E., Crowe, J. E., Jr., et al. (2019). Protective antibodies against Eastern equine encephalitis virus bind to epitopes in domains A and B of the E2 glycoprotein. Nat Microbiol 4, 187-197.
Ko, S. Y., Akahata, W., Yang, E. S., Kong, W. P., Burke, C. W., Honnold, S. P., Nichols, D. K., Huang, Y. S., Schieber, G. L., Carlton, K., et al. (2019). A virus-like particle vaccine prevents equine encephalitis virus infection in nonhuman primates. Sci Transl Med 11, eaav3113.
Mastronarde, D. N. (2005). Automated electron microscope tomography using robust prediction of specimen movements. J Struct Biol 152, 36-51.
Metcalf, T. U., Baxter, V. K., Nilaratanakul, V., and Griffin, D. E. (2013). Recruitment and retention of B cells in the central nervous system in response to alphavirus encephalomyelitis. J Virol 87, 2420-2429.
Metcalf, T. U., and Griffin, D. E. (2011). Alphavirus-induced encephalomyelitis: antibody-secreting cells and viral clearance from the nervous system. J Virol 85, 11490-11501.
Morens, D. M., Folkers, G. K., and Fauci, A. S. (2019). Eastern Equine Encephalitis Virus-another emergent arbovirus in the United States. N Engl J Med 381, 1989-1992.
Mukhopadhyay, S., Zhang, W., Gabler, S., Chipman, P. R., Strauss, E. G., Strauss, J. H., Baker, T. S., Kuhn, R. J., and Rossmann, M. G. (2006). Mapping the structure and function of the E1 and E2 glycoproteins in alphaviruses. Structure 14, 63-73.
Neves V, A.-d.-S. F., Corte-Real S, A. R. B. Castanho M (2016). Antibody approaches to treat brain diseases. Trends in Biotechnology 34, 36-48.
Ohi, M., Li, Y., Cheng, Y., and Walz, T. (2004). Negative staining and image classification-powerful tools in modern electron microscopy. Biol Proced Online 6, 23-34.
Pettersen, E. F., Goddard, T. D., Huang, C. C., Couch, G. S., Greenblatt, D. M., Meng, E. C., and Ferrin, T. E. (2004). UCSF Chimera—a visualization system for exploratory research and analysis. J Comput Chem 25, 1605-1612.
Phelps, A. L., O'Brien, L. M., Eastaugh, L. S., Davies, C., Lever, M. S., Ennis, J., Zeitlin, L., Nunez, A., and Ulaeto, D. O. (2019). Aerosol infection of Balb/c mice with eastern equine encephalitis virus; susceptibility and lethality. Virol J 16, 2.
Pulgar, V. M. (2018). Transcytosis to cross the blood brain barrier, new advancements and challenges. Front Neurosci 12, 1019.
Rohou, A., and Grigorieff, N. (2015). CTFFIND4: Fast and accurate defocus estimation from electron micrographs. J Struct Biol 192, 216-221.
Salimi H, Cain M D, Jiang X, Roth R A, Beatty W L, Sun C, Klimstra W B, Hou J, and Klein R S (2020). Encephalitic Alphaviruses Exploit Caveola-Mediated Transcytosis at the Blood-Brain Barrier for Central Nervous System Entry. *mBio* 11, e02731-19.
Scheres, S. H. (2012). RELION: implementation of a Bayesian approach to cryo-EM structure determination. J Struct Biol 180, 519-530.
Scheres, S. H., and Chen, S. (2012). Prevention of overfitting in cryo-EM structure determination. Nat Methods 9, 853-854.
Sorzano, C. O., de la Rosa Trevin, J. M., Oton, J., Vega, J. J., Cuenca, J., Zaldivar-Peraza, A., Gomez-Blanco, J., Vargas, J., Quintana, A., Marabini, R., et al. (2013). Semiautomatic, high-throughput, high-resolution protocol for three-dimensional reconstruction of single particles in electron microscopy. Methods Mol Biol 950, 171-193.
Sun, E., Zhao, J., Sun, L., Xu, Q., Yang, T., Qin, Y., Wang, W., Wei, P., Sun, J., and Wu, D. (2013a). Comprehensive mapping of common immunodominant epitopes in the eastern equine encephalitis virus E2 protein recognized by avian antibody responses. PLOS One 8, e69349.
Sun, S., Xiang, Y., Akahata, W., Holdaway, H., Pal, P., Zhang, X., Diamond, M. S., Nabel, G. J., and Rossmann, M. G. (2013b). Structural analyses at pseudo atomic resolution of Chikungunya virus and antibodies show mechanisms of neutralization. Elife 2, e00435.
Sun C, Gardner C L, Watson A M, Ryman K D, and Klimstra W B (2014). Stable, high-level expression of reporter proteins from improved alphavirus expression vectors to track replication and dissemination during encephalitic and arthritogenic disease. J Virol 88, 2035-2046.
Trobaugh, D. W., Sun, C., Dunn, M. D., Reed, D. S., and Klimstra, W. B. (2019). Rational design of a live-attenuated eastern equine encephalitis virus vaccine through informed mutation of virulence determinants. PLOS Pathog 15, e1007584.
Turchaninova, M. A., Davydov, A., Britanova, O. V., Shugay, M., Bikos, V., Egorov, E. S., Kirgizova, V. I., Merzlyak, E. M., Staroverov, D. B., Bolotin, D. A., et al. (2016). High-quality full-length immunoglobulin profiling with unique molecular barcoding. Nat Protoc 11, 1599-1616.
Turula, H., and Wobus, C. E. (2018). The Role of the Polymeric Immunoglobulin Receptor and Secretory Immunoglobulins during Mucosal Infection and Immunity. Viruses 10, 237.
Wirawan, M., Fibriansah, G., Marzinek, J. K., Lim, X. X., Ng, T. S., Sim, A. Y. L., Zhang, Q., Kostyuchenko, V. A., Shi, J., Smith, S. A., et al. (2019). Mechanism of enhanced immature Dengue virus attachment to endosomal membrane induced by prM Antibody. Structure 27, 253-267 e258.
Yu, X., McGraw, P. A., House, F. S., and Crowe, J. E., Jr. (2008a). An optimized electrofusion-based protocol for generating virus-specific human monoclonal antibodies. J Immunol Methods 336, 142-151.
Yu, X., Tsibane, T., McGraw, P. A., House, F. S., Keefer, C. J., Hicar, M. D., Tumpey, T. M., Pappas, C., Perrone, L. A., Martinez, O., et al. (2008b). Neutralizing antibodies derived from the B cells of 1918 influenza pandemic survivors. Nature 455, 532-536.
Zhang, K. (2016). Gctf: Real-time CTF determination and correction. J Struct Biol 193, 1-12.
Zhang, R., Kim, A. S., Fox, J. M., Nair, S., Basore, K., Klimstra, W. B., Rimkunas, R., Fong, R. H., Lin, H., Poddar, S., et al. (2018). Mxra8 is a receptor for multiple arthritogenic alphaviruses. Nature 557, 570-574.
Zheng, S. Q., Palovcak, E., Armache, J. P., Verba, K. A., Cheng, Y., and Agard, D. A. (2017). MotionCor2: anisotropic correction of beam-induced motion for improved cryo-electron microscopy. Nat Methods 14, 331-332.
Zivanov, J., Nakane, T., Forsberg, B. O., Kimanius, D., Hagen, W. J., Lindahl, E., and Scheres, S. H. (2018). New tools for automated high-resolution cryo-EM structure determination in RELION-3. Elife 7, e42166.

What is claimed is:

1. A method of reducing the likelihood of infection of a subject at risk of contracting alphavirus, comprising delivering to said subject an antibody or antibody fragment comprising heavy and light chain variables regions comprising the heavy chain CDR sequences and the light chain CDR sequences, respectively, of SEQ ID NOS: 364-366 and SEQ ID NOS: 553-555, respectively, or SEQ ID NOS: 286-288 and SEQ ID NOS: 475-477, respectively.

2. The method of claim 1, wherein the heavy and the light chain variable regions of said antibody or antibody fragment are encoded by the nucleic acid sequences of SEQ ID NOS: 75 and 76, respectively, or SEQ ID NOS: 23 and 24, respectively.

3. The method of claim 1, wherein the heavy and the light chain variable regions of said antibody or antibody fragment are encoded by the nucleic acid sequences having 95% identity to SEQ ID NOS: 75 and 76, respectively, or SEQ ID NOS: 23 and 24, respectively.

4. The method of claim 1, wherein the heavy and light chain regions of said antibody or antibody fragment are encoded by the nucleic acid sequences having 90% identity to SEQ ID NOS: 75 and 76, respectively, or SEQ ID NOS: 23 and 24, respectively.

5. The method of claim 1, wherein the heavy and light chain variable region amino acid sequences of said antibody or antibody fragment comprise SEQ ID NOS: 201 and 202, respectively, or SEQ ID NOS: 149 and 150, respectively.

6. The method of claim 1, wherein the heavy and light chain variable region amino acid sequences of said antibody or antibody fragment have 90% identity to SEQ ID NOS: 201 and 202, respectively, or SEQ ID NOS: 149 and 150, respectively.

7. The method of claim 1, wherein the heavy and light variable region amino acid sequences of said antibody or antibody fragment have 95% identity to SEQ ID NOS: 201 and 202, respectively, or SEQ ID NOS: 149 and 150, respectively.

8. The method of claim 1, wherein said antibody is a chimeric antibody or a bispecific antibody, or wherein the antibody fragment is a recombinant scFv (single chain fragment variable) antibody, Fab fragment, $F(ab')_2$ fragment, or Fv fragment.

9. The method of claim 1, wherein said antibody is an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising a mutated Fc portion comprising a LALA mutation, a N297 mutation, a GASD/ALIE mutation, a YTE mutation, an LS mutation, an enzymatic or chemical addition glycan modification, removal of a glycan modification or results from expression in a cell line engineered with a defined glycosylating pattern glycan modification.

10. The method of claim 1, wherein said antibody or antibody fragment is administered prior to infection or after infection.

11. The method of claim 1, wherein said subject is a pregnant female, a sexually active female, or a female undergoing fertility treatments.

12. The method of claim 1, wherein delivering the antibody or antibody fragment comprises administration of said antibody or antibody fragment to said subject.

13. The method of claim 1, wherein the alphavirus is eastern equine encephalitis virus, western equine encephalitis virus, or Venezuelan equine encephalitis virus.

14. The method of claim 1, wherein delivering said antibody or antibody fragment comprises administration of a RNA or DNA or vector nucleic acid sequence that encodes said antibody or antibody fragment to said subject.

15. A method of treating a subject infected with alphavirus comprising delivering to said subject an antibody or antibody fragment comprising heavy and light chain variable regions comprising the heavy chain CDR sequences and the light chain CDR sequences, respectively, of SEQ ID NOS:

364-366 and SEQ ID NOS: 553-555, respectively, or SEQ ID NOS: 286-288 and SEQ ID NOS: 475-477, respectively, or SEQ ID NOS: 259-261 and SEQ ID NOS: 448-450, or SEQ ID NOS: 355-357 and SEQ ID NOS: 544-546, or SEQ ID NOS: 346-348 and SEQ ID NOS: 535-537, or SEQ ID NOS: 265-267 and SEQ ID NOS: 454-456, respectively.

16. The method of claim 15, wherein the heavy and the light chain variable regions of said antibody or antibody fragment are encoded by the nucleic acid sequences of SEQ ID NOS: 75 and 76, respectively, or SEQ ID NOS: 23 and 24, respectively, or SEQ ID NOS: 5 and 6, respectively, or SEQ ID NOS: 69 and 70, respectively, or SEQ ID NOS: 63 and 64, respectively, or SEQ ID NOS: 9 and 10, respectively.

17. The method of claim 15, wherein the heavy and the light chain variable regions of said antibody or antibody fragment are encoded by the nucleic acid sequences having 95% identity to SEQ ID NOS: 75 and 76, respectively, or SEQ ID NOS: 23 and 24, respectively, or SEQ ID NOS: 5 and 6, respectively, or SEQ ID NOS: 69 and 70, respectively, or SEQ ID NOS: 63 and 64, respectively, or SEQ ID NOS: 9 and 10, respectively.

18. The method of claim 15, wherein the heavy and light chain variable regions of said antibody or antibody fragment are encoded by the nucleic acid sequences having 90% identity to SEQ ID NOS: 75 and 76, respectively, or SEQ ID NOS: 23 and 24, respectively, or SEQ ID NOS: 5 and 6, respectively, or SEQ ID NOS: 69 and 70, respectively, or SEQ ID NOS: 63 and 64, respectively, or SEQ ID NOS: 9 and 10, respectively.

19. The method of claim 15, wherein the heavy and light chain variable region amino acid sequences of said antibody or antibody fragment comprises SEQ ID NOS: 201 and 202, respectively, or SEQ ID NOS: 149 and 150, or respectively, SEQ ID NOS: 131 and 132, respectively, or SEQ ID NOS: 195 and 196, respectively, or SEQ ID NOS: 189 and 190, respectively, or SEQ ID NOS: 135 and 136, respectively.

20. The method of claim 15, wherein the heavy and light chain variable region amino acid sequences of said antibody or antibody fragment have 90% identity to SEQ ID NOS: 201 and 202, respectively, or SEQ ID NOS: 149 and 150, respectively, or SEQ ID NOS: 131 and 132, respectively, or SEQ ID NOS: 195 and 196, respectively, or SEQ ID NOS: 189 and 190, respectively, or SEQ ID NOS: 135 and 136, respectively.

21. The method of claim 15, wherein the heavy and light chain variable region amino acid sequences of said antibody or antibody fragment have 95% identity to SEQ ID NOS: 201 and 202, respectively, or SEQ ID NOS: 149 and 150, respectively or SEQ ID NOS: 131 and 132, respectively, or SEQ ID NOS: 195 and 196, respectively, or SEQ ID NOS: 189 and 190, respectively, or SEQ ID NOS: 135 and 136, respectively.

22. The method of claim 15, wherein said antibody is a chimeric antibody or a bispecific antibody, or wherein the antibody fragment is a recombinant scFv (single chain fragment variable) antibody, Fab fragment, $F(ab')_2$ fragment, or Fv fragment.

23. The method of claim 15, wherein said antibody is an IgG, IgA, IgM, polymeric IgA, or polymeric IgM antibody, or a recombinant IgG, IgA, IgM, polymeric IgA, or polymeric IgM antibody or IgG, IgA, IgM, polymeric IgA, or polymeric IgM antibody fragment comprising a mutated Fc portion comprising a LALA mutation, a N297 mutation, a GASD/ALIE mutation, a YTE mutation, an LS mutation, an enzymatic or chemical addition glycan modification, removal of a glycan modification or results from expression in a cell line engineered with a defined glycosylating pattern glycan modification.

24. The method of claim 15, wherein said subject is a pregnant female, a sexually active female, or a female undergoing fertility treatments.

25. The method of claim 15, wherein delivering the antibody or antibody fragment comprises administration of said antibody or antibody fragment to said subject.

26. The method of claim 15, wherein the alphavirus is eastern equine encephalitis virus, western equine encephalitis virus, or Venezuelan equine encephalitis virus.

27. The method of claim 15, wherein delivering said antibody or antibody fragment comprises administration of a RNA or DNA sequence or vector nucleic acid sequence that encodes said antibody or antibody fragment to said subject.

* * * * *

SEQUENCE LISTING

<160> NUMBER OF SEQ ID NOS: 630

<210> SEQ ID NO 1
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtggagtc tgggggaggc gtggtccagc ctgggaggtc cctgagactc 60
tcttgtgcag cgtctggatt ccacttcggt agttatggaa tgcactggtt ccgccaggct 120
ccaggcaagg gactggagtg ggtggcagtt acgtggtatg atggaagtaa taaagactat 180
gtagactccg tgaagggccg attcaccatc tccagagaca attccgagaa cacattgtat 240
ctgcaaatga ccagcctgag agccgaggac acggctgtat attactgtgc gagagatgga 300
ggcagtacct ggccccctga ttattggggc cagggaaccc tggtcatcgt ctcctca 357

<210> SEQ ID NO 2
<211> LENGTH: 309
<212> TYPE: DNA
<213> ORGANISM: Artificial sequence
<220> FEATURE:
<223> OTHER INFORMATION: Synthetic oligonucleotide

<400> SEQUENCE: 2
cagtctccag ccaccctgtc tgtgtctccg ggggaaagag ccaccctctc ctgcagggcc 60
agtcaaagtg ttaacagaaa cttagcctgg taccagcaca aacctggcca ggctcccagg 120
ctcctcatct atggtgcatc caccagggtc actgatatcc cagccaggtt cagtggcagt 180
gggtctggga cagagttcac tctcaccatc agcagcctgc agtctgaaga ttttgcaatt 240
tattactgtc agcagtataa taactggcct cgattcactt tcggccctgg gaccaaagtg 300
gatatcaaa 309

<210> SEQ ID NO 3
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 3
caggtgcagc tggtgcagtc tggggctgag gtgaagaagc ctggggcctc agtgaaggtc 60
tcctgcaagg cttctggata caccttcacc gactactata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gtgcgtggat 300
acagctatgg gctggggctt tgactactgg ggccagggaa ccctggtcac cgtctcctca 360

<210> SEQ ID NO 4
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 4
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
ccggctttcg gcggagggac caaggtggag atcaaa 336

<210> SEQ ID NO 5
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 5
caggtgcagc tgcaggagtc gggcccagga ctggtgaagc cttcacagac cctgtccctc 60
acctgcactg tctctggtgg ctccgtcagc agtggtgatt actactggaa ttggatccgc 120
cagcacccac agaagggcct ggagtggatt gggtacatct ttaacggtgg gagtaccaac 180
tacaacccgt ccgtccagag tcgagccacc atatcggttg acacgtctaa gaacgtgctc 240
tccctgcagc tgacttctgt gactgccgcg gacagtgccg tgtattattg tgcgagagat 300
tgggaacact gtttcaatgg tatatgctac tactactttg actactgggg ccagggaacc 360
ctggtcaccg tctcctcc 378

<210> SEQ ID NO 6
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 6
gacatccaga tgacccagtc tccatcctcc ctgtctgcat ctgtaggaga cagagtcacc 60
atcacttgcc gggcaagtca gagcattaag aactatttaa attggtatca acagaaacca 120
gggacagccc ctaaggtcct gatctttggt gcatctagtt tgcaaagtgg ggtcccatca 180
aggttcagtg gcagtggatc tgggacagat ttcactctca ccatcagcag tctgcaacct 240
gaagattttg caacttacta ttgtcaacag agttacagta ccctccggac tttcggcgga 300
gggaccaagg tgaacatcaa a 321

<210> SEQ ID NO 7
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 7
caggtgcagc tggtggagtc tgggggaggc gtggtccagc ctgggaggtc cctgagactc 60
tcctgtgcag cgtctggctt caccttgaat aattatggca ttcactgggt ccgtcaggct 120
ccaggcaagg ggctggagtg ggtggcactt atatggtttg atgggactac caaatacaac 180
ggagactcca tgaagggccg attcaccatc tccagagaca attccaagaa cacagtttat 240
ctgcaaatga acagcctgag agccgaggac acggctgtgt attattgtgc gagagccaca 300 tacgatttt ggagtggcga gcccattggc cactactaca tggacgtctg gggcaagggg 360
accacggtca ccgtctcctc a 381

<210> SEQ ID NO 8
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 8
cagactgtgg tgactcagga gccctcactg actgtgtccc caggagggac agtcactctc 60
acctgtgctt ccaacactgg agcagtcacc agtgatttct atccaaactg gttccagcag 120
aaacctggac aagcacccag ggcattgatt tatagtacaa acaacaaaca ctcttggacc 180
cctgcccggt tctcaggctc cctccttggg ggcaaagctg ccctgacagt gtcaggtgtg 240
cagcctgagg acgaggctga gtattactgc ctgctctact atggtggggc tcaggtctat 300
gtcttcggaa ctgggaccaa ggtcaccgtc cta 333

<210> SEQ ID NO 9
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 9
gaggtgcagc tgttggagtc tgggggaggc ttggtacagc ctgggggtc cctgagactc 60 tcctgtgcag cctctggatt catctttgac atctatgcca tgaactgggt ccgccaggct 120
ccagggaagg ggctggagtg ggtctcggct attagtggta gtggtagtac tacatactat 180
gcagattctc tgaagggccg attcaccatt tccagagaca attccaagaa cgcggtgtat 240
ctacaaatga agagcctgag agtcgacgac acggccgtat attactgtgc gaaaggttct 300
ggggagcagc gctattactt ctaccccttg gacttctggg gcacagggac cacggtcacc 360
gtctcctca 369

<210> SEQ ID NO 10
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 10
tcatatgtgc tgactcagcc accctcggtg tcagtggccc caggacagac ggccaggata 60
acctgtgggg aagacaacat tggaagtaaa agtgtgcact ggtaccagca gaggccaggc 120
caggcccctg ttctggtcgt ctatgatgat aagtatcggc cctcagggat ccctgagcga 180
ttctctggct ccaactctgg gaacacggcc accctgacca tcagcaggat cgaagccggg 240
gatgaggccg actattactg tcaggtgtgg gatagtcgtt atgatcgtca tgtggttttc 300
ggcggaggga ccaagctgac cgtccta 327

<210> SEQ ID NO 11
<211> LENGTH: 351
<212> TYPE: DNA
<213> ORGANISM: Artificial sequence
<220> FEATURE:

<223> OTHER INFORMATION: Synthetic oligonucleotide

<400> SEQUENCE: 11
caggtgcagc tggtggagtc tgggggaggc gtggtccagc ctgggaggtc cctgagactc 60
tcctgtgaag cgtctggatt ctacttcaat agttatggca tgcactgggt ccgccaggct 120
ccaggcaagg ggctggagtg ggtggcagtt atatggtatg atggaagtac gaagacctat 180
gtagagtccg tgatgggccg attcaccatc tccagagaca attccaagaa cacgctgtat 240
ctacaaatga acagcctgag agtcgaggac acggctgtgt attactgtgc gagggccagt 300
ggctgggaga ttgactactg gggccaggga actctggtca ccgtctactc a 351

<210> SEQ ID NO 12
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 12
cagtctgccc tgactcagcc tgcctccgtg tctgggtctc ctggacagtc gatcaccatc 60
tcctgcactg gaaccagcag tgacgttggt ggttataatt atgtctcctg gtaccaacag 120
cacccaggca aagcccccaa actcatcatt tttgatgtca ataatcggcc ctcaggggtt 180
tctaatcgct tctctggctc caagtctgtc aacacggcct ccctgaccat ctctgggctc 240
cgggctgagg acgaggctga ttattactgc agctcatata cagccagcag cactctcgta 300
ttcggcgggg ggaccaagct gaccgtccta 330

<210> SEQ ID NO 13
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 13
caggtgcagc tggtgcagtc tggggctgag gtgaggaagc cggggtcctc ggtgaaggtc 60
tcctgcaagg cttctggagg caccttcagc aattatgata tcaactgggt gcggcaggcc 120
cctggacaag ggcttgagtg gatgggaggg atcatcccta tctttgatac accaaactac 180
gcacagaagt tccagggcag agtcaccatt accgcggacg agtccacgac gaaagcctac 240
atggagctga gcagcctgag atctgaagac acggccgtgt attactgtgc gagaggggcg 300
tcccgatatt gtaatagcac cagctgctat agaatttttg actactgggg ccagggaagc 360
ctggtcaccg tctcctca 378

<210> SEQ ID NO 14
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 14
gacatccaga tgacccagtc tccttccacc ctgtctgcat ctgtaggaga cagagtcact 60
atcacttgcc gggccagtca gactattggt gattggctgg cctggtatca gcagaaacca 120
gggaaagccc ctaaactcct gatctataag gcgtcttttt tagaaggtgg ggtcccatca 180
aggttcagcg gcagtggatc tgggacaaca ttcactctca ccatcagcag cctgcagcct 240
gatgactttg caacttatta ctgccaacac tataacacct atgcgtacag ttttggccag 300
gggaccaagc tggagatcaa a 321

<210> SEQ ID NO 15
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 15
caggtgcagc tggtgcagtc gggggctgag gtgaagaagc ctgggtcctc ggtgaaggtc 60
tcctgcaagg cttctggagg caccttcagc gactatagta tcaactgggt gcgacaggcc 120
cctggacaag ggcttgagtg gatgggaggg atcatcccta tcgttggatc agtcaactac 180
gcacagaagt tccagggcag agtcacgatt accgcggacg actccacgag cacagcctac 240
atggaactga gcagcctgag atctgaagac acggccgtat attactgtgc gacagaaata 300
gggatagcag tggctggtac gatctactac ggtatggacg tctggggcca agggaccacg 360
gtcaccgtct cctca 375

<210> SEQ ID NO 16
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 16
gaaattgtgt tgacacagtc tccagccacc ctgtctttgt ctccagggga aagagccacc 60
ctctcctgca gggccagtca gagtgttagc agctacttag cctggtacca acagaaacct 120
ggccaggctc ccaggctcct catctatgat ccatccaaca gggccactgg catcccagcc 180
aggttcagtg gcagtgggtc tgggacagac ttcactctca ccatcagcag cctagagcct 240
gaagattttg cagtttatta ctgtcagcac cgtagcaact ggcctccggg aacgtacact 300
tttggccagg ggaccaagct ggagatcaaa 330

<210> SEQ ID NO 17
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 17
caggtgcagc tggtggagtc tgggggaggc gtggtccagc ctgggaggtc cctgagactc 60
tcctgtgcag cctctggatt caccttcagt acctatgcta tgcactgggt ccgccaggct 120
ccaggcaagg ggctggagtg ggtggcactt ctatcatatg atggaagtag taaatactac 180
gcagactccg tgaagggccg attcaccatc tccagagaca attccaagaa cacgctgtat 240
ctgcaaatga gcagcctgag agctgacgac acggctatat attactgtgc gaaaatacct 300
gttagtatgg ttcggggagt tatggagtac gctatggacg tctggggcca agggaccacg 360
gtcaccgtct cctca 375

<210> SEQ ID NO 18
<211> LENGTH: 324
<212> TYPE: DNA

<213> ORGANISM: Artificial sequence
<220> FEATURE:
<223> OTHER INFORMATION: Synthetic oligonucleotide

<400> SEQUENCE: 18
tcctatgtgc tgactcagcc accctcggtg tcagtggccc caggacagac ggccaggatt 60
acctgtgggg gaaacaacat tggaagtaac actgtgcact ggtaccagca gaagccaggc 120
caggcccctg tgctggtcgt ctatggtgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgatcatgt ggtattcggc 300
ggagggacca agctgaccgt ccta 324

<210> SEQ ID NO 19
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 19
caggttcaac tggtgcagtc tggaactgag gtgaagaagc ctggggcctc agtgaaggtc 60
tcctgcaagg cctctggtta cacttttacc agttatggtt tcacctgggt gcgacaggcc 120
cctgggcaag ggcttgagtg gatggggtgg atcagttctt ataataataa cacaaactat 180
gcacagaagt tccagggcag agtcaccatg accacagaca catccacgag cacagcctac 240
atggagctga ggagcctgag atctgacgac acggccgtct tttactgtgc gagagatcgt 300
tttagtggct acgatttggg ctactggggc cagggaaccc tagtcaccgt ctcctca 357

<210> SEQ ID NO 20
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 20
cagtctgccc tgactcagcc tgcctccgtg tctgggtctc ctggacagtc gatcaccatc 60
tcctgcactg gaaccagcag tgatgttggg agttataacc ttgtctcctg gtaccaacag 120
cacccaggca aagcccccaa actcatgatt tatgaggtca ctaagcggcc ctcaggggtt 180
tctaatcgct tctctggctc caagtctggc aacacggcct ccctgacaat ctctgggctc 240
caggctgagg acgaggctga ttattactgc tgctcatttg caggtaggag cgctccattc 300
ggtactggga ccaaggtcac cgtccta 327

<210> SEQ ID NO 21
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 21
caggtgcagc tggtgcagtc tggggctgag gtgaagaagc ctggatcctc ggtgaaggtc 60
tcctgcaagg tttctggggg caccttcagt cactttgcca tcatctgggt gcgacaggcc 120
cctggacagg gacttgagtg gatgggaggg atcatcccag tctttggcac aacaaactac 180
gtagagaagt tccaggggag agtcacgatt accgcggacg agtccaggag cacagcctac 240
atggagttga ctagactgac ctttgaagac acggccgtct attactgtgc gaaaggcttt 300
agggcgggag gagctaatac cgacttcgac tactggggcc agggaaccct ggtcaccgtc 360
tcctca 366

<210> SEQ ID NO 22
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 22
cagcttgtag tgactcaatc gccctctgcc tctgcctccc tgggagcctc ggtcaagttc 60
acctgcactc tgagcagtgg gcacagcacc tactccatcg cctggcatca gcaacaccca 120
gcgaggggcc ctcggtattt gatgagggtt aacagtgatg gcagccacac caagggggac 180
gggatccctg atcgcttctc aggctccagc tctggggctg atcgcttcct caccatctcc 240
agactccagt ctgaggatga ggctgactat tactgtcaga cctggggcac tggcattcaa 300
gttgttttcg gcggaggaag caagttgacc gtccta 336

<210> SEQ ID NO 23
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 23
caggtgcagc tggtggagtc tgggggaggc gtggtccagc ctgggaggtc cctgagactc 60
tcctgtgcag cctctggatt caccttcagt aattatggca tccactgggt ccgccaggct 120
ccaggcaagg ggctggagtg ggtggcagtt atctcatatg atggaagaca taaatacata 180
gcagaccccg tgaagggccg attcaccatc tccagagaca attccaagaa catgctgtat 240
ctgcaaatga acagcctgag aactgaggac acggctgtct attactgtgc gaaggatacc 300
agtggctggt acgaattctt tgactcctgg ggccagggaa tcccggtcac cgtctcctca 360

<210> SEQ ID NO 24
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 24
gaaatagtga tgacgcagtc tccagccacc ctgtctgtgt ctccagggga gagagccacc 60
ctctcttgta gggccagtca gagtgttgcc accaacgtgg cctggtacca gcagaaacct 120
ggccaggctc ccaggctcct catctatggt gcatccacca gggccactgg aatcccggcc 180
aggttcagtg gcagtgggtc tgggacagag ttcactctca ccatcagcag cctgcagtct 240
gaggattttg cagtttatta ttgtcagcag tgcaatgact ggctgacgtt cggccaaggg 300
accaaggtgg aaatcaaa 318

<210> SEQ ID NO 25
<211> LENGTH: 381
<212> TYPE: DNA
<213> ORGANISM: Artificial sequence
<220> FEATURE:

<223> OTHER INFORMATION: Synthetic oligonucleotide

<400> SEQUENCE: 25
caggttcagc tggtgcagtc tggagctgag gtgacgaagc ctggggcctc agtgaaggtc 60
tcctgcaaga cttctggtta cacctttacc tactataata tcagttgggt gcgacaggcc 120
cctggacaag ggcttgagtg gatgggatgg atcagcgctt acagtggtaa cacacactat 180
gcacagaaac tccagggcag agtcaccatg accatagaca catccacgag cacagcctac 240
atggagctga ggagcctgag atctgacgac acggccgtgt attactgtgc gagagatgga 300
gcctcagtac taccacctgc ttccgtctac tactcctaca tggacgtctg gggcaaaggg 360
accacggtca ccgtctcctc a 381

<210> SEQ ID NO 26
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 26
gacatccaga tgacccagtc tccatcctcc ctgtctgcat ctgtaggaga cagagtcacc 60
atcagttgtc gggcaagtca gaacattagc agctatttaa attggtatca gcagaaacca 120
gggaaagccc ctaaggtctt gatctatgct gcatccagtt tgcaaagagg ggtcccatca 180
aggttcagtg gcagtggatc tgggacagat ttcactctca ccatcagcag tctgcaacct 240
gaagattttg cgacttacta ctgtcaacag agttacagta cccctcggac ttttggccag 300
gggaccaagg tggagatcaa a 321

<210> SEQ ID NO 27
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 27
gaggtgcagc tggtggagtc tgggagaggc ttggtccagc ctgggggtc cctgagactc 60 tcctgtgcag cctctggatt cacctttaat atctattgga tgagctgggt ccgccaggct 120
ccagggaagg ggctggagtg ggtggccaac ataaaacaag acggaagtga gaaatattat 180
gtgaattctg tgaagggccg attcaccatc tccagagaca acgccaagta ctcactgtat 240
ctgcaaatga atagcctgag agccgaggac acggctgtgt attactgtgc gagaggattc 300
ataggatatt gtaatagtaa aacctgctca tatgactttg actactgggg ccagggagcc 360
ctggtcaccg tctcctca 378

<210> SEQ ID NO 28
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 28
tcttctgaac tgactcagga ccctgctgtg tctgtggcct tgggacagac agtcaggatc 60
acatgccaag gagacagcct cagaagtttt tatgcaagct ggtaccagca gaagccaggg 120
caggcccctc tacttgtcat ctacaatgaa aacaaccggc cctcaggaat cccagaccga 180
ttctctggct ccagctcagg aaacacagct tccttgacca tcactgggac tcaggcggca 240
gatgacgctg actattactg tagttcccgg gacagcagtg gtaaccatgt gctcttcggc 300
ggagggacca agctgaccgt ccta 324

<210> SEQ ID NO 29
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 29
caggttcagc tggtgcagtc tggagctgag gtgaagaagc ctggggcctc agtgaaggtc 60
tcctgcaagg cctctggtta cacctttacc aactatggta tcacgtgggt gcgacaggcc 120
cctggacagg ggcttgagtg gatgggatgg atcagcgctt acaatggtaa cacagattat 180
gcgcagaagc tccagggcag agtcaccatg accacagaca catccacgag cacagcctac 240
atggaactgg ggagcctcag atctgacgac acggccgtgt attactgtgc gagggaacta 300
tggttcgggg acttgggcta ctggggccag ggaaccctgg tcaccgtctc ctca 354

<210> SEQ ID NO 30
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 30
gaaattgtgt tgacgcagtc tccaggcacc ctgtctttgt ctccagggga aagagccacc 60
ctctcctgca gggccagtca gagtgtgagc cgcagcagca gcagctactt agcctggtac 120
cagcagaaac ctggccaggc tcccaggctc ctcatctatg gtgcatccag cagggccact 180
ggcatcccag acaggttcag tggcagtggg tctgggacag acttcactct caccatcagc 240
agactggagc ctgaagatgt tgcagtgtat tactgtcagc agtatggaag ttcacctcag 300
acttttggcc aggggaccaa gctggagatc aaa 333

<210> SEQ ID NO 31
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 31
gaagtgcacc tggtggactc tgggggaggc ttggaacagc ctggcaggtc cctgagactc 60
tcctgtgcag cctctggatt cacctttagt gattatgcca tgcactgggt ccggcaagct 120
ccagggaagg gcctggagtg ggtctcaagt attagttgga atagtggtaa cataggctat 180
gcggactctg tgaagggccg attcaccatc tccagagaca acgccaagaa ctccctgtat 240
ctacaaatga acactctgaa aactgaggac acggccttct attactgtgc aagaggccct 300
tttttcaact ggaatcccac taactacttt gaccactggg gccagggaac cctggtcacc 360
gtctcctca 369

<210> SEQ ID NO 32
<211> LENGTH: 330
<212> TYPE: DNA

<213> ORGANISM: Artificial sequence
<220> FEATURE:
<223> OTHER INFORMATION: Synthetic oligonucleotide

<400> SEQUENCE: 32
gaaattgtgt tgacgcagtc tccaggcacc ctgtctttgt ctccagggga aagagccacc 60
ctctcctgca gggccagtca gagtgttccc agcagctact tagcctggta ccagcacaaa 120
cctggccagg ctcccaggct cctcatctat ggtgcatcca gcagggccac tggcatccca 180
gacaggttca gtggcagtgg gtctgggaca gacttcactc taaccatccg cagactggag 240
cctgaggatt ttgcagtgta ctactgtcag cagtatggta cgtcaccccc catgtacact 300
tttggccagg ggaccaagct ggagatcaaa 330

<210> SEQ ID NO 33
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 33
caggtgcaag tggtggagtc tgggggaggc gtggtccagc ctgggaggtc cctgagactc 60
tcctgtgcag cctctggatt cacctttact agttatggta tacactgggt ccgccaggct 120
ccaggcaagg ggctggaatg ggtggcagtt atatcgtatg atggaagtaa tagattctac 180
gcagactccg tgaagggccg attcaccatc tccagagaca attctaagaa cacgttgtat 240
ctgcaaatga acagcctgag agttgaggac acggctgtgt attattgtgc gagagggagg 300
ctttgtgttg gtgatagttg ccactcgggg ccacttgact actggggcca gggaaccctg 360
gtcaccgtct cctca 375

<210> SEQ ID NO 34
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 34
tcgtttgagc tgacgcagcc accctcaatg tccgtgtccc caggacagac agccaggatc 60
tcctgctctg gagatacatt ggggaataaa tatgcttact ggtatcaaca gaagccaggg 120
cagtcccctg tgctggtcat ctatcaagat aacaagcggc cctcagggat tcctgagcga 180
ttctctggct ccaactctgg aaacacagcc actctgacca tcagcgggac ccaggctatg 240
gattcggctg actattactg tcaggcgtgg gacagcagcg ctcattatgt cttcggaact 300
gggaccaagg tcaccgtcct a 321

<210> SEQ ID NO 35
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 35
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atgaaagtaa taaatactat 180
tcagactccg tgaagggccg attcaccatc tccagagaca attccaagaa cacgctgtat 240
ctgcaaatga acagcctgag agctgaggac acggctgtgt attactgtgc gaaaaagggc 300
tgtagtggtg gtaactgtga cgagggcttt gactactggg gccagggaac cctggtcacc 360
gtctcctca 369

<210> SEQ ID NO 36
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 36
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctcatcgct tctctggctc caagtctggc aacacggcct ccctgaccat ctctgggctc 240
caggctgagg acgaggctga ttattactgc atctcatata gaagcagcag cactctttat 300
gtcttcggaa ctgggaccaa ggtcaccgtc cta 333

<210> SEQ ID NO 37
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 37
caggtgcagc tggtggagtc tgggggaggc gtggtccagc ctgggaggtc cctgagactc 60
tcctgtgcag cgtctggatt ctacttcagt agctatggca tgcactgggt ccgccaggct 120
ccaggcaagg ggctggagtg ggtggcagtt atatggtatg atggaagtaa taaatactat 180
gtagactccg tgaagggccg attcaccatc tccagagaca attccaagaa cacgctgtat 240
ctgcaaatga acagcctgag agccgaggac acggctgtgt attactgtgc gagagcggat 300
ggctacaatt ttgactactg gggccaggga accctggtca ccgtctcctc a 351

<210> SEQ ID NO 38
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 38
tcttctgagc tgactcagga ccctgctgtg tctgtggcct tgggacagac agtcaggatc 60
acatgccagg gagacagcct cagaagctat tttgcaagct ggtaccagca gaagccagga 120
caggcccctg tagttgtcat ctttgataga aacaaccggc cctcagggat cccagaccga 180
ttctctggct ccagctcagg aagcacagct tccttgacca tcactggggc tcaggcggaa 240
gatgaggctg actattactg taactcccgg gacagcagtg gtaaccttta tgtcttcgga 300
actgggacca aggtcaccgt ccta 324

<210> SEQ ID NO 39
<211> LENGTH: 384
<212> TYPE: DNA

<213> ORGANISM: Artificial sequence
<220> FEATURE:
<223> OTHER INFORMATION: Synthetic oligonucleotide

<400> SEQUENCE: 39
caggtcacct tgaaggagtc tggtcctgtg ctggtgaaac ccacagagac cctcacgctg 60
acctgcagcg tctctgggtt ctcactcagc agtgctagaa tgggtgtgag ctggatccgt 120
cagccccctg ggaaggccct ggagtggctt gcacacattt tttcgagtga cgaaaaatcc 180
tacagcacat ctctgaagag caggctctcc atctccaagg acacctccaa aagccaggtg 240
gtccttacct tgaccaacct ggaccctgtg gacacagcca catattactg tgcacggata 300
cgtggcccta gttattacca ccaaaactac tactacttcg gtatggacgt ctggggccaa 360
gggaccacgg tcaccgtctc ctca 384

<210> SEQ ID NO 40
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 40
gatattgtga tgactcagtc tccactctcc ctgcccgtca cccctggaga gccggcctcc 60
atctcctgca ggtcaagtca gagcctccta catagtaatg gatacaacta tttggattgg 120
tacctgcaga agccagggca gtctccacag ctcctgatct atctgggttc taatcgggcc 180
tccggggtcc ctgacaggtt cagtggcagt ggatcaggca cagattttac actgcaaatt 240
agcagagtgg aggctgagga tgttggagtt tattactgca tgcaagctct acaagctccg 300
tggacgttcg gccaagggac caaggtggaa atcaaa 336

<210> SEQ ID NO 41
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 41
caggtgcagc tgcaggagtc gggcccagga ctggtgaagc cttcacagac cctgtccctc 60
acctgcgtag tctctggtgc ctccatcagc agtgctgatt cctactggag ttggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgacctctct aactgccgcg gacacggccg tgtattactg tgcgagaggg 300
ggaccttatt gtggtggtga ctgctatcgg tggggccagg gaaccctggt caccgtctcc 360
tca 363

<210> SEQ ID NO 42
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 42
gacatccagc tgacccagtc tccatcctcc ctgtctgcat ctgtaggaga cagagtcacc 60
atcacttgcc aggcgagtca ggacattagc aacttttaa attggtatca gcagaaacca 120
gggaaagccc ctaagctcct gatctacgat gcagccaatt tggatacagg ggtcccatca 180
aggttcagtg gaagtggatc tgagacagat tttactttca ccatcagcag cctgcagcct 240
gaagatattg caacatatta ctgtcaacag tatgatagtc tcccttggac gttcggccaa 300
gggaccaagg tggaaatcaa a 321

<210> SEQ ID NO 43
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 43
caggtgcagc tgcgggagtc gggcccagga ctggttaagc cttcggagac cctgtccctc 60
acctgcactg tctctaatgg ctccattagt agttactact ggagctggat ccggcagccc 120
gccgggaagg gactggagtg gattgggcgt atttatagta gtgggagcac caattacaat 180
ccctccctca agagtcgagt caccatgtca gtagacacgt cgaagaacca gttctccctg 240
aggctgaggt ctgtgaccgc cgcggacacg gccgtatatt attgtgcgag agatttgagg 300
gcgtggattc agttgcacag ggccagtctc tactactact acatggacgt ctggggcaaa 360
gggaccacgg tcaccgtctc ctca 384

<210> SEQ ID NO 44
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 44
tcttctgagc tgactcagga ccctgctgtg tctgtggcct tgggacagac agtcaggatc 60
acatgccaag gagacagcct cagaagcttt tatacaacct ggtaccagca gaagccagga 120
caggcccctg tacttgtcat ctatggtaca aacaaccggc cctcagggat cccagagcga 180
ttctctggct ccagttcagg aaacacagct tccttgacca tcactggggc tcaggcggat 240
gatgaggctg actattactg tgactcccgg gacagcagtg gtgaactttg gctgttcggc 300
ggagggacca agctgaccgt ccta 324

<210> SEQ ID NO 45
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 45
gaggtgcagc tgttggagtc tgggggaggc ttggtacagc cggggggggtc actgagactc 60 tcctgtgtag cctctggatt cagctttgga agctatggca tgagctgggt ccggcaggct 120
ccagggaagg ggctggagtg ggtctcaggt attggtggca ggggtgacag cacatacttc 180
gcagactccg tgaagggccg attcagcatc tccagagaca actccaagaa tacattgtat 240
ctacaaatga acttcctgag agccgaggac acggccgtat attattgtgc gaaagaagga 300
tttggtagtg gtcatttcca cgggagtaat gactattggg gccaggggac cctggtcacc 360
gtgtcctca 369

<210> SEQ ID NO 46
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 46
gacatccaga tgacccaatc tccatcttcc ctgtctgcat ctgtaggaga cagagtcacc 60
atcgcttgcc agacgagtca cgacattagc aactatttaa attggtatca acagaaacca 120
gggagagccc ctaaactcct gatctacgat gcatccaatt tgcaaacagg ggtcccatct 180
aggttcagtg gaagtggctc tgggacagat tttactctca ccatcagcag cctgcagcct 240
gaagatattg caacatatta ctgtcaacag tttgacagtc tcccactcac tttcggcgga 300
gggaccaagg tgggggtcaa a 321

<210> SEQ ID NO 47
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 47
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgagtg gatgggatgg atgaacccta acagtggtaa cacaggctac 180
gcacagaagt tccagggcag agtcaccatg accaggaaca cctccataag cacagcctac 240
atggagctga gcagcctgag atctgatgac acggccgtat attactgtgc gagattttac 300
gatttttgga gtggtttaga catagacgtc tggggcaaag ggaccacggt caccgtcttc 360
tca 363

<210> SEQ ID NO 48
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 48
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcat cactcgagtc 300
ttcggaactg ggaccaaggt caccgtccta 330

<210> SEQ ID NO 49
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 49
caggtgcagc tggtgcagtc tggggctgag gtgaagaagc ctgggtcctc ggtgaaggtt 60
tcctgcaagg cttctggagg caccttcagc aactatggta tcagctgggt gcgacaggcc 120
cctggacaag ggcttgagtg gatgggaggg gtcatcccca tctttggaac aacaaagtac 180
gcaaagaagt tccagggcag agtcacggtt accgcggaca aatccacggg cacagcctac 240
atggagctga gcagcctgat atctgaggac acggccgtgt attactgtgc gagagatgat 300
ggagcagcag ctggcacggg ctactacggc atggccgtct ggggccaagg gaccacggtc 360
accgtctcct ca 372

<210> SEQ ID NO 50
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 50
gaaatagtga tgacgcagtc tccagccacc ctgtctgtgt ctccagggga aagagccacc 60
ctctcctgca gggccagtca gagtgttagc agctacttag cctggtacca gcagaagcct 120
ggccaggctc ccaggctcct catctatggt gcatccacca gggccactgg tatcccagcc 180
aggttcagtg gcagtgggtc tgggacagag ttcactctca ccatcagcag cctgcagtct 240
ggagattttg cagtttatta ctgtcagcag tatgttaact ggccccagta cacttttggc 300
caggggacca agctggagat caaa 324

<210> SEQ ID NO 51
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 51
caggtgcagc ttctgcagtc tggggctgag gtgaagaagc ctgggtcctc ggtgaaggtc 60
tcctgcaagg cttctggagg caccttcagc aacattggta tcagctgggt gcgacaggcc 120
cctcgacaag ggcttgagtg gatgggaggg atcatccctc tctttgctac aacaaactac 180
gcacagaact tccagggcag actcactatt accgcggaca agtccacgac cacagcctac 240
atggagctga acagcctgag atctgacgac acgggcgtgt atttctgtgc gagacaactg 300
gggtgggcat attgtaatag tagcacctgc tccaagggct ggttcaaccc ctggggccag 360
ggaaccctgg tcaccgtctc ctca 384

<210> SEQ ID NO 52
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 52
gatattgtga tgacccagac tccactctcc ctgcccgtca cccctggaga gccggcctcc 60
atttcctgca ggtctagtca gagcctcttg gatagtgatg atggaaacac ctatttggac 120
tggtacctgc agaagccagg gcagtctcca cacctcctga tctatacggt ttcctatcgg 180
gcctctggag tcccagacag gttcagtggc agtgggtcag gcactgattt cacactgaag 240
atcagcacgg tggaggctga ggatgttgga gtttattact gcatgcaacg tacagagttt 300
ccttacactt ttggccaggg gaccaagctg gaaatc 336

<210> SEQ ID NO 53
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 53
caggtgcagc tgcaggagtc gggcccagga ctggtgaagc cttcacagac cctgtccctc 60
agttgcagtg tctctggtgg ctccatcagc actggtggat actactggag ctggatccgc 120
cagaagtcag ggaagggcct ggagtggatt gggtacatct ctaacattgg gaacacctac 180
tacaacccgt cgctcaagag tcgagttgcc atttcgttag acacgtctaa gaatcagttc 240
tccctgaagt tgagctctgt gactgccgcg gacacggccg tgtattactg tgcgaaagcc 300
ccgcccgatg cctatgattc ggggacttat tatctcgcct actacatgga cgtctggggc 360
aaagggacca cggtcgccgt ctcctca 387

<210> SEQ ID NO 54
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 54
gacatccaga tgacccagtt tccctccacc ctgtctgcat ctgtaggaga cagagtcacc 60
atcacttgtc gggccagtca gagtattagt agctggttgg cctggtatca gcagaaacca 120
gggaaagccc ctaacctcct gatctataag gcgtctagtt tagaaagtgg ggtcccatca 180
aggttcagcg gcagtggatc tgggacagaa ttcactctca ccatcagcag cctgcagcct 240
gatgattttg caagttatta ctgccaacag tataatagtt atccgtacac ttttggccag 300
gggaccaagt tggagatcaa a 321

<210> SEQ ID NO 55
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 55
caggtgcagc tggtggagtc tgggggaggc gtggtccagc ctgggaggtc cctgagactc 60
tcctgtacag cctctggatt caccttcagt aactatggca tgcagtgggt ccgccaggct 120
ccaggcaagg ggctggagtg ggtggcagtt atatcatatc atggaaataa taactataca 180
gactccgtga agggccgatt caccatctcc agagacaatt ccaagaacac gctgtatctg 240
caaatgaaca gcctgagagc tgaggacacg gctgtgtatt actgtgccac aggtttagag 300
ggtgaatact ggggccaggg aaccctggtc accgtctcct ca 342

<210> SEQ ID NO 56
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 56
tcctatgagc tgacacagcc atcctcagtg tcagtgtctc cgggacagac agccaggatc 60
acctgctcag gagatttact ggcaaaaata tatgctcggt ggttccagca gaagccaggc 120
caggcccctg aactggtgat ttataaagac agtgagcggc cctcagggat ccctgagcga 180
ttctccggct ccagctcagg gaccacagtc accttgacca tcagcggggc ccaggttgag 240
gatgaggctg actattactg ttactctgcg actgacaaca atggagtgtt cggcggaggg 300
accaagctga ccgtccta 318

<210> SEQ ID NO 57
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 57
caggtgcagc tgcaggagtc gggcccagga ctggtgaagc cttcacagac cctgtccctc 60
acctgcactg tctctggtgg ctccatcagc agtggtgatt actactggag ctggatccgc 120
cagcacccag ggaagggcct agagtggatt gggtacatct attacaatgg gaacacctac 180
tccaacccgt ccctcaagag tcgagttacc atatcagtag acacgtctaa gaaccagttc 240
tccctgaggc tgacctctgt gactgccgcg gacacggccg tgtattactg tgcgagaggg 300
gggaggatac gatttttgga gtggtatgac tactggggcc agggaaccct ggtcaccgtc 360
tcctca 366

<210> SEQ ID NO 58
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 58
gacatccaga tgacccagtc tccatcctcc ctgtctgcat ctgtaggaga cagagtcacc 60
atcacttgcc gggcaagtca gagcattagc aactatttaa attggtatca gcagaaacca 120
gggaaagccc ctaagctcct gatctatgct gcgtccagtt tgcaaagtgg ggtcccatca 180
aggttcagtg gcagtggatc tgggacagat ttcactctca ccatcagcac tctgcaacct 240
gaagattttg caacttacta ctgtcaacag agttacagtt cccctcgaac ttttggcctg 300
gggaccaagc tggagatcaa a 321

<210> SEQ ID NO 59
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 59
caggtgcagc tggtggagtc tgggggaggc gtggtccagc ctgggaggtc cctgagactc 60
tcctgtgcag cgtctggatt cagtttcaat agctatggca tgcattgggt ccgccaggct 120
ccaggcaagg ggctggagtg ggtggcactt acatggtatg atggaagtaa taaatattat 180
gcagagtccg tgaagggccg attcaccatc tccagagaca attccaagaa cacgctgtat 240
ctgcaaatga acagcctgag agccgaagac acggctgtgt attactgtgc gagagatcag 300
ggatgtagtg gtggtagctg ctactccgag ggttggttcg acccctgggg ccagggaacc 360
ctggtcaccg tctcctca 378

<210> SEQ ID NO 60
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 60
cagtctgtgc tgactcagcc accctcagcg tctgggaccc ccgggcagag ggtcaccatc 60
tcttgttctg gaagcagctc caatatcgga ggtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tgccgtggta 300
ttcggcggag ggaccaagct gaccgtccta 330

<210> SEQ ID NO 61
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 61
cagatcacct tgaaggagtc tggtcctacg ctggtgaaac ccacacagac cctcacgctg 60
acctgcacct tttctgggtt ctcactcagt agtagtggag agggtctggg ctggatccgt 120
cagcccccag gaaaggccct ggagtggctt gctctcattt atggggatga tgataagcgc 180
tacagccctt ctctgaagag taggctcacc atcaccaagg acacctccaa aaatcaggtg 240
gtccttacaa tgaccaacat ggaccctgtg gacacagcca catattactg tgcacacagg 300
agcggatatt gtagtggtgg tgattgctac tcgagattag gctggttcga cccctggggc 360
ctgggaaccc tggtcaccgt ctcctca 387

<210> SEQ ID NO 62
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 62
gaaattgtgt tgacgcagtc tccaggcacc ctgtctttgt ctccagggga aagagccacc 60
ctctcctgca gggccagtca gagtgttagc aacaactact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag caatatggta ggtcactttt cactttcggc 300
cctgggacca aagtggatat caaa 324

<210> SEQ ID NO 63
<211> LENGTH: 396
<212> TYPE: DNA
<213> ORGANISM: Artificial sequence
<220> FEATURE:
<223> OTHER INFORMATION: Synthetic oligonucleotide

<400> SEQUENCE: 63
caggtgcagc tggtggagtc tgggggaggc gtggtccagc ctgggaggtc cctgagactc 60
tcctgtgcag cctctggatt caccttcagg acctatgctc tgcactgggt ccgccaggct 120
ccaggcaagg ggctggagtg ggtggcagtc atctcatatg atggaagcaa taaatactac 180
gcagactccg tgaagggccg attcaccatc tccagagaca attccaagaa cacgctgttt 240
gtgcaaatga atagcctgag acctgaggac acggctgtgt attactgtac gagagtcgtt 300
aattttggag tggcttttat ccgagatggg gtgtatgggc actactacta cggtatggac 360
gtctggggcc aagggaccac ggtcaccgtc tcctca 396

<210> SEQ ID NO 64
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 64
cagtctgtgt tgacgcagcc gccctcagtg tctgcggccc caggacagaa ggtcagcatc 60
tcctgctctg gaagcacctc caacattggg aataattatg tatcctggta ccggcagttc 120
ccaggaacag cccccaaatt cctcatttat gacaatgata agcgaccctc agggattcct 180
gaccgattct ctggctccaa gtctggcacg tcagccaccc tgggcatcac cggactccag 240
actggggacg aggccgatta ttactgcgga acatgggata gcagcctgag tgtttgggtg 300
ttcggcggag ggaccaagct gaccgtccta 330

<210> SEQ ID NO 65
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 65
caggtgcaag tgcaggagtc gggcccagga ctggtgaaga cctcggagac cctgtccctc 60
acctgcactg tctctggtgg atccatcagt agttactact ggagttggat ccggcaggcc 120
gccgggaagg gactggagtg gattggcgg acatatagtg gtgggagtcc caattacaac 180
ccctccctca ggagtcgagt caccgtgtca gtggacacgt ccaagaacca gttctccctg 240
atcctgacct ctgtgaccgc cgcggacacg gccgtgtatt tctgtgcgcg agaagaccac 300
ggattacgac agaaatttta ctactacatg gacctctggg gcaaagggac tgcggtcacc 360
gtctcctca 369

<210> SEQ ID NO 66
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 66
tcctatgtgc tgactcagcc accctccgtg tcagtggccc caggaaagac ggccaagatt 60
acctgtgggg gaagcaacat tggaagtaaa agtgtgcact ggtaccagca gaagccaggc 120
caggcccctg tgttggtcat ctattatgat agtgaccggc cctcagggat ccctgaccga 180
ttctctggct ccaactctgg gaacacggcc accctgacca tcagcagggt cgaagccggg 240
gatgaggccg actattcctg tcaggtgtgg gatagttctc ctgatcactc ccctgtggtt 300
tttggcggag ggaccaagct gaccgtccta 330

<210> SEQ ID NO 67
<211> LENGTH: 383
<212> TYPE: DNA
<213> ORGANISM: Artificial sequence
<220> FEATURE:
<223> OTHER INFORMATION: Synthetic oligonucleotide

<400> SEQUENCE: 67
caggtgcagc tgcaggagtc gggcccagga ctggtgaagc cttcggagac cctgtccctc 60
acttgtattg tctctggtgg ctccatcaat agttactact ggagttggat ccggcagccc 120
gccgggaagg cactggagtg gattgggcgg atatatacca gtgggagcac caactataac 180
ccctccctca agagtcgagt caccatgtca gtagacatgt ccaagaacca gttctccctg 240
aagctgacct ctgtgaccgc cgcggacacg gccgtgtatt actgtgcgag agcccctcgt 300
ataccagtat ctgtagaggg tcattactac taccactact acatggacgt ctggggcaaa 360
gggaccacgg tcaccgtctc ctc 383

<210> SEQ ID NO 68
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 68
tcttctgtgc tgactcagga ccctgctgtg tctgtggcct tgggacagac agtcaggatc 60
acatgccaag gagacagcct cagaacctat tatgcaagct ggtaccagca gaagccagga 120
caggccccta tacttgtcat ctatgctaaa aaccaccggc cctcagggat cccagaccga 180
ttctctggct ccagctcagg aaacacagct tccttgacca tcactggggc tcaggcggaa 240
gatgaggctg actattactg taactcccag gacagcagtg gtaaccatct aggattcggc 300
ggagggacca agctgaccgt cctag 325

<210> SEQ ID NO 69
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 69
gaggtgcagc tgttggagtc tgggggaggc ttggtacagc ctggggggtc cctgagactc 60
tcctgtgcag cctctggatt caccattagc agatatgccg tgacctgggt ccgccaggct 120
ccagggaagg ggctggagtg ggtctcaact atcactggta gtggtggtag gacatactac 180
gcagactccg tgaagggccg gttcaccgtc tccagagaca gttccaagaa cacactgtat 240
ctgcaaatga acaccctgag agccgaagac tcggccatat attactgtgc gaaagggatt 300
gtagtggtcc tagtgggacc cccctacttc ggtatggacg tctggggcca agggaccacg 360
gtcaccgtct cctca 375

<210> SEQ ID NO 70
<211> LENGTH: 325

<212> TYPE: DNA
<213> ORGANISM: Artificial sequence
<220> FEATURE:
<223> OTHER INFORMATION: Synthetic oligonucleotide

<400> SEQUENCE: 70
tcctatgtgc tgactcagcc accctcggtg tcagtggccc caggacagac ggccaggatt 60
ccctgtgggg gaaacaacat tggaactaaa actgtacact ggtaccagca gaagccaggc 120
caggcccctg tgctggtcgt ctatgatgat agcgaccggc cctcagggat ccctgagcga 180
ttctctggct ccaattctgg gaacacggcc accctgacca tcagcagtgt cgaagccggg 240
gatgaggccg actatcactg tcaggtgtgg gatagtagta gtgatctcgt ggttttcggc 300
ggagggacca agctgaccgt cctag 325

<210> SEQ ID NO 71
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 71
cagctgcagc tgcaggagtc cggctcagga ctggtgaagc cttcacagac cctgtccctc 60
acctgcgctg tctctggtgg ttccattagt agtggtgttt attcctggag ctggatccgg 120
cagccaccag ggaagggcct ggagtggatt gggtacatct atcatagtgg gagcacctac 180
tacaacccgt ccctcaagag tcgagtcacc atatcagtag acaggtccaa gaaccagttc 240
tccctgaagc tgagctctgt gaccgccgcg gacacggccg tgtattactg tgccagagag 300
agtgtagcaa actactttga ctactggggc cagggaaccc tggtcaccgt ctcctca 357

<210> SEQ ID NO 72
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 72
gaaattgtgt tgacacagtc tccagccacc ctgtctttgt ctccagggga aagtgccacc 60
ctctcctgca gggccagtca gagtgttgac agctacttag cctggtacca acagaaacct 120
ggccaggctc ccaggctcct catctatgat gcatccaaca gggcctctgg catcccagcc 180
aggttcagtg gcagtgggtc tgggacagac ttcactctca ccatcagcag cctagagcct 240
gaagattttg cagtttatta ctgtcagcag cgtagcgact ggccattcac tttcggccct 300
gggaccaaag tggatatcaa ac 322

<210> SEQ ID NO 73
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 73
caggtgcagc tggtggagtc tgggactgag gtgaagaagc ctggggcctc agtgaaggtc 60
tcctgcaagg cttctgaata caccttcacc gcctactata tacactgggt gcggcaggcc 120
cctggacaag ggcttgagtg gatgggatgg atcaacccta acagtggtgg cacaaactat 180
gcacagaagt ttcagggccg ggtcaccatg accggggaca cgtccatcac cacagcctac 240
atggagctga gcaggctgag atctgacgac acggccgttt attactgtgc ttcggattac 300
tttgatagta gtggttatca tgactactgg ggccagggaa ctctggtcac cgtctcctcc 360
g 361

<210> SEQ ID NO 74
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 74
cagtctgccc tgactcagcc tgcctccgtg tctgggtctc ctggacagtc gatcaccatc 60
tcctgcactg gaaccagcag tgatattggg aattataacc ttgtctcctg gtaccaacaa 120
cacccaggca aagcccccaa actcatgatt tttgaggtca gtaagcggcc ctcaggggtt 180
tctaatcgct tctctggctc caagtctggc aacacggcct ccctgactat ctctgggctc 240
caggctgaag acgaggctca ttattactgc tgctcatatg tggatgattg ggtattcggc 300
ggagggacca aactgaccgt cctg 324

<210> SEQ ID NO 75
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 75
caggtcacct tgaaggagtc tggtcctgcg ctggtgaaac ccacacagac cctcacactg 60
acctgcacct tctctgggtt ctcactcagc actagtggaa tgcgtgtgag ctggatccgt 120
cagcccccag ggaaggccct ggagtggctt gcacgcattg attgggatga tgataaattc 180
tacagcacat ctctgaagac caggctcacc atctccaagg acacctccaa aaaccaggtg 240
gtccttagaa tgaccaacat ggaccctgtg gacacagcca cgtattactg tgcacggata 300
ctcccgggat attgtagtgg aggtagctgc tactacaatt accactttga ctactggggc 360
cagggaactc tggtcaccgt ctcctca 387

<210> SEQ ID NO 76
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 76
tcctatgtgc tgactcagcc accctcggtg tcagtggccc caggacagac ggccaggatt 60
acctgtgggg gaaacaacat tggaagtaaa agtgtgcact ggtaccagca gaagccaggc 120
caggcccctg tgctggtcgt ctatcatgat agcgaccggc cctcagggat ccctgagcga 180
ttctctggct ccaactctgg gaacacggcc accctgacca tcagcagggt cgaagccggg 240
gatgaggccg actattactg tcaggtgtgg gatagtagta gtgaccctta tgtcttcgga 300
actgggacca aggtcaccgt cctag 325

<210> SEQ ID NO 77
<211> LENGTH: 373

<212> TYPE: DNA
<213> ORGANISM: Artificial sequence
<220> FEATURE:
<223> OTHER INFORMATION: Synthetic oligonucleotide

<400> SEQUENCE: 77
caggtgcagc tggtggagtc tgggggaggc gtggtccagc ctgggaggtc cctgagactc 60
tcctgtgcag cgtctggatt caccttcagt tcctatggca tgcactgggt ccgccaggct 120
ccaggcaagg ggctggagtg ggtggcagtt atatggtatg atggaataaa taaatactat 180
tcagactccg tgaagggccg attcaccatc tccagagaca attccaagaa cacgctgtat 240
ctgcaaatga acagcctgag agccgaggac aaggctgtct attattgtgc gagagagggg 300
gggggccagc acggtgacta tgcgagctgg ttcgacccct ggggccaggg aaccctggtc 360
accgtgtcct cag 373

<210> SEQ ID NO 78
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 78
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatact gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttatagta aagggaggac tttcggccct 300
gggaccaaag tggatatcaa ac 322

<210> SEQ ID NO 79
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 79
caggtgcagc tggtgcagtc tggggctgag gtgaagaagc ctgggtcctc ggtgaaagtc 60
tcatgcaagg cttctggagg ctccttcaga agttatgcta tcagttgggt gcgacaggcc 120
cctggacaag ggcttgagtg gatgggaatg atcatcccta tttttgacac gacaaactac 180
gcacagaagt tccagggcag agtcacgatt accgcggaca aatccacgag cacaacgtac 240
atggagctga acagcctaaa atctgaggac acggccgtat attactgtgc gagagatcta 300
aatcatttct atgctagtag tgggccaaat gacctctggg gccagggaac cctggtcacc 360
gtgtcctcag 370

<210> SEQ ID NO 80
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 80
gaaattgtgt tgacgcagtc tccaggcacc ctgtctttgt ctccagggga aagagccacc 60
ctctcctgca gggccagtca gagtgttagc agcaacttct tagcctggta ccagcagaaa 120
cctggccagg ctcccaggct cctcatctat ggtacatcta gcagggccac tggcatccca 180
gacaggttca gtggcagtgg gtctgggaca gatttcactc tcaccatcag cagactggag 240
cctgaagatt ttgcagtgta ttactgtcag cagtatggtg gctcaccggg gacgttcggc 300
caagggacca aggtggaaat caaac 325

<210> SEQ ID NO 81
<211> LENGTH: 379
<212> TYPE: DNA
<213> ORGANISM: Artificial sequence
<220> FEATURE:
<223> OTHER INFORMATION: Synthetic oligonucleotide

<400> SEQUENCE: 81
caggtcacct tgaaggagtc tggtcctgcg ctggtgagac ccacacagac cctcacactg 60
acctgcacct tctctgggtt ctcactcacc actagtggaa tgcgtgtgag ctggatccgt 120
cagcccccag ggaaggccct ggagtggctt gcacgcattg attgggatga tgataaattc 180
tacagtacat ctctgaagac caggctcacc atctccaagg acacctccaa aaaccaggtg 240
gtccttacac tgaccaacat ggaccctgtg gacacagcca cgtattactg tgcacggtcc 300
atgtatgata gtagtggtta ttatcctccg actccttttg atatctgggg ccaagggaca 360
atggtcaccg tctcttcag 379

<210> SEQ ID NO 82
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 82
gacatccaga tgacccagtc tccatcctcc ctgtctgcat ctgtaggaga cagagtcacc 60
atcacttgcc gggcaagtca gagcattagc aggtacttaa attggtatca gcagaaacca 120
gggaaagccc ctaagctcct gatctatgct gcatccgctt tgcaaagtgg ggtcccatca 180
aggttcagtg gcagtggatc tgggacagat ttcactctca ccatcagcag tctgcaacct 240
gaagattttg caacttactc ctgtcaacaa agtttcaata ccccattcac tttcggccct 300
gggaccaaag tggatatcaa ac 322

<210> SEQ ID NO 83
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 83
gaggtgcagt tgttggagtc tgggggaggc ttgatacagc ctggggggtc cctgagactc 60
tcctgtgcag cctctggatt cacctttacc aactatgcca tgaactgggt ccgccaggct 120
ccagggaagg ggctggagtg ggtctcagtt attagtggta gtggtggtac ctcatattac 180
gcagactccg tgaagggccg gttcaccatc tccagagaca attccaagaa caccctgtat 240
ctgcaaatga acagcctgag agccgaggac acggccgtat attactgtgc caaaggggct 300
actctgatag tggtggttct tcgaccggat gtttttgata tctggggcca aggcacaatg 360
gtcaccgtct cttca 375

<210> SEQ ID NO 84
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 84
tcctatgagc tgactcagcc accctcagtg tccgtgtccc caggacagac agccagcatc 60
acctgctctg gagataaatt gggggataaa catgcttgct ggtatcgaca gaagccaggc 120
cagtcccctg tcctggtcat ctatcaagat agcaagcggc cctcagggat ccctgagcga 180
ttctctggct ccaactctgg gaacacagcc actctgacca tcagcgggac ccaggctatg 240
gatgaggctg actattactg tcaggcgtgg gacagcaaca ctgctcatta tgtcttcgga 300
actgggacca aggtcaccgt ctta 324

<210> SEQ ID NO 85
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 85
caggtgcagc tggtggagtc tgggggaggc gtggtccagc ctgggaggtc cctgagactc 60
tcctgtgcag cgtctggatt caggttcagt agctatggca tgcactgggt ccgccaggct 120
ccaggcaagg ggctggagtg ggtgggagtt atatggtatg atggaagtaa taaatactac 180
gcagactccg tgaagggccg atgcaccatc tccagagaca atgccaagaa cactctgtat 240
ctgcaaatga acagcctgag agccgaggac acggctatgt attactgtgc gagagtctcc 300
cggggagccg acgattggga ctactactac tacatggacg tctggggcaa agggaccacg 360
gtcaccgtct cctca 375

<210> SEQ ID NO 86
<211> LENGTH: 340
<212> TYPE: DNA
<213> ORGANISM: Artificial sequence
<220> FEATURE:
<223> OTHER INFORMATION: Synthetic oligonucleotide

<400> SEQUENCE: 86
gacatcgtga tgacccagtc tccagactcc ctggctgtgt ctctgggcga gagggccacc 60
atcaactgca agtccagtca cagtgtttta tatttctcca acaacaagaa ctgcttagct 120
tggtatcagc agaaaccagg acagcctcct aagttgctca tttactgggc atctacccgg 180
gagtccgggg tccctgaccg attcagtggc agcgggtctg ggacagattt cactctcacc 240
atcagcagcc tgcaggctga agatgtggca gtttattact gtcagcaata ttatagtact 300
cctttcactt tcggccctgg gaccaaagtg gatatcagac 340

<210> SEQ ID NO 87
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 87
caggtgcagc tggtggagtc tgggggaggc gtggtccagc ctgggaggtc cctgagactc 60
tcctgtgcag cgtctggatt catgttcagt agctatggca tgcactgggt ccgccaggct 120
ccaggcaagg ggctggagtg ggtggcagtt atatggtatg atggaagtaa taaatactat 180
gcagactccg tgaagggccg attcagcatc tccagagaca attccaagaa caccctgtat 240
ctgcaaatga acagtctgag agccgaggac acggctgtgt attactgtgc gagagtagtg 300
gggggggagt ttgactactg gggccaggga accctggtca ccgtctcctc a 351

<210> SEQ ID NO 88
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 88
aattttatgc tgactcagcc gcactctgtg tcggagtctc cggggaagac ggtaaccatc 60
tcctgcaccc gcagcagtgg cagcattgcc agcaactatg tgcagtggta ccaacagcgc 120
ccgggcagtg cccccaccac tgtgatctat gaggataacc aaagaccctc tggggtccct 180
gatcggttct ctggctccag cgacagctcc tccaactctg cctccctcac catctctgga 240
ctgaagactg aggacgaggc tgactactac tgtcagtctt ataatagcag caattgggtg 300
ttcggcggag ggaccaagct gaccgtccta g 331

<210> SEQ ID NO 89
<211> LENGTH: 358
<212> TYPE: DNA
<213> ORGANISM: Artificial sequence
<220> FEATURE:
<223> OTHER INFORMATION: Synthetic oligonucleotide

<400> SEQUENCE: 89
caggtgcagc tggtggagtc tgggggaggc gtggtccagc ctgggaggtc cctgagactc 60
tcctgtacag cgtctggatt cacattcagt agctatggca tgcactgggt ccgccagact 120
ccagacaagg ggctggagtg ggtggcactt atatggtatg atggaagtaa taaatattat 180
gcagactccg tgaagggccg cttcaccatc tccagagaca attccaagaa cacactgtat 240
ctgcaaatgg agaccctgag agccgaggac acggccgttt attactgtgc gagagttggg 300
ggagttggat gggaagggga cttctggggc cagggaacct tggtcaccgt ctcctcag 358

<210> SEQ ID NO 90
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 90
cagtctgccc tgactcagcc tgcctccgtg tctgggtctc ctggacagtc gatcaccatc 60
tcctgcgctg gatccagcag tgacgttggt gctaataact atgtctcctg gtaccaacag 120
gacccaggcc aagcccccaa actcatgatt tatgaggtca attatcggcc ctcaggggtt 180
cctaatcgct tctctggctc caagtctggc aacacggcct acctgaccat ctctgggctc 240
caggctgagg acgaggctaa ttatttctgc agctcatatt caagcgccac cactctccga 300
ttcggcggag ggaccaaact gaccgtccta g 331

<210> SEQ ID NO 91
<211> LENGTH: 358
<212> TYPE: DNA
<213> ORGANISM: Artificial sequence
<220> FEATURE:
<223> OTHER INFORMATION: Synthetic oligonucleotide

<400> SEQUENCE: 91
caggttcagt tggtccagtc tggagctgag gtgaagaagc caggggcctc agtgaaggtc 60
tcctgcaaga cttctggtta catcttttcc aactatgata ttagttgggt gcgacaggcc 120
cctggccagg ggcttgagtg gatgggatgg atcagcgctt acagtggtga aaaaaagtat 180
tcacagaagt tccaggtcag actcaccatg accgcagaca ctgccacgag cacagcctac 240
atggaactga ggagcctgag atctgacgac acggccgtgt attattgtgc gcgagaccct 300
actgtggtcc atgctttgga tatctggggc caggggacaa tggtcaccgt ctcttcag 358

<210> SEQ ID NO 92
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 92
gacatccaga tgacccagtc tccatcctcc ctgtctgcat ctgtaggaga cagagtcacc 60
atcacttgcc aggcgagtca cgacattagt aactttttaa attggtatca acagaaacca 120
gggaaagccc ctaaactcct gatcttcgat gcatccaatt tggaaccagg ggtcccatca 180
aggttcagtg gaagtggatc tgggacagat ttcactttca ccatcaacag cctgcagcct 240
gaagatattg caacatacta ctgtcaacag tatgatgatc tcgtgtacac ttttggccag 300
gggaccaagc tggagatcaa ac 322

<210> SEQ ID NO 93
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 93
gaggtgcagc tggtggagtc tgggggaggc ttggtacagc cggggggtc cctgagactc 60 tcctgtgcag cctctggatt caccttcagt agctatacca tgaattgggt ccgccaggct 120
ccagggaagg ggctggaatg ggtttcatat attactaata gtagtagtgc catatactac 180
gcagactctg tgaagggccg attcaccatc tccagagaca atgccaagaa ctcactgtat 240
ctacaaatga acagcctgag agacgaggac acggctgtgt attactgtgc gagagatctt 300
gctcggcccc atcggtacta tgataatagt gcttattttg aggtgtttga ctcctggggc 360
cagggaaccc tggtcaccgt ctcctca 387

<210> SEQ ID NO 94
<211> LENGTH: 328
<212> TYPE: DNA
<213> ORGANISM: Artificial sequence
<220> FEATURE:
<223> OTHER INFORMATION: Synthetic oligonucleotide

<400> SEQUENCE: 94
tcttctgagc tgactcagga ccctgctgtg tctgtggcct tgggacagac agtcaggatc 60
acatgccaag gagacagcct cagaaactat tatgcaagct ggtaccagca gaagccagga 120
caggcccctg ttcttgtcat ctatggtaaa aataaccggc cctcagggat cccagaccga 180
ttctctggct ccaactcagg aaacacagct tccttgacca tcactggggc tcaggcggaa 240
gatgagggtg actattactg tagctcccgg gacagcagtg gtaactatct gagagtcttc 300
ggaactggga ccaaggtcac cgtcctag 328

<210> SEQ ID NO 95
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 95
caggtgcagc tggtggagtc tgggggaggc gtggtccagc ctgggaggtc cctgagactc 60
tcctgtgcag cgtctggatt caccttcaat agctatggca tgcactgggt ccgccagact 120
ccaggcaagg ggctggagtg ggtggcaatt atatggtatg atggaagtca aaaatactat 180
gcagactccg tgaagggccg attcaccatc tccagagaca attccaagaa cacgctgtat 240
ctgcaaatga acagcctgag agccgaggac acggctgtgt attactgtgc gagagacgag 300
gggagctatg acttagacta ctggggccag ggaaccctgg tcaccgtctc ctca 354

<210> SEQ ID NO 96
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 96
cagtctgccc tgattcagcc tgcctccgtg tctgggtctc ctggacagtc gatcaccatc 60
tcctgcactg gaaccaaaag tgacgttggt ggttataact atgtctcctg gtaccaacaa 120
tacccaggca aaacacccaa acgcatgatt ttcgaggtca gtaatcggcc ctcaggggct 180
tctaatcgct tctctggctc caagtctggc aacacggcct ccctgaccat ctctgggctc 240
caggctgagg acgaggctga ttattattgc acctcatata caagtagcag cactctggtc 300
ttcggcggag ggaccaagct gaccgtccta 330

<210> SEQ ID NO 97
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 97
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggcatg acggcagtaa taaatactat 180
ggagactccg tgaagggccg attcaccatc tccagagaca actccaagaa cacgctatat 240
ttgcaaatga acggcctgag agccgaggac acggctgtgt attactgtgc gagagtagaa 300
ggtgggagct actcaggtga ctactggggc cagggaaccc tggtcaccgt ctcctca 357

<210> SEQ ID NO 98
<211> LENGTH: 330

<212> TYPE: DNA
<213> ORGANISM: Artificial sequence
<220> FEATURE:
<223> OTHER INFORMATION: Synthetic oligonucleotide

<400> SEQUENCE: 98
cagtctgccc tgactcagcc tgcctccgtg tctgggtctc ctggacagtc gatcaccatc 60
tcctgcactg gaaccagcag tgacattggt gcttataact ctgtctcctg gtaccaacag 120
cacccaggca aagcccccaa actcatgatt tatgatgtca gtaatcggcc ctcaggggtt 180
tctaatcgct tctctggctc caagtctggc aacacggcct ccctgaccat ctctgggctc 240
caggctgagg acgaggctga ttattactgc agttccttta caaacaccgt ctctgtggtg 300
ttcggcggag ggaccaagct gaccgtccta 330

<210> SEQ ID NO 99
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 99
caggtgcaac tggtggagtc tgggggaggc ttggtcaagc ctggagggtc cctgagactc 60
tcctgtgcag cctctgggtt catcttcagt gactactcca tgaattggat ccgccaggct 120
ccagggaagg gtctggagtg gatttcatca attagtcata gtgagactta cacatactac 180
gcagactctg tgaagggccg attcaccatc tccagagaca acgccaagaa ctcactttat 240
ctgcaaatgc acagcctgag agccgaagac acgggtgtct attactgtgc gagacctcta 300
gaggcaatga tgtgggagga atttcacttc tggggccagg gaatcctggt cagcgtctcc 360
tca 363

<210> SEQ ID NO 100
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 100
cagtctgtgc tgactcagcc accctccgcg tctgggaccc ccgggcagag ggtcaccatc 60
tcttgttctg gaagcacctc caacatcggg actaattatg tctactggta ccaccacctc 120
ccaggaacgg cccccaaact cctcatctat aggactaatc agcggccctc aggggtccct 180
gaccgattct ctggctccaa gtctggcacc tcagcctccc tggtcatcag tgggctccgg 240
tccgaggatg aggctgatta ttactgtgcg tcatgggatg gcagcctgag tggggtgcta 300
ttcggcggag ggaccaagct gaccgtccta g 331

<210> SEQ ID NO 101
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 101
caggtgcagc tggtgcagtc tggggctgag gtgaggaagc cggggtcctc ggtgaaggtc 60
tcctgcaagg cttctggagg caccttcagc aattatgata tcaactgggt gcggcaggcc 120

```
cctggacaag ggcttgagtg gatgggaggg atcatcccta tctttgatac accaaactac    180

gcacagaagt tccagggcag agtcaccatt accgcggacg agtccacgac gaaagcctac    240

atggagctga gcagcctgag atctgaagac acggccgtgt attactgtgc gagaggggcg    300

tcccgatatt gtaatagcac cagctgctat agaatttttg actactgggg ccagggaagc    360

ctggtcaccg tctcctca                                                  378
```

<210> SEQ ID NO 102
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 102

```
cagtctgtgc tgactcagcc accctccgcg tctgggaccc ccgggcagag ggtcaccatc     60

tcttgttctg gaagcacctc caacatcggg actaattatg tctactggta ccaccacctc    120

ccaggaacgg cccccaaact cctcatctat aggactaatc agcggccctc aggggtccct    180

gaccgattct ctggctccaa gtctggcacc tcagcctccc tggtcatcag tgggctccgg    240

tccgaggatg aggctgatta ttactgtgcg tcatgggatg gcagcctgag tggggtgcta    300

ttcggcggag ggaccaagct gaccgtccta g                                   331
```

<210> SEQ ID NO 103
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 103

```
caggtgcagc tgcaggagtc gggcccagga ctggtgaagc cttcggagac cctgtccctc     60

acctgcactg tctctggtta ctccatcagc agtggttact actggggctg gatccggcag    120

cccccaggga agggcctgga gtggattggg agtgtctatc atagtgggac cacttactac    180

aacccgtccc tcaggagtcg agtcaccata tcatcagaca cgtccaagaa ccagttctcc    240

ctgaggctga gctctgtgac cgccgcagac acggccgtgt attactgtgc gggctctcgg    300

ttggtttccg atatatggcc cctcgtggac gtctggggca cagggaccac ggtcaccgtc    360

tcctca                                                               366
```

<210> SEQ ID NO 104
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 104

```
gaaattgtgt tgacgcagtc tccaggcacc ctgtctttgt ctccaggtga aagagccacc     60

ctctcctgca gggccagtca gagtgttagc agcagctact tagcctggta ccagcagaaa    120

cctggccagg ctcccaggct cctcatctat ggtgcatcca gcagggccac tggcatccca    180

gacaggttca gtggcagtgg gtctgggaca gacttcactc tcaccttcag cagactggag    240

cctgaagatt ttgccgtgta ttactgtcag cagtatggta gctcaccgtg gacgttcggc    300

caagggacca aggtggaaat caaa                                           324
```

<210> SEQ ID NO 105
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 105
gaggtgcagc tggtggagtc tgggggaggc ttggtaaagc ctgggggtc ccttagactc 60 tcctgtgcag cctctggatt cactttcagt aacgtctgga tgagctgggt ccgccaggct 120
ccagggaagg ggctggagtg ggttggccgt attaaaagca aaattgatgg tgggacaaca 180
gactacgctg tattcgtgaa aggcagattc atcatctcaa gagatgattc aaaaaatatg 240
ttgtatctgc aaatgaacag cctgaaaacc gaggacacag ccgtgtatta ctgtaccaca 300
gaggattata attacgtttg ggggggtctc ccggcgccgt acggtttgga cgtctggggc 360
caagggacca cggtcaccgt ctcctca 387

<210> SEQ ID NO 106
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 106
gaaattgtgt tgacgcagtc tccaggcacc ctgtctttgt ctccaggtga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccttcag cagactggag 240
cctgaagatt ttgccgtgta ttactgtcag cagtatggta gctcaccgtg gacgttcggc 300
caagggacca aggtggaaat caaa 324

<210> SEQ ID NO 107
<211> LENGTH: 379
<212> TYPE: DNA
<213> ORGANISM: Artificial sequence
<220> FEATURE:
<223> OTHER INFORMATION: Synthetic oligonucleotide

<400> SEQUENCE: 107
caggtgcagc tgcaggagtc gggcccagga ctggtgaaga cttcacagac cctgtccctc 60
acctgcactg tctctggtgg ctccgtcata agtggtgatt actactggag ttggatccgc 120
cagcccccag ggaagggcct ggagtggatt gggtacatct ttaatagtgg gagcaccaac 180
tacaacccgt ccctcaagag tcgagtcacc atttcagcag ataagtccaa gaagcagctc 240
tcccttaagc tgacctctgt gactgccgca gacacggccg tgtattactg tgccagagac 300
tatgagggat gtactaatgg tgtatgctat acgtacttag acttctgggg ccagggaacc 360
ctggtcaccg tctcctcag 379

<210> SEQ ID NO 108
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 108

```
gacatccaga tgacccagtc tccatcctcc ctgtctgcat ctgtaggaga cagagtcatg     60

atcacttgcc gggcaagtca gaacattaaa aactatttaa attggtatca gcagaaatca    120

gcgacagccc ctgagctcct gatatatggt gcttccagtg tgcaaagtgg ggtcccatca    180

aggttcagtg gcagtggatc tgggacagaa ttcactctca ccatcagcag tctgcaaccc    240

gaagattttg caacttacta ctgtcaacag agttacagta ccctccggac tttcggcgga    300

gggaccaagg tggagatcaa ac                                             322


<210> SEQ ID NO 109
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 109

caggtgcagc tggtgcagtc tggggctgag gtgaagaagc ctggggcctc aatgaaggtc     60

tcctgcaaga cttctggata caccttcacc gactactata tgcactgggt gcgacaggcc    120

cctggacaag ggcgtgagtg gatgggatgg atcaacccta aaagtggtgt cgcaaactat    180

gcacagaaat ttcaggacag ggtcaccatg accagggaca cgtccatcac cacagcctac    240

atggaggtga ccaggctgag atctgacgac acggccgtgt attactgtgc gagagatcgg    300

gggatttttg gaggttacta cggtttggac gtctggggcc aagggaccac ggtcaccgtc    360

tcctca                                                               366


<210> SEQ ID NO 110
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 110

cagtctgtgt tgacgcagcc gccctcagtg tctgcggccc caggacagaa ggtcaccatc     60

tcctgctctg gaagcagctc caacattgtg aataattatg tatcctggta ccggcagctc    120

ccaggaacag cccccaaact cctcatttat gacaataata agcgaccctc agggattcct    180

gaccgattct ctggctccaa gtctggcgcg tcagccaccc tgggcatcac cggactccag    240

actggggacg aggccgatta ttactgcgga acatgggata gcagcctgag tgctgtggtc    300

ttcggcgaag ggaccaaggt gaccgtccta                                     330


<210> SEQ ID NO 111
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 111

caggtgcaac tggtggagtc tgggggaggc gtggtccagc ctgggaggtc cctgagactc     60

tcctgtgcag cgtctggatt cagcttcagt gactatggca tgcactgggt ccgccaggct    120

ccaggcaagg ggctggagtg ggtggcaatt gtatggtttg atggaagtaa taaatactat    180

gcagactccg tgaagggccg attcaccatc tccagagaca attccaggaa cacactgtat    240

ctgcaaatga acagcctgag aggcgaggac acggctgtgt atcactgtgc gagagatttt    300

accccaacgg cggtagctct tgactactgg ggccagggaa ccctggtcac cgtctcctca    360
```

<210> SEQ ID NO 112
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 112
cagtctgtgc tgacgcagcc ccactctgtg tcggagtctc cggggaagac ggtaaccatc 60
tcctgcaccc gcagcagtgg cagcatttcc cgcaactatg tgcagtggta ccagcagcgc 120
ccgggcagtg cccccaccac tgtgatctat gaggataacc aaaggccctc tggggtccct 180
gatcggttct ctggctccat cgacagctcc tccaactctg cctccctcac catctctgga 240
ctgaagactg aggacgaggc tgactactac tgtcagtctt atgatagcag ccctacctgg 300
gtgttcggcg gagggaccaa gctgaccgtc cta 333

<210> SEQ ID NO 113
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 113
caggtgcaac tggtggagtc tgggggaggc gtggtccagc ctgggaggtc cctgagactc 60
tcctgtgcag cgtctggatt cagcttcagt gactatggca tgcactgggt ccgccaggct 120
ccaggcaagg ggctggagtg ggtggcaatt gtatggtttg atggaagtaa taaatactat 180
gcagactccg tgaagggccg attcaccatc tccagagaca attccaggaa cacactgtat 240
ctgcaaatga acagcctgag aggcgaggac acggctgtgt atcactgtgc gagagatttt 300
accccaacgg cggtagctct tgactactgg ggccagggaa ccctggtcac cgtctcctca 360

<210> SEQ ID NO 114
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 114
aattttatgc tgactcagcc ccactctgtg tcggagtctc cggggaagac ggtaaccatc 60
tcctgcaccc gcagcagtgg cagcatttcc cgcaactatg tgcagtggta ccagcagcgc 120
ccgggcagtg cccccaccac tgtgatctat gaggataacc aaaggccctc tggggtccct 180
gatcggttct ctggctccat cgacagctcc tccaactctg cctccctcac catctctgga 240
ctgaagactg aggacgaggc tgactactac tgtcagtctt atgatagcag ccctacctgg 300
gtgttcggcg gagggaccaa gctgaccgtc cta 333

<210> SEQ ID NO 115
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 115
caggtgcagc tgcaggagtc gggcccagga ctggtgaagc cttcggagac cctgtccctc 60
acctgcgctg tctctggtta ctccatcaac agtggttact actgggcctg gatccggcag 120
cccccaggga aggggctaga gtggattgga aatatctatc aaagtgggag cacctactac 180
aacccgtccc tcatgagtcg agtcaccata tcagtagacg cgtccaagaa ccagttattc 240
ctgaacctga gctctgtgac cgccgcagag acggccgtgt attactgtgc gacctgtcac 300
tcgttgggaa caagtgcctg gccgctcccg gactactggg gccagggaac ccttgtcacc 360
gtctcctca 369

<210> SEQ ID NO 116
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 116
gaaattgtgt tgacgcagtc tccaggcacc ctgtctttgt ctccagggga aagagccacc 60
ctctcctgca agaccagtca gagtattagc agcgactact tagcctggta ccagcagaga 120
cctggccagg ctccctggct cctcatcttt ggtgcatcga gcagggccac tggtacccca 180
gacaggttca gtggcagtgg gtctgggaca gacttcactc tcaccatcag cagactggag 240
cctgaagatt ttgcagtgta tttctgtcag cagtatggta gttcaccgtt cacttttggc 300
caggggacca acctggagat caaa 324

<210> SEQ ID NO 117
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 117
gaggtgcagc tggtggagtc tgggggaggc ttggtaaagc ctggggggtc ccttagactc 60
tcctgtgcag cctctggatt cactttcagt aacgtctgga tgagctgggt ccgccaggct 120
ccagggaagg ggctggagtg ggttggccgt attaaaagca aaattgatgg tgggacaaca 180
gactacgctg tattcgtgaa aggcagattc atcatctcaa gagatgattc aaaaaatatg 240
ttgtatctgc aaatgaacag cctgaaaacc gaggacacag ccgtgtatta ctgtaccaca 300
gaggattata attacgtttg ggggggtctc ccggcgccgt acggtttgga cgtctggggc 360
caagggacca cggtcaccgt ctcctca 387

<210> SEQ ID NO 118
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 118
cagtctgccc tgactcagcc tccctccgtg tccgggtctc ctggacagtc agtcaccatc 60
tcctgcactg gaaccagcag tgacgttggt agttataacc gtgtctcctg gtaccagcag 120
cccccaggca cagcccccaa actcatgatt tatgaggtca gtaatcggcc ctcaggggtc 180
cctgatcgct tctctgggtc caagtctggc aacacggcct ccctgaccat ctctgggctc 240
caggctgagg acgaggctga ttattactgc agcttatata cagtcagcag caatgtggta 300
ttcggcggag ggaccaagct gaccgtcctg 330

<210> SEQ ID NO 119
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 119
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggcacatct attacagtgg gaacacctac 180
tacaacccgt ccctcaagag tcgagtaacc atatcagtag acacgtctaa gaaccagttc 240
tccctgaagc tgagctctgt gactgccgcg gacacggccg tgtattactg tgcgagagaa 300
acccatagtg ggagctacgg ctactggggc cagggaaccc tggtcaccgt ctcctca 357

<210> SEQ ID NO 120
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 120
cagtctgccc tgactcagcc tccctccgcg tccgggtctc ctggacagtc agtaaccatc 60
tcctgcactg gaaccagcag tgacgttggt ggttataact atgtctcctg gtaccaacag 120
cacccaggca aagcccccaa actcatgatt tatgaggtca gtaagcggcc ctcaggtgtc 180
cctgatcgct tctctggctc caagtctggc aacacggcct ccctgaccgt ctctgggctc 240
caggctgagg atgaggctga ttattactgc agctcatatg caggcagcaa cgtttgggtg 300
ttcggcggag ggaccaagct gaccgtccta 330

<210> SEQ ID NO 121
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 121
caggtgcagc tggtggagtc tgggggaggc gtggtccagc ctgggaggtc cctgagactc 60
tcctgtgcag cctctgggtt cgtcttcact aattatgtta tgcactgggt ccgccaggct 120
ccaggcaagg cgctggagtg ggtgacactt atatcatatg atggaaacaa taaatactac 180
acagactccg tgaagggccg attcaccatc tccagagaca attccaagaa cacgctgtat 240
ctgcaaatga acagcctgag agctgaggac acggctttat attactgtgc gagatctccg 300
cacggtgacg tccctgacta ctacttcgat ctctggggcc gtggcaccct ggtcactgtc 360
tcctca 366

<210> SEQ ID NO 122
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 122

```
gacatccaga tgacccagtc tccttccacc ctgtctgcat ctgtaggaga cagagtcacc     60

atcacttgcc gggccagtca gagtattagt agctggttgg cctggtatca gcacaaacca    120

gggaaacccc ctaagctcct gatctataag gcgtctagtt tacaaagtgg ggtcccatca    180

aggttcagcg gcagtggatc tgggacagaa ttcactctca ccatcagcag cctgcagcct    240

gatgattttg caacttatta ctgccaacag tataatactt atcgggcgtt cggcctaggg    300

accaaggtgg agatcaaa                                                  318


<210> SEQ ID NO 123
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 123

caggtgcagc tggtgcagtc aggggctgag gtgaggaagc ctgggtcctc ggtgaaggtc     60

tcctgcgtgg cttctggagg caccttcagg aactatgcta tcagctgggt gcgacgggcc    120

cctggacaag ggcttgagtg gatgggaggg atcatcccta tctttggtac aacaaactac    180

gcacagaagt tccagggcag agtcacgatt tccgcggacg agtccacgag cacagcctac    240

atggagctga gcagcctgag atctgaggac acggccgtct attactgtgc gagagattac    300

tatgagagga ctgattatta caccccgggc tactggggcc agggaaccct ggtcaccgtc    360

tcctca                                                               366


<210> SEQ ID NO 124
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 124

tcctatgtgc tgactcagcc accctcagtg tcagtggccc caggaaagac ggccaggatt     60

acctgtgggg gaaacaacat tgaaagtaca agtgttcact ggtaccagca gaagccaggc    120

caggcccctg tgctggtcat ctattttgat agcgaccggc cctcagggat ccctgagcga    180

ttctctggct ccaactctgg aaacacggcc accctgaccc tcagcagggt cgaagccggg    240

gatgaggccg actattactg tcaggtgtgg gatagtagta gtgatcatgt ggtattcggc    300

ggagggacca agctgaccgt ccta                                           324


<210> SEQ ID NO 125
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 125

caggtgcagc tgcaggagtc gggcccagga ctggtgaagc catcggagac cctgtccctc     60

acctgctctg tctctaatta ctccattacc agtacttact actgggggtg gatccggcag    120

cccccaggga aggggctgga gtggattggg agtgtttatc atactgggag cacttattac    180

aacccgtccc tcaagagtcg agtcaccata tcagtagaca cgtccaagaa ccggttctcc    240

ctgaggctgc gctctgtgac cgccgcagac acggccgttt attactgtgc gagagagata    300

ccggcatgga tttactactt ggacgtctgg ggcaaagggg ccacggtcac cgtctcctcg    360
```

<210> SEQ ID NO 126
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 126
cagtctgtgt tgacgcagcc gccctcagtg tctgcggccc ctgggcagca ggtcaccatc 60
tcctgctctg taagcagctc caacattggg accacttatg tatcctggta ccagcaactc 120
ccaggaacag cccccaaact cctcatttat gacaacaata ggcgaccctc agggattcct 180
gaccgattct ctggctccaa gtctggcacg tcagccaccc tgggcatcac cggactccag 240
actggggacg aggccgatta ttactgcgga gcatgggata gcagcctgag tgctggggtg 300
ttcggcgggg ggaccaagct gaccgtccta 330

<210> SEQ ID NO 127
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 127

Gln Val Gln Leu Val Glu Ser Gly Gly Gly Val Val Gln Pro Gly Arg
1 5 10 15

Ser Leu Arg Leu Ser Cys Ala Ala Ser Gly Phe His Phe Gly Ser Tyr
20 25 30

Gly Met His Trp Phe Arg Gln Ala Pro Gly Lys Gly Leu Glu Trp Val
35 40 45

Ala Val Thr Trp Tyr Asp Gly Ser Asn Lys Asp Tyr Val Asp Ser Val
50 55 60

Lys Gly Arg Phe Thr Ile Ser Arg Asp Asn Ser Glu Asn Thr Leu Tyr
65 70 75 80

Leu Gln Met Thr Ser Leu Arg Ala Glu Asp Thr Ala Val Tyr Tyr Cys
85 90 95

Ala Arg Asp Gly Gly Ser Thr Trp Pro Pro Asp Tyr Trp Gly Gln Gly
100 105 110

Thr Leu Val Ile Val Ser Ser
115

<210> SEQ ID NO 128
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 128

Gln Ser Pro Ala Thr Leu Ser Val Ser Pro Gly Glu Arg Ala Thr Leu
1 5 10 15

Ser Cys Arg Ala Ser Gln Ser Val Asn Arg Asn Leu Ala Trp Tyr Gln
20 25 30

His Lys Pro Gly Gln Ala Pro Arg Leu Leu Ile Tyr Gly Ala Ser Thr
35 40 45

Arg Val Thr Asp Ile Pro Ala Arg Phe Ser Gly Ser Gly Ser Gly Thr
50 55 60

Glu Phe Thr Leu Thr Ile Ser Ser Leu Gln Ser Glu Asp Phe Ala Ile
65 70 75 80

Tyr Tyr Cys Gln Gln Tyr Asn Asn Trp Pro Arg Phe Thr Phe Gly Pro
85 90 95

Gly Thr Lys Val Asp Ile Lys
100

<210> SEQ ID NO 129
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 129

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Cys Val Asp Thr Ala Met Gly Trp Gly Phe Asp Tyr Trp Gly Gln
100 105 110

Gly Thr Leu Val Thr Val Ser Ser
115 120

<210> SEQ ID NO 130
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 130

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Pro Ala Phe Gly Gly Gly Thr Lys Val Glu Ile Lys
100 105 110

<210> SEQ ID NO 131
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 131

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Ser Gly
            20                  25                  30

Asp Tyr Tyr Trp Asn Trp Ile Arg Gln His Pro Gln Lys Gly Leu Glu
        35                  40                  45

Trp Ile Gly Tyr Ile Phe Asn Gly Gly Ser Thr Asn Tyr Asn Pro Ser
    50                  55                  60

Val Gln Ser Arg Ala Thr Ile Ser Val Asp Thr Ser Lys Asn Val Leu
65                  70                  75                  80

Ser Leu Gln Leu Thr Ser Val Thr Ala Ala Asp Ser Ala Val Tyr Tyr
                85                  90                  95

Cys Ala Arg Asp Trp Glu His Cys Phe Asn Gly Ile Cys Tyr Tyr Tyr
            100                 105                 110

Phe Asp Tyr Trp Gly Gln Gly Thr Leu Val Thr Val Ser Ser
        115                 120                 125

<210> SEQ ID NO 132
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys Asn Tyr
            20                  25                  30

Leu Asn Trp Tyr Gln Gln Lys Pro Gly Thr Ala Pro Lys Val Leu Ile
        35                  40                  45

Phe Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Arg
                85                  90                  95

Thr Phe Gly Gly Gly Thr Lys Val Asn Ile Lys
            100                 105

<210> SEQ ID NO 133
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 133

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Asn Asn Tyr
            20                  25                  30

Gly Ile His Trp Val Arg Gln Ala Pro Gly Lys Gly Leu Glu Trp Val
        35                  40                  45

```
Ala Leu Ile Trp Phe Asp Gly Thr Thr Lys Tyr Asn Gly Asp Ser Met
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Ala Thr Tyr Asp Phe Trp Ser Gly Glu Pro Ile Gly His Tyr
            100                 105                 110

Tyr Met Asp Val Trp Gly Lys Gly Thr Thr Val Thr Val Ser Ser
        115                 120                 125


<210> SEQ ID NO 134
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 134

Gln Thr Val Val Thr Gln Glu Pro Ser Leu Thr Val Ser Pro Gly Gly
1               5                   10                  15

Thr Val Thr Leu Thr Cys Ala Ser Asn Thr Gly Ala Val Thr Ser Asp
            20                  25                  30

Phe Tyr Pro Asn Trp Phe Gln Gln Lys Pro Gly Gln Ala Pro Arg Ala
        35                  40                  45

Leu Ile Tyr Ser Thr Asn Asn Lys His Ser Trp Thr Pro Ala Arg Phe
    50                  55                  60

Ser Gly Ser Leu Leu Gly Gly Lys Ala Ala Leu Thr Val Ser Gly Val
65                  70                  75                  80

Gln Pro Glu Asp Glu Ala Glu Tyr Tyr Cys Leu Leu Tyr Tyr Gly Gly
                85                  90                  95

Ala Gln Val Tyr Val Phe Gly Thr Gly Thr Lys Val Thr Val Leu
            100                 105                 110


<210> SEQ ID NO 135
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Asp Ile Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Ser Thr Thr Tyr Tyr Ala Asp Ser Leu
    50                  55                  60

Lys Gly Arg Phe Thr Ile Ser Arg Asp Asn Ser Lys Asn Ala Val Tyr
65                  70                  75                  80

Leu Gln Met Lys Ser Leu Arg Val Asp Asp Thr Ala Val Tyr Tyr Cys
                85                  90                  95

Ala Lys Gly Ser Gly Glu Gln Arg Tyr Tyr Phe Tyr Pro Leu Asp Phe
            100                 105                 110

Trp Gly Thr Gly Thr Thr Val Thr Val Ser Ser
        115                 120
```

<210> SEQ ID NO 136
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 136

Ser Tyr Val Leu Thr Gln Pro Pro Ser Val Ser Val Ala Pro Gly Gln
1               5                   10                  15

Thr Ala Arg Ile Thr Cys Gly Glu Asp Asn Ile Gly Ser Lys Ser Val
            20                  25                  30

His Trp Tyr Gln Gln Arg Pro Gly Gln Ala Pro Val Leu Val Val Tyr
        35                  40                  45

Asp Asp Lys Tyr Arg Pro Ser Gly Ile Pro Glu Arg Phe Ser Gly Ser
    50                  55                  60

Asn Ser Gly Asn Thr Ala Thr Leu Thr Ile Ser Arg Ile Glu Ala Gly
65                  70                  75                  80

Asp Glu Ala Asp Tyr Tyr Cys Gln Val Trp Asp Ser Arg Tyr Asp Arg
                85                  90                  95

His Val Val Phe Gly Gly Gly Thr Lys Leu Thr Val Leu
            100                 105

<210> SEQ ID NO 137
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 137

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Tyr Phe Asn Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Thr Lys Thr Tyr Val Glu Ser Val
    50                  55                  60

Met Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Ala Ser Gly Trp Glu Ile Asp Tyr Trp Gly Gln Gly Thr Leu
            100                 105                 110

Val Thr Val Tyr Ser
        115

<210> SEQ ID NO 138
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 138

Gln Ser Ala Leu Thr Gln Pro Ala Ser Val Ser Gly Ser Pro Gly Gln
1               5                   10                  15

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Ile Ile Phe Asp Val Asn Asn Arg Pro Ser Gly Val Ser Asn Arg Phe
    50                  55                  60

Ser Gly Ser Lys Ser Val Asn Thr Ala Ser Leu Thr Ile Ser Gly Leu
65                  70                  75                  80

Arg Ala Glu Asp Glu Ala Asp Tyr Tyr Cys Ser Ser Tyr Thr Ala Ser
                85                  90                  95

Ser Thr Leu Val Phe Gly Gly Gly Thr Lys Leu Thr Val Leu
            100                 105                 110


<210> SEQ ID NO 139
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 139

Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Asn Tyr
            20                  25                  30

Asp Ile Asn Trp Val Arg Gln Ala Pro Gly Gln Gly Leu Glu Trp Met
        35                  40                  45

Gly Gly Ile Ile Pro Ile Phe Asp Thr Pro Asn Tyr Ala Gln Lys Phe
    50                  55                  60

Gln Gly Arg Val Thr Ile Thr Ala Asp Glu Ser Thr Thr Lys Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Arg Tyr Cys Asn Ser Thr Ser Cys Tyr Arg Ile
            100                 105                 110

Phe Asp Tyr Trp Gly Gln Gly Ser Leu Val Thr Val Ser Ser
        115                 120                 125


<210> SEQ ID NO 140
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 140

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Gly Asp Trp
            20                  25                  30

Leu Ala Trp Tyr Gln Gln Lys Pro Gly Lys Ala Pro Lys Leu Leu Ile
        35                  40                  45

Tyr Lys Ala Ser Phe Leu Glu Gly Gly Val Pro Ser Arg Phe Ser Gly
    50                  55                  60

Ser Gly Ser Gly Thr Thr Phe Thr Leu Thr Ile Ser Ser Leu Gln Pro
65                  70                  75                  80

Asp Asp Phe Ala Thr Tyr Tyr Cys Gln His Tyr Asn Thr Tyr Ala Tyr
                85                  90                  95
```

```
Ser Phe Gly Gln Gly Thr Lys Leu Glu Ile Lys
            100                 105


<210> SEQ ID NO 141
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ser Ile Asn Trp Val Arg Gln Ala Pro Gly Gln Gly Leu Glu Trp Met
        35                  40                  45

Gly Gly Ile Ile Pro Ile Val Gly Ser Val Asn Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ile Gly Ile Ala Val Ala Gly Thr Ile Tyr Tyr Gly Met
            100                 105                 110

Asp Val Trp Gly Gln Gly Thr Thr Val Thr Val Ser Ser
        115                 120                 125


<210> SEQ ID NO 142
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 142

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Pro Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Gly Thr Tyr Thr Phe Gly Gln Gly Thr Lys Leu Glu Ile Lys
            100                 105                 110


<210> SEQ ID NO 143
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 143
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Leu Leu Ser Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Asp Asp Thr Ala Ile Tyr Tyr Cys
                85                  90                  95

Ala Lys Ile Pro Val Ser Met Val Arg Gly Val Met Glu Tyr Ala Met
            100                 105                 110

Asp Val Trp Gly Gln Gly Thr Thr Val Thr Val Ser Ser
        115                 120                 125


<210> SEQ ID NO 144
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 144

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Asn Thr Val
            20                  25                  30

His Trp Tyr Gln Gln Lys Pro Gly Gln Ala Pro Val Leu Val Val Tyr
        35                  40                  45

Gly Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 145
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 145

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Thr Trp Val Arg Gln Ala Pro Gly Gln Gly Leu Glu Trp Met
        35                  40                  45

Gly Trp Ile Ser Ser Tyr Asn Asn Asn Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Phe Tyr Cys
                85                  90                  95

Ala Arg Asp Arg Phe Ser Gly Tyr Asp Leu Gly Tyr Trp Gly Gln Gly
            100                 105                 110

Thr Leu Val Thr Val Ser Ser
        115


<210> SEQ ID NO 146
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 146

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Phe Ala Gly Arg
                85                  90                  95

Ser Ala Pro Phe Gly Thr Gly Thr Lys Val Thr Val Leu
            100                 105


<210> SEQ ID NO 147
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Val Ser Gly Gly Thr Phe Ser His Phe
            20                  25                  30

Ala Ile Ile Trp Val Arg Gln Ala Pro Gly Gln Gly Leu Glu Trp Met
        35                  40                  45

Gly Gly Ile Ile Pro Val Phe Gly Thr Thr Asn Tyr Val Glu Lys Phe
    50                  55                  60

Gln Gly Arg Val Thr Ile Thr Ala Asp Glu Ser Arg Ser Thr Ala Tyr
65                  70                  75                  80

Met Glu Leu Thr Arg Leu Thr Phe Glu Asp Thr Ala Val Tyr Tyr Cys
                85                  90                  95

Ala Lys Gly Phe Arg Ala Gly Gly Ala Asn Thr Asp Phe Asp Tyr Trp
            100                 105                 110

Gly Gln Gly Thr Leu Val Thr Val Ser Ser
        115                 120


<210> SEQ ID NO 148
<211> LENGTH: 112
<212> TYPE: PRT
```

<213> ORGANISM: Artificial sequence
<220> FEATURE:
<223> OTHER INFORMATION: Synthetic polypeptide

<400> SEQUENCE: 148

Gln Leu Val Val Thr Gln Ser Pro Ser Ala Ser Ala Ser Leu Gly Ala
1 5 10 15

Ser Val Lys Phe Thr Cys Thr Leu Ser Ser Gly His Ser Thr Tyr Ser
20 25 30

Ile Ala Trp His Gln Gln His Pro Ala Arg Gly Pro Arg Tyr Leu Met
35 40 45

Arg Val Asn Ser Asp Gly Ser His Thr Lys Gly Asp Gly Ile Pro Asp
50 55 60

Arg Phe Ser Gly Ser Ser Ser Gly Ala Asp Arg Phe Leu Thr Ile Ser
65 70 75 80

Arg Leu Gln Ser Glu Asp Glu Ala Asp Tyr Tyr Cys Gln Thr Trp Gly
85 90 95

Thr Gly Ile Gln Val Val Phe Gly Gly Gly Ser Lys Leu Thr Val Leu
100 105 110

<210> SEQ ID NO 149
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 149

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Ile His Trp Val Arg Gln Ala Pro Gly Lys Gly Leu Glu Trp Val
35 40 45

Ala Val Ile Ser Tyr Asp Gly Arg His Lys Tyr Ile Ala Asp Pro Val
50 55 60

Lys Gly Arg Phe Thr Ile Ser Arg Asp Asn Ser Lys Asn Met Leu Tyr
65 70 75 80

Leu Gln Met Asn Ser Leu Arg Thr Glu Asp Thr Ala Val Tyr Tyr Cys
85 90 95

Ala Lys Asp Thr Ser Gly Trp Tyr Glu Phe Phe Asp Ser Trp Gly Gln
100 105 110

Gly Ile Pro Val Thr Val Ser Ser
115 120

<210> SEQ ID NO 150
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 150

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ala Thr Asn
20 25 30

Val Ala Trp Tyr Gln Gln Lys Pro Gly Gln Ala Pro Arg Leu Leu Ile
35 40 45

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Cys Asn Asp Trp Leu Thr
                85                  90                  95

Phe Gly Gln Gly Thr Lys Val Glu Ile Lys
            100                 105
```

<210> SEQ ID NO 151
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 151

```
Gln Val Gln Leu Val Gln Ser Gly Ala Glu Val Thr Lys Pro Gly Ala
1               5                   10                  15

Ser Val Lys Val Ser Cys Lys Thr Ser Gly Tyr Thr Phe Thr Tyr Tyr
            20                  25                  30

Asn Ile Ser Trp Val Arg Gln Ala Pro Gly Gln Gly Leu Glu Trp Met
        35                  40                  45

Gly Trp Ile Ser Ala Tyr Ser Gly Asn Thr His Tyr Ala Gln Lys Leu
    50                  55                  60

Gln Gly Arg Val Thr Met Thr Ile Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Ala Ser Val Leu Pro Pro Ala Ser Val Tyr Tyr Ser
            100                 105                 110

Tyr Met Asp Val Trp Gly Lys Gly Thr Thr Val Thr Val Ser Ser
        115                 120                 125
```

<210> SEQ ID NO 152
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 152

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asn Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105
```

<210> SEQ ID NO 153
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 153

```
Glu Val Gln Leu Val Glu Ser Gly Arg Gly Leu Val Gln Pro Gly Gly
1               5                   10                  15

Ser Leu Arg Leu Ser Cys Ala Ala Ser Gly Phe Thr Phe Asn Ile Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asn Ser Val
    50                  55                  60

Lys Gly Arg Phe Thr Ile Ser Arg Asp Asn Ala Lys Tyr Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Ile Gly Tyr Cys Asn Ser Lys Thr Cys Ser Tyr Asp
            100                 105                 110

Phe Asp Tyr Trp Gly Gln Gly Ala Leu Val Thr Val Ser Ser
        115                 120                 125
```

<210> SEQ ID NO 154
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 154

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Phe Tyr Ala
            20                  25                  30

Ser Trp Tyr Gln Gln Lys Pro Gly Gln Ala Pro Leu Leu Val Ile Tyr
        35                  40                  45

Asn Glu Asn Asn Arg Pro Ser Gly Ile Pro Asp Arg Phe Ser Gly Ser
    50                  55                  60

Ser Ser Gly Asn Thr Ala Ser Leu Thr Ile Thr Gly Thr Gln Ala Ala
65                  70                  75                  80

Asp Asp Ala Asp Tyr Tyr Cys Ser Ser Arg Asp Ser Ser Gly Asn His
                85                  90                  95

Val Leu Phe Gly Gly Gly Thr Lys Leu Thr Val Leu
            100                 105
```

<210> SEQ ID NO 155
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 155

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Gly Ile Thr Trp Val Arg Gln Ala Pro Gly Gln Gly Leu Glu Trp Met
35 40 45

Gly Trp Ile Ser Ala Tyr Asn Gly Asn Thr Asp Tyr Ala Gln Lys Leu
50 55 60

Gln Gly Arg Val Thr Met Thr Thr Asp Thr Ser Thr Ser Thr Ala Tyr
65 70 75 80

Met Glu Leu Gly Ser Leu Arg Ser Asp Asp Thr Ala Val Tyr Tyr Cys
85 90 95

Ala Arg Glu Leu Trp Phe Gly Asp Leu Gly Tyr Trp Gly Gln Gly Thr
100 105 110

Leu Val Thr Val Ser Ser
115

<210> SEQ ID NO 156
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 156

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Ser
20 25 30

Ser Ser Ser Tyr Leu Ala Trp Tyr Gln Gln Lys Pro Gly Gln Ala Pro
35 40 45

Arg Leu Leu Ile Tyr Gly Ala Ser Ser Arg Ala Thr Gly Ile Pro Asp
50 55 60

Arg Phe Ser Gly Ser Gly Ser Gly Thr Asp Phe Thr Leu Thr Ile Ser
65 70 75 80

Arg Leu Glu Pro Glu Asp Val Ala Val Tyr Tyr Cys Gln Gln Tyr Gly
85 90 95

Ser Ser Pro Gln Thr Phe Gly Gln Gly Thr Lys Leu Glu Ile Lys
100 105 110

<210> SEQ ID NO 157
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 157

Glu Val His Leu Val Asp Ser Gly Gly Gly Leu Glu Gln Pro Gly Arg
1 5 10 15

Ser Leu Arg Leu Ser Cys Ala Ala Ser Gly Phe Thr Phe Ser Asp Tyr
20 25 30

Ala Met His Trp Val Arg Gln Ala Pro Gly Lys Gly Leu Glu Trp Val
35 40 45

Ser Ser Ile Ser Trp Asn Ser Gly Asn Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Thr Leu Lys Thr Glu Asp Thr Ala Phe Tyr Tyr Cys
85 90 95

Ala Arg Gly Pro Phe Phe Asn Trp Asn Pro Thr Asn Tyr Phe Asp His

```
            100                 105                 110

Trp Gly Gln Gly Thr Leu Val Thr Val Ser Ser
        115                 120


<210> SEQ ID NO 158
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 158

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Tyr Leu Ala Trp Tyr Gln His Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Thr Ser Pro
                85                  90                  95

Pro Met Tyr Thr Phe Gly Gln Gly Thr Lys Leu Glu Ile Lys
            100                 105                 110


<210> SEQ ID NO 159
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 159

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Arg Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Gly Arg Leu Cys Val Gly Asp Ser Cys His Ser Gly Pro Leu
            100                 105                 110

Asp Tyr Trp Gly Gln Gly Thr Leu Val Thr Val Ser Ser
        115                 120                 125


<210> SEQ ID NO 160
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 160
```

```
Ser Phe Glu Leu Thr Gln Pro Pro Ser Met Ser Val Ser Pro Gly Gln
1               5                   10                  15

Thr Ala Arg Ile Ser Cys Ser Gly Asp Thr Leu Gly Asn Lys Tyr Ala
            20                  25                  30

Tyr Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Ser Ala Asp Tyr Tyr Cys Gln Ala Trp Asp Ser Ser Ala His Tyr
                85                  90                  95

Val Phe Gly Thr Gly Thr Lys Val Thr Val Leu
            100                 105
```

```
<210> SEQ ID NO 161
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 161

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Glu Ser Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Gly Cys Ser Gly Gly Asn Cys Asp Glu Gly Phe Asp Tyr
            100                 105                 110

Trp Gly Gln Gly Thr Leu Val Thr Val Ser Ser
        115                 120
```

```
<210> SEQ ID NO 162
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 162

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser His Arg Phe
    50                  55                  60

Ser Gly Ser Lys Ser Gly Asn Thr Ala Ser Leu Thr Ile Ser Gly Leu
```

```
65                  70                  75                  80

Gln Ala Glu Asp Glu Ala Asp Tyr Tyr Cys Ile Ser Tyr Arg Ser Ser
                85                  90                  95

Ser Thr Leu Tyr Val Phe Gly Thr Gly Thr Lys Val Thr Val Leu
            100                 105                 110


<210> SEQ ID NO 163
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 163

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Tyr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Gly Tyr Asn Phe Asp Tyr Trp Gly Gln Gly Thr Leu
            100                 105                 110

Val Thr Val Ser Ser
        115


<210> SEQ ID NO 164
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 164

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Phe Ala
            20                  25                  30

Ser Trp Tyr Gln Gln Lys Pro Gly Gln Ala Pro Val Val Val Ile Phe
        35                  40                  45

Asp Arg Asn Asn Arg Pro Ser Gly Ile Pro Asp Arg Phe Ser Gly Ser
    50                  55                  60

Ser Ser Gly Ser Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Leu
                85                  90                  95

Tyr Val Phe Gly Thr Gly Thr Lys Val Thr Val Leu
            100                 105


<210> SEQ ID NO 165
<211> LENGTH: 128
<212> TYPE: PRT
<213> ORGANISM: Artificial sequence
<220> FEATURE:
```

<223> OTHER INFORMATION: Synthetic polypeptide

<400> SEQUENCE: 165

Gln Val Thr Leu Lys Glu Ser Gly Pro Val Leu Val Lys Pro Thr Glu
1 5 10 15

Thr Leu Thr Leu Thr Cys Ser Val Ser Gly Phe Ser Leu Ser Ser Ala
20 25 30

Arg Met Gly Val Ser Trp Ile Arg Gln Pro Pro Gly Lys Ala Leu Glu
35 40 45

Trp Leu Ala His Ile Phe Ser Ser Asp Glu Lys Ser Tyr Ser Thr Ser
50 55 60

Leu Lys Ser Arg Leu Ser Ile Ser Lys Asp Thr Ser Lys Ser Gln Val
65 70 75 80

Val Leu Thr Leu Thr Asn Leu Asp Pro Val Asp Thr Ala Thr Tyr Tyr
85 90 95

Cys Ala Arg Ile Arg Gly Pro Ser Tyr Tyr His Gln Asn Tyr Tyr Tyr
100 105 110

Phe Gly Met Asp Val Trp Gly Gln Gly Thr Thr Val Thr Val Ser Ser
115 120 125

<210> SEQ ID NO 166
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 166

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Gln Ile
65 70 75 80

Ser Arg Val Glu Ala Glu Asp Val Gly Val Tyr Tyr Cys Met Gln Ala
85 90 95

Leu Gln Ala Pro Trp Thr Phe Gly Gln Gly Thr Lys Val Glu Ile Lys
100 105 110

<210> SEQ ID NO 167
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 167

Gln Val Gln Leu Gln Glu Ser Gly Pro Gly Leu Val Lys Pro Ser Gln
1 5 10 15

Thr Leu Ser Leu Thr Cys Val Val Ser Gly Ala Ser Ile Ser Ser Ala
20 25 30

Asp Ser Tyr Trp Ser Trp Ile Arg Gln His Pro Gly Lys Gly Leu Glu
35 40 45

Trp Ile Gly Tyr Ile Tyr Tyr Ser Gly Ser Thr Tyr Tyr Asn Pro Ser

```
    50                  55                  60

Leu Lys Ser Arg Val Thr Ile Ser Val Asp Thr Ser Lys Asn Gln Phe
65                  70                  75                  80

Ser Leu Lys Leu Thr Ser Leu Thr Ala Ala Asp Thr Ala Val Tyr Tyr
                85                  90                  95

Cys Ala Arg Gly Gly Pro Tyr Cys Gly Gly Asp Cys Tyr Arg Trp Gly
            100                 105                 110

Gln Gly Thr Leu Val Thr Val Ser Ser
        115                 120


<210> SEQ ID NO 168
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 168

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Asp Ala Ala Asn Leu Asp Thr Gly Val Pro Ser Arg Phe Ser Gly
    50                  55                  60

Ser Gly Ser Glu Thr Asp Phe Thr Phe Thr Ile Ser Ser Leu Gln Pro
65                  70                  75                  80

Glu Asp Ile Ala Thr Tyr Tyr Cys Gln Gln Tyr Asp Ser Leu Pro Trp
                85                  90                  95

Thr Phe Gly Gln Gly Thr Lys Val Glu Ile Lys
            100                 105


<210> SEQ ID NO 169
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 169

Gln Val Gln Leu Arg Glu Ser Gly Pro Gly Leu Val Lys Pro Ser Glu
1               5                   10                  15

Thr Leu Ser Leu Thr Cys Thr Val Ser Asn Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Ser Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Asp Leu Arg Ala Trp Ile Gln Leu His Arg Ala Ser Leu Tyr Tyr
            100                 105                 110

Tyr Tyr Met Asp Val Trp Gly Lys Gly Thr Thr Val Thr Val Ser Ser
        115                 120                 125
```

<210> SEQ ID NO 170
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 170

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Phe Tyr Thr
20 25 30

Thr Trp Tyr Gln Gln Lys Pro Gly Gln Ala Pro Val Leu Val Ile Tyr
35 40 45

Gly Thr Asn Asn Arg Pro Ser Gly Ile Pro Glu Arg Phe Ser Gly Ser
50 55 60

Ser Ser Gly Asn Thr Ala Ser Leu Thr Ile Thr Gly Ala Gln Ala Asp
65 70 75 80

Asp Glu Ala Asp Tyr Tyr Cys Asp Ser Arg Asp Ser Ser Gly Glu Leu
85 90 95

Trp Leu Phe Gly Gly Gly Thr Lys Leu Thr Val Leu
100 105

<210> SEQ ID NO 171
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 171

Glu Val Gln Leu Leu Glu Ser Gly Gly Gly Leu Val Gln Pro Gly Gly
1 5 10 15

Ser Leu Arg Leu Ser Cys Val Ala Ser Gly Phe Ser Phe Gly Ser Tyr
20 25 30

Gly Met Ser Trp Val Arg Gln Ala Pro Gly Lys Gly Leu Glu Trp Val
35 40 45

Ser Gly Ile Gly Gly Arg Gly Asp Ser Thr Tyr Phe Ala Asp Ser Val
50 55 60

Lys Gly Arg Phe Ser Ile Ser Arg Asp Asn Ser Lys Asn Thr Leu Tyr
65 70 75 80

Leu Gln Met Asn Phe Leu Arg Ala Glu Asp Thr Ala Val Tyr Tyr Cys
85 90 95

Ala Lys Glu Gly Phe Gly Ser Gly His Phe His Gly Ser Asn Asp Tyr
100 105 110

Trp Gly Gln Gly Thr Leu Val Thr Val Ser Ser
115 120

<210> SEQ ID NO 172
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 172

Asp Ile Gln Met Thr Gln Ser Pro Ser Ser Leu Ser Ala Ser Val Gly
1 5 10 15

Asp Arg Val Thr Ile Ala Cys Gln Thr Ser His Asp Ile Ser Asn Tyr

```
            20                  25                  30

Leu Asn Trp Tyr Gln Gln Lys Pro Gly Arg Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Phe Asp Ser Leu Pro Leu
                85                  90                  95

Thr Phe Gly Gly Gly Thr Lys Val Gly Val Lys
            100                 105


<210> SEQ ID NO 173
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Phe Tyr Asp Phe Trp Ser Gly Leu Asp Ile Asp Val Trp Gly
            100                 105                 110

Lys Gly Thr Thr Val Thr Val Phe Ser
        115                 120


<210> SEQ ID NO 174
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 174

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

```
Ile Thr Arg Val Phe Gly Thr Gly Thr Lys Val Thr Val Leu
            100                 105                 110


<210> SEQ ID NO 175
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 175

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Gly Ile Ser Trp Val Arg Gln Ala Pro Gly Gln Gly Leu Glu Trp Met
        35                  40                  45

Gly Gly Val Ile Pro Ile Phe Gly Thr Thr Lys Tyr Ala Lys Lys Phe
    50                  55                  60

Gln Gly Arg Val Thr Val Thr Ala Asp Lys Ser Thr Gly Thr Ala Tyr
65                  70                  75                  80

Met Glu Leu Ser Ser Leu Ile Ser Glu Asp Thr Ala Val Tyr Tyr Cys
                85                  90                  95

Ala Arg Asp Asp Gly Ala Ala Ala Gly Thr Gly Tyr Tyr Gly Met Ala
            100                 105                 110

Val Trp Gly Gln Gly Thr Thr Val Thr Val Ser Ser
        115                 120


<210> SEQ ID NO 176
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 176

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Gly Asp Phe Ala Val Tyr Tyr Cys Gln Gln Tyr Val Asn Trp Pro Gln
                85                  90                  95

Tyr Thr Phe Gly Gln Gly Thr Lys Leu Glu Ile Lys
            100                 105


<210> SEQ ID NO 177
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 177

Gln Val Gln Leu Leu Gln Ser Gly Ala Glu Val Lys Lys Pro Gly Ser
```

```
1               5                   10                  15

Ser Val Lys Val Ser Cys Lys Ala Ser Gly Gly Thr Phe Ser Asn Ile
            20                  25                  30

Gly Ile Ser Trp Val Arg Gln Ala Pro Arg Gln Gly Leu Glu Trp Met
        35                  40                  45

Gly Gly Ile Ile Pro Leu Phe Ala Thr Thr Asn Tyr Ala Gln Asn Phe
    50                  55                  60

Gln Gly Arg Leu Thr Ile Thr Ala Asp Lys Ser Thr Thr Thr Ala Tyr
65                  70                  75                  80

Met Glu Leu Asn Ser Leu Arg Ser Asp Asp Thr Gly Val Tyr Phe Cys
                85                  90                  95

Ala Arg Gln Leu Gly Trp Ala Tyr Cys Asn Ser Ser Thr Cys Ser Lys
            100                 105                 110

Gly Trp Phe Asn Pro Trp Gly Gln Gly Thr Leu Val Thr Val Ser Ser
        115                 120                 125


<210> SEQ ID NO 178
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 178

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro His Leu Leu Ile Tyr Thr Val Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Thr Val Glu Ala Glu Asp Val Gly Val Tyr Tyr Cys Met Gln
                85                  90                  95

Arg Thr Glu Phe Pro Tyr Thr Phe Gly Gln Gly Thr Lys Leu Glu Ile
            100                 105                 110


<210> SEQ ID NO 179
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 179

Gln Val Gln Leu Gln Glu Ser Gly Pro Gly Leu Val Lys Pro Ser Gln
1               5                   10                  15

Thr Leu Ser Leu Ser Cys Ser Val Ser Gly Gly Ser Ile Ser Thr Gly
            20                  25                  30

Gly Tyr Tyr Trp Ser Trp Ile Arg Gln Lys Ser Gly Lys Gly Leu Glu
        35                  40                  45

Trp Ile Gly Tyr Ile Ser Asn Ile Gly Asn Thr Tyr Tyr Asn Pro Ser
    50                  55                  60

Leu Lys Ser Arg Val Ala Ile Ser Leu Asp Thr Ser Lys Asn Gln Phe
65                  70                  75                  80
```

Ser Leu Lys Leu Ser Ser Val Thr Ala Ala Asp Thr Ala Val Tyr Tyr
85 90 95

Cys Ala Lys Ala Pro Pro Asp Ala Tyr Asp Ser Gly Thr Tyr Tyr Leu
100 105 110

Ala Tyr Tyr Met Asp Val Trp Gly Lys Gly Thr Thr Val Ala Val Ser
115 120 125

Ser

<210> SEQ ID NO 180
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 180

Asp Ile Gln Met Thr Gln Phe Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Asn Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Ser Tyr Tyr Cys Gln Gln Tyr Asn Ser Tyr Pro Tyr
85 90 95

Thr Phe Gly Gln Gly Thr Lys Leu Glu Ile Lys
100 105

<210> SEQ ID NO 181
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 181

Gln Val Gln Leu Val Glu Ser Gly Gly Gly Val Val Gln Pro Gly Arg
1 5 10 15

Ser Leu Arg Leu Ser Cys Thr Ala Ser Gly Phe Thr Phe Ser Asn Tyr
20 25 30

Gly Met Gln Trp Val Arg Gln Ala Pro Gly Lys Gly Leu Glu Trp Val
35 40 45

Ala Val Ile Ser Tyr His Gly Asn Asn Asn Tyr Thr Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Thr Gly Leu Glu Gly Glu Tyr Trp Gly Gln Gly Thr Leu Val Thr Val
100 105 110

Ser Ser

<210> SEQ ID NO 182
<211> LENGTH: 106
<212> TYPE: PRT

<213> ORGANISM: Artificial sequence
<220> FEATURE:
<223> OTHER INFORMATION: Synthetic polypeptide

<400> SEQUENCE: 182

```
Ser Tyr Glu Leu Thr Gln Pro Ser Ser Val Ser Val Ser Pro Gly Gln
1               5                   10                  15

Thr Ala Arg Ile Thr Cys Ser Gly Asp Leu Leu Ala Lys Ile Tyr Ala
            20                  25                  30

Arg Trp Phe Gln Gln Lys Pro Gly Gln Ala Pro Glu Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Thr Asp Asn Asn Gly Val
                85                  90                  95

Phe Gly Gly Gly Thr Lys Leu Thr Val Leu
            100                 105
```

<210> SEQ ID NO 183
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 183

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Asn Gly Asn Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Ala Arg Gly Gly Arg Ile Arg Phe Leu Glu Trp Tyr Asp Tyr Trp
            100                 105                 110

Gly Gln Gly Thr Leu Val Thr Val Ser Ser
        115                 120
```

<210> SEQ ID NO 184
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 184

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ser Tyr Ser Ser Pro Arg
                85                  90                  95

Thr Phe Gly Leu Gly Thr Lys Leu Glu Ile Lys
            100                 105
```

<210> SEQ ID NO 185
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 185

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Asn Ser Tyr
            20                  25                  30

Gly Met His Trp Val Arg Gln Ala Pro Gly Lys Gly Leu Glu Trp Val
        35                  40                  45

Ala Leu Thr Trp Tyr Asp Gly Ser Asn Lys Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Cys Ser Gly Gly Ser Cys Tyr Ser Glu Gly Trp
            100                 105                 110

Phe Asp Pro Trp Gly Gln Gly Thr Leu Val Thr Val Ser Ser
        115                 120                 125
```

<210> SEQ ID NO 186
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 186

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Val Val Phe Gly Gly Gly Thr Lys Leu Thr Val Leu
            100                 105                 110
```

<210> SEQ ID NO 187
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 187

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Ser Ser
            20                  25                  30

Gly Glu Gly Leu Gly Trp Ile Arg Gln Pro Pro Gly Lys Ala Leu Glu
        35                  40                  45

Trp Leu Ala Leu Ile Tyr Gly Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Ser Gly Tyr Cys Ser Gly Gly Asp Cys Tyr Ser Arg
            100                 105                 110

Leu Gly Trp Phe Asp Pro Trp Gly Leu Gly Thr Leu Val Thr Val Ser
        115                 120                 125

Ser

<210> SEQ ID NO 188
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 188

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Phe Thr Phe Gly Pro Gly Thr Lys Val Asp Ile Lys
            100                 105

<210> SEQ ID NO 189
<211> LENGTH: 132
<212> TYPE: PRT
<213> ORGANISM: Artificial sequence
<220> FEATURE:
<223> OTHER INFORMATION: Synthetic polypeptide

<400> SEQUENCE: 189

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Ala Leu His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Val Gln Met Asn Ser Leu Arg Pro Glu Asp Thr Ala Val Tyr Tyr Cys
                85                  90                  95

Thr Arg Val Val Asn Phe Gly Val Ala Phe Ile Arg Asp Gly Val Tyr
            100                 105                 110

Gly His Tyr Tyr Tyr Gly Met Asp Val Trp Gly Gln Gly Thr Thr Val
        115                 120                 125

Thr Val Ser Ser
    130

<210> SEQ ID NO 190
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 190

Gln Ser Val Leu Thr Gln Pro Pro Ser Val Ser Ala Ala Pro Gly Gln
1               5                   10                  15

Lys Val Ser Ile Ser Cys Ser Gly Ser Thr Ser Asn Ile Gly Asn Asn
            20                  25                  30

Tyr Val Ser Trp Tyr Arg Gln Phe Pro Gly Thr Ala Pro Lys Phe Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Val Trp Val Phe Gly Gly Gly Thr Lys Leu Thr Val Leu
            100                 105                 110

<210> SEQ ID NO 191
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 191

Gln Val Gln Val Gln Glu Ser Gly Pro Gly Leu Val Lys Thr Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ala Ala Gly Lys Gly Leu Glu Trp Ile
        35                  40                  45

Gly Arg Thr Tyr Ser Gly Gly Ser Pro Asn Tyr Asn Pro Ser Leu Arg
    50                  55                  60

Ser Arg Val Thr Val Ser Val Asp Thr Ser Lys Asn Gln Phe Ser Leu
65                  70                  75                  80

Ile Leu Thr Ser Val Thr Ala Ala Asp Thr Ala Val Tyr Phe Cys Ala
85 90 95

Arg Glu Asp His Gly Leu Arg Gln Lys Phe Tyr Tyr Tyr Met Asp Leu
100 105 110

Trp Gly Lys Gly Thr Ala Val Thr Val Ser Ser
115 120

<210> SEQ ID NO 192
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 192

Ser Tyr Val Leu Thr Gln Pro Pro Ser Val Ser Val Ala Pro Gly Lys
1 5 10 15

Thr Ala Lys Ile Thr Cys Gly Gly Ser Asn Ile Gly Ser Lys Ser Val
20 25 30

His Trp Tyr Gln Gln Lys Pro Gly Gln Ala Pro Val Leu Val Ile Tyr
35 40 45

Tyr Asp Ser Asp Arg Pro Ser Gly Ile Pro Asp Arg Phe Ser Gly Ser
50 55 60

Asn Ser Gly Asn Thr Ala Thr Leu Thr Ile Ser Arg Val Glu Ala Gly
65 70 75 80

Asp Glu Ala Asp Tyr Ser Cys Gln Val Trp Asp Ser Ser Pro Asp His
85 90 95

Ser Pro Val Val Phe Gly Gly Gly Thr Lys Leu Thr Val Leu
100 105 110

<210> SEQ ID NO 193
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 193

Gln Val Gln Leu Gln Glu Ser Gly Pro Gly Leu Val Lys Pro Ser Glu
1 5 10 15

Thr Leu Ser Leu Thr Cys Ile Val Ser Gly Gly Ser Ile Asn Ser Tyr
20 25 30

Tyr Trp Ser Trp Ile Arg Gln Pro Ala Gly Lys Ala Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Val Asp Met Ser Lys Asn Gln Phe Ser Leu
65 70 75 80

Lys Leu Thr Ser Val Thr Ala Ala Asp Thr Ala Val Tyr Tyr Cys Ala
85 90 95

Arg Ala Pro Arg Ile Pro Val Ser Val Glu Gly His Tyr Tyr Tyr His
100 105 110

Tyr Tyr Met Asp Val Trp Gly Lys Gly Thr Thr Val Thr Val Ser
115 120 125

<210> SEQ ID NO 194
<211> LENGTH: 108
<212> TYPE: PRT

<213> ORGANISM: Artificial sequence
<220> FEATURE:
<223> OTHER INFORMATION: Synthetic polypeptide

<400> SEQUENCE: 194

```
Ser Ser Val Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Ile Leu Val Ile Tyr
        35                  40                  45

Ala Lys Asn His Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Gln Asp Ser Ser Gly Asn His
                85                  90                  95

Leu Gly Phe Gly Gly Gly Thr Lys Leu Thr Val Leu
            100                 105
```

<210> SEQ ID NO 195
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 195

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Arg Tyr
            20                  25                  30

Ala Val Thr Trp Val Arg Gln Ala Pro Gly Lys Gly Leu Glu Trp Val
        35                  40                  45

Ser Thr Ile Thr Gly Ser Gly Gly Arg Thr Tyr Tyr Ala Asp Ser Val
    50                  55                  60

Lys Gly Arg Phe Thr Val Ser Arg Asp Ser Ser Lys Asn Thr Leu Tyr
65                  70                  75                  80

Leu Gln Met Asn Thr Leu Arg Ala Glu Asp Ser Ala Ile Tyr Tyr Cys
                85                  90                  95

Ala Lys Gly Ile Val Val Val Leu Val Gly Pro Pro Tyr Phe Gly Met
            100                 105                 110

Asp Val Trp Gly Gln Gly Thr Thr Val Thr Val Ser Ser
        115                 120                 125
```

<210> SEQ ID NO 196
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 196

```
Ser Tyr Val Leu Thr Gln Pro Pro Ser Val Ser Val Ala Pro Gly Gln
1               5                   10                  15

Thr Ala Arg Ile Pro Cys Gly Gly Asn Asn Ile Gly Thr Lys Thr Val
            20                  25                  30

His Trp Tyr Gln Gln Lys Pro Gly Gln Ala Pro Val Leu Val Val Tyr
        35                  40                  45
```

```
Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Ser Val Glu Ala Gly
65                  70                  75                  80

Asp Glu Ala Asp Tyr His Cys Gln Val Trp Asp Ser Ser Ser Asp Leu
                85                  90                  95

Val Val Phe Gly Gly Gly Thr Lys Leu Thr Val Leu
            100                 105


<210> SEQ ID NO 197
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 197

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Val Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Val Ala Asn Tyr Phe Asp Tyr Trp Gly Gln Gly
            100                 105                 110

Thr Leu Val Thr Val Ser Ser
        115


<210> SEQ ID NO 198
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 198

Glu Ile Val Leu Thr Gln Ser Pro Ala Thr Leu Ser Leu Ser Pro Gly
1               5                   10                  15

Glu Ser Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Phe
                85                  90                  95

Thr Phe Gly Pro Gly Thr Lys Val Asp Ile Lys
            100                 105
```

<210> SEQ ID NO 199
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 199

Gln Val Gln Leu Val Glu Ser Gly Thr Glu Val Lys Lys Pro Gly Ala
1 5 10 15

Ser Val Lys Val Ser Cys Lys Ala Ser Glu Tyr Thr Phe Thr Ala Tyr
20 25 30

Tyr Ile His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Gly Asp Thr Ser Ile Thr Thr Ala Tyr
65 70 75 80

Met Glu Leu Ser Arg Leu Arg Ser Asp Asp Thr Ala Val Tyr Tyr Cys
85 90 95

Ala Ser Asp Tyr Phe Asp Ser Ser Gly Tyr His Asp Tyr Trp Gly Gln
100 105 110

Gly Thr Leu Val Thr Val Ser Ser
115 120

<210> SEQ ID NO 200
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 200

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Ile Gly Asn Tyr
20 25 30

Asn Leu Val Ser Trp Tyr Gln Gln His Pro Gly Lys Ala Pro Lys Leu
35 40 45

Met Ile Phe Glu Val Ser Lys Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala His Tyr Tyr Cys Cys Ser Tyr Val Asp Asp
85 90 95

Trp Val Phe Gly Gly Gly Thr Lys Leu Thr Val Leu
100 105

<210> SEQ ID NO 201
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 201

Gln Val Thr Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Thr Ser
20 25 30

```
Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Arg Met Thr Asn Met Asp Pro Val Asp Thr Ala Thr Tyr Tyr
                85                  90                  95

Cys Ala Arg Ile Leu Pro Gly Tyr Cys Ser Gly Gly Ser Cys Tyr Tyr
            100                 105                 110

Asn Tyr His Phe Asp Tyr Trp Gly Gln Gly Thr Leu Val Thr Val Ser
        115                 120                 125

Ser


<210> SEQ ID NO 202
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 202

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

His Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Pro
                85                  90                  95

Tyr Val Phe Gly Thr Gly Thr Lys Val Thr Val Leu
            100                 105


<210> SEQ ID NO 203
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 203

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ile Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Lys Ala Val Tyr Tyr Cys
                85                  90                  95
```

Ala Arg Glu Gly Gly Gly Gln His Gly Asp Tyr Ala Ser Trp Phe Asp
100 105 110

Pro Trp Gly Gln Gly Thr Leu Val Thr Val Ser Ser
115 120

<210> SEQ ID NO 204
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 204

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Thr Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Lys Gly Arg
85 90 95

Thr Phe Gly Pro Gly Thr Lys Val Asp Ile Lys
100 105

<210> SEQ ID NO 205
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 205

Gln Val Gln Leu Val Gln Ser Gly Ala Glu Val Lys Lys Pro Gly Ser
1 5 10 15

Ser Val Lys Val Ser Cys Lys Ala Ser Gly Gly Ser Phe Arg Ser Tyr
20 25 30

Ala Ile Ser Trp Val Arg Gln Ala Pro Gly Gln Gly Leu Glu Trp Met
35 40 45

Gly Met Ile Ile Pro Ile Phe Asp Thr Thr Asn Tyr Ala Gln Lys Phe
50 55 60

Gln Gly Arg Val Thr Ile Thr Ala Asp Lys Ser Thr Ser Thr Thr Tyr
65 70 75 80

Met Glu Leu Asn Ser Leu Lys Ser Glu Asp Thr Ala Val Tyr Tyr Cys
85 90 95

Ala Arg Asp Leu Asn His Phe Tyr Ala Ser Ser Gly Pro Asn Asp Leu
100 105 110

Trp Gly Gln Gly Thr Leu Val Thr Val Ser Ser
115 120

<210> SEQ ID NO 206
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 206

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Asn
20 25 30

Phe Leu Ala Trp Tyr Gln Gln Lys Pro Gly Gln Ala Pro Arg Leu Leu
35 40 45

Ile Tyr Gly Thr Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Gly Ser Pro
85 90 95

Gly Thr Phe Gly Gln Gly Thr Lys Val Glu Ile Lys
100 105

<210> SEQ ID NO 207
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 207

Gln Val Thr Leu Lys Glu Ser Gly Pro Ala Leu Val Arg Pro Thr Gln
1 5 10 15

Thr Leu Thr Leu Thr Cys Thr Phe Ser Gly Phe Ser Leu Thr Thr Ser
20 25 30

Gly Met Arg Val Ser Trp Ile Arg Gln Pro Pro Gly Lys Ala Leu Glu
35 40 45

Trp Leu Ala Arg Ile Asp Trp Asp Asp Asp Lys Phe Tyr Ser Thr Ser
50 55 60

Leu Lys Thr Arg Leu Thr Ile Ser Lys Asp Thr Ser Lys Asn Gln Val
65 70 75 80

Val Leu Thr Leu Thr Asn Met Asp Pro Val Asp Thr Ala Thr Tyr Tyr
85 90 95

Cys Ala Arg Ser Met Tyr Asp Ser Ser Gly Tyr Tyr Pro Pro Thr Pro
100 105 110

Phe Asp Ile Trp Gly Gln Gly Thr Met Val Thr Val Ser Ser
115 120 125

<210> SEQ ID NO 208
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 208

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Arg Tyr
20 25 30

Leu Asn Trp Tyr Gln Gln Lys Pro Gly Lys Ala Pro Lys Leu Leu Ile
35 40 45

Tyr Ala Ala Ser Ala Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Ser Cys Gln Gln Ser Phe Asn Thr Pro Phe
85 90 95

Thr Phe Gly Pro Gly Thr Lys Val Asp Ile Lys
100 105

<210> SEQ ID NO 209
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 209

Glu Val Gln Leu Leu Glu Ser Gly Gly Gly Leu Ile Gln Pro Gly Gly
1 5 10 15

Ser Leu Arg Leu Ser Cys Ala Ala Ser Gly Phe Thr Phe Thr Asn Tyr
20 25 30

Ala Met Asn Trp Val Arg Gln Ala Pro Gly Lys Gly Leu Glu Trp Val
35 40 45

Ser Val Ile Ser Gly Ser Gly Gly Thr Ser Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Ala Thr Leu Ile Val Val Val Leu Arg Pro Asp Val Phe
100 105 110

Asp Ile Trp Gly Gln Gly Thr Met Val Thr Val Ser Ser
115 120 125

<210> SEQ ID NO 210
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 210

Ser Tyr Glu Leu Thr Gln Pro Pro Ser Val Ser Val Ser Pro Gly Gln
1 5 10 15

Thr Ala Ser Ile Thr Cys Ser Gly Asp Lys Leu Gly Asp Lys His Ala
20 25 30

Cys Trp Tyr Arg Gln Lys Pro Gly Gln Ser Pro Val Leu Val Ile Tyr
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Asp Ser Asn Thr Ala His
85 90 95

Tyr Val Phe Gly Thr Gly Thr Lys Val Thr Val Leu
100 105

<210> SEQ ID NO 211
<211> LENGTH: 125
<212> TYPE: PRT

<213> ORGANISM: Artificial sequence
<220> FEATURE:
<223> OTHER INFORMATION: Synthetic polypeptide

<400> SEQUENCE: 211

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Arg Phe Ser Ser Tyr
            20                  25                  30

Gly Met His Trp Val Arg Gln Ala Pro Gly Lys Gly Leu Glu Trp Val
        35                  40                  45

Gly Val Ile Trp Tyr Asp Gly Ser Asn Lys Tyr Tyr Ala Asp Ser Val
    50                  55                  60

Lys Gly Arg Cys Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Val Ser Arg Gly Ala Asp Asp Trp Asp Tyr Tyr Tyr Tyr Met
            100                 105                 110

Asp Val Trp Gly Lys Gly Thr Thr Val Thr Val Ser Ser
        115                 120                 125
```

<210> SEQ ID NO 212
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 212

```
Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Phe
            20                  25                  30

Ser Asn Asn Lys Asn Cys Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Arg
```

<210> SEQ ID NO 213
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 213

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Met Phe Ser Ser Tyr
            20                  25                  30
```

```
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Gly Gly Glu Phe Asp Tyr Trp Gly Gln Gly Thr Leu
            100                 105                 110

Val Thr Val Ser Ser
        115


<210> SEQ ID NO 214
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 214

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ser Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asn Ser
                85                  90                  95

Ser Asn Trp Val Phe Gly Gly Gly Thr Lys Leu Thr Val Leu
            100                 105                 110


<210> SEQ ID NO 215
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 215

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Thr Pro Asp Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Glu Thr Leu Arg Ala Glu Asp Thr Ala Val Tyr Tyr Cys
                85                  90                  95

Ala Arg Val Gly Gly Val Gly Trp Glu Gly Asp Phe Trp Gly Gln Gly
            100                 105                 110
```

Thr Leu Val Thr Val Ser Ser
115

<210> SEQ ID NO 216
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 216

Gln Ser Ala Leu Thr Gln Pro Ala Ser Val Ser Gly Ser Pro Gly Gln
1 5 10 15

Ser Ile Thr Ile Ser Cys Ala Gly Ser Ser Ser Asp Val Gly Ala Asn
20 25 30

Asn Tyr Val Ser Trp Tyr Gln Gln Asp Pro Gly Gln Ala Pro Lys Leu
35 40 45

Met Ile Tyr Glu Val Asn Tyr Arg Pro Ser Gly Val Pro Asn Arg Phe
50 55 60

Ser Gly Ser Lys Ser Gly Asn Thr Ala Tyr Leu Thr Ile Ser Gly Leu
65 70 75 80

Gln Ala Glu Asp Glu Ala Asn Tyr Phe Cys Ser Ser Tyr Ser Ser Ala
85 90 95

Thr Thr Leu Arg Phe Gly Gly Gly Thr Lys Leu Thr Val Leu
100 105 110

<210> SEQ ID NO 217
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 217

Gln Val Gln Leu Val Gln Ser Gly Ala Glu Val Lys Lys Pro Gly Ala
1 5 10 15

Ser Val Lys Val Ser Cys Lys Thr Ser Gly Tyr Ile Phe Ser Asn Tyr
20 25 30

Asp Ile Ser Trp Val Arg Gln Ala Pro Gly Gln Gly Leu Glu Trp Met
35 40 45

Gly Trp Ile Ser Ala Tyr Ser Gly Glu Lys Lys Tyr Ser Gln Lys Phe
50 55 60

Gln Val Arg Leu Thr Met Thr Ala Asp Thr Ala Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Pro Thr Val Val His Ala Leu Asp Ile Trp Gly Gln Gly
100 105 110

Thr Met Val Thr Val Ser Ser
115

<210> SEQ ID NO 218
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Ser Asn Phe
            20                  25                  30

Leu Asn Trp Tyr Gln Gln Lys Pro Gly Lys Ala Pro Lys Leu Leu Ile
        35                  40                  45

Phe Asp Ala Ser Asn Leu Glu Pro Gly Val Pro Ser Arg Phe Ser Gly
    50                  55                  60

Ser Gly Ser Gly Thr Asp Phe Thr Phe Thr Ile Asn Ser Leu Gln Pro
65                  70                  75                  80

Glu Asp Ile Ala Thr Tyr Tyr Cys Gln Gln Tyr Asp Asp Leu Val Tyr
                85                  90                  95

Thr Phe Gly Gln Gly Thr Lys Leu Glu Ile Lys
            100                 105


<210> SEQ ID NO 219
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Tyr Ile Thr Asn Ser Ser Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Leu Ala Arg Pro His Arg Tyr Tyr Asp Asn Ser Ala Tyr
            100                 105                 110

Phe Glu Val Phe Asp Ser Trp Gly Gln Gly Thr Leu Val Thr Val Ser
        115                 120                 125

Ser


<210> SEQ ID NO 220
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 220

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60
```

Asn Ser Gly Asn Thr Ala Ser Leu Thr Ile Thr Gly Ala Gln Ala Glu
65 70 75 80

Asp Glu Gly Asp Tyr Tyr Cys Ser Ser Arg Asp Ser Ser Gly Asn Tyr
85 90 95

Leu Arg Val Phe Gly Thr Gly Thr Lys Val Thr Val Leu
100 105

<210> SEQ ID NO 221
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 221

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Asn Ser Tyr
20 25 30

Gly Met His Trp Val Arg Gln Thr Pro Gly Lys Gly Leu Glu Trp Val
35 40 45

Ala Ile Ile Trp Tyr Asp Gly Ser Gln Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Glu Gly Ser Tyr Asp Leu Asp Tyr Trp Gly Gln Gly Thr
100 105 110

Leu Val Thr Val Ser Ser
115

<210> SEQ ID NO 222
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 222

Gln Ser Ala Leu Ile Gln Pro Ala Ser Val Ser Gly Ser Pro Gly Gln
1 5 10 15

Ser Ile Thr Ile Ser Cys Thr Gly Thr Lys Ser Asp Val Gly Gly Tyr
20 25 30

Asn Tyr Val Ser Trp Tyr Gln Gln Tyr Pro Gly Lys Thr Pro Lys Arg
35 40 45

Met Ile Phe Glu Val Ser Asn Arg Pro Ser Gly Ala Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Thr Ser Tyr Thr Ser Ser
85 90 95

Ser Thr Leu Val Phe Gly Gly Gly Thr Lys Leu Thr Val Leu
100 105 110

<210> SEQ ID NO 223
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 223

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Arg Val Glu Gly Gly Ser Tyr Ser Gly Asp Tyr Trp Gly Gln Gly
            100                 105                 110

Thr Leu Val Thr Val Ser Ser
        115

<210> SEQ ID NO 224
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 224

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Tyr
            20                  25                  30

Asn Ser Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Asn Thr
                85                  90                  95

Val Ser Val Val Phe Gly Gly Gly Thr Lys Leu Thr Val Leu
            100                 105                 110

<210> SEQ ID NO 225
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 225

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Ser Met Asn Trp Ile Arg Gln Ala Pro Gly Lys Gly Leu Glu Trp Ile
        35                  40                  45

Ser Ser Ile Ser His Ser Glu Thr Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met His Ser Leu Arg Ala Glu Asp Thr Gly Val Tyr Tyr Cys
85 90 95

Ala Arg Pro Leu Glu Ala Met Met Trp Glu Glu Phe His Phe Trp Gly
100 105 110

Gln Gly Ile Leu Val Ser Val Ser Ser
115 120

<210> SEQ ID NO 226
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 226

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Asn
20 25 30

Tyr Val Tyr Trp Tyr His His Leu Pro Gly Thr Ala Pro Lys Leu Leu
35 40 45

Ile Tyr Arg Thr Asn Gln Arg Pro Ser Gly Val Pro Asp Arg Phe Ser
50 55 60

Gly Ser Lys Ser Gly Thr Ser Ala Ser Leu Val Ile Ser Gly Leu Arg
65 70 75 80

Ser Glu Asp Glu Ala Asp Tyr Tyr Cys Ala Ser Trp Asp Gly Ser Leu
85 90 95

Ser Gly Val Leu Phe Gly Gly Gly Thr Lys Leu Thr Val Leu
100 105 110

<210> SEQ ID NO 227
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 227

Gln Val Gln Leu Val Gln Ser Gly Ala Glu Val Arg Lys Pro Gly Ser
1 5 10 15

Ser Val Lys Val Ser Cys Lys Ala Ser Gly Gly Thr Phe Ser Asn Tyr
20 25 30

Asp Ile Asn Trp Val Arg Gln Ala Pro Gly Gln Gly Leu Glu Trp Met
35 40 45

Gly Gly Ile Ile Pro Ile Phe Asp Thr Pro Asn Tyr Ala Gln Lys Phe
50 55 60

Gln Gly Arg Val Thr Ile Thr Ala Asp Glu Ser Thr Thr Lys Ala Tyr
65 70 75 80

Met Glu Leu Ser Ser Leu Arg Ser Glu Asp Thr Ala Val Tyr Tyr Cys
85 90 95

Ala Arg Gly Ala Ser Arg Tyr Cys Asn Ser Thr Ser Cys Tyr Arg Ile
100 105 110

Phe Asp Tyr Trp Gly Gln Gly Ser Leu Val Thr Val Ser Ser
115 120 125

<210> SEQ ID NO 228
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 228

Gln Ser Val Leu Thr Gln Pro Pro Ser Ala Ser Gly Thr Pro Gly Gln
1 5 10 15

Arg Val Thr Ile Ser Cys Ser Gly Ser Thr Ser Asn Ile Gly Thr Asn
20 25 30

Tyr Val Tyr Trp Tyr His His Leu Pro Gly Thr Ala Pro Lys Leu Leu
35 40 45

Ile Tyr Arg Thr Asn Gln Arg Pro Ser Gly Val Pro Asp Arg Phe Ser
50 55 60

Gly Ser Lys Ser Gly Thr Ser Ala Ser Leu Val Ile Ser Gly Leu Arg
65 70 75 80

Ser Glu Asp Glu Ala Asp Tyr Tyr Cys Ala Ser Trp Asp Gly Ser Leu
85 90 95

Ser Gly Val Leu Phe Gly Gly Gly Thr Lys Leu Thr Val Leu
100 105 110

<210> SEQ ID NO 229
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 229

Gln Val Gln Leu Gln Glu Ser Gly Pro Gly Leu Val Lys Pro Ser Glu
1 5 10 15

Thr Leu Ser Leu Thr Cys Thr Val Ser Gly Tyr Ser Ile Ser Ser Gly
20 25 30

Tyr Tyr Trp Gly Trp Ile Arg Gln Pro Pro Gly Lys Gly Leu Glu Trp
35 40 45

Ile Gly Ser Val Tyr His Ser Gly Thr Thr Tyr Tyr Asn Pro Ser Leu
50 55 60

Arg Ser Arg Val Thr Ile Ser Ser Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Gly Ser Arg Leu Val Ser Asp Ile Trp Pro Leu Val Asp Val Trp
100 105 110

Gly Thr Gly Thr Thr Val Thr Val Ser Ser
115 120

<210> SEQ ID NO 230
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 230

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Phe Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 231
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 231

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Val
20 25 30

Trp Met Ser Trp Val Arg Gln Ala Pro Gly Lys Gly Leu Glu Trp Val
35 40 45

Gly Arg Ile Lys Ser Lys Ile Asp Gly Gly Thr Thr Asp Tyr Ala Val
50 55 60

Phe Val Lys Gly Arg Phe Ile Ile Ser Arg Asp Asp Ser Lys Asn Met
65 70 75 80

Leu Tyr Leu Gln Met Asn Ser Leu Lys Thr Glu Asp Thr Ala Val Tyr
85 90 95

Tyr Cys Thr Thr Glu Asp Tyr Asn Tyr Val Trp Gly Gly Leu Pro Ala
100 105 110

Pro Tyr Gly Leu Asp Val Trp Gly Gln Gly Thr Thr Val Thr Val Ser
115 120 125

Ser

<210> SEQ ID NO 232
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 232

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Phe Ser Arg Leu Glu
65 70 75 80

```
Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 233
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 233

Gln Val Gln Leu Gln Glu Ser Gly Pro Gly Leu Val Lys Thr Ser Gln
1               5                   10                  15

Thr Leu Ser Leu Thr Cys Thr Val Ser Gly Gly Ser Val Ile Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Phe Asn Ser Gly Ser Thr Asn Tyr Asn Pro Ser
    50                  55                  60

Leu Lys Ser Arg Val Thr Ile Ser Ala Asp Lys Ser Lys Lys Gln Leu
65                  70                  75                  80

Ser Leu Lys Leu Thr Ser Val Thr Ala Ala Asp Thr Ala Val Tyr Tyr
                85                  90                  95

Cys Ala Arg Asp Tyr Glu Gly Cys Thr Asn Gly Val Cys Tyr Thr Tyr
            100                 105                 110

Leu Asp Phe Trp Gly Gln Gly Thr Leu Val Thr Val Ser Ser
        115                 120                 125


<210> SEQ ID NO 234
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 234

Asp Ile Gln Met Thr Gln Ser Pro Ser Ser Leu Ser Ala Ser Val Gly
1               5                   10                  15

Asp Arg Val Met Ile Thr Cys Arg Ala Ser Gln Asn Ile Lys Asn Tyr
            20                  25                  30

Leu Asn Trp Tyr Gln Gln Lys Ser Ala Thr Ala Pro Glu Leu Leu Ile
        35                  40                  45

Tyr Gly Ala Ser Ser Val Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Arg
                85                  90                  95

Thr Phe Gly Gly Gly Thr Lys Val Glu Ile Lys
            100                 105


<210> SEQ ID NO 235
<211> LENGTH: 122
<212> TYPE: PRT
<213> ORGANISM: Artificial sequence
<220> FEATURE:
<223> OTHER INFORMATION: Synthetic polypeptide
```

<400> SEQUENCE: 235

Gln Val Gln Leu Val Gln Ser Gly Ala Glu Val Lys Lys Pro Gly Ala
1               5                   10                  15

Ser Met Lys Val Ser Cys Lys Thr Ser Gly Tyr Thr Phe Thr Asp Tyr
            20                  25                  30

Tyr Met His Trp Val Arg Gln Ala Pro Gly Gln Gly Arg Glu Trp Met
        35                  40                  45

Gly Trp Ile Asn Pro Lys Ser Gly Val Ala Asn Tyr Ala Gln Lys Phe
    50                  55                  60

Gln Asp Arg Val Thr Met Thr Arg Asp Thr Ser Ile Thr Thr Ala Tyr
65                  70                  75                  80

Met Glu Val Thr Arg Leu Arg Ser Asp Asp Thr Ala Val Tyr Tyr Cys
                85                  90                  95

Ala Arg Asp Arg Gly Ile Phe Gly Gly Tyr Tyr Gly Leu Asp Val Trp
            100                 105                 110

Gly Gln Gly Thr Thr Val Thr Val Ser Ser
        115                 120

<210> SEQ ID NO 236
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 236

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Val Asn Asn
            20                  25                  30

Tyr Val Ser Trp Tyr Arg Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Ala Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Glu Gly Thr Lys Val Thr Val Leu
            100                 105                 110

<210> SEQ ID NO 237
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 237

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Asp Tyr
            20                  25                  30

Gly Met His Trp Val Arg Gln Ala Pro Gly Lys Gly Leu Glu Trp Val
        35                  40                  45

Ala Ile Val Trp Phe Asp Gly Ser Asn Lys Tyr Tyr Ala Asp Ser Val
    50                  55                  60

Lys Gly Arg Phe Thr Ile Ser Arg Asp Asn Ser Arg Asn Thr Leu Tyr
65 70 75 80

Leu Gln Met Asn Ser Leu Arg Gly Glu Asp Thr Ala Val Tyr His Cys
85 90 95

Ala Arg Asp Phe Thr Pro Thr Ala Val Ala Leu Asp Tyr Trp Gly Gln
100 105 110

Gly Thr Leu Val Thr Val Ser Ser
115 120

<210> SEQ ID NO 238
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 238

Gln Ser Val Leu Thr Gln Pro His Ser Val Ser Glu Ser Pro Gly Lys
1 5 10 15

Thr Val Thr Ile Ser Cys Thr Arg Ser Ser Gly Ser Ile Ser Arg Asn
20 25 30

Tyr Val Gln Trp Tyr Gln Gln Arg Pro Gly Ser Ala Pro Thr Thr Val
35 40 45

Ile Tyr Glu Asp Asn Gln Arg Pro Ser Gly Val Pro Asp Arg Phe Ser
50 55 60

Gly Ser Ile Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Tyr Asp Ser
85 90 95

Ser Pro Thr Trp Val Phe Gly Gly Gly Thr Lys Leu Thr Val Leu
100 105 110

<210> SEQ ID NO 239
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 239

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Asp Tyr
20 25 30

Gly Met His Trp Val Arg Gln Ala Pro Gly Lys Gly Leu Glu Trp Val
35 40 45

Ala Ile Val Trp Phe Asp Gly Ser Asn Lys Tyr Tyr Ala Asp Ser Val
50 55 60

Lys Gly Arg Phe Thr Ile Ser Arg Asp Asn Ser Arg Asn Thr Leu Tyr
65 70 75 80

Leu Gln Met Asn Ser Leu Arg Gly Glu Asp Thr Ala Val Tyr His Cys
85 90 95

Ala Arg Asp Phe Thr Pro Thr Ala Val Ala Leu Asp Tyr Trp Gly Gln
100 105 110

Gly Thr Leu Val Thr Val Ser Ser
115 120

<210> SEQ ID NO 240

<211> LENGTH: 111
<212> TYPE: PRT
<213> ORGANISM: Artificial sequence
<220> FEATURE:
<223> OTHER INFORMATION: Synthetic polypeptide

<400> SEQUENCE: 240

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ser Arg Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Pro Thr Trp Val Phe Gly Gly Gly Thr Lys Leu Thr Val Leu
            100                 105                 110

<210> SEQ ID NO 241
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 241

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Asn Ser Gly
            20                  25                  30

Tyr Tyr Trp Ala Trp Ile Arg Gln Pro Pro Gly Lys Gly Leu Glu Trp
        35                  40                  45

Ile Gly Asn Ile Tyr Gln Ser Gly Ser Thr Tyr Tyr Asn Pro Ser Leu
    50                  55                  60

Met Ser Arg Val Thr Ile Ser Val Asp Ala Ser Lys Asn Gln Leu Phe
65                  70                  75                  80

Leu Asn Leu Ser Ser Val Thr Ala Ala Glu Thr Ala Val Tyr Tyr Cys
                85                  90                  95

Ala Thr Cys His Ser Leu Gly Thr Ser Ala Trp Pro Leu Pro Asp Tyr
            100                 105                 110

Trp Gly Gln Gly Thr Leu Val Thr Val Ser Ser
        115                 120

<210> SEQ ID NO 242
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 242

Glu Ile Val Leu Thr Gln Ser Pro Gly Thr Leu Ser Leu Ser Pro Gly
1               5                   10                  15

Glu Arg Ala Thr Leu Ser Cys Lys Thr Ser Gln Ser Ile Ser Ser Asp
            20                  25                  30

```
Tyr Leu Ala Trp Tyr Gln Gln Arg Pro Gly Gln Ala Pro Trp Leu Leu
        35                  40                  45

Ile Phe Gly Ala Ser Ser Arg Ala Thr Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Ser Ser Pro
                85                  90                  95

Phe Thr Phe Gly Gln Gly Thr Asn Leu Glu Ile Lys
            100                 105


<210> SEQ ID NO 243
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 243

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Val
            20                  25                  30

Trp Met Ser Trp Val Arg Gln Ala Pro Gly Lys Gly Leu Glu Trp Val
        35                  40                  45

Gly Arg Ile Lys Ser Lys Ile Asp Gly Gly Thr Thr Asp Tyr Ala Val
    50                  55                  60

Phe Val Lys Gly Arg Phe Ile Ile Ser Arg Asp Asp Ser Lys Asn Met
65                  70                  75                  80

Leu Tyr Leu Gln Met Asn Ser Leu Lys Thr Glu Asp Thr Ala Val Tyr
                85                  90                  95

Tyr Cys Thr Thr Glu Asp Tyr Asn Tyr Val Trp Gly Gly Leu Pro Ala
            100                 105                 110

Pro Tyr Gly Leu Asp Val Trp Gly Gln Gly Thr Thr Val Thr Val Ser
        115                 120                 125

Ser


<210> SEQ ID NO 244
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 244

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Val Ser
                85                  90                  95
```

Ser Asn Val Val Phe Gly Gly Gly Thr Lys Leu Thr Val Leu
100 105 110

<210> SEQ ID NO 245
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 245

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly His Ile Tyr Tyr Ser Gly Asn Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Thr His Ser Gly Ser Tyr Gly Tyr Trp Gly Gln Gly
100 105 110

Thr Leu Val Thr Val Ser Ser
115

<210> SEQ ID NO 246
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 246

Gln Ser Ala Leu Thr Gln Pro Pro Ser Ala Ser Gly Ser Pro Gly Gln
1 5 10 15

Ser Val Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Lys Arg Pro Ser Gly Val Pro Asp Arg Phe
50 55 60

Ser Gly Ser Lys Ser Gly Asn Thr Ala Ser Leu Thr Val Ser Gly Leu
65 70 75 80

Gln Ala Glu Asp Glu Ala Asp Tyr Tyr Cys Ser Ser Tyr Ala Gly Ser
85 90 95

Asn Val Trp Val Phe Gly Gly Gly Thr Lys Leu Thr Val Leu
100 105 110

<210> SEQ ID NO 247
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 247

Gln Val Gln Leu Val Glu Ser Gly Gly Gly Val Val Gln Pro Gly Arg

```
1               5                   10                  15

Ser Leu Arg Leu Ser Cys Ala Ala Ser Gly Phe Val Phe Thr Asn Tyr
            20                  25                  30

Val Met His Trp Val Arg Gln Ala Pro Gly Lys Ala Leu Glu Trp Val
        35                  40                  45

Thr Leu Ile Ser Tyr Asp Gly Asn Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Ser Pro His Gly Asp Val Pro Asp Tyr Tyr Phe Asp Leu Trp
            100                 105                 110

Gly Arg Gly Thr Leu Val Thr Val Ser Ser
        115                 120
```

<210> SEQ ID NO 248
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 248

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln His Lys Pro Gly Lys Pro Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Arg Ala
                85                  90                  95

Phe Gly Leu Gly Thr Lys Val Glu Ile Lys
            100                 105
```

<210> SEQ ID NO 249
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 249

```
Gln Val Gln Leu Val Gln Ser Gly Ala Glu Val Arg Lys Pro Gly Ser
1               5                   10                  15

Ser Val Lys Val Ser Cys Val Ala Ser Gly Gly Thr Phe Arg Asn Tyr
            20                  25                  30

Ala Ile Ser Trp Val Arg Arg Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Ser Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Asp Tyr Tyr Glu Arg Thr Asp Tyr Tyr Thr Pro Gly Tyr Trp
            100                 105                 110

Gly Gln Gly Thr Leu Val Thr Val Ser Ser
        115                 120
```

<210> SEQ ID NO 250
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 250

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Glu Ser Thr Ser Val
            20                  25                  30

His Trp Tyr Gln Gln Lys Pro Gly Gln Ala Pro Val Leu Val Ile Tyr
        35                  40                  45

Phe Asp Ser Asp Arg Pro Ser Gly Ile Pro Glu Arg Phe Ser Gly Ser
    50                  55                  60

Asn Ser Gly Asn Thr Ala Thr Leu Thr Leu Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 251
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 251

```
Gln Val Gln Leu Gln Glu Ser Gly Pro Gly Leu Val Lys Pro Ser Glu
1               5                   10                  15

Thr Leu Ser Leu Thr Cys Ser Val Ser Asn Tyr Ser Ile Thr Ser Thr
            20                  25                  30

Tyr Tyr Trp Gly Trp Ile Arg Gln Pro Pro Gly Lys Gly Leu Glu Trp
        35                  40                  45

Ile Gly Ser Val Tyr His Thr Gly Ser Thr Tyr Tyr Asn Pro Ser Leu
    50                  55                  60

Lys Ser Arg Val Thr Ile Ser Val Asp Thr Ser Lys Asn Arg Phe Ser
65                  70                  75                  80

Leu Arg Leu Arg Ser Val Thr Ala Ala Asp Thr Ala Val Tyr Tyr Cys
                85                  90                  95

Ala Arg Glu Ile Pro Ala Trp Ile Tyr Tyr Leu Asp Val Trp Gly Lys
            100                 105                 110

Gly Ala Thr Val Thr Val Ser Ser
        115                 120
```

<210> SEQ ID NO 252
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 252

```
Gln Ser Val Leu Thr Gln Pro Pro Ser Val Ser Ala Ala Pro Gly Gln
1               5                   10                  15

Gln Val Thr Ile Ser Cys Ser Val Ser Ser Ser Asn Ile Gly Thr Thr
            20                  25                  30

Tyr Val Ser Trp Tyr Gln Gln Leu Pro Gly Thr Ala Pro Lys Leu Leu
        35                  40                  45

Ile Tyr Asp Asn Asn Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ala Trp Asp Ser Ser Leu
                85                  90                  95

Ser Ala Gly Val Phe Gly Gly Gly Thr Lys Leu Thr Val Leu
            100                 105                 110
```

<210> SEQ ID NO 253
<211> LENGTH: 8
<212> TYPE: PRT
<213> ORGANISM: Artificial sequence
<220> FEATURE:
<223> OTHER INFORMATION: Synthetic peptide

<400> SEQUENCE: 253

```
Gly Phe His Phe Gly Ser Tyr Gly
1               5
```

<210> SEQ ID NO 254
<211> LENGTH: 8
<212> TYPE: PRT
<213> ORGANISM: Artificial sequence
<220> FEATURE:
<223> OTHER INFORMATION: Synthetic peptide

<400> SEQUENCE: 254

```
Thr Trp Tyr Asp Gly Ser Asn Lys
1               5
```

<210> SEQ ID NO 255
<211> LENGTH: 12
<212> TYPE: PRT
<213> ORGANISM: Artificial sequence
<220> FEATURE:
<223> OTHER INFORMATION: Synthetic peptide

<400> SEQUENCE: 255

```
Ala Arg Asp Gly Gly Ser Thr Trp Pro Pro Asp Tyr
1               5                   10
```

<210> SEQ ID NO 256
<211> LENGTH: 8
<212> TYPE: PRT
<213> ORGANISM: Artificial sequence
<220> FEATURE:
<223> OTHER INFORMATION: Synthetic peptide

<400> SEQUENCE: 256

```
Gly Tyr Thr Phe Thr Asp Tyr Tyr
1               5
```

<210> SEQ ID NO 257
<211> LENGTH: 8
<212> TYPE: PRT
<213> ORGANISM: Artificial sequence
<220> FEATURE:
<223> OTHER INFORMATION: Synthetic peptide

<400> SEQUENCE: 257

Ile Asn Pro Asn Ser Gly Gly Thr
1 5

<210> SEQ ID NO 258
<211> LENGTH: 13
<212> TYPE: PRT
<213> ORGANISM: Artificial sequence
<220> FEATURE:
<223> OTHER INFORMATION: Synthetic peptide

<400> SEQUENCE: 258

Ala Cys Val Asp Thr Ala Met Gly Trp Gly Phe Asp Tyr
1 5 10

<210> SEQ ID NO 259
<211> LENGTH: 10
<212> TYPE: PRT
<213> ORGANISM: Artificial sequence
<220> FEATURE:
<223> OTHER INFORMATION: Synthetic peptide

<400> SEQUENCE: 259

Gly Gly Ser Val Ser Ser Gly Asp Tyr Tyr
1 5 10

<210> SEQ ID NO 260
<211> LENGTH: 7
<212> TYPE: PRT
<213> ORGANISM: Artificial sequence
<220> FEATURE:
<223> OTHER INFORMATION: Synthetic peptide

<400> SEQUENCE: 260

Ile Phe Asn Gly Gly Ser Thr
1 5

<210> SEQ ID NO 261
<211> LENGTH: 16
<212> TYPE: PRT
<213> ORGANISM: Artificial sequence
<220> FEATURE:
<223> OTHER INFORMATION: Synthetic peptide

<400> SEQUENCE: 261

Ala Arg Asp Trp Glu His Cys Phe Asn Gly Ile Cys Tyr Tyr Tyr Phe
1 5 10 15

<210> SEQ ID NO 262
<211> LENGTH: 8
<212> TYPE: PRT
<213> ORGANISM: Artificial sequence
<220> FEATURE:
<223> OTHER INFORMATION: Synthetic peptide

<400> SEQUENCE: 262

Gly Phe Thr Leu Asn Asn Tyr Gly
1 5

<210> SEQ ID NO 263

<211> LENGTH: 8
<212> TYPE: PRT
<213> ORGANISM: Artificial sequence
<220> FEATURE:
<223> OTHER INFORMATION: Synthetic peptide

<400> SEQUENCE: 263

Ile Trp Phe Asp Gly Thr Thr Lys
1               5

<210> SEQ ID NO 264
<211> LENGTH: 20
<212> TYPE: PRT
<213> ORGANISM: Artificial sequence
<220> FEATURE:
<223> OTHER INFORMATION: Synthetic peptide

<400> SEQUENCE: 264

Ala Arg Ala Thr Tyr Asp Phe Trp Ser Gly Glu Pro Ile Gly His Tyr
1               5                   10                  15

Tyr Met Asp Val
            20

<210> SEQ ID NO 265
<211> LENGTH: 8
<212> TYPE: PRT
<213> ORGANISM: Artificial sequence
<220> FEATURE:
<223> OTHER INFORMATION: Synthetic peptide

<400> SEQUENCE: 265

Gly Phe Ile Phe Asp Ile Tyr Ala
1               5

<210> SEQ ID NO 266
<211> LENGTH: 8
<212> TYPE: PRT
<213> ORGANISM: Artificial sequence
<220> FEATURE:
<223> OTHER INFORMATION: Synthetic peptide

<400> SEQUENCE: 266

Ile Ser Gly Ser Gly Ser Thr Thr
1               5

<210> SEQ ID NO 267
<211> LENGTH: 16
<212> TYPE: PRT
<213> ORGANISM: Artificial sequence
<220> FEATURE:
<223> OTHER INFORMATION: Synthetic peptide

<400> SEQUENCE: 267

Ala Lys Gly Ser Gly Glu Gln Arg Tyr Tyr Phe Tyr Pro Leu Asp Phe
1               5                   10                  15

<210> SEQ ID NO 268
<211> LENGTH: 8
<212> TYPE: PRT
<213> ORGANISM: Artificial sequence
<220> FEATURE:
<223> OTHER INFORMATION: Synthetic peptide

<400> SEQUENCE: 268

Gly Phe Tyr Phe Asn Ser Tyr Gly
1               5

<210> SEQ ID NO 269
<211> LENGTH: 8
<212> TYPE: PRT
<213> ORGANISM: Artificial sequence
<220> FEATURE:
<223> OTHER INFORMATION: Synthetic peptide

<400> SEQUENCE: 269

Ile Trp Tyr Asp Gly Ser Thr Lys
1               5

<210> SEQ ID NO 270
<211> LENGTH: 10
<212> TYPE: PRT
<213> ORGANISM: Artificial sequence
<220> FEATURE:
<223> OTHER INFORMATION: Synthetic peptide

<400> SEQUENCE: 270

Ala Arg Ala Ser Gly Trp Glu Ile Asp Tyr
1               5                   10

<210> SEQ ID NO 271
<211> LENGTH: 8
<212> TYPE: PRT
<213> ORGANISM: Artificial sequence
<220> FEATURE:
<223> OTHER INFORMATION: Synthetic peptide

<400> SEQUENCE: 271

Gly Gly Thr Phe Ser Asn Tyr Asp
1               5

<210> SEQ ID NO 272
<211> LENGTH: 8
<212> TYPE: PRT
<213> ORGANISM: Artificial sequence
<220> FEATURE:
<223> OTHER INFORMATION: Synthetic peptide

<400> SEQUENCE: 272

Ile Ile Pro Ile Phe Asp Thr Pro
1               5

<210> SEQ ID NO 273
<211> LENGTH: 19
<212> TYPE: PRT
<213> ORGANISM: Artificial sequence
<220> FEATURE:
<223> OTHER INFORMATION: Synthetic peptide

<400> SEQUENCE: 273

Ala Arg Gly Ala Ser Arg Tyr Cys Asn Ser Thr Ser Cys Tyr Arg Ile
1               5                   10                  15

Phe Asp Tyr

<210> SEQ ID NO 274
<211> LENGTH: 8
<212> TYPE: PRT
<213> ORGANISM: Artificial sequence
<220> FEATURE:
<223> OTHER INFORMATION: Synthetic peptide

<400> SEQUENCE: 274

Gly Gly Thr Phe Ser Asp Tyr Ser
1               5

<210> SEQ ID NO 275
<211> LENGTH: 8
<212> TYPE: PRT
<213> ORGANISM: Artificial sequence
<220> FEATURE:
<223> OTHER INFORMATION: Synthetic peptide

<400> SEQUENCE: 275

Ile Ile Pro Ile Val Gly Ser Val
1 5

<210> SEQ ID NO 276
<211> LENGTH: 18
<212> TYPE: PRT
<213> ORGANISM: Artificial sequence
<220> FEATURE:
<223> OTHER INFORMATION: Synthetic peptide

<400> SEQUENCE: 276

Ala Thr Glu Ile Gly Ile Ala Val Ala Gly Thr Ile Tyr Tyr Gly Met
1 5 10 15

Asp Val

<210> SEQ ID NO 277
<211> LENGTH: 8
<212> TYPE: PRT
<213> ORGANISM: Artificial sequence
<220> FEATURE:
<223> OTHER INFORMATION: Synthetic peptide

<400> SEQUENCE: 277

Gly Phe Thr Phe Ser Thr Tyr Ala
1 5

<210> SEQ ID NO 278
<211> LENGTH: 8
<212> TYPE: PRT
<213> ORGANISM: Artificial sequence
<220> FEATURE:
<223> OTHER INFORMATION: Synthetic peptide

<400> SEQUENCE: 278

Leu Ser Tyr Asp Gly Ser Ser Lys
1 5

<210> SEQ ID NO 279
<211> LENGTH: 18
<212> TYPE: PRT
<213> ORGANISM: Artificial sequence
<220> FEATURE:
<223> OTHER INFORMATION: Synthetic peptide

<400> SEQUENCE: 279

Ala Lys Ile Pro Val Ser Met Val Arg Gly Val Met Glu Tyr Ala Met
1 5 10 15

Asp Val

<210> SEQ ID NO 280
<211> LENGTH: 8
<212> TYPE: PRT
<213> ORGANISM: Artificial sequence
<220> FEATURE:
<223> OTHER INFORMATION: Synthetic peptide

<400> SEQUENCE: 280

Gly Tyr Thr Phe Thr Ser Tyr Gly
1 5

<210> SEQ ID NO 281
<211> LENGTH: 8
<212> TYPE: PRT
<213> ORGANISM: Artificial sequence
<220> FEATURE:
<223> OTHER INFORMATION: Synthetic peptide

<400> SEQUENCE: 281

Ile Ser Ser Tyr Asn Asn Asn Thr
1 5

<210> SEQ ID NO 282
<211> LENGTH: 12
<212> TYPE: PRT
<213> ORGANISM: Artificial sequence
<220> FEATURE:
<223> OTHER INFORMATION: Synthetic peptide

<400> SEQUENCE: 282

Ala Arg Asp Arg Phe Ser Gly Tyr Asp Leu Gly Tyr
1 5 10

<210> SEQ ID NO 283
<211> LENGTH: 8
<212> TYPE: PRT
<213> ORGANISM: Artificial sequence
<220> FEATURE:
<223> OTHER INFORMATION: Synthetic peptide

<400> SEQUENCE: 283

Gly Gly Thr Phe Ser His Phe Ala
1 5

<210> SEQ ID NO 284
<211> LENGTH: 8
<212> TYPE: PRT
<213> ORGANISM: Artificial sequence
<220> FEATURE:
<223> OTHER INFORMATION: Synthetic peptide

<400> SEQUENCE: 284

Ile Ile Pro Val Phe Gly Thr Thr
1 5

<210> SEQ ID NO 285
<211> LENGTH: 15
<212> TYPE: PRT
<213> ORGANISM: Artificial sequence
<220> FEATURE:
<223> OTHER INFORMATION: Synthetic peptide

<400> SEQUENCE: 285

Ala Lys Gly Phe Arg Ala Gly Gly Ala Asn Thr Asp Phe Asp Tyr
1 5 10 15

<210> SEQ ID NO 286
<211> LENGTH: 8
<212> TYPE: PRT
<213> ORGANISM: Artificial sequence
<220> FEATURE:
<223> OTHER INFORMATION: Synthetic peptide

<400> SEQUENCE: 286

Gly Phe Thr Phe Ser Asn Tyr Gly
1               5

<210> SEQ ID NO 287
<211> LENGTH: 8
<212> TYPE: PRT
<213> ORGANISM: Artificial sequence
<220> FEATURE:
<223> OTHER INFORMATION: Synthetic peptide

<400> SEQUENCE: 287

Ile Ser Tyr Asp Gly Arg His Lys
1               5

<210> SEQ ID NO 288
<211> LENGTH: 13
<212> TYPE: PRT
<213> ORGANISM: Artificial sequence
<220> FEATURE:
<223> OTHER INFORMATION: Synthetic peptide

<400> SEQUENCE: 288

Ala Lys Asp Thr Ser Gly Trp Tyr Glu Phe Phe Asp Ser
1               5                   10

<210> SEQ ID NO 289
<211> LENGTH: 8
<212> TYPE: PRT
<213> ORGANISM: Artificial sequence
<220> FEATURE:
<223> OTHER INFORMATION: Synthetic peptide

<400> SEQUENCE: 289

Gly Tyr Thr Phe Thr Tyr Tyr Asn
1               5

<210> SEQ ID NO 290
<211> LENGTH: 8
<212> TYPE: PRT
<213> ORGANISM: Artificial sequence
<220> FEATURE:
<223> OTHER INFORMATION: Synthetic peptide

<400> SEQUENCE: 290

Ile Ser Ala Tyr Ser Gly Asn Thr
1               5

<210> SEQ ID NO 291
<211> LENGTH: 20
<212> TYPE: PRT
<213> ORGANISM: Artificial sequence
<220> FEATURE:
<223> OTHER INFORMATION: Synthetic peptide

<400> SEQUENCE: 291

Ala Arg Asp Gly Ala Ser Val Leu Pro Pro Ala Ser Val Tyr Tyr Ser
1               5                   10                  15

Tyr Met Asp Val
            20

<210> SEQ ID NO 292
<211> LENGTH: 8
<212> TYPE: PRT
<213> ORGANISM: Artificial sequence
<220> FEATURE:
<223> OTHER INFORMATION: Synthetic peptide

<400> SEQUENCE: 292

Gly Phe Thr Phe Asn Ile Tyr Trp
1               5

<210> SEQ ID NO 293
<211> LENGTH: 8
<212> TYPE: PRT
<213> ORGANISM: Artificial sequence
<220> FEATURE:
<223> OTHER INFORMATION: Synthetic peptide

<400> SEQUENCE: 293

Ile Lys Gln Asp Gly Ser Glu Lys
1               5

<210> SEQ ID NO 294
<211> LENGTH: 19
<212> TYPE: PRT
<213> ORGANISM: Artificial sequence
<220> FEATURE:
<223> OTHER INFORMATION: Synthetic peptide

<400> SEQUENCE: 294

Ala Arg Gly Phe Ile Gly Tyr Cys Asn Ser Lys Thr Cys Ser Tyr Asp
1               5                   10                  15

Phe Asp Tyr

<210> SEQ ID NO 295
<211> LENGTH: 8
<212> TYPE: PRT
<213> ORGANISM: Artificial sequence
<220> FEATURE:
<223> OTHER INFORMATION: Synthetic peptide

<400> SEQUENCE: 295

Gly Tyr Thr Phe Thr Asn Tyr Gly
1               5

<210> SEQ ID NO 296
<211> LENGTH: 8
<212> TYPE: PRT
<213> ORGANISM: Artificial sequence
<220> FEATURE:
<223> OTHER INFORMATION: Synthetic peptide

<400> SEQUENCE: 296

Ile Ser Ala Tyr Asn Gly Asn Thr
1               5

<210> SEQ ID NO 297
<211> LENGTH: 11
<212> TYPE: PRT
<213> ORGANISM: Artificial sequence
<220> FEATURE:
<223> OTHER INFORMATION: Synthetic peptide

<400> SEQUENCE: 297

Ala Arg Glu Leu Trp Phe Gly Asp Leu Gly Tyr
1               5                   10

<210> SEQ ID NO 298
<211> LENGTH: 8
<212> TYPE: PRT
<213> ORGANISM: Artificial sequence
<220> FEATURE:
<223> OTHER INFORMATION: Synthetic peptide

<400> SEQUENCE: 298

Gly Phe Thr Phe Ser Asp Tyr Ala
1 5

<210> SEQ ID NO 299
<211> LENGTH: 8
<212> TYPE: PRT
<213> ORGANISM: Artificial sequence
<220> FEATURE:
<223> OTHER INFORMATION: Synthetic peptide

<400> SEQUENCE: 299

Ile Ser Trp Asn Ser Gly Asn Ile
1 5

<210> SEQ ID NO 300
<211> LENGTH: 16
<212> TYPE: PRT
<213> ORGANISM: Artificial sequence
<220> FEATURE:
<223> OTHER INFORMATION: Synthetic peptide

<400> SEQUENCE: 300

Ala Arg Gly Pro Phe Phe Asn Trp Asn Pro Thr Asn Tyr Phe Asp His
1 5 10 15

<210> SEQ ID NO 301
<211> LENGTH: 8
<212> TYPE: PRT
<213> ORGANISM: Artificial sequence
<220> FEATURE:
<223> OTHER INFORMATION: Synthetic peptide

<400> SEQUENCE: 301

Gly Phe Thr Phe Thr Ser Tyr Gly
1 5

<210> SEQ ID NO 302
<211> LENGTH: 8
<212> TYPE: PRT
<213> ORGANISM: Artificial sequence
<220> FEATURE:
<223> OTHER INFORMATION: Synthetic peptide

<400> SEQUENCE: 302

Ile Ser Tyr Asp Gly Ser Asn Arg
1 5

<210> SEQ ID NO 303
<211> LENGTH: 18
<212> TYPE: PRT
<213> ORGANISM: Artificial sequence
<220> FEATURE:
<223> OTHER INFORMATION: Synthetic peptide

<400> SEQUENCE: 303

Ala Arg Gly Arg Leu Cys Val Gly Asp Ser Cys His Ser Gly Pro Leu
1 5 10 15

Asp Tyr

<210> SEQ ID NO 304
<211> LENGTH: 8
<212> TYPE: PRT
<213> ORGANISM: Artificial sequence
<220> FEATURE:

<223> OTHER INFORMATION: Synthetic peptide

<400> SEQUENCE: 304

Gly Phe Thr Phe Ser Ser Tyr Gly
1 5

<210> SEQ ID NO 305
<211> LENGTH: 8
<212> TYPE: PRT
<213> ORGANISM: Artificial sequence
<220> FEATURE:
<223> OTHER INFORMATION: Synthetic peptide

<400> SEQUENCE: 305

Ile Ser Tyr Asp Glu Ser Asn Lys
1 5

<210> SEQ ID NO 306
<211> LENGTH: 16
<212> TYPE: PRT
<213> ORGANISM: Artificial sequence
<220> FEATURE:
<223> OTHER INFORMATION: Synthetic peptide

<400> SEQUENCE: 306

Ala Lys Lys Gly Cys Ser Gly Gly Asn Cys Asp Glu Gly Phe Asp Tyr
1 5 10 15

<210> SEQ ID NO 307
<211> LENGTH: 8
<212> TYPE: PRT
<213> ORGANISM: Artificial sequence
<220> FEATURE:
<223> OTHER INFORMATION: Synthetic peptide

<400> SEQUENCE: 307

Gly Phe Tyr Phe Ser Ser Tyr Gly
1 5

<210> SEQ ID NO 308
<211> LENGTH: 8
<212> TYPE: PRT
<213> ORGANISM: Artificial sequence
<220> FEATURE:
<223> OTHER INFORMATION: Synthetic peptide

<400> SEQUENCE: 308

Ile Trp Tyr Asp Gly Ser Asn Lys
1 5

<210> SEQ ID NO 309
<211> LENGTH: 10
<212> TYPE: PRT
<213> ORGANISM: Artificial sequence
<220> FEATURE:
<223> OTHER INFORMATION: Synthetic peptide

<400> SEQUENCE: 309

Ala Arg Ala Asp Gly Tyr Asn Phe Asp Tyr
1 5 10

<210> SEQ ID NO 310
<211> LENGTH: 10
<212> TYPE: PRT
<213> ORGANISM: Artificial sequence
<220> FEATURE:
<223> OTHER INFORMATION: Synthetic peptide

<400> SEQUENCE: 310

Gly Phe Ser Leu Ser Ser Ala Arg Met Gly
1               5                   10

<210> SEQ ID NO 311
<211> LENGTH: 7
<212> TYPE: PRT
<213> ORGANISM: Artificial sequence
<220> FEATURE:
<223> OTHER INFORMATION: Synthetic peptide

<400> SEQUENCE: 311

Ile Phe Ser Ser Asp Glu Lys
1               5

<210> SEQ ID NO 312
<211> LENGTH: 20
<212> TYPE: PRT
<213> ORGANISM: Artificial sequence
<220> FEATURE:
<223> OTHER INFORMATION: Synthetic peptide

<400> SEQUENCE: 312

Ala Arg Ile Arg Gly Pro Ser Tyr Tyr His Gln Asn Tyr Tyr Tyr Phe
1               5                   10                  15

Gly Met Asp Val
            20

<210> SEQ ID NO 313
<211> LENGTH: 10
<212> TYPE: PRT
<213> ORGANISM: Artificial sequence
<220> FEATURE:
<223> OTHER INFORMATION: Synthetic peptide

<400> SEQUENCE: 313

Gly Ala Ser Ile Ser Ser Ala Asp Ser Tyr
1               5                   10

<210> SEQ ID NO 314
<211> LENGTH: 7
<212> TYPE: PRT
<213> ORGANISM: Artificial sequence
<220> FEATURE:
<223> OTHER INFORMATION: Synthetic peptide

<400> SEQUENCE: 314

Ile Tyr Tyr Ser Gly Ser Thr
1               5

<210> SEQ ID NO 315
<211> LENGTH: 13
<212> TYPE: PRT
<213> ORGANISM: Artificial sequence
<220> FEATURE:
<223> OTHER INFORMATION: Synthetic peptide

<400> SEQUENCE: 315

Ala Arg Gly Gly Pro Tyr Cys Gly Gly Asp Cys Tyr Arg
1               5                   10

<210> SEQ ID NO 316
<211> LENGTH: 8
<212> TYPE: PRT
<213> ORGANISM: Artificial sequence
<220> FEATURE:
<223> OTHER INFORMATION: Synthetic peptide

<400> SEQUENCE: 316

Asn Gly Ser Ile Ser Ser Tyr Tyr
1               5

<210> SEQ ID NO 317
<211> LENGTH: 7
<212> TYPE: PRT
<213> ORGANISM: Artificial sequence
<220> FEATURE:
<223> OTHER INFORMATION: Synthetic peptide

<400> SEQUENCE: 317

Ile Tyr Ser Ser Gly Ser Thr
1               5

<210> SEQ ID NO 318
<211> LENGTH: 22
<212> TYPE: PRT
<213> ORGANISM: Artificial sequence
<220> FEATURE:
<223> OTHER INFORMATION: Synthetic peptide

<400> SEQUENCE: 318

Ala Arg Asp Leu Arg Ala Trp Ile Gln Leu His Arg Ala Ser Leu Tyr
1               5                   10                  15

Tyr Tyr Tyr Met Asp Val
            20

<210> SEQ ID NO 319
<211> LENGTH: 8
<212> TYPE: PRT
<213> ORGANISM: Artificial sequence
<220> FEATURE:
<223> OTHER INFORMATION: Synthetic peptide

<400> SEQUENCE: 319

Gly Phe Ser Phe Gly Ser Tyr Gly
1               5

<210> SEQ ID NO 320
<211> LENGTH: 8
<212> TYPE: PRT
<213> ORGANISM: Artificial sequence
<220> FEATURE:
<223> OTHER INFORMATION: Synthetic peptide

<400> SEQUENCE: 320

Ile Gly Gly Arg Gly Asp Ser Thr
1               5

<210> SEQ ID NO 321
<211> LENGTH: 16
<212> TYPE: PRT
<213> ORGANISM: Artificial sequence
<220> FEATURE:
<223> OTHER INFORMATION: Synthetic peptide

<400> SEQUENCE: 321

Ala Lys Glu Gly Phe Gly Ser Gly His Phe His Gly Ser Asn Asp Tyr
1               5                   10                  15

<210> SEQ ID NO 322
<211> LENGTH: 8

<212> TYPE: PRT
<213> ORGANISM: Artificial sequence
<220> FEATURE:
<223> OTHER INFORMATION: Synthetic peptide

<400> SEQUENCE: 322

Gly Tyr Thr Phe Thr Ser Tyr Asp
1               5

<210> SEQ ID NO 323
<211> LENGTH: 8
<212> TYPE: PRT
<213> ORGANISM: Artificial sequence
<220> FEATURE:
<223> OTHER INFORMATION: Synthetic peptide

<400> SEQUENCE: 323

Met Asn Pro Asn Ser Gly Asn Thr
1               5

<210> SEQ ID NO 324
<211> LENGTH: 14
<212> TYPE: PRT
<213> ORGANISM: Artificial sequence
<220> FEATURE:
<223> OTHER INFORMATION: Synthetic peptide

<400> SEQUENCE: 324

Ala Arg Phe Tyr Asp Phe Trp Ser Gly Leu Asp Ile Asp Val
1               5                   10

<210> SEQ ID NO 325
<211> LENGTH: 8
<212> TYPE: PRT
<213> ORGANISM: Artificial sequence
<220> FEATURE:
<223> OTHER INFORMATION: Synthetic peptide

<400> SEQUENCE: 325

Gly Gly Thr Phe Ser Asn Tyr Gly
1               5

<210> SEQ ID NO 326
<211> LENGTH: 8
<212> TYPE: PRT
<213> ORGANISM: Artificial sequence
<220> FEATURE:
<223> OTHER INFORMATION: Synthetic peptide

<400> SEQUENCE: 326

Val Ile Pro Ile Phe Gly Thr Thr
1               5

<210> SEQ ID NO 327
<211> LENGTH: 17
<212> TYPE: PRT
<213> ORGANISM: Artificial sequence
<220> FEATURE:
<223> OTHER INFORMATION: Synthetic peptide

<400> SEQUENCE: 327

Ala Arg Asp Asp Gly Ala Ala Ala Gly Thr Gly Tyr Tyr Gly Met Ala
1               5                   10                  15

Val

<210> SEQ ID NO 328

<211> LENGTH: 8
<212> TYPE: PRT
<213> ORGANISM: Artificial sequence
<220> FEATURE:
<223> OTHER INFORMATION: Synthetic peptide

<400> SEQUENCE: 328

Gly Gly Thr Phe Ser Asn Ile Gly
1 5

<210> SEQ ID NO 329
<211> LENGTH: 8
<212> TYPE: PRT
<213> ORGANISM: Artificial sequence
<220> FEATURE:
<223> OTHER INFORMATION: Synthetic peptide

<400> SEQUENCE: 329

Ile Ile Pro Leu Phe Ala Thr Thr
1 5

<210> SEQ ID NO 330
<211> LENGTH: 21
<212> TYPE: PRT
<213> ORGANISM: Artificial sequence
<220> FEATURE:
<223> OTHER INFORMATION: Synthetic peptide

<400> SEQUENCE: 330

Ala Arg Gln Leu Gly Trp Ala Tyr Cys Asn Ser Ser Thr Cys Ser Lys
1 5 10 15

Gly Trp Phe Asn Pro
20

<210> SEQ ID NO 331
<211> LENGTH: 10
<212> TYPE: PRT
<213> ORGANISM: Artificial sequence
<220> FEATURE:
<223> OTHER INFORMATION: Synthetic peptide

<400> SEQUENCE: 331

Gly Gly Ser Ile Ser Thr Gly Gly Tyr Tyr
1 5 10

<210> SEQ ID NO 332
<211> LENGTH: 7
<212> TYPE: PRT
<213> ORGANISM: Artificial sequence
<220> FEATURE:
<223> OTHER INFORMATION: Synthetic peptide

<400> SEQUENCE: 332

Ile Ser Asn Ile Gly Asn Thr
1 5

<210> SEQ ID NO 333
<211> LENGTH: 21
<212> TYPE: PRT
<213> ORGANISM: Artificial sequence
<220> FEATURE:
<223> OTHER INFORMATION: Synthetic peptide

<400> SEQUENCE: 333

Ala Lys Ala Pro Pro Asp Ala Tyr Asp Ser Gly Thr Tyr Tyr Leu Ala
1 5 10 15

Tyr Tyr Met Asp Val
            20

<210> SEQ ID NO 334
<211> LENGTH: 8
<212> TYPE: PRT
<213> ORGANISM: Artificial sequence
<220> FEATURE:
<223> OTHER INFORMATION: Synthetic peptide

<400> SEQUENCE: 334

Gly Phe Thr Phe Ser Asn Tyr Gly
1               5

<210> SEQ ID NO 335
<211> LENGTH: 8
<212> TYPE: PRT
<213> ORGANISM: Artificial sequence
<220> FEATURE:
<223> OTHER INFORMATION: Synthetic peptide

<400> SEQUENCE: 335

Ile Ser Tyr His Gly Asn Asn Asn
1               5

<210> SEQ ID NO 336
<211> LENGTH: 8
<212> TYPE: PRT
<213> ORGANISM: Artificial sequence
<220> FEATURE:
<223> OTHER INFORMATION: Synthetic peptide

<400> SEQUENCE: 336

Ala Thr Gly Leu Glu Gly Glu Tyr
1               5

<210> SEQ ID NO 337
<211> LENGTH: 10
<212> TYPE: PRT
<213> ORGANISM: Artificial sequence
<220> FEATURE:
<223> OTHER INFORMATION: Synthetic peptide

<400> SEQUENCE: 337

Gly Gly Ser Ile Ser Ser Gly Asp Tyr Tyr
1               5                   10

<210> SEQ ID NO 338
<211> LENGTH: 7
<212> TYPE: PRT
<213> ORGANISM: Artificial sequence
<220> FEATURE:
<223> OTHER INFORMATION: Synthetic peptide

<400> SEQUENCE: 338

Ile Tyr Tyr Asn Gly Asn Thr
1               5

<210> SEQ ID NO 339
<211> LENGTH: 14
<212> TYPE: PRT
<213> ORGANISM: Artificial sequence
<220> FEATURE:
<223> OTHER INFORMATION: Synthetic peptide

<400> SEQUENCE: 339

Ala Arg Gly Gly Arg Ile Arg Phe Leu Glu Trp Tyr Asp Tyr 1 5 10

<210> SEQ ID NO 340
<211> LENGTH: 8
<212> TYPE: PRT
<213> ORGANISM: Artificial sequence
<220> FEATURE:
<223> OTHER INFORMATION: Synthetic peptide

<400> SEQUENCE: 340

Gly Phe Ser Phe Asn Ser Tyr Gly
1 5

<210> SEQ ID NO 341
<211> LENGTH: 8
<212> TYPE: PRT
<213> ORGANISM: Artificial sequence
<220> FEATURE:
<223> OTHER INFORMATION: Synthetic peptide

<400> SEQUENCE: 341

Thr Trp Tyr Asp Gly Ser Asn Lys
1 5

<210> SEQ ID NO 342
<211> LENGTH: 19
<212> TYPE: PRT
<213> ORGANISM: Artificial sequence
<220> FEATURE:
<223> OTHER INFORMATION: Synthetic peptide

<400> SEQUENCE: 342

Ala Arg Asp Gln Gly Cys Ser Gly Gly Ser Cys Tyr Ser Glu Gly Trp
1 5 10 15

Phe Asp Pro

<210> SEQ ID NO 343
<211> LENGTH: 10
<212> TYPE: PRT
<213> ORGANISM: Artificial sequence
<220> FEATURE:
<223> OTHER INFORMATION: Synthetic peptide

<400> SEQUENCE: 343

Gly Phe Ser Leu Ser Ser Ser Gly Glu Gly
1 5 10

<210> SEQ ID NO 344
<211> LENGTH: 7
<212> TYPE: PRT
<213> ORGANISM: Artificial sequence
<220> FEATURE:
<223> OTHER INFORMATION: Synthetic peptide

<400> SEQUENCE: 344

Ile Tyr Gly Asp Asp Asp Lys
1 5

<210> SEQ ID NO 345
<211> LENGTH: 21
<212> TYPE: PRT
<213> ORGANISM: Artificial sequence
<220> FEATURE:
<223> OTHER INFORMATION: Synthetic peptide

<400> SEQUENCE: 345

Ala His Arg Ser Gly Tyr Cys Ser Gly Gly Asp Cys Tyr Ser Arg Leu
1 5 10 15

Gly Trp Phe Asp Pro
20

<210> SEQ ID NO 346
<211> LENGTH: 8
<212> TYPE: PRT
<213> ORGANISM: Artificial sequence
<220> FEATURE:
<223> OTHER INFORMATION: Synthetic peptide

<400> SEQUENCE: 346

Gly Phe Thr Phe Arg Thr Tyr Ala
1 5

<210> SEQ ID NO 347
<211> LENGTH: 8
<212> TYPE: PRT
<213> ORGANISM: Artificial sequence
<220> FEATURE:
<223> OTHER INFORMATION: Synthetic peptide

<400> SEQUENCE: 347

Ile Ser Tyr Asp Gly Ser Asn Lys
1 5

<210> SEQ ID NO 348
<211> LENGTH: 25
<212> TYPE: PRT
<213> ORGANISM: Artificial sequence
<220> FEATURE:
<223> OTHER INFORMATION: Synthetic peptide

<400> SEQUENCE: 348

Thr Arg Val Val Asn Phe Gly Val Ala Phe Ile Arg Asp Gly Val Tyr
1 5 10 15

Gly His Tyr Tyr Tyr Gly Met Asp Val
20 25

<210> SEQ ID NO 349
<211> LENGTH: 8
<212> TYPE: PRT
<213> ORGANISM: Artificial sequence
<220> FEATURE:
<223> OTHER INFORMATION: Synthetic peptide

<400> SEQUENCE: 349

Gly Gly Ser Ile Ser Ser Tyr Tyr
1 5

<210> SEQ ID NO 350
<211> LENGTH: 7
<212> TYPE: PRT
<213> ORGANISM: Artificial sequence
<220> FEATURE:
<223> OTHER INFORMATION: Synthetic peptide

<400> SEQUENCE: 350

Thr Tyr Ser Gly Gly Ser Pro
1 5

<210> SEQ ID NO 351
<211> LENGTH: 17
<212> TYPE: PRT
<213> ORGANISM: Artificial sequence
<220> FEATURE:
<223> OTHER INFORMATION: Synthetic peptide

<400> SEQUENCE: 351

Ala Arg Glu Asp His Gly Leu Arg Gln Lys Phe Tyr Tyr Tyr Met Asp
1               5                   10                  15

Leu

<210> SEQ ID NO 352
<211> LENGTH: 8
<212> TYPE: PRT
<213> ORGANISM: Artificial sequence
<220> FEATURE:
<223> OTHER INFORMATION: Synthetic peptide

<400> SEQUENCE: 352

Gly Gly Ser Ile Asn Ser Tyr Tyr
1               5

<210> SEQ ID NO 353
<211> LENGTH: 7
<212> TYPE: PRT
<213> ORGANISM: Artificial sequence
<220> FEATURE:
<223> OTHER INFORMATION: Synthetic peptide

<400> SEQUENCE: 353

Ile Tyr Thr Ser Gly Ser Thr
1               5

<210> SEQ ID NO 354
<211> LENGTH: 22
<212> TYPE: PRT
<213> ORGANISM: Artificial sequence
<220> FEATURE:
<223> OTHER INFORMATION: Synthetic peptide

<400> SEQUENCE: 354

Ala Arg Ala Pro Arg Ile Pro Val Ser Val Glu Gly His Tyr Tyr Tyr
1               5                   10                  15

His Tyr Tyr Met Asp Val
            20

<210> SEQ ID NO 355
<211> LENGTH: 8
<212> TYPE: PRT
<213> ORGANISM: Artificial sequence
<220> FEATURE:
<223> OTHER INFORMATION: Synthetic peptide

<400> SEQUENCE: 355

Gly Phe Thr Ile Ser Arg Tyr Ala
1               5

<210> SEQ ID NO 356
<211> LENGTH: 8
<212> TYPE: PRT
<213> ORGANISM: Artificial sequence
<220> FEATURE:
<223> OTHER INFORMATION: Synthetic peptide

<400> SEQUENCE: 356

Ile Thr Gly Ser Gly Gly Arg Thr
1               5

<210> SEQ ID NO 357
<211> LENGTH: 18
<212> TYPE: PRT
<213> ORGANISM: Artificial sequence
<220> FEATURE:
<223> OTHER INFORMATION: Synthetic peptide

<400> SEQUENCE: 357

Ala Lys Gly Ile Val Val Val Leu Val Gly Pro Pro Tyr Phe Gly Met
1 5 10 15

Asp Val

<210> SEQ ID NO 358
<211> LENGTH: 10
<212> TYPE: PRT
<213> ORGANISM: Artificial sequence
<220> FEATURE:
<223> OTHER INFORMATION: Synthetic peptide

<400> SEQUENCE: 358

Gly Gly Ser Ile Ser Ser Gly Val Tyr Ser
1 5 10

<210> SEQ ID NO 359
<211> LENGTH: 7
<212> TYPE: PRT
<213> ORGANISM: Artificial sequence
<220> FEATURE:
<223> OTHER INFORMATION: Synthetic peptide

<400> SEQUENCE: 359

Ile Tyr His Ser Gly Ser Thr
1 5

<210> SEQ ID NO 360
<211> LENGTH: 11
<212> TYPE: PRT
<213> ORGANISM: Artificial sequence
<220> FEATURE:
<223> OTHER INFORMATION: Synthetic peptide

<400> SEQUENCE: 360

Ala Arg Glu Ser Val Ala Asn Tyr Phe Asp Tyr
1 5 10

<210> SEQ ID NO 361
<211> LENGTH: 8
<212> TYPE: PRT
<213> ORGANISM: Artificial sequence
<220> FEATURE:
<223> OTHER INFORMATION: Synthetic peptide

<400> SEQUENCE: 361

Glu Tyr Thr Phe Thr Ala Tyr Tyr
1 5

<210> SEQ ID NO 362
<211> LENGTH: 8
<212> TYPE: PRT
<213> ORGANISM: Artificial sequence
<220> FEATURE:
<223> OTHER INFORMATION: Synthetic peptide

<400> SEQUENCE: 362

Ile Asn Pro Asn Ser Gly Gly Thr
1 5

<210> SEQ ID NO 363
<211> LENGTH: 13
<212> TYPE: PRT
<213> ORGANISM: Artificial sequence
<220> FEATURE:
<223> OTHER INFORMATION: Synthetic peptide

<400> SEQUENCE: 363

Ala Ser Asp Tyr Phe Asp Ser Ser Gly Tyr His Asp Tyr
1 5 10

<210> SEQ ID NO 364
<211> LENGTH: 10
<212> TYPE: PRT
<213> ORGANISM: Artificial sequence
<220> FEATURE:
<223> OTHER INFORMATION: Synthetic peptide

<400> SEQUENCE: 364

Gly Phe Ser Leu Ser Thr Ser Gly Met Arg
1 5 10

<210> SEQ ID NO 365
<211> LENGTH: 7
<212> TYPE: PRT
<213> ORGANISM: Artificial sequence
<220> FEATURE:
<223> OTHER INFORMATION: Synthetic peptide

<400> SEQUENCE: 365

Ile Asp Trp Asp Asp Asp Lys
1 5

<210> SEQ ID NO 366
<211> LENGTH: 21
<212> TYPE: PRT
<213> ORGANISM: Artificial sequence
<220> FEATURE:
<223> OTHER INFORMATION: Synthetic peptide

<400> SEQUENCE: 366

Ala Arg Ile Leu Pro Gly Tyr Cys Ser Gly Gly Ser Cys Tyr Tyr Asn
1 5 10 15

Tyr His Phe Asp Tyr
20

<210> SEQ ID NO 367
<211> LENGTH: 8
<212> TYPE: PRT
<213> ORGANISM: Artificial sequence
<220> FEATURE:
<223> OTHER INFORMATION: Synthetic peptide

<400> SEQUENCE: 367

Gly Phe Thr Phe Ser Ser Tyr Gly
1 5

<210> SEQ ID NO 368
<211> LENGTH: 8
<212> TYPE: PRT
<213> ORGANISM: Artificial sequence
<220> FEATURE:
<223> OTHER INFORMATION: Synthetic peptide

<400> SEQUENCE: 368

Ile Trp Tyr Asp Gly Ile Asn Lys 1 5

<210> SEQ ID NO 369
<211> LENGTH: 17
<212> TYPE: PRT
<213> ORGANISM: Artificial sequence
<220> FEATURE:
<223> OTHER INFORMATION: Synthetic peptide

<400> SEQUENCE: 369

Ala Arg Glu Gly Gly Gly Gln His Gly Asp Tyr Ala Ser Trp Phe Asp
1 5 10 15

Pro

<210> SEQ ID NO 370
<211> LENGTH: 8
<212> TYPE: PRT
<213> ORGANISM: Artificial sequence
<220> FEATURE:
<223> OTHER INFORMATION: Synthetic peptide

<400> SEQUENCE: 370

Gly Gly Ser Phe Arg Ser Tyr Ala
1 5

<210> SEQ ID NO 371
<211> LENGTH: 8
<212> TYPE: PRT
<213> ORGANISM: Artificial sequence
<220> FEATURE:
<223> OTHER INFORMATION: Synthetic peptide

<400> SEQUENCE: 371

Ile Ile Pro Ile Phe Asp Thr Thr
1 5

<210> SEQ ID NO 372
<211> LENGTH: 16
<212> TYPE: PRT
<213> ORGANISM: Artificial sequence
<220> FEATURE:
<223> OTHER INFORMATION: Synthetic peptide

<400> SEQUENCE: 372

Ala Arg Asp Leu Asn His Phe Tyr Ala Ser Ser Gly Pro Asn Asp Leu
1 5 10 15

<210> SEQ ID NO 373
<211> LENGTH: 10
<212> TYPE: PRT
<213> ORGANISM: Artificial sequence
<220> FEATURE:
<223> OTHER INFORMATION: Synthetic peptide

<400> SEQUENCE: 373

Gly Phe Ser Leu Thr Thr Ser Gly Met Arg
1 5 10

<210> SEQ ID NO 374
<211> LENGTH: 7
<212> TYPE: PRT
<213> ORGANISM: Artificial sequence
<220> FEATURE:
<223> OTHER INFORMATION: Synthetic peptide

<400> SEQUENCE: 374

Ile Asp Trp Asp Asp Asp Lys
1 5

<210> SEQ ID NO 375
<211> LENGTH: 18
<212> TYPE: PRT
<213> ORGANISM: Artificial sequence
<220> FEATURE:
<223> OTHER INFORMATION: Synthetic peptide

<400> SEQUENCE: 375

Ala Arg Ser Met Tyr Asp Ser Ser Gly Tyr Tyr Pro Pro Thr Pro Phe
1 5 10 15

Asp Ile

<210> SEQ ID NO 376
<211> LENGTH: 8
<212> TYPE: PRT
<213> ORGANISM: Artificial sequence
<220> FEATURE:
<223> OTHER INFORMATION: Synthetic peptide

<400> SEQUENCE: 376

Gly Phe Thr Phe Thr Asn Tyr Ala
1 5

<210> SEQ ID NO 377
<211> LENGTH: 8
<212> TYPE: PRT
<213> ORGANISM: Artificial sequence
<220> FEATURE:
<223> OTHER INFORMATION: Synthetic peptide

<400> SEQUENCE: 377

Ile Ser Gly Ser Gly Gly Thr Ser
1 5

<210> SEQ ID NO 378
<211> LENGTH: 18
<212> TYPE: PRT
<213> ORGANISM: Artificial sequence
<220> FEATURE:
<223> OTHER INFORMATION: Synthetic peptide

<400> SEQUENCE: 378

Ala Lys Gly Ala Thr Leu Ile Val Val Val Leu Arg Pro Asp Val Phe
1 5 10 15

Asp Ile

<210> SEQ ID NO 379
<211> LENGTH: 8
<212> TYPE: PRT
<213> ORGANISM: Artificial sequence
<220> FEATURE:
<223> OTHER INFORMATION: Synthetic peptide

<400> SEQUENCE: 379

Gly Phe Arg Phe Ser Ser Tyr Gly
1 5

<210> SEQ ID NO 380
<211> LENGTH: 8
<212> TYPE: PRT
<213> ORGANISM: Artificial sequence
<220> FEATURE:
<223> OTHER INFORMATION: Synthetic peptide

<400> SEQUENCE: 380

Ile Trp Tyr Asp Gly Ser Asn Lys
1               5

<210> SEQ ID NO 381
<211> LENGTH: 18
<212> TYPE: PRT
<213> ORGANISM: Artificial sequence
<220> FEATURE:
<223> OTHER INFORMATION: Synthetic peptide

<400> SEQUENCE: 381

Ala Arg Val Ser Arg Gly Ala Asp Asp Trp Asp Tyr Tyr Tyr Tyr Met
1               5                   10                  15

Asp Val

<210> SEQ ID NO 382
<211> LENGTH: 8
<212> TYPE: PRT
<213> ORGANISM: Artificial sequence
<220> FEATURE:
<223> OTHER INFORMATION: Synthetic peptide

<400> SEQUENCE: 382

Gly Phe Met Phe Ser Ser Tyr Gly
1               5

<210> SEQ ID NO 383
<211> LENGTH: 8
<212> TYPE: PRT
<213> ORGANISM: Artificial sequence
<220> FEATURE:
<223> OTHER INFORMATION: Synthetic peptide

<400> SEQUENCE: 383

Ile Trp Tyr Asp Gly Ser Asn Lys
1               5

<210> SEQ ID NO 384
<211> LENGTH: 10
<212> TYPE: PRT
<213> ORGANISM: Artificial sequence
<220> FEATURE:
<223> OTHER INFORMATION: Synthetic peptide

<400> SEQUENCE: 384

Ala Arg Val Val Gly Gly Glu Phe Asp Tyr
1               5                   10

<210> SEQ ID NO 385
<211> LENGTH: 8
<212> TYPE: PRT
<213> ORGANISM: Artificial sequence
<220> FEATURE:
<223> OTHER INFORMATION: Synthetic peptide

<400> SEQUENCE: 385

Gly Phe Thr Phe Ser Ser Tyr Gly
1               5

<210> SEQ ID NO 386
<211> LENGTH: 8
<212> TYPE: PRT
<213> ORGANISM: Artificial sequence
<220> FEATURE:

<223> OTHER INFORMATION: Synthetic peptide

<400> SEQUENCE: 386

Ile Trp Tyr Asp Gly Ser Asn Lys
1               5

<210> SEQ ID NO 387
<211> LENGTH: 12
<212> TYPE: PRT
<213> ORGANISM: Artificial sequence
<220> FEATURE:
<223> OTHER INFORMATION: Synthetic peptide

<400> SEQUENCE: 387

Ala Arg Val Gly Gly Val Gly Trp Glu Gly Asp Phe
1               5                   10

<210> SEQ ID NO 388
<211> LENGTH: 8
<212> TYPE: PRT
<213> ORGANISM: Artificial sequence
<220> FEATURE:
<223> OTHER INFORMATION: Synthetic peptide

<400> SEQUENCE: 388

Gly Tyr Ile Phe Ser Asn Tyr Asp
1               5

<210> SEQ ID NO 389
<211> LENGTH: 8
<212> TYPE: PRT
<213> ORGANISM: Artificial sequence
<220> FEATURE:
<223> OTHER INFORMATION: Synthetic peptide

<400> SEQUENCE: 389

Ile Ser Ala Tyr Ser Gly Glu Lys
1               5

<210> SEQ ID NO 390
<211> LENGTH: 12
<212> TYPE: PRT
<213> ORGANISM: Artificial sequence
<220> FEATURE:
<223> OTHER INFORMATION: Synthetic peptide

<400> SEQUENCE: 390

Ala Arg Asp Pro Thr Val Val His Ala Leu Asp Ile
1               5                   10

<210> SEQ ID NO 391
<211> LENGTH: 8
<212> TYPE: PRT
<213> ORGANISM: Artificial sequence
<220> FEATURE:
<223> OTHER INFORMATION: Synthetic peptide

<400> SEQUENCE: 391

Gly Phe Thr Phe Ser Ser Tyr Thr
1               5

<210> SEQ ID NO 392
<211> LENGTH: 8
<212> TYPE: PRT
<213> ORGANISM: Artificial sequence
<220> FEATURE:
<223> OTHER INFORMATION: Synthetic peptide

<400> SEQUENCE: 392

Ile Thr Asn Ser Ser Ser Ala Ile
1 5

<210> SEQ ID NO 393
<211> LENGTH: 22
<212> TYPE: PRT
<213> ORGANISM: Artificial sequence
<220> FEATURE:
<223> OTHER INFORMATION: Synthetic peptide

<400> SEQUENCE: 393

Ala Arg Asp Leu Ala Arg Pro His Arg Tyr Tyr Asp Asn Ser Ala Tyr
1 5 10 15

Phe Glu Val Phe Asp Ser
20

<210> SEQ ID NO 394
<211> LENGTH: 8
<212> TYPE: PRT
<213> ORGANISM: Artificial sequence
<220> FEATURE:
<223> OTHER INFORMATION: Synthetic peptide

<400> SEQUENCE: 394

Gly Phe Thr Phe Asn Ser Tyr Gly
1 5

<210> SEQ ID NO 395
<211> LENGTH: 8
<212> TYPE: PRT
<213> ORGANISM: Artificial sequence
<220> FEATURE:
<223> OTHER INFORMATION: Synthetic peptide

<400> SEQUENCE: 395

Ile Trp Tyr Asp Gly Ser Gln Lys
1 5

<210> SEQ ID NO 396
<211> LENGTH: 11
<212> TYPE: PRT
<213> ORGANISM: Artificial sequence
<220> FEATURE:
<223> OTHER INFORMATION: Synthetic peptide

<400> SEQUENCE: 396

Ala Arg Asp Glu Gly Ser Tyr Asp Leu Asp Tyr
1 5 10

<210> SEQ ID NO 397
<211> LENGTH: 8
<212> TYPE: PRT
<213> ORGANISM: Artificial sequence
<220> FEATURE:
<223> OTHER INFORMATION: Synthetic peptide

<400> SEQUENCE: 397

Gly Phe Thr Phe Ser Ser Tyr Gly
1 5

<210> SEQ ID NO 398
<211> LENGTH: 8
<212> TYPE: PRT
<213> ORGANISM: Artificial sequence
<220> FEATURE:
<223> OTHER INFORMATION: Synthetic peptide

<400> SEQUENCE: 398

Ile Trp His Asp Gly Ser Asn Lys
1               5

<210> SEQ ID NO 399
<211> LENGTH: 12
<212> TYPE: PRT
<213> ORGANISM: Artificial sequence
<220> FEATURE:
<223> OTHER INFORMATION: Synthetic peptide

<400> SEQUENCE: 399

Ala Arg Val Glu Gly Gly Ser Tyr Ser Gly Asp Tyr
1               5                   10

<210> SEQ ID NO 400
<211> LENGTH: 8
<212> TYPE: PRT
<213> ORGANISM: Artificial sequence
<220> FEATURE:
<223> OTHER INFORMATION: Synthetic peptide

<400> SEQUENCE: 400

Gly Phe Ile Phe Ser Asp Tyr Ser
1               5

<210> SEQ ID NO 401
<211> LENGTH: 8
<212> TYPE: PRT
<213> ORGANISM: Artificial sequence
<220> FEATURE:
<223> OTHER INFORMATION: Synthetic peptide

<400> SEQUENCE: 401

Ile Ser His Ser Glu Thr Tyr Thr
1               5

<210> SEQ ID NO 402
<211> LENGTH: 14
<212> TYPE: PRT
<213> ORGANISM: Artificial sequence
<220> FEATURE:
<223> OTHER INFORMATION: Synthetic peptide

<400> SEQUENCE: 402

Ala Arg Pro Leu Glu Ala Met Met Trp Glu Glu Phe His Phe
1               5                   10

<210> SEQ ID NO 403
<211> LENGTH: 8
<212> TYPE: PRT
<213> ORGANISM: Artificial sequence
<220> FEATURE:
<223> OTHER INFORMATION: Synthetic peptide

<400> SEQUENCE: 403

Gly Gly Thr Phe Ser Asn Tyr Asp
1               5

<210> SEQ ID NO 404
<211> LENGTH: 8
<212> TYPE: PRT
<213> ORGANISM: Artificial sequence
<220> FEATURE:

<223> OTHER INFORMATION: Synthetic peptide

<400> SEQUENCE: 404

Ile Ile Pro Ile Phe Asp Thr Pro
1 5

<210> SEQ ID NO 405
<211> LENGTH: 19
<212> TYPE: PRT
<213> ORGANISM: Artificial sequence
<220> FEATURE:
<223> OTHER INFORMATION: Synthetic peptide

<400> SEQUENCE: 405

Ala Arg Gly Ala Ser Arg Tyr Cys Asn Ser Thr Ser Cys Tyr Arg Ile
1 5 10 15

Phe Asp Tyr

<210> SEQ ID NO 406
<211> LENGTH: 9
<212> TYPE: PRT
<213> ORGANISM: Artificial sequence
<220> FEATURE:
<223> OTHER INFORMATION: Synthetic peptide

<400> SEQUENCE: 406

Gly Tyr Ser Ile Ser Ser Gly Tyr Tyr
1 5

<210> SEQ ID NO 407
<211> LENGTH: 7
<212> TYPE: PRT
<213> ORGANISM: Artificial sequence
<220> FEATURE:
<223> OTHER INFORMATION: Synthetic peptide

<400> SEQUENCE: 407

Val Tyr His Ser Gly Thr Thr
1 5

<210> SEQ ID NO 408
<211> LENGTH: 15
<212> TYPE: PRT
<213> ORGANISM: Artificial sequence
<220> FEATURE:
<223> OTHER INFORMATION: Synthetic peptide

<400> SEQUENCE: 408

Ala Gly Ser Arg Leu Val Ser Asp Ile Trp Pro Leu Val Asp Val
1 5 10 15

<210> SEQ ID NO 409
<211> LENGTH: 8
<212> TYPE: PRT
<213> ORGANISM: Artificial sequence
<220> FEATURE:
<223> OTHER INFORMATION: Synthetic peptide

<400> SEQUENCE: 409

Gly Phe Thr Phe Ser Asn Val Trp
1 5

<210> SEQ ID NO 410
<211> LENGTH: 10
<212> TYPE: PRT
<213> ORGANISM: Artificial sequence
<220> FEATURE:
<223> OTHER INFORMATION: Synthetic peptide

<400> SEQUENCE: 410

Ile Lys Ser Lys Ile Asp Gly Gly Thr Thr
1               5                   10

<210> SEQ ID NO 411
<211> LENGTH: 20
<212> TYPE: PRT
<213> ORGANISM: Artificial sequence
<220> FEATURE:
<223> OTHER INFORMATION: Synthetic peptide

<400> SEQUENCE: 411

Thr Thr Glu Asp Tyr Asn Tyr Val Trp Gly Gly Leu Pro Ala Pro Tyr
1               5                   10                  15

Gly Leu Asp Val
            20

<210> SEQ ID NO 412
<211> LENGTH: 10
<212> TYPE: PRT
<213> ORGANISM: Artificial sequence
<220> FEATURE:
<223> OTHER INFORMATION: Synthetic peptide

<400> SEQUENCE: 412

Gly Gly Ser Val Ile Ser Gly Asp Tyr Tyr
1               5                   10

<210> SEQ ID NO 413
<211> LENGTH: 7
<212> TYPE: PRT
<213> ORGANISM: Artificial sequence
<220> FEATURE:
<223> OTHER INFORMATION: Synthetic peptide

<400> SEQUENCE: 413

Ile Phe Asn Ser Gly Ser Thr
1               5

<210> SEQ ID NO 414
<211> LENGTH: 18
<212> TYPE: PRT
<213> ORGANISM: Artificial sequence
<220> FEATURE:
<223> OTHER INFORMATION: Synthetic peptide

<400> SEQUENCE: 414

Ala Arg Asp Tyr Glu Gly Cys Thr Asn Gly Val Cys Tyr Thr Tyr Leu
1               5                   10                  15

Asp Phe

<210> SEQ ID NO 415
<211> LENGTH: 8
<212> TYPE: PRT
<213> ORGANISM: Artificial sequence
<220> FEATURE:
<223> OTHER INFORMATION: Synthetic peptide

<400> SEQUENCE: 415

Gly Tyr Thr Phe Thr Asp Tyr Tyr
1               5

<210> SEQ ID NO 416
<211> LENGTH: 8
<212> TYPE: PRT
<213> ORGANISM: Artificial sequence
<220> FEATURE:
<223> OTHER INFORMATION: Synthetic peptide

<400> SEQUENCE: 416

Ile Asn Pro Lys Ser Gly Val Ala
1 5

<210> SEQ ID NO 417
<211> LENGTH: 15
<212> TYPE: PRT
<213> ORGANISM: Artificial sequence
<220> FEATURE:
<223> OTHER INFORMATION: Synthetic peptide

<400> SEQUENCE: 417

Ala Arg Asp Arg Gly Ile Phe Gly Gly Tyr Tyr Gly Leu Asp Val
1 5 10 15

<210> SEQ ID NO 418
<211> LENGTH: 8
<212> TYPE: PRT
<213> ORGANISM: Artificial sequence
<220> FEATURE:
<223> OTHER INFORMATION: Synthetic peptide

<400> SEQUENCE: 418

Gly Phe Ser Phe Ser Asp Tyr Gly
1 5

<210> SEQ ID NO 419
<211> LENGTH: 8
<212> TYPE: PRT
<213> ORGANISM: Artificial sequence
<220> FEATURE:
<223> OTHER INFORMATION: Synthetic peptide

<400> SEQUENCE: 419

Val Trp Phe Asp Gly Ser Asn Lys
1 5

<210> SEQ ID NO 420
<211> LENGTH: 13
<212> TYPE: PRT
<213> ORGANISM: Artificial sequence
<220> FEATURE:
<223> OTHER INFORMATION: Synthetic peptide

<400> SEQUENCE: 420

Ala Arg Asp Phe Thr Pro Thr Ala Val Ala Leu Asp Tyr
1 5 10

<210> SEQ ID NO 421
<211> LENGTH: 8
<212> TYPE: PRT
<213> ORGANISM: Artificial sequence
<220> FEATURE:
<223> OTHER INFORMATION: Synthetic peptide

<400> SEQUENCE: 421

Gly Phe Ser Phe Ser Asp Tyr Gly
1 5

<210> SEQ ID NO 422

<211> LENGTH: 8
<212> TYPE: PRT
<213> ORGANISM: Artificial sequence
<220> FEATURE:
<223> OTHER INFORMATION: Synthetic peptide

<400> SEQUENCE: 422

Val Trp Phe Asp Gly Ser Asn Lys
1 5

<210> SEQ ID NO 423
<211> LENGTH: 13
<212> TYPE: PRT
<213> ORGANISM: Artificial sequence
<220> FEATURE:
<223> OTHER INFORMATION: Synthetic peptide

<400> SEQUENCE: 423

Ala Arg Asp Phe Thr Pro Thr Ala Val Ala Leu Asp Tyr
1 5 10

<210> SEQ ID NO 424
<211> LENGTH: 9
<212> TYPE: PRT
<213> ORGANISM: Artificial sequence
<220> FEATURE:
<223> OTHER INFORMATION: Synthetic peptide

<400> SEQUENCE: 424

Gly Tyr Ser Ile Asn Ser Gly Tyr Tyr
1 5

<210> SEQ ID NO 425
<211> LENGTH: 7
<212> TYPE: PRT
<213> ORGANISM: Artificial sequence
<220> FEATURE:
<223> OTHER INFORMATION: Synthetic peptide

<400> SEQUENCE: 425

Ile Tyr Gln Ser Gly Ser Thr
1 5

<210> SEQ ID NO 426
<211> LENGTH: 16
<212> TYPE: PRT
<213> ORGANISM: Artificial sequence
<220> FEATURE:
<223> OTHER INFORMATION: Synthetic peptide

<400> SEQUENCE: 426

Ala Thr Cys His Ser Leu Gly Thr Ser Ala Trp Pro Leu Pro Asp Tyr
1 5 10 15

<210> SEQ ID NO 427
<211> LENGTH: 8
<212> TYPE: PRT
<213> ORGANISM: Artificial sequence
<220> FEATURE:
<223> OTHER INFORMATION: Synthetic peptide

<400> SEQUENCE: 427

Gly Phe Thr Phe Ser Asn Val Trp
1 5

<210> SEQ ID NO 428
<211> LENGTH: 10

<212> TYPE: PRT
<213> ORGANISM: Artificial sequence
<220> FEATURE:
<223> OTHER INFORMATION: Synthetic peptide

<400> SEQUENCE: 428

Ile Lys Ser Lys Ile Asp Gly Gly Thr Thr
1 5 10

<210> SEQ ID NO 429
<211> LENGTH: 20
<212> TYPE: PRT
<213> ORGANISM: Artificial sequence
<220> FEATURE:
<223> OTHER INFORMATION: Synthetic peptide

<400> SEQUENCE: 429

Thr Thr Glu Asp Tyr Asn Tyr Val Trp Gly Gly Leu Pro Ala Pro Tyr
1 5 10 15

Gly Leu Asp Val
20

<210> SEQ ID NO 430
<211> LENGTH: 10
<212> TYPE: PRT
<213> ORGANISM: Artificial sequence
<220> FEATURE:
<223> OTHER INFORMATION: Synthetic peptide

<400> SEQUENCE: 430

Gly Gly Ser Ile Ser Ser Gly Gly Tyr Tyr
1 5 10

<210> SEQ ID NO 431
<211> LENGTH: 7
<212> TYPE: PRT
<213> ORGANISM: Artificial sequence
<220> FEATURE:
<223> OTHER INFORMATION: Synthetic peptide

<400> SEQUENCE: 431

Ile Tyr Tyr Ser Gly Asn Thr
1 5

<210> SEQ ID NO 432
<211> LENGTH: 11
<212> TYPE: PRT
<213> ORGANISM: Artificial sequence
<220> FEATURE:
<223> OTHER INFORMATION: Synthetic peptide

<400> SEQUENCE: 432

Ala Arg Glu Thr His Ser Gly Ser Tyr Gly Tyr
1 5 10

<210> SEQ ID NO 433
<211> LENGTH: 8
<212> TYPE: PRT
<213> ORGANISM: Artificial sequence
<220> FEATURE:
<223> OTHER INFORMATION: Synthetic peptide

<400> SEQUENCE: 433

Gly Phe Val Phe Thr Asn Tyr Val
1 5

<210> SEQ ID NO 434
<211> LENGTH: 8
<212> TYPE: PRT
<213> ORGANISM: Artificial sequence
<220> FEATURE:
<223> OTHER INFORMATION: Synthetic peptide

<400> SEQUENCE: 434

Ile Ser Tyr Asp Gly Asn Asn Lys
1               5

<210> SEQ ID NO 435
<211> LENGTH: 15
<212> TYPE: PRT
<213> ORGANISM: Artificial sequence
<220> FEATURE:
<223> OTHER INFORMATION: Synthetic peptide

<400> SEQUENCE: 435

Ala Arg Ser Pro His Gly Asp Val Pro Asp Tyr Tyr Phe Asp Leu
1               5                   10                  15

<210> SEQ ID NO 436
<211> LENGTH: 8
<212> TYPE: PRT
<213> ORGANISM: Artificial sequence
<220> FEATURE:
<223> OTHER INFORMATION: Synthetic peptide

<400> SEQUENCE: 436

Gly Gly Thr Phe Arg Asn Tyr Ala
1               5

<210> SEQ ID NO 437
<211> LENGTH: 8
<212> TYPE: PRT
<213> ORGANISM: Artificial sequence
<220> FEATURE:
<223> OTHER INFORMATION: Synthetic peptide

<400> SEQUENCE: 437

Ile Ile Pro Ile Phe Gly Thr Thr
1               5

<210> SEQ ID NO 438
<211> LENGTH: 15
<212> TYPE: PRT
<213> ORGANISM: Artificial sequence
<220> FEATURE:
<223> OTHER INFORMATION: Synthetic peptide

<400> SEQUENCE: 438

Ala Arg Asp Tyr Tyr Glu Arg Thr Asp Tyr Tyr Thr Pro Gly Tyr
1               5                   10                  15

<210> SEQ ID NO 439
<211> LENGTH: 9
<212> TYPE: PRT
<213> ORGANISM: Artificial sequence
<220> FEATURE:
<223> OTHER INFORMATION: Synthetic peptide

<400> SEQUENCE: 439

Asn Tyr Ser Ile Thr Ser Thr Tyr Tyr
1               5

<210> SEQ ID NO 440

<211> LENGTH: 7
<212> TYPE: PRT
<213> ORGANISM: Artificial sequence
<220> FEATURE:
<223> OTHER INFORMATION: Synthetic peptide

<400> SEQUENCE: 440

Val Tyr His Thr Gly Ser Thr
1 5

<210> SEQ ID NO 441
<211> LENGTH: 13
<212> TYPE: PRT
<213> ORGANISM: Artificial sequence
<220> FEATURE:
<223> OTHER INFORMATION: Synthetic peptide

<400> SEQUENCE: 441

Ala Arg Glu Ile Pro Ala Trp Ile Tyr Tyr Leu Asp Val
1 5 10

<210> SEQ ID NO 442
<211> LENGTH: 6
<212> TYPE: PRT
<213> ORGANISM: Artificial sequence
<220> FEATURE:
<223> OTHER INFORMATION: Synthetic peptide

<400> SEQUENCE: 442

Gln Ser Val Asn Arg Asn
1 5

<210> SEQ ID NO 443
<211> LENGTH: 3
<212> TYPE: PRT
<213> ORGANISM: Artificial sequence
<220> FEATURE:
<223> OTHER INFORMATION: Synthetic peptide

<400> SEQUENCE: 443

Gly Ala Ser
1

<210> SEQ ID NO 444
<211> LENGTH: 10
<212> TYPE: PRT
<213> ORGANISM: Artificial sequence
<220> FEATURE:
<223> OTHER INFORMATION: Synthetic peptide

<400> SEQUENCE: 444

Gln Gln Tyr Asn Asn Trp Pro Arg Phe Thr
1 5 10

<210> SEQ ID NO 445
<211> LENGTH: 11
<212> TYPE: PRT
<213> ORGANISM: Artificial sequence
<220> FEATURE:
<223> OTHER INFORMATION: Synthetic peptide

<400> SEQUENCE: 445

Gln Ser Leu Val Tyr Ser Asp Gly Asn Thr Tyr
1 5 10

<210> SEQ ID NO 446
<211> LENGTH: 3

<212> TYPE: PRT
<213> ORGANISM: Artificial sequence
<220> FEATURE:
<223> OTHER INFORMATION: Synthetic peptide

<400> SEQUENCE: 446

Lys Val Ser
1

<210> SEQ ID NO 447
<211> LENGTH: 9
<212> TYPE: PRT
<213> ORGANISM: Artificial sequence
<220> FEATURE:
<223> OTHER INFORMATION: Synthetic peptide

<400> SEQUENCE: 447

Met Gln Gly Thr His Trp Pro Pro Ala
1               5

<210> SEQ ID NO 448
<211> LENGTH: 6
<212> TYPE: PRT
<213> ORGANISM: Artificial sequence
<220> FEATURE:
<223> OTHER INFORMATION: Synthetic peptide

<400> SEQUENCE: 448

Gln Ser Ile Lys Asn Tyr
1               5

<210> SEQ ID NO 449
<211> LENGTH: 3
<212> TYPE: PRT
<213> ORGANISM: Artificial sequence
<220> FEATURE:
<223> OTHER INFORMATION: Synthetic peptide

<400> SEQUENCE: 449

Gly Ala Ser
1

<210> SEQ ID NO 450
<211> LENGTH: 9
<212> TYPE: PRT
<213> ORGANISM: Artificial sequence
<220> FEATURE:
<223> OTHER INFORMATION: Synthetic peptide

<400> SEQUENCE: 450

Gln Gln Ser Tyr Ser Thr Leu Arg Thr
1               5

<210> SEQ ID NO 451
<211> LENGTH: 9
<212> TYPE: PRT
<213> ORGANISM: Artificial sequence
<220> FEATURE:
<223> OTHER INFORMATION: Synthetic peptide

<400> SEQUENCE: 451

Thr Gly Ala Val Thr Ser Asp Phe Tyr
1               5

<210> SEQ ID NO 452
<211> LENGTH: 3
<212> TYPE: PRT

<213> ORGANISM: Artificial sequence
<220> FEATURE:
<223> OTHER INFORMATION: Synthetic peptide

<400> SEQUENCE: 452

Ser Thr Asn
1

<210> SEQ ID NO 453
<211> LENGTH: 11
<212> TYPE: PRT
<213> ORGANISM: Artificial sequence
<220> FEATURE:
<223> OTHER INFORMATION: Synthetic peptide

<400> SEQUENCE: 453

Leu Leu Tyr Tyr Gly Gly Ala Gln Val Tyr Val
1 5 10

<210> SEQ ID NO 454
<211> LENGTH: 6
<212> TYPE: PRT
<213> ORGANISM: Artificial sequence
<220> FEATURE:
<223> OTHER INFORMATION: Synthetic peptide

<400> SEQUENCE: 454

Asn Ile Gly Ser Lys Ser
1 5

<210> SEQ ID NO 455
<211> LENGTH: 3
<212> TYPE: PRT
<213> ORGANISM: Artificial sequence
<220> FEATURE:
<223> OTHER INFORMATION: Synthetic peptide

<400> SEQUENCE: 455

Asp Asp Lys
1

<210> SEQ ID NO 456
<211> LENGTH: 12
<212> TYPE: PRT
<213> ORGANISM: Artificial sequence
<220> FEATURE:
<223> OTHER INFORMATION: Synthetic peptide

<400> SEQUENCE: 456

Gln Val Trp Asp Ser Arg Tyr Asp Arg His Val Val
1 5 10

<210> SEQ ID NO 457
<211> LENGTH: 9
<212> TYPE: PRT
<213> ORGANISM: Artificial sequence
<220> FEATURE:
<223> OTHER INFORMATION: Synthetic peptide

<400> SEQUENCE: 457

Ser Ser Asp Val Gly Gly Tyr Asn Tyr
1 5

<210> SEQ ID NO 458
<211> LENGTH: 3
<212> TYPE: PRT
<213> ORGANISM: Artificial sequence
<220> FEATURE:
<223> OTHER INFORMATION: Synthetic peptide

<400> SEQUENCE: 458

Asp Val Asn
1

<210> SEQ ID NO 459
<211> LENGTH: 10
<212> TYPE: PRT
<213> ORGANISM: Artificial sequence
<220> FEATURE:
<223> OTHER INFORMATION: Synthetic peptide

<400> SEQUENCE: 459

Ser Ser Tyr Thr Ala Ser Ser Thr Leu Val
1 5 10

<210> SEQ ID NO 460
<211> LENGTH: 6
<212> TYPE: PRT
<213> ORGANISM: Artificial sequence
<220> FEATURE:
<223> OTHER INFORMATION: Synthetic peptide

<400> SEQUENCE: 460

Gln Thr Ile Gly Asp Trp
1 5

<210> SEQ ID NO 461
<211> LENGTH: 3
<212> TYPE: PRT
<213> ORGANISM: Artificial sequence
<220> FEATURE:
<223> OTHER INFORMATION: Synthetic peptide

<400> SEQUENCE: 461

Lys Ala Ser
1

<210> SEQ ID NO 462
<211> LENGTH: 9
<212> TYPE: PRT
<213> ORGANISM: Artificial sequence
<220> FEATURE:
<223> OTHER INFORMATION: Synthetic peptide

<400> SEQUENCE: 462

Gln His Tyr Asn Thr Tyr Ala Tyr Ser
1 5

<210> SEQ ID NO 463
<211> LENGTH: 6
<212> TYPE: PRT
<213> ORGANISM: Artificial sequence
<220> FEATURE:
<223> OTHER INFORMATION: Synthetic peptide

<400> SEQUENCE: 463

Gln Ser Val Ser Ser Tyr
1 5

<210> SEQ ID NO 464
<211> LENGTH: 3
<212> TYPE: PRT
<213> ORGANISM: Artificial sequence
<220> FEATURE:

<223> OTHER INFORMATION: Synthetic peptide

<400> SEQUENCE: 464

Asp Pro Ser
1

<210> SEQ ID NO 465
<211> LENGTH: 12
<212> TYPE: PRT
<213> ORGANISM: Artificial sequence
<220> FEATURE:
<223> OTHER INFORMATION: Synthetic peptide

<400> SEQUENCE: 465

Gln His Arg Ser Asn Trp Pro Pro Gly Thr Tyr Thr
1               5                   10

<210> SEQ ID NO 466
<211> LENGTH: 6
<212> TYPE: PRT
<213> ORGANISM: Artificial sequence
<220> FEATURE:
<223> OTHER INFORMATION: Synthetic peptide

<400> SEQUENCE: 466

Asn Ile Gly Ser Asn Thr
1               5

<210> SEQ ID NO 467
<211> LENGTH: 3
<212> TYPE: PRT
<213> ORGANISM: Artificial sequence
<220> FEATURE:
<223> OTHER INFORMATION: Synthetic peptide

<400> SEQUENCE: 467

Gly Asp Ser
1

<210> SEQ ID NO 468
<211> LENGTH: 11
<212> TYPE: PRT
<213> ORGANISM: Artificial sequence
<220> FEATURE:
<223> OTHER INFORMATION: Synthetic peptide

<400> SEQUENCE: 468

Gln Val Trp Asp Ser Ser Ser Asp His Val Val
1               5                   10

<210> SEQ ID NO 469
<211> LENGTH: 9
<212> TYPE: PRT
<213> ORGANISM: Artificial sequence
<220> FEATURE:
<223> OTHER INFORMATION: Synthetic peptide

<400> SEQUENCE: 469

Ser Ser Asp Val Gly Ser Tyr Asn Leu
1               5

<210> SEQ ID NO 470
<211> LENGTH: 3
<212> TYPE: PRT
<213> ORGANISM: Artificial sequence
<220> FEATURE:
<223> OTHER INFORMATION: Synthetic peptide

<400> SEQUENCE: 470

Glu Val Thr
1

<210> SEQ ID NO 471
<211> LENGTH: 9
<212> TYPE: PRT
<213> ORGANISM: Artificial sequence
<220> FEATURE:
<223> OTHER INFORMATION: Synthetic peptide

<400> SEQUENCE: 471

Cys Ser Phe Ala Gly Arg Ser Ala Pro
1 5

<210> SEQ ID NO 472
<211> LENGTH: 7
<212> TYPE: PRT
<213> ORGANISM: Artificial sequence
<220> FEATURE:
<223> OTHER INFORMATION: Synthetic peptide

<400> SEQUENCE: 472

Ser Gly His Ser Thr Tyr Ser
1 5

<210> SEQ ID NO 473
<211> LENGTH: 7
<212> TYPE: PRT
<213> ORGANISM: Artificial sequence
<220> FEATURE:
<223> OTHER INFORMATION: Synthetic peptide

<400> SEQUENCE: 473

Val Asn Ser Asp Gly Ser His
1 5

<210> SEQ ID NO 474
<211> LENGTH: 10
<212> TYPE: PRT
<213> ORGANISM: Artificial sequence
<220> FEATURE:
<223> OTHER INFORMATION: Synthetic peptide

<400> SEQUENCE: 474

Gln Thr Trp Gly Thr Gly Ile Gln Val Val
1 5 10

<210> SEQ ID NO 475
<211> LENGTH: 6
<212> TYPE: PRT
<213> ORGANISM: Artificial sequence
<220> FEATURE:
<223> OTHER INFORMATION: Synthetic peptide

<400> SEQUENCE: 475

Gln Ser Val Ala Thr Asn
1 5

<210> SEQ ID NO 476
<211> LENGTH: 3
<212> TYPE: PRT
<213> ORGANISM: Artificial sequence
<220> FEATURE:
<223> OTHER INFORMATION: Synthetic peptide

<400> SEQUENCE: 476

Gly Ala Ser
1

<210> SEQ ID NO 477
<211> LENGTH: 8
<212> TYPE: PRT
<213> ORGANISM: Artificial sequence
<220> FEATURE:
<223> OTHER INFORMATION: Synthetic peptide

<400> SEQUENCE: 477

Gln Gln Cys Asn Asp Trp Leu Thr
1 5

<210> SEQ ID NO 478
<211> LENGTH: 6
<212> TYPE: PRT
<213> ORGANISM: Artificial sequence
<220> FEATURE:
<223> OTHER INFORMATION: Synthetic peptide

<400> SEQUENCE: 478

Gln Asn Ile Ser Ser Tyr
1 5

<210> SEQ ID NO 479
<211> LENGTH: 3
<212> TYPE: PRT
<213> ORGANISM: Artificial sequence
<220> FEATURE:
<223> OTHER INFORMATION: Synthetic peptide

<400> SEQUENCE: 479

Ala Ala Ser
1

<210> SEQ ID NO 480
<211> LENGTH: 9
<212> TYPE: PRT
<213> ORGANISM: Artificial sequence
<220> FEATURE:
<223> OTHER INFORMATION: Synthetic peptide

<400> SEQUENCE: 480

Gln Gln Ser Tyr Ser Thr Pro Arg Thr
1 5

<210> SEQ ID NO 481
<211> LENGTH: 6
<212> TYPE: PRT
<213> ORGANISM: Artificial sequence
<220> FEATURE:
<223> OTHER INFORMATION: Synthetic peptide

<400> SEQUENCE: 481

Ser Leu Arg Ser Phe Tyr
1 5

<210> SEQ ID NO 482
<211> LENGTH: 3
<212> TYPE: PRT
<213> ORGANISM: Artificial sequence
<220> FEATURE:
<223> OTHER INFORMATION: Synthetic peptide

<400> SEQUENCE: 482

Asn Glu Asn
1

<210> SEQ ID NO 483
<211> LENGTH: 11
<212> TYPE: PRT
<213> ORGANISM: Artificial sequence
<220> FEATURE:
<223> OTHER INFORMATION: Synthetic peptide

<400> SEQUENCE: 483

Ser Ser Arg Asp Ser Ser Gly Asn His Val Leu
1 5 10

<210> SEQ ID NO 484
<211> LENGTH: 10
<212> TYPE: PRT
<213> ORGANISM: Artificial sequence
<220> FEATURE:
<223> OTHER INFORMATION: Synthetic peptide

<400> SEQUENCE: 484

Gln Ser Val Ser Arg Ser Ser Ser Ser Tyr
1 5 10

<210> SEQ ID NO 485
<211> LENGTH: 3
<212> TYPE: PRT
<213> ORGANISM: Artificial sequence
<220> FEATURE:
<223> OTHER INFORMATION: Synthetic peptide

<400> SEQUENCE: 485

Gly Ala Ser
1

<210> SEQ ID NO 486
<211> LENGTH: 9
<212> TYPE: PRT
<213> ORGANISM: Artificial sequence
<220> FEATURE:
<223> OTHER INFORMATION: Synthetic peptide

<400> SEQUENCE: 486

Gln Gln Tyr Gly Ser Ser Pro Gln Thr
1 5

<210> SEQ ID NO 487
<211> LENGTH: 7
<212> TYPE: PRT
<213> ORGANISM: Artificial sequence
<220> FEATURE:
<223> OTHER INFORMATION: Synthetic peptide

<400> SEQUENCE: 487

Gln Ser Val Pro Ser Ser Tyr
1 5

<210> SEQ ID NO 488
<211> LENGTH: 3
<212> TYPE: PRT
<213> ORGANISM: Artificial sequence
<220> FEATURE:
<223> OTHER INFORMATION: Synthetic peptide

<400> SEQUENCE: 488

Gly Ala Ser
1

<210> SEQ ID NO 489
<211> LENGTH: 11
<212> TYPE: PRT
<213> ORGANISM: Artificial sequence
<220> FEATURE:
<223> OTHER INFORMATION: Synthetic peptide

<400> SEQUENCE: 489

Gln Gln Tyr Gly Thr Ser Pro Pro Met Tyr Thr
1 5 10

<210> SEQ ID NO 490
<211> LENGTH: 6
<212> TYPE: PRT
<213> ORGANISM: Artificial sequence
<220> FEATURE:
<223> OTHER INFORMATION: Synthetic peptide

<400> SEQUENCE: 490

Thr Leu Gly Asn Lys Tyr
1 5

<210> SEQ ID NO 491
<211> LENGTH: 3
<212> TYPE: PRT
<213> ORGANISM: Artificial sequence
<220> FEATURE:
<223> OTHER INFORMATION: Synthetic peptide

<400> SEQUENCE: 491

Gln Asp Asn
1

<210> SEQ ID NO 492
<211> LENGTH: 10
<212> TYPE: PRT
<213> ORGANISM: Artificial sequence
<220> FEATURE:
<223> OTHER INFORMATION: Synthetic peptide

<400> SEQUENCE: 492

Gln Ala Trp Asp Ser Ser Ala His Tyr Val
1 5 10

<210> SEQ ID NO 493
<211> LENGTH: 9
<212> TYPE: PRT
<213> ORGANISM: Artificial sequence
<220> FEATURE:
<223> OTHER INFORMATION: Synthetic peptide

<400> SEQUENCE: 493

Ser Ser Asp Val Gly Gly Tyr Asn Tyr
1 5

<210> SEQ ID NO 494
<211> LENGTH: 3
<212> TYPE: PRT
<213> ORGANISM: Artificial sequence
<220> FEATURE:
<223> OTHER INFORMATION: Synthetic peptide

<400> SEQUENCE: 494

Glu Val Ser

1

<210> SEQ ID NO 495
<211> LENGTH: 11
<212> TYPE: PRT
<213> ORGANISM: Artificial sequence
<220> FEATURE:
<223> OTHER INFORMATION: Synthetic peptide

<400> SEQUENCE: 495

Ile Ser Tyr Arg Ser Ser Ser Thr Leu Tyr Val
1 5 10

<210> SEQ ID NO 496
<211> LENGTH: 6
<212> TYPE: PRT
<213> ORGANISM: Artificial sequence
<220> FEATURE:
<223> OTHER INFORMATION: Synthetic peptide

<400> SEQUENCE: 496

Ser Leu Arg Ser Tyr Phe
1 5

<210> SEQ ID NO 497
<211> LENGTH: 3
<212> TYPE: PRT
<213> ORGANISM: Artificial sequence
<220> FEATURE:
<223> OTHER INFORMATION: Synthetic peptide

<400> SEQUENCE: 497

Asp Arg Asn
1

<210> SEQ ID NO 498
<211> LENGTH: 11
<212> TYPE: PRT
<213> ORGANISM: Artificial sequence
<220> FEATURE:
<223> OTHER INFORMATION: Synthetic peptide

<400> SEQUENCE: 498

Asn Ser Arg Asp Ser Ser Gly Asn Leu Tyr Val
1 5 10

<210> SEQ ID NO 499
<211> LENGTH: 11
<212> TYPE: PRT
<213> ORGANISM: Artificial sequence
<220> FEATURE:
<223> OTHER INFORMATION: Synthetic peptide

<400> SEQUENCE: 499

Gln Ser Leu Leu His Ser Asn Gly Tyr Asn Tyr
1 5 10

<210> SEQ ID NO 500
<211> LENGTH: 3
<212> TYPE: PRT
<213> ORGANISM: Artificial sequence
<220> FEATURE:
<223> OTHER INFORMATION: Synthetic peptide

<400> SEQUENCE: 500

Leu Gly Ser
1

<210> SEQ ID NO 501
<211> LENGTH: 9
<212> TYPE: PRT
<213> ORGANISM: Artificial sequence
<220> FEATURE:
<223> OTHER INFORMATION: Synthetic peptide

<400> SEQUENCE: 501

Met Gln Ala Leu Gln Ala Pro Trp Thr
1               5

<210> SEQ ID NO 502
<211> LENGTH: 6
<212> TYPE: PRT
<213> ORGANISM: Artificial sequence
<220> FEATURE:
<223> OTHER INFORMATION: Synthetic peptide

<400> SEQUENCE: 502

Gln Asp Ile Ser Asn Phe
1               5

<210> SEQ ID NO 503
<211> LENGTH: 3
<212> TYPE: PRT
<213> ORGANISM: Artificial sequence
<220> FEATURE:
<223> OTHER INFORMATION: Synthetic peptide

<400> SEQUENCE: 503

Asp Ala Ala
1

<210> SEQ ID NO 504
<211> LENGTH: 9
<212> TYPE: PRT
<213> ORGANISM: Artificial sequence
<220> FEATURE:
<223> OTHER INFORMATION: Synthetic peptide

<400> SEQUENCE: 504

Gln Gln Tyr Asp Ser Leu Pro Trp Thr
1               5

<210> SEQ ID NO 505
<211> LENGTH: 6
<212> TYPE: PRT
<213> ORGANISM: Artificial sequence
<220> FEATURE:
<223> OTHER INFORMATION: Synthetic peptide

<400> SEQUENCE: 505

Ser Leu Arg Ser Phe Tyr
1               5

<210> SEQ ID NO 506
<211> LENGTH: 3
<212> TYPE: PRT
<213> ORGANISM: Artificial sequence
<220> FEATURE:
<223> OTHER INFORMATION: Synthetic peptide

<400> SEQUENCE: 506

Gly Thr Asn
1

<210> SEQ ID NO 507
<211> LENGTH: 11
<212> TYPE: PRT
<213> ORGANISM: Artificial sequence
<220> FEATURE:
<223> OTHER INFORMATION: Synthetic peptide

<400> SEQUENCE: 507

Asp Ser Arg Asp Ser Ser Gly Glu Leu Trp Leu
1               5                   10

<210> SEQ ID NO 508
<211> LENGTH: 6
<212> TYPE: PRT
<213> ORGANISM: Artificial sequence
<220> FEATURE:
<223> OTHER INFORMATION: Synthetic peptide

<400> SEQUENCE: 508

His Asp Ile Ser Asn Tyr
1               5

<210> SEQ ID NO 509
<211> LENGTH: 3
<212> TYPE: PRT
<213> ORGANISM: Artificial sequence
<220> FEATURE:
<223> OTHER INFORMATION: Synthetic peptide

<400> SEQUENCE: 509

Asp Ala Ser
1

<210> SEQ ID NO 510
<211> LENGTH: 9
<212> TYPE: PRT
<213> ORGANISM: Artificial sequence
<220> FEATURE:
<223> OTHER INFORMATION: Synthetic peptide

<400> SEQUENCE: 510

Gln Gln Phe Asp Ser Leu Pro Leu Thr
1               5

<210> SEQ ID NO 511
<211> LENGTH: 9
<212> TYPE: PRT
<213> ORGANISM: Artificial sequence
<220> FEATURE:
<223> OTHER INFORMATION: Synthetic peptide

<400> SEQUENCE: 511

Ser Ser Asp Val Gly Gly Tyr Asn Tyr
1               5

<210> SEQ ID NO 512
<211> LENGTH: 3
<212> TYPE: PRT
<213> ORGANISM: Artificial sequence
<220> FEATURE:
<223> OTHER INFORMATION: Synthetic peptide

<400> SEQUENCE: 512

Glu Val Ser
1

<210> SEQ ID NO 513
<211> LENGTH: 10
<212> TYPE: PRT
<213> ORGANISM: Artificial sequence
<220> FEATURE:
<223> OTHER INFORMATION: Synthetic peptide

<400> SEQUENCE: 513

Ser Ser Tyr Thr Ser Ser Ile Thr Arg Val
1               5                   10

<210> SEQ ID NO 514
<211> LENGTH: 6
<212> TYPE: PRT
<213> ORGANISM: Artificial sequence
<220> FEATURE:
<223> OTHER INFORMATION: Synthetic peptide

<400> SEQUENCE: 514

Gln Ser Val Ser Ser Tyr
1               5

<210> SEQ ID NO 515
<211> LENGTH: 3
<212> TYPE: PRT
<213> ORGANISM: Artificial sequence
<220> FEATURE:
<223> OTHER INFORMATION: Synthetic peptide

<400> SEQUENCE: 515

Gly Ala Ser
1

<210> SEQ ID NO 516
<211> LENGTH: 10
<212> TYPE: PRT
<213> ORGANISM: Artificial sequence
<220> FEATURE:
<223> OTHER INFORMATION: Synthetic peptide

<400> SEQUENCE: 516

Gln Gln Tyr Val Asn Trp Pro Gln Tyr Thr
1               5                   10

<210> SEQ ID NO 517
<211> LENGTH: 12
<212> TYPE: PRT
<213> ORGANISM: Artificial sequence
<220> FEATURE:
<223> OTHER INFORMATION: Synthetic peptide

<400> SEQUENCE: 517

Gln Ser Leu Leu Asp Ser Asp Asp Gly Asn Thr Tyr
1               5                   10

<210> SEQ ID NO 518
<211> LENGTH: 3
<212> TYPE: PRT
<213> ORGANISM: Artificial sequence
<220> FEATURE:
<223> OTHER INFORMATION: Synthetic peptide

<400> SEQUENCE: 518

Thr Val Ser
1

<210> SEQ ID NO 519

<211> LENGTH: 9
<212> TYPE: PRT
<213> ORGANISM: Artificial sequence
<220> FEATURE:
<223> OTHER INFORMATION: Synthetic peptide

<400> SEQUENCE: 519

Met Gln Arg Thr Glu Phe Pro Tyr Thr
1 5

<210> SEQ ID NO 520
<211> LENGTH: 6
<212> TYPE: PRT
<213> ORGANISM: Artificial sequence
<220> FEATURE:
<223> OTHER INFORMATION: Synthetic peptide

<400> SEQUENCE: 520

Gln Ser Ile Ser Ser Trp
1 5

<210> SEQ ID NO 521
<211> LENGTH: 3
<212> TYPE: PRT
<213> ORGANISM: Artificial sequence
<220> FEATURE:
<223> OTHER INFORMATION: Synthetic peptide

<400> SEQUENCE: 521

Lys Ala Ser
1

<210> SEQ ID NO 522
<211> LENGTH: 9
<212> TYPE: PRT
<213> ORGANISM: Artificial sequence
<220> FEATURE:
<223> OTHER INFORMATION: Synthetic peptide

<400> SEQUENCE: 522

Gln Gln Tyr Asn Ser Tyr Pro Tyr Thr
1 5

<210> SEQ ID NO 523
<211> LENGTH: 6
<212> TYPE: PRT
<213> ORGANISM: Artificial sequence
<220> FEATURE:
<223> OTHER INFORMATION: Synthetic peptide

<400> SEQUENCE: 523

Leu Leu Ala Lys Ile Tyr
1 5

<210> SEQ ID NO 524
<211> LENGTH: 3
<212> TYPE: PRT
<213> ORGANISM: Artificial sequence
<220> FEATURE:
<223> OTHER INFORMATION: Synthetic peptide

<400> SEQUENCE: 524

Lys Asp Ser
1

<210> SEQ ID NO 525
<211> LENGTH: 9

<212> TYPE: PRT
<213> ORGANISM: Artificial sequence
<220> FEATURE:
<223> OTHER INFORMATION: Synthetic peptide

<400> SEQUENCE: 525

Tyr Ser Ala Thr Asp Asn Asn Gly Val
1 5

<210> SEQ ID NO 526
<211> LENGTH: 6
<212> TYPE: PRT
<213> ORGANISM: Artificial sequence
<220> FEATURE:
<223> OTHER INFORMATION: Synthetic peptide

<400> SEQUENCE: 526

Gln Ser Ile Ser Asn Tyr
1 5

<210> SEQ ID NO 527
<211> LENGTH: 3
<212> TYPE: PRT
<213> ORGANISM: Artificial sequence
<220> FEATURE:
<223> OTHER INFORMATION: Synthetic peptide

<400> SEQUENCE: 527

Ala Ala Ser
1

<210> SEQ ID NO 528
<211> LENGTH: 9
<212> TYPE: PRT
<213> ORGANISM: Artificial sequence
<220> FEATURE:
<223> OTHER INFORMATION: Synthetic peptide

<400> SEQUENCE: 528

Gln Gln Ser Tyr Ser Ser Pro Arg Thr
1 5

<210> SEQ ID NO 529
<211> LENGTH: 8
<212> TYPE: PRT
<213> ORGANISM: Artificial sequence
<220> FEATURE:
<223> OTHER INFORMATION: Synthetic peptide

<400> SEQUENCE: 529

Ser Ser Asn Ile Gly Gly Asn Thr
1 5

<210> SEQ ID NO 530
<211> LENGTH: 3
<212> TYPE: PRT
<213> ORGANISM: Artificial sequence
<220> FEATURE:
<223> OTHER INFORMATION: Synthetic peptide

<400> SEQUENCE: 530

Ser Asn Asn
1

<210> SEQ ID NO 531
<211> LENGTH: 11
<212> TYPE: PRT

<213> ORGANISM: Artificial sequence
<220> FEATURE:
<223> OTHER INFORMATION: Synthetic peptide

<400> SEQUENCE: 531

Ala Ala Trp Asp Asp Ser Leu Asn Ala Val Val
1 5 10

<210> SEQ ID NO 532
<211> LENGTH: 7
<212> TYPE: PRT
<213> ORGANISM: Artificial sequence
<220> FEATURE:
<223> OTHER INFORMATION: Synthetic peptide

<400> SEQUENCE: 532

Gln Ser Val Ser Asn Asn Tyr
1 5

<210> SEQ ID NO 533
<211> LENGTH: 3
<212> TYPE: PRT
<213> ORGANISM: Artificial sequence
<220> FEATURE:
<223> OTHER INFORMATION: Synthetic peptide

<400> SEQUENCE: 533

Gly Ala Ser
1

<210> SEQ ID NO 534
<211> LENGTH: 9
<212> TYPE: PRT
<213> ORGANISM: Artificial sequence
<220> FEATURE:
<223> OTHER INFORMATION: Synthetic peptide

<400> SEQUENCE: 534

Gln Gln Tyr Gly Arg Ser Leu Phe Thr
1 5

<210> SEQ ID NO 535
<211> LENGTH: 8
<212> TYPE: PRT
<213> ORGANISM: Artificial sequence
<220> FEATURE:
<223> OTHER INFORMATION: Synthetic peptide

<400> SEQUENCE: 535

Thr Ser Asn Ile Gly Asn Asn Tyr
1 5

<210> SEQ ID NO 536
<211> LENGTH: 3
<212> TYPE: PRT
<213> ORGANISM: Artificial sequence
<220> FEATURE:
<223> OTHER INFORMATION: Synthetic peptide

<400> SEQUENCE: 536

Asp Asn Asp
1

<210> SEQ ID NO 537
<211> LENGTH: 11
<212> TYPE: PRT
<213> ORGANISM: Artificial sequence
<220> FEATURE:
<223> OTHER INFORMATION: Synthetic peptide

<400> SEQUENCE: 537

Gly Thr Trp Asp Ser Ser Leu Ser Val Trp Val
1 5 10

<210> SEQ ID NO 538
<211> LENGTH: 6
<212> TYPE: PRT
<213> ORGANISM: Artificial sequence
<220> FEATURE:
<223> OTHER INFORMATION: Synthetic peptide

<400> SEQUENCE: 538

Asn Ile Gly Ser Lys Ser
1 5

<210> SEQ ID NO 539
<211> LENGTH: 3
<212> TYPE: PRT
<213> ORGANISM: Artificial sequence
<220> FEATURE:
<223> OTHER INFORMATION: Synthetic peptide

<400> SEQUENCE: 539

Tyr Asp Ser
1

<210> SEQ ID NO 540
<211> LENGTH: 13
<212> TYPE: PRT
<213> ORGANISM: Artificial sequence
<220> FEATURE:
<223> OTHER INFORMATION: Synthetic peptide

<400> SEQUENCE: 540

Gln Val Trp Asp Ser Ser Pro Asp His Ser Pro Val Val
1 5 10

<210> SEQ ID NO 541
<211> LENGTH: 6
<212> TYPE: PRT
<213> ORGANISM: Artificial sequence
<220> FEATURE:
<223> OTHER INFORMATION: Synthetic peptide

<400> SEQUENCE: 541

Ser Leu Arg Thr Tyr Tyr
1 5

<210> SEQ ID NO 542
<211> LENGTH: 3
<212> TYPE: PRT
<213> ORGANISM: Artificial sequence
<220> FEATURE:
<223> OTHER INFORMATION: Synthetic peptide

<400> SEQUENCE: 542

Ala Lys Asn
1

<210> SEQ ID NO 543
<211> LENGTH: 11
<212> TYPE: PRT
<213> ORGANISM: Artificial sequence
<220> FEATURE:

<223> OTHER INFORMATION: Synthetic peptide

<400> SEQUENCE: 543

Asn Ser Gln Asp Ser Ser Gly Asn His Leu Gly
1               5                   10

<210> SEQ ID NO 544
<211> LENGTH: 6
<212> TYPE: PRT
<213> ORGANISM: Artificial sequence
<220> FEATURE:
<223> OTHER INFORMATION: Synthetic peptide

<400> SEQUENCE: 544

Asn Ile Gly Thr Lys Thr
1               5

<210> SEQ ID NO 545
<211> LENGTH: 3
<212> TYPE: PRT
<213> ORGANISM: Artificial sequence
<220> FEATURE:
<223> OTHER INFORMATION: Synthetic peptide

<400> SEQUENCE: 545

Asp Asp Ser
1

<210> SEQ ID NO 546
<211> LENGTH: 11
<212> TYPE: PRT
<213> ORGANISM: Artificial sequence
<220> FEATURE:
<223> OTHER INFORMATION: Synthetic peptide

<400> SEQUENCE: 546

Gln Val Trp Asp Ser Ser Ser Asp Leu Val Val
1               5                   10

<210> SEQ ID NO 547
<211> LENGTH: 6
<212> TYPE: PRT
<213> ORGANISM: Artificial sequence
<220> FEATURE:
<223> OTHER INFORMATION: Synthetic peptide

<400> SEQUENCE: 547

Gln Ser Val Asp Ser Tyr
1               5

<210> SEQ ID NO 548
<211> LENGTH: 3
<212> TYPE: PRT
<213> ORGANISM: Artificial sequence
<220> FEATURE:
<223> OTHER INFORMATION: Synthetic peptide

<400> SEQUENCE: 548

Asp Ala Ser
1

<210> SEQ ID NO 549
<211> LENGTH: 9
<212> TYPE: PRT
<213> ORGANISM: Artificial sequence
<220> FEATURE:
<223> OTHER INFORMATION: Synthetic peptide

<400> SEQUENCE: 549

Gln Gln Arg Ser Asp Trp Pro Phe Thr
1 5

<210> SEQ ID NO 550
<211> LENGTH: 9
<212> TYPE: PRT
<213> ORGANISM: Artificial sequence
<220> FEATURE:
<223> OTHER INFORMATION: Synthetic peptide

<400> SEQUENCE: 550

Ser Ser Asp Ile Gly Asn Tyr Asn Leu
1 5

<210> SEQ ID NO 551
<211> LENGTH: 3
<212> TYPE: PRT
<213> ORGANISM: Artificial sequence
<220> FEATURE:
<223> OTHER INFORMATION: Synthetic peptide

<400> SEQUENCE: 551

Glu Val Ser
1

<210> SEQ ID NO 552
<211> LENGTH: 8
<212> TYPE: PRT
<213> ORGANISM: Artificial sequence
<220> FEATURE:
<223> OTHER INFORMATION: Synthetic peptide

<400> SEQUENCE: 552

Cys Ser Tyr Val Asp Asp Trp Val
1 5

<210> SEQ ID NO 553
<211> LENGTH: 6
<212> TYPE: PRT
<213> ORGANISM: Artificial sequence
<220> FEATURE:
<223> OTHER INFORMATION: Synthetic peptide

<400> SEQUENCE: 553

Asn Ile Gly Ser Lys Ser
1 5

<210> SEQ ID NO 554
<211> LENGTH: 3
<212> TYPE: PRT
<213> ORGANISM: Artificial sequence
<220> FEATURE:
<223> OTHER INFORMATION: Synthetic peptide

<400> SEQUENCE: 554

His Asp Ser
1

<210> SEQ ID NO 555
<211> LENGTH: 11
<212> TYPE: PRT
<213> ORGANISM: Artificial sequence
<220> FEATURE:
<223> OTHER INFORMATION: Synthetic peptide

<400> SEQUENCE: 555

Gln Val Trp Asp Ser Ser Ser Asp Pro Tyr Val
1               5                   10

<210> SEQ ID NO 556
<211> LENGTH: 6
<212> TYPE: PRT
<213> ORGANISM: Artificial sequence
<220> FEATURE:
<223> OTHER INFORMATION: Synthetic peptide

<400> SEQUENCE: 556

Gln Ser Ile Ser Ser Tyr
1               5

<210> SEQ ID NO 557
<211> LENGTH: 3
<212> TYPE: PRT
<213> ORGANISM: Artificial sequence
<220> FEATURE:
<223> OTHER INFORMATION: Synthetic peptide

<400> SEQUENCE: 557

Thr Ala Ser
1

<210> SEQ ID NO 558
<211> LENGTH: 9
<212> TYPE: PRT
<213> ORGANISM: Artificial sequence
<220> FEATURE:
<223> OTHER INFORMATION: Synthetic peptide

<400> SEQUENCE: 558

Gln Gln Ser Tyr Ser Lys Gly Arg Thr
1               5

<210> SEQ ID NO 559
<211> LENGTH: 7
<212> TYPE: PRT
<213> ORGANISM: Artificial sequence
<220> FEATURE:
<223> OTHER INFORMATION: Synthetic peptide

<400> SEQUENCE: 559

Gln Ser Val Ser Ser Asn Phe
1               5

<210> SEQ ID NO 560
<211> LENGTH: 3
<212> TYPE: PRT
<213> ORGANISM: Artificial sequence
<220> FEATURE:
<223> OTHER INFORMATION: Synthetic peptide

<400> SEQUENCE: 560

Gly Thr Ser
1

<210> SEQ ID NO 561
<211> LENGTH: 9
<212> TYPE: PRT
<213> ORGANISM: Artificial sequence
<220> FEATURE:
<223> OTHER INFORMATION: Synthetic peptide

<400> SEQUENCE: 561

Gln Gln Tyr Gly Gly Ser Pro Gly Thr
1 5

<210> SEQ ID NO 562
<211> LENGTH: 6
<212> TYPE: PRT
<213> ORGANISM: Artificial sequence
<220> FEATURE:
<223> OTHER INFORMATION: Synthetic peptide

<400> SEQUENCE: 562

Gln Ser Ile Ser Arg Tyr
1 5

<210> SEQ ID NO 563
<211> LENGTH: 3
<212> TYPE: PRT
<213> ORGANISM: Artificial sequence
<220> FEATURE:
<223> OTHER INFORMATION: Synthetic peptide

<400> SEQUENCE: 563

Ala Ala Ser
1

<210> SEQ ID NO 564
<211> LENGTH: 9
<212> TYPE: PRT
<213> ORGANISM: Artificial sequence
<220> FEATURE:
<223> OTHER INFORMATION: Synthetic peptide

<400> SEQUENCE: 564

Gln Gln Ser Phe Asn Thr Pro Phe Thr
1 5

<210> SEQ ID NO 565
<211> LENGTH: 6
<212> TYPE: PRT
<213> ORGANISM: Artificial sequence
<220> FEATURE:
<223> OTHER INFORMATION: Synthetic peptide

<400> SEQUENCE: 565

Lys Leu Gly Asp Lys His
1 5

<210> SEQ ID NO 566
<211> LENGTH: 3
<212> TYPE: PRT
<213> ORGANISM: Artificial sequence
<220> FEATURE:
<223> OTHER INFORMATION: Synthetic peptide

<400> SEQUENCE: 566

Gln Asp Ser
1

<210> SEQ ID NO 567
<211> LENGTH: 11
<212> TYPE: PRT
<213> ORGANISM: Artificial sequence
<220> FEATURE:
<223> OTHER INFORMATION: Synthetic peptide

<400> SEQUENCE: 567

```
Gln Ala Trp Asp Ser Asn Thr Ala His Tyr Val
1               5                   10


<210> SEQ ID NO 568
<211> LENGTH: 12
<212> TYPE: PRT
<213> ORGANISM: Artificial sequence
<220> FEATURE:
<223> OTHER INFORMATION: Synthetic peptide

<400> SEQUENCE: 568

His Ser Val Leu Tyr Phe Ser Asn Asn Lys Asn Cys
1               5                   10


<210> SEQ ID NO 569
<211> LENGTH: 3
<212> TYPE: PRT
<213> ORGANISM: Artificial sequence
<220> FEATURE:
<223> OTHER INFORMATION: Synthetic peptide

<400> SEQUENCE: 569

Trp Ala Ser
1


<210> SEQ ID NO 570
<211> LENGTH: 9
<212> TYPE: PRT
<213> ORGANISM: Artificial sequence
<220> FEATURE:
<223> OTHER INFORMATION: Synthetic peptide

<400> SEQUENCE: 570

Gln Gln Tyr Tyr Ser Thr Pro Phe Thr
1               5


<210> SEQ ID NO 571
<211> LENGTH: 8
<212> TYPE: PRT
<213> ORGANISM: Artificial sequence
<220> FEATURE:
<223> OTHER INFORMATION: Synthetic peptide

<400> SEQUENCE: 571

Ser Gly Ser Ile Ala Ser Asn Tyr
1               5


<210> SEQ ID NO 572
<211> LENGTH: 3
<212> TYPE: PRT
<213> ORGANISM: Artificial sequence
<220> FEATURE:
<223> OTHER INFORMATION: Synthetic peptide

<400> SEQUENCE: 572

Glu Asp Asn
1


<210> SEQ ID NO 573
<211> LENGTH: 9
<212> TYPE: PRT
<213> ORGANISM: Artificial sequence
<220> FEATURE:
<223> OTHER INFORMATION: Synthetic peptide

<400> SEQUENCE: 573

Gln Ser Tyr Asn Ser Ser Asn Trp Val
```

1 5

<210> SEQ ID NO 574
<211> LENGTH: 9
<212> TYPE: PRT
<213> ORGANISM: Artificial sequence
<220> FEATURE:
<223> OTHER INFORMATION: Synthetic peptide

<400> SEQUENCE: 574

Ser Ser Asp Val Gly Ala Asn Asn Tyr
1 5

<210> SEQ ID NO 575
<211> LENGTH: 3
<212> TYPE: PRT
<213> ORGANISM: Artificial sequence
<220> FEATURE:
<223> OTHER INFORMATION: Synthetic peptide

<400> SEQUENCE: 575

Glu Val Asn
1

<210> SEQ ID NO 576
<211> LENGTH: 10
<212> TYPE: PRT
<213> ORGANISM: Artificial sequence
<220> FEATURE:
<223> OTHER INFORMATION: Synthetic peptide

<400> SEQUENCE: 576

Ser Ser Tyr Ser Ser Ala Thr Thr Leu Arg
1 5 10

<210> SEQ ID NO 577
<211> LENGTH: 6
<212> TYPE: PRT
<213> ORGANISM: Artificial sequence
<220> FEATURE:
<223> OTHER INFORMATION: Synthetic peptide

<400> SEQUENCE: 577

His Asp Ile Ser Asn Phe
1 5

<210> SEQ ID NO 578
<211> LENGTH: 3
<212> TYPE: PRT
<213> ORGANISM: Artificial sequence
<220> FEATURE:
<223> OTHER INFORMATION: Synthetic peptide

<400> SEQUENCE: 578

Asp Ala Ser
1

<210> SEQ ID NO 579
<211> LENGTH: 9
<212> TYPE: PRT
<213> ORGANISM: Artificial sequence
<220> FEATURE:
<223> OTHER INFORMATION: Synthetic peptide

<400> SEQUENCE: 579

Gln Gln Tyr Asp Asp Leu Val Tyr Thr
1 5

<210> SEQ ID NO 580
<211> LENGTH: 6
<212> TYPE: PRT
<213> ORGANISM: Artificial sequence
<220> FEATURE:
<223> OTHER INFORMATION: Synthetic peptide

<400> SEQUENCE: 580

Ser Leu Arg Asn Tyr Tyr
1 5

<210> SEQ ID NO 581
<211> LENGTH: 3
<212> TYPE: PRT
<213> ORGANISM: Artificial sequence
<220> FEATURE:
<223> OTHER INFORMATION: Synthetic peptide

<400> SEQUENCE: 581

Gly Lys Asn
1

<210> SEQ ID NO 582
<211> LENGTH: 12
<212> TYPE: PRT
<213> ORGANISM: Artificial sequence
<220> FEATURE:
<223> OTHER INFORMATION: Synthetic peptide

<400> SEQUENCE: 582

Ser Ser Arg Asp Ser Ser Gly Asn Tyr Leu Arg Val
1 5 10

<210> SEQ ID NO 583
<211> LENGTH: 9
<212> TYPE: PRT
<213> ORGANISM: Artificial sequence
<220> FEATURE:
<223> OTHER INFORMATION: Synthetic peptide

<400> SEQUENCE: 583

Lys Ser Asp Val Gly Gly Tyr Asn Tyr
1 5

<210> SEQ ID NO 584
<211> LENGTH: 3
<212> TYPE: PRT
<213> ORGANISM: Artificial sequence
<220> FEATURE:
<223> OTHER INFORMATION: Synthetic peptide

<400> SEQUENCE: 584

Glu Val Ser
1

<210> SEQ ID NO 585
<211> LENGTH: 10
<212> TYPE: PRT
<213> ORGANISM: Artificial sequence
<220> FEATURE:
<223> OTHER INFORMATION: Synthetic peptide

<400> SEQUENCE: 585

Thr Ser Tyr Thr Ser Ser Ser Thr Leu Val
1 5 10

<210> SEQ ID NO 586
<211> LENGTH: 9
<212> TYPE: PRT
<213> ORGANISM: Artificial sequence
<220> FEATURE:
<223> OTHER INFORMATION: Synthetic peptide

<400> SEQUENCE: 586

Ser Ser Asp Ile Gly Ala Tyr Asn Ser
1               5

<210> SEQ ID NO 587
<211> LENGTH: 3
<212> TYPE: PRT
<213> ORGANISM: Artificial sequence
<220> FEATURE:
<223> OTHER INFORMATION: Synthetic peptide

<400> SEQUENCE: 587

Asp Val Ser
1

<210> SEQ ID NO 588
<211> LENGTH: 10
<212> TYPE: PRT
<213> ORGANISM: Artificial sequence
<220> FEATURE:
<223> OTHER INFORMATION: Synthetic peptide

<400> SEQUENCE: 588

Ser Ser Phe Thr Asn Thr Val Ser Val Val
1               5                   10

<210> SEQ ID NO 589
<211> LENGTH: 8
<212> TYPE: PRT
<213> ORGANISM: Artificial sequence
<220> FEATURE:
<223> OTHER INFORMATION: Synthetic peptide

<400> SEQUENCE: 589

Thr Ser Asn Ile Gly Thr Asn Tyr
1               5

<210> SEQ ID NO 590
<211> LENGTH: 3
<212> TYPE: PRT
<213> ORGANISM: Artificial sequence
<220> FEATURE:
<223> OTHER INFORMATION: Synthetic peptide

<400> SEQUENCE: 590

Arg Thr Asn
1

<210> SEQ ID NO 591
<211> LENGTH: 11
<212> TYPE: PRT
<213> ORGANISM: Artificial sequence
<220> FEATURE:
<223> OTHER INFORMATION: Synthetic peptide

<400> SEQUENCE: 591

Ala Ser Trp Asp Gly Ser Leu Ser Gly Val Leu
1               5                   10

<210> SEQ ID NO 592
<211> LENGTH: 8
<212> TYPE: PRT
<213> ORGANISM: Artificial sequence
<220> FEATURE:
<223> OTHER INFORMATION: Synthetic peptide

<400> SEQUENCE: 592

Thr Ser Asn Ile Gly Thr Asn Tyr
1 5

<210> SEQ ID NO 593
<211> LENGTH: 3
<212> TYPE: PRT
<213> ORGANISM: Artificial sequence
<220> FEATURE:
<223> OTHER INFORMATION: Synthetic peptide

<400> SEQUENCE: 593

Arg Thr Asn
1

<210> SEQ ID NO 594
<211> LENGTH: 11
<212> TYPE: PRT
<213> ORGANISM: Artificial sequence
<220> FEATURE:
<223> OTHER INFORMATION: Synthetic peptide

<400> SEQUENCE: 594

Ala Ser Trp Asp Gly Ser Leu Ser Gly Val Leu
1 5 10

<210> SEQ ID NO 595
<211> LENGTH: 7
<212> TYPE: PRT
<213> ORGANISM: Artificial sequence
<220> FEATURE:
<223> OTHER INFORMATION: Synthetic peptide

<400> SEQUENCE: 595

Gln Ser Val Ser Ser Ser Tyr
1 5

<210> SEQ ID NO 596
<211> LENGTH: 3
<212> TYPE: PRT
<213> ORGANISM: Artificial sequence
<220> FEATURE:
<223> OTHER INFORMATION: Synthetic peptide

<400> SEQUENCE: 596

Gly Ala Ser
1

<210> SEQ ID NO 597
<211> LENGTH: 9
<212> TYPE: PRT
<213> ORGANISM: Artificial sequence
<220> FEATURE:
<223> OTHER INFORMATION: Synthetic peptide

<400> SEQUENCE: 597

Gln Gln Tyr Gly Ser Ser Pro Trp Thr
1 5

<210> SEQ ID NO 598

<211> LENGTH: 7
<212> TYPE: PRT
<213> ORGANISM: Artificial sequence
<220> FEATURE:
<223> OTHER INFORMATION: Synthetic peptide

<400> SEQUENCE: 598

Gln Ser Val Ser Ser Ser Tyr
1               5

<210> SEQ ID NO 599
<211> LENGTH: 3
<212> TYPE: PRT
<213> ORGANISM: Artificial sequence
<220> FEATURE:
<223> OTHER INFORMATION: Synthetic peptide

<400> SEQUENCE: 599

Gly Ala Ser
1

<210> SEQ ID NO 600
<211> LENGTH: 9
<212> TYPE: PRT
<213> ORGANISM: Artificial sequence
<220> FEATURE:
<223> OTHER INFORMATION: Synthetic peptide

<400> SEQUENCE: 600

Gln Gln Tyr Gly Ser Ser Pro Trp Thr
1               5

<210> SEQ ID NO 601
<211> LENGTH: 6
<212> TYPE: PRT
<213> ORGANISM: Artificial sequence
<220> FEATURE:
<223> OTHER INFORMATION: Synthetic peptide

<400> SEQUENCE: 601

Gln Asn Ile Lys Asn Tyr
1               5

<210> SEQ ID NO 602
<211> LENGTH: 3
<212> TYPE: PRT
<213> ORGANISM: Artificial sequence
<220> FEATURE:
<223> OTHER INFORMATION: Synthetic peptide

<400> SEQUENCE: 602

Gly Ala Ser
1

<210> SEQ ID NO 603
<211> LENGTH: 9
<212> TYPE: PRT
<213> ORGANISM: Artificial sequence
<220> FEATURE:
<223> OTHER INFORMATION: Synthetic peptide

<400> SEQUENCE: 603

Gln Gln Ser Tyr Ser Thr Leu Arg Thr
1               5

<210> SEQ ID NO 604
<211> LENGTH: 8

<212> TYPE: PRT
<213> ORGANISM: Artificial sequence
<220> FEATURE:
<223> OTHER INFORMATION: Synthetic peptide

<400> SEQUENCE: 604

Ser Ser Asn Ile Val Asn Asn Tyr
1 5

<210> SEQ ID NO 605
<211> LENGTH: 3
<212> TYPE: PRT
<213> ORGANISM: Artificial sequence
<220> FEATURE:
<223> OTHER INFORMATION: Synthetic peptide

<400> SEQUENCE: 605

Asp Asn Asn
1

<210> SEQ ID NO 606
<211> LENGTH: 11
<212> TYPE: PRT
<213> ORGANISM: Artificial sequence
<220> FEATURE:
<223> OTHER INFORMATION: Synthetic peptide

<400> SEQUENCE: 606

Gly Thr Trp Asp Ser Ser Leu Ser Ala Val Val
1 5 10

<210> SEQ ID NO 607
<211> LENGTH: 8
<212> TYPE: PRT
<213> ORGANISM: Artificial sequence
<220> FEATURE:
<223> OTHER INFORMATION: Synthetic peptide

<400> SEQUENCE: 607

Ser Gly Ser Ile Ser Arg Asn Tyr
1 5

<210> SEQ ID NO 608
<211> LENGTH: 3
<212> TYPE: PRT
<213> ORGANISM: Artificial sequence
<220> FEATURE:
<223> OTHER INFORMATION: Synthetic peptide

<400> SEQUENCE: 608

Glu Asp Asn
1

<210> SEQ ID NO 609
<211> LENGTH: 10
<212> TYPE: PRT
<213> ORGANISM: Artificial sequence
<220> FEATURE:
<223> OTHER INFORMATION: Synthetic peptide

<400> SEQUENCE: 609

Gln Ser Tyr Asp Ser Ser Pro Thr Trp Val
1 5 10

<210> SEQ ID NO 610
<211> LENGTH: 8
<212> TYPE: PRT

<213> ORGANISM: Artificial sequence
<220> FEATURE:
<223> OTHER INFORMATION: Synthetic peptide

<400> SEQUENCE: 610

Ser Gly Ser Ile Ser Arg Asn Tyr
1               5

<210> SEQ ID NO 611
<211> LENGTH: 3
<212> TYPE: PRT
<213> ORGANISM: Artificial sequence
<220> FEATURE:
<223> OTHER INFORMATION: Synthetic peptide

<400> SEQUENCE: 611

Glu Asp Asn
1

<210> SEQ ID NO 612
<211> LENGTH: 10
<212> TYPE: PRT
<213> ORGANISM: Artificial sequence
<220> FEATURE:
<223> OTHER INFORMATION: Synthetic peptide

<400> SEQUENCE: 612

Gln Ser Tyr Asp Ser Ser Pro Thr Trp Val
1               5                   10

<210> SEQ ID NO 613
<211> LENGTH: 7
<212> TYPE: PRT
<213> ORGANISM: Artificial sequence
<220> FEATURE:
<223> OTHER INFORMATION: Synthetic peptide

<400> SEQUENCE: 613

Gln Ser Ile Ser Ser Asp Tyr
1               5

<210> SEQ ID NO 614
<211> LENGTH: 3
<212> TYPE: PRT
<213> ORGANISM: Artificial sequence
<220> FEATURE:
<223> OTHER INFORMATION: Synthetic peptide

<400> SEQUENCE: 614

Gly Ala Ser
1

<210> SEQ ID NO 615
<211> LENGTH: 9
<212> TYPE: PRT
<213> ORGANISM: Artificial sequence
<220> FEATURE:
<223> OTHER INFORMATION: Synthetic peptide

<400> SEQUENCE: 615

Gln Gln Tyr Gly Ser Ser Pro Phe Thr
1               5

<210> SEQ ID NO 616
<211> LENGTH: 9
<212> TYPE: PRT
<213> ORGANISM: Artificial sequence
<220> FEATURE:
<223> OTHER INFORMATION: Synthetic peptide

<400> SEQUENCE: 616

Ser Ser Asp Val Gly Ser Tyr Asn Arg
1               5

<210> SEQ ID NO 617
<211> LENGTH: 3
<212> TYPE: PRT
<213> ORGANISM: Artificial sequence
<220> FEATURE:
<223> OTHER INFORMATION: Synthetic peptide

<400> SEQUENCE: 617

Glu Val Ser
1

<210> SEQ ID NO 618
<211> LENGTH: 10
<212> TYPE: PRT
<213> ORGANISM: Artificial sequence
<220> FEATURE:
<223> OTHER INFORMATION: Synthetic peptide

<400> SEQUENCE: 618

Ser Leu Tyr Thr Val Ser Ser Asn Val Val
1               5                   10

<210> SEQ ID NO 619
<211> LENGTH: 9
<212> TYPE: PRT
<213> ORGANISM: Artificial sequence
<220> FEATURE:
<223> OTHER INFORMATION: Synthetic peptide

<400> SEQUENCE: 619

Ser Ser Asp Val Gly Gly Tyr Asn Tyr
1               5

<210> SEQ ID NO 620
<211> LENGTH: 3
<212> TYPE: PRT
<213> ORGANISM: Artificial sequence
<220> FEATURE:
<223> OTHER INFORMATION: Synthetic peptide

<400> SEQUENCE: 620

Glu Val Ser
1

<210> SEQ ID NO 621
<211> LENGTH: 10
<212> TYPE: PRT
<213> ORGANISM: Artificial sequence
<220> FEATURE:
<223> OTHER INFORMATION: Synthetic peptide

<400> SEQUENCE: 621

Ser Ser Tyr Ala Gly Ser Asn Val Trp Val
1               5                   10

<210> SEQ ID NO 622
<211> LENGTH: 6
<212> TYPE: PRT
<213> ORGANISM: Artificial sequence
<220> FEATURE:

<223> OTHER INFORMATION: Synthetic peptide

<400> SEQUENCE: 622

Gln Ser Ile Ser Ser Trp
1 5

<210> SEQ ID NO 623
<211> LENGTH: 3
<212> TYPE: PRT
<213> ORGANISM: Artificial sequence
<220> FEATURE:
<223> OTHER INFORMATION: Synthetic peptide

<400> SEQUENCE: 623

Lys Ala Ser
1

<210> SEQ ID NO 624
<211> LENGTH: 8
<212> TYPE: PRT
<213> ORGANISM: Artificial sequence
<220> FEATURE:
<223> OTHER INFORMATION: Synthetic peptide

<400> SEQUENCE: 624

Gln Gln Tyr Asn Thr Tyr Arg Ala
1 5

<210> SEQ ID NO 625
<211> LENGTH: 6
<212> TYPE: PRT
<213> ORGANISM: Artificial sequence
<220> FEATURE:
<223> OTHER INFORMATION: Synthetic peptide

<400> SEQUENCE: 625

Asn Ile Glu Ser Thr Ser
1 5

<210> SEQ ID NO 626
<211> LENGTH: 3
<212> TYPE: PRT
<213> ORGANISM: Artificial sequence
<220> FEATURE:
<223> OTHER INFORMATION: Synthetic peptide

<400> SEQUENCE: 626

Phe Asp Ser
1

<210> SEQ ID NO 627
<211> LENGTH: 11
<212> TYPE: PRT
<213> ORGANISM: Artificial sequence
<220> FEATURE:
<223> OTHER INFORMATION: Synthetic peptide

<400> SEQUENCE: 627

Gln Val Trp Asp Ser Ser Ser Asp His Val Val
1 5 10

<210> SEQ ID NO 628
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 628

Ser Ser Asn Ile Gly Thr Thr Tyr
1               5


<210> SEQ ID NO 629
<211> LENGTH: 3
<212> TYPE: PRT
<213> ORGANISM: Artificial sequence
<220> FEATURE:
<223> OTHER INFORMATION: Synthetic peptide

<400> SEQUENCE: 629

Asp Asn Asn
1


<210> SEQ ID NO 630
<211> LENGTH: 11
<212> TYPE: PRT
<213> ORGANISM: Artificial sequence
<220> FEATURE:
<223> OTHER INFORMATION: Synthetic peptide

<400> SEQUENCE: 630

Gly Ala Trp Asp Ser Ser Leu Ser Ala Gly Val
1               5                   10
```